(12) United States Patent
Brimble et al.

(10) Patent No.: US 11,691,949 B2
(45) Date of Patent: Jul. 4, 2023

(54) QUINOLINE SULFONAMIDE COMPOUNDS AND THEIR USE AS ANTIBACTERIAL AGENTS

(71) Applicant: OTAGO INNOVATION LIMITED, Dunedin (NZ)

(72) Inventors: Margaret Anne Brimble, Auckland (NZ); Greg Murray Cook, Dunedin (NZ); Scott Andrew Ferguson, Dunedin (NZ); Adam Heikal, Kolsås (NZ); David Rennison, Auckland (NZ)

(73) Assignee: OTAGO INNOVATION LIMITED, Dunedin (NZ)

( * ) Notice: Subject to any disclaimer, the term of this patent is extended or adjusted under 35 U.S.C. 154(b) by 0 days.

(21) Appl. No.: 15/733,250

(22) PCT Filed: Dec. 20, 2018

(86) PCT No.: PCT/NZ2018/050182
§ 371 (c)(1),
(2) Date: Jun. 17, 2020

(87) PCT Pub. No.: WO2019/125185
PCT Pub. Date: Jun. 27, 2019

(65) Prior Publication Data
US 2020/0385354 A1    Dec. 10, 2020

Related U.S. Application Data

(60) Provisional application No. 62/608,141, filed on Dec. 20, 2017.

(51) Int. Cl.
| | |
|---|---|
| *C07D 215/40* | (2006.01) |
| *C07D 401/12* | (2006.01) |
| *A61K 45/06* | (2006.01) |
| *C07D 401/14* | (2006.01) |
| *C07D 405/12* | (2006.01) |
| *C07D 409/12* | (2006.01) |
| *C07D 413/12* | (2006.01) |
| *C07D 417/12* | (2006.01) |

(52) U.S. Cl.
CPC ......... *C07D 215/40* (2013.01); *C07D 401/12* (2013.01); *C07D 401/14* (2013.01); *C07D 405/12* (2013.01); *C07D 409/12* (2013.01); *C07D 413/12* (2013.01); *C07D 417/12* (2013.01); *A61K 45/06* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,147,704 B2 * | 12/2006 | Ueno | ................. | C09B 67/0033 106/498 |
| 9,102,688 B2 * | 8/2015 | Buhr | ......................... | A61P 7/06 |
| 2015/0158895 A1 | 6/2015 | Leblond et al. | | |
| 2016/0310528 A1 | 10/2016 | Simpson et al. | | |
| 2017/0151225 A1 | 6/2017 | Dahl | | |

FOREIGN PATENT DOCUMENTS

| | | |
|---|---|---|
| CN | 101768151 A | 7/2010 |
| CN | 103409135 A | 11/2013 |
| WO | 2010051064 A1 | 5/2010 |
| WO | 2012110603 A1 | 8/2012 |
| WO | 2012122534 A2 | 9/2012 |
| WO | 2014071044 A1 | 5/2014 |
| WO | WO-2014071044 A1 * | 5/2014 ................ A61P 3/00 |

OTHER PUBLICATIONS

Xue, G. et al. Tetrahedron 2002 vol. 58 pp. 4809-4815.*
International Search Report for PCT/NZ2018/050182, dated Apr. 1, 2019.
Yasuye, Masakazu, "Syntheses of sulfonilamides of the quinoline series. II. Synthesis of quinoline derivatives:", J. Pharm. Soc. Japan (1942), vol. 62, pp. 520-524. (English machine translation included).
Xue, Guoping et al.: 'The synthesis of azacrown ethers with quinoline-based sidearms as potential zinc(II) Tuorophores', Tetrahedron (2002), 58(24), 4809-4815.
Pagani, G., et al.. Antimicrobial activity of 8-aminoquinoline bidentate chelates Farmaco, Edizione Scientifica (1971), vol. 26, No. 2, pp. 118-131 (English machine translation attached).
Bompiani, Kristin M.; Caglic, Dejan; Krutein, Michelle C.; Benoni, Galit; Hrones, Morgan; Lairson, Luke L.; Bian, Haiyan; Smith, Garry R.; Dickerson, Tobin J (2016). High-Throughput Screening Uncovers Novel Botulinum Neurotoxin Inhibitor Chemotypes. ACS Combinatorial Science, ( ), acscombsci.6b00033-.doi:10.1021/acscombsci.6b00033.

(Continued)

*Primary Examiner* — Sikarl A Witherspoon
(74) *Attorney, Agent, or Firm* — Ryan L. Marshall; Barnes & Thornburg LLP

(57) ABSTRACT

The invention provides novel quinoline sulfonamide compounds of Formula I:

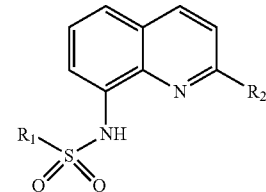

Formula I and their use for the treatment or prevention of bacterial infections caused by both Gram positive and Gram negative bacteria such as, for example, infections caused by one or more bacteria from the Enterobactericeae, Staphylococcaceae, or Streptococcaceae families. The compounds described and claimed herein may be formulated in one or more pharmaceutical or veterinary compositions for use in animal husbandry, and in particular in relation to the treatment of mastitis by directly targeting mastitis causing bacteria in a bovine herd. In certain embodiments described herein the pharmaceutical or veterinary compositions are formulated as a spray for direct administration to the udder of the bovine animal such as a cow.

15 Claims, 1 Drawing Sheet

(56) References Cited

OTHER PUBLICATIONS

Chai, Sergio C.; Ye, Qi-Zhuang (2009). Metal-mediated inhibition is a viable approach for inhibiting cellular methionine aminopeptidase. , 19(24), 6862-6864.doi:10.1016/j.bmcl.2009.10.082.

Xie, Y., Gong, G., Liu, Y., Deng, S., Rinderspacher, A., Branden, L.J., & Landry, D.W. (2008). Convenient preparation of N-8-quinolinyl benzenesultams as novel NF-κB inhibitors. Tetrahedron Letters, 49, 2320-2323.

* cited by examiner

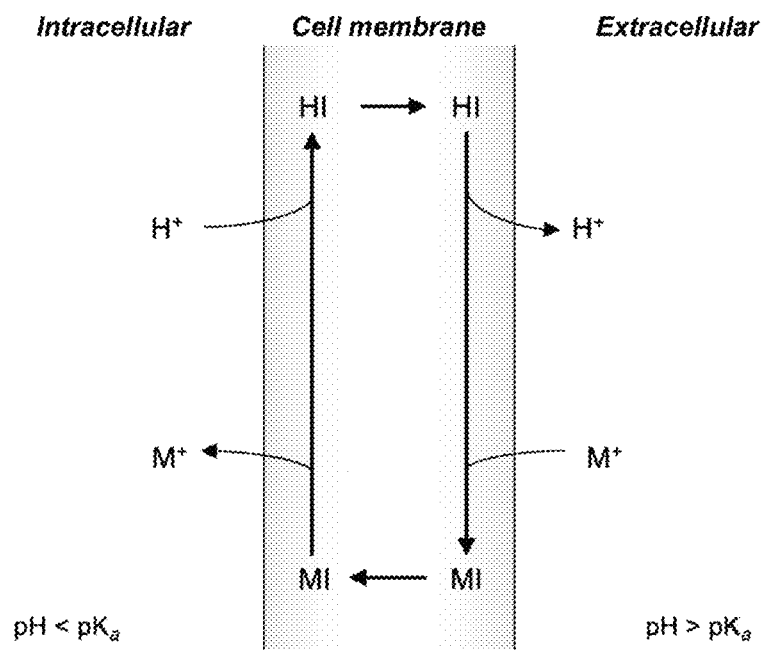

QUINOLINE SULFONAMIDE COMPOUNDS AND THEIR USE AS ANTIBACTERIAL AGENTS

CROSS REFERENCE TO RELATED APPLICATIONS

This application is a 371 national phase of PCT/NZ2018/050182, filed Dec. 20, 2018, which claims the benefit of the filing date of U.S. Application No. 62/608,141, filed Dec. 20, 2017, the disclosures of which are incorporated, in their entirety, by this reference.

TECHNICAL FIELD

The invention relates to quinoline sulfonamide compounds and their use for the treatment or prevention of bacterial infections. In particular, the invention relates to novel sulfonamide quinoline compounds substituted at the 2-position of the quinoline ring.

BACKGROUND OF THE INVENTION

Bacterial Infections in humans and other animals continue to present a threat to human and animal health and well-being. Despite the evolution of several classes of antibiotics over the last century, bacterial resistance to commonly used antibiotics is a globally recognised problem to which there are few solutions at present.

Antibiotic resistance is present in every country. In February 2017, the World Health Organisation listed priority human pathogens for which research and development of new antibiotics is most critical, these being *Acinetobacter baumannii* (carbapenem-resistant), *Pseudomonas aeruginosa* (carbapenem-resistant), and Enterobacteraceae (carbapenem-resistant, ESBL-producing). Animals, particularly in food production, are also susceptible to a wide range of bacterial infections, e.g. Gram-negative respiratory disease, foot-rot, and mastitis including acute *E. coli* mastitis, and *Pseudomonas* mastitis. In New Zealand, dairy cattle, antibiotics are used primarily during dry cow therapy and for the treatment of mastitis, where the most commonly used antibiotics are penicillin-based products. Worldwide the widespread use of antibiotics in animal food has driven the rise of antibiotic-resistant strains of bacteria.

Antibiotics are used in livestock production for both disease prevention and treatment of disease. Approximately 80% of the antibiotics used in the United States is through their use in the animal food industry, and many of these antibiotics are important in human medicine. While the development of antibiotic resistance by bacteria is a natural process, the widespread use of antibiotics in the animal food and agricultural industries raises the possibility of antibiotic-resistant bacteria of animal origin contributing to infections in humans. As such, it is crucial that new antibacterial agents are developed that are targeted specifically at the agricultural industry, to protect the use of essential human antibiotics.

One example of a problematic bacterial infection in animals is bovine mastitis, a bacterial infection of the udder. Bovine mastitis is the most significant production limiting disease for dairying worldwide, and costs the New Zealand dairy industry NZ$280M each year. Bovine mastitis is not only a disease of economic importance, but one with possible implications for public health. Mastitis is recognised as the most common reason for antibiotic use in the dairy industry, both within New Zealand and worldwide.

Preventative teat sprays containing sanitisers such as chlorhexidine and iodine are vital tools in managing mastitis. These sanitisers are applied to cows after every milking. However, chlorhexidine and iodine are essential human medicines used for the control of infection. They appear on the World Health Organisation (WHO) Model List of Essential Medicines. As bacterial tolerance to chlorhexidine has already been reported in *Staphylococcus aureus, Klebsiella pneumonae*, and *Pseudomonas aeruginosa*, it is crucial that new non-medical alternative sanitisers are developed for use in the agricultural industry.

An ionophore is a chemical species that reversibly binds ions. Many ionophores are lipid-soluble entities that transport ions across a cell membrane. An ionophore binds a metal, transports it across a lipid bilayer, releases the metal, and then re-engages with metal ions not yet transported across the membrane, repeating the process. Ionophores have been used as growth promotants in agriculture for decades. Monensin is the most widely used, and is included in animal feed to improve weight gain of beef cattle through a mechanism that alters rumen fermentation, in turn increasing milk yield and reducing milk fat content. Current evidence indicates that ionophores are unlikely to contribute to the spread of antibiotic resistance in humans because ionophores are not used in human medicine and have a distinct mode of action compared to antibiotic used in humans.

In the search for improved antibacterial agents, the applicant has found that ionophores able to bind zinc are potential candidates because they show rapid killing of certain bacteria. Notably, these bacteria are mastitis-causing bacteria and ionophores that bind zinc are not used in human medicine to treat bacterial infections. Taking advantage of zinc as a means to control mastitis offers two advantages: zinc homeostasis is critical to bacterial survival, and excess zinc accumulation in bacteria results in cellular toxicity.

8-Hydroxy quinoline compounds are examples of ionophores. They have the general structure:

They are known to have varied antibacterial activity against a number of clinically-relevant bacterial species, including *E. coli, S. aureus, C. difficile, S. mutans*, and *Mycobacterium* species. The acidic phenolic hydrogen is thought to be important for activity because it can be ionised relatively easily. Adding electron withdrawing substituents to the phenol ring (e.g. chlorine atoms) decreases the $pK_a$ of the phenolic hydrogen and can affect antibacterial activity. Sulfonamide quinoline compounds (where the hydroxyl group of the phenol ring has been replaced with a sulfonamide group) are also effective as antibacterial agents through their ionophore activity. The $pK_a$ of the sulfonamide hydrogen can be tailored by changing the substituent on the sulfonamide moiety.

Examples of known 8-sulfonamide quinoline compounds include:

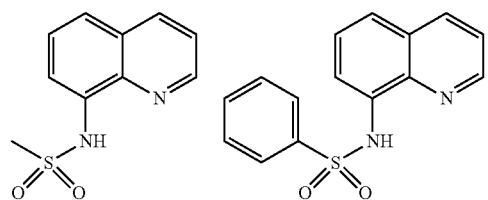

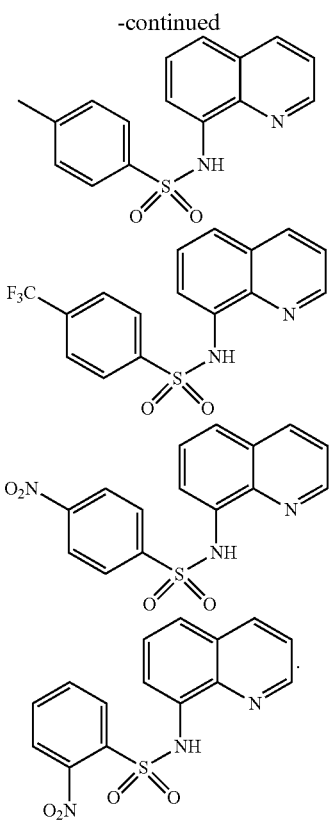

The applicant has now found that certain substituted sulfonamide quinoline compounds exhibit inhibitory (antibacterial) activity against several groups of bacteria (including Gram-positive and Gram-negative bacteria). It is therefore an object of the invention to provide novel quinoline compounds as potential antibacterial agents, or to at least provide a useful alternative to current antibiotics.

SUMMARY OF THE INVENTION

In one aspect of the invention there is provided a compound of Formula I:

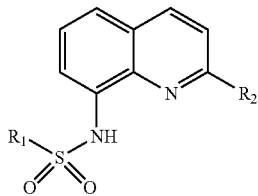

Formula I wherein $R_1$ is selected from the group comprising alkyl, cycloalkyl, alkenyl, alkynyl, aryl, alkylaryl, alkoxyaryl, heterocyclyl, alkylheterocyclyl, alkoxyheterocyclyl, heteroaryl, alkylheteroaryl, alkoxyheteroaryl, $C_1$-$C_6$ alkyl(cycloalkyl), aralkyl, $C_1$-$C_6$ alkyl(alkylaryl), $C_1$-$C_6$ alkyl(alkoxyaryl), $C_1$-$C_6$ alkyl(heterocyclyl), $C_1$-$C_6$ alkyl(alkylheterocyclyl), $C_1$-$C_6$ alkyl(alkoxyheterocyclyl), $C_1$-$C_6$ alkyl(heteroaryl), $C_1$-$C_6$ alkyl(alkylheteroaryl), and $C_1$-$C_6$ alkyl(alkoxyheteroaryl), each of which is optionally substituted with one or more of halogen, $OR_3$, OCHO, OC(=O)$R_3$, $SR_3$, $SCF_3$, SC(=O)$R_3$, S(=O)$R_3$, $SO_2R_3$, $SO_3H$, $SO_2NR_3R_4$, $NR_3R_4$, $NR_3$CHO, $NR_3COR_4$, $NR_3CO_2R_4$, $NR_3SO_2R_4$, $NO_2$, CN, CHO, $COR_3$, $CO_2H$, $CO_2R_3$, and $CONR_3R_4$;

$R_2$ is selected from the group comprising alkyl, cycloalkyl, alkenyl, alkynyl, aryl, alkylaryl, alkoxyaryl, heterocyclyl, alkylheterocyclyl, alkoxyheterocyclyl, heteroaryl, alkylheteroaryl, alkoxyheteroaryl, $C_1$-$C_6$ alkyl(cycloalkyl), aralkyl, $C_1$-$C_6$ alkyl(alkylaryl), $C_1$-$C_6$ alkyl(alkoxyaryl), $C_1$-$C_6$ alkyl(heterocyclyl), $C_1$-$C_6$ alkyl(alkylheterocyclyl), $C_1$-$C_6$ alkyl(alkoxyheterocyclyl), $C_1$-$C_6$ alkyl(heteroaryl), $C_1$-$C_6$ alkyl(alkylheteroaryl), $C_1$-$C_6$ alkyl(alkoxyheteroaryl), ($C_1$-$C_6$ alkyl)$NR_7R_8$, ($C_1$-$C_6$ alkyl)$NR_7$($C_1$-$C_6$ alkyl)$NR_8R_9$, ($C_1$-$C_6$ alkyl)N(($C_1$-$C_6$ alkyl)$NR_8R_9$)$_2$, ($C_1$-$C_6$ alkyl)$NR_7$($C_1$-$C_6$ alkyl)$OR_8$, ($C_1$-$C_6$ alkyl)$NR_7$($C_1$-$C_6$ alkyl)O($C_1$-$C_6$ alkyl)$OR_8$, ($C_1$-$C_6$ alkyl)$NR_7$C(=O)$R_8$, ($C_1$-$C_6$ alkyl)$NR_7$($C_1$-$C_6$ alkyl)C(=O)$NR_8R_9$, ($C_0$-$C_3$ alkyl)CH=$NOR_7$, CH=$NNR_7R_8$, ($C_0$-$C_3$ alkyl)CH=$NNR_7R_8$, ($C_0$-$C_3$ alkyl)CH=$NNR_3$C(=O)$R_7$, ($C_0$-$C_3$alkyl)CH=$NNR_3$C(=S)$R_7$, ($C_0$-$C_3$alkyl)CH=$NNR_3$C(=O)$NR_7R_8$, ($C_0$-$C_3$ alkyl)CH=$NNR_3$C(=S)$NR_7R_8$, ($C_0$-$C_3$ alkyl)CH=$NNR_3$C(=O)C(=$NOR_7$)$R_8$, ($C_0$-$C_3$ alkyl)CH=$NR_3$C(=O)C(=O)$NR_7R_8$, ($C_0$-$C_3$ alkyl)C(=O)$NR_7R_8$, ($C_0$-$C_3$ alkyl)C(=O)$NR_3OR_7$, ($C_0$-$C_3$ alkyl)C(=O)$NR_3NR_7R_8$, each of which is optionally substituted with one or more of each of halogen, alkyl, $OR_3$, OCHO, OC(=O)$R_3$, $SR_3$, SC(=O)$R_3$, S(=O)$R_3$, $S_2R_3$, $SO_3H$, $SO_2NR_3R_4$, $NR_3R_4$, $NR_3$CHO, $NR_3COR_4$, $NR_3CO_2R_4$, $NR_3$C(=O)$NR_4R_5$, $NR_3$C(=S)$NR_4R_5$, $NR_3$C(=$NR_4$)$NR_5R_6$, $NR_3$C(=$NNO_2$)$NR_4R_5$, $NR_3$C(=NCN)$NR_4R_5$, $NR_3$C(=$CHNO_2$)$NR_4R_5$, $NR_3$C(=$NR_4$)$R_5$, $NR_3SO_2R_4$, $NO_2$, CN, CHO, $COR_3$, $CO_2H$, $C_2R_3$, $CONR_3R_4$, C(=O)$NR_3OR_3$, C(=O)$NR_3NR_4R_5$, C(=O)$NR_3$CN, or wherein $R_2$ is CHO;

$R_3$, $R_4$, $R_5$ and $R_6$ are each selected from the group comprising hydrogen, alkyl, aryl and aralkyl; and $R_7$, $R_8$ and $R_9$ are each selected from the group comprising hydrogen, hydroxyl, alkyl, cycloalkyl, alkenyl, alkynyl, aryl, alkylaryl, alkoxyaryl, heterocyclyl, alkylheterocyclyl, alkoxyheterocyl, heteroaryl, alkylheteroaryl, alkoxyheteroaryl, $C_1$-$C_6$ alkyl(cycloalkyl), aralkyl, $C_1$-$C_6$ alkyl(alkylaryl), $C_1$-$C_6$ alkyl(alkoxyaryl), $C_1$-$C_6$ alkyl(heterocyclyl), $C_1$-$C_6$ alkyl(alkylheterocyclyl), $C_1$-$C_6$ alkyl(alkoxyheterocyclyl), $C_1$-$C_6$ alkyl(heteroaryl), $C_1$-$C_6$ alkyl(alkylheteroaryl), $C_1$-$C_6$ alkyl(alkoxyheteroaryl), monosaccharide, disaccharide, each of which is optionally substituted with one or more of halogen, $OR_3$, OCHO, OC(=O)$R_3$, $SR_3$, SC(=O)$R_3$, S(=O)$R_3$, $SO_2R_3$, $SO_3H$, $SO_2NR_3R_4$, $NR_3R_4$, $NR_3$CHO, $NR_3COR_4$, $NR_3CO_2R_4$, $NR_3$C(=O)$NR_4R_5$, $NR_3$C(=S)$NR_4R_5$, $NR_3$C(=$NR_4$)$NR_5R_6$, $NR_3$C(=$NNO_2$) $NR_4R_5$, $NR_3$C(=NCN)$NR_4R_5$, $NR_3$C(=$CHNO_2$)$NR_4R_5$, $NR_3$C(=$NR_4$)$R_5$, $NR_3S_2R_4$, $NO_2$, CN, CHO, $COR_3$, $CO_2H$, $CO_2R_3$, $CONR_3R_4$, C(=O)$NR_3OR_3$, C(=O)$NR_3NR_4R_5$, C(=O)$NR_3$CN; or a pharmaceutically acceptable salt or hydrate thereof.

In certain embodiments, $R_2$ is not an unsubstituted group selected from the following: methyl, pyridyl, formyl, 1-2-[(1-ethyl-6,7-dimethoxy-4-isoquinolinyl)methyl, 3-(trifluoromethyl)phenyl, 3-(trifluoromethoxy)phenyl, or 3,5-dimethyl-1H-pyrazol-1-yl.

In certain embodiments, where $R_1$ is an unsubstituted aminosulfonylphenyl, $R_2$ is not unsubstituted 2-(diethylamino)ethyl.

In certain embodiments the compound is a compound of Formula I wherein $R_1$ and $R_2$ are not both unsubstituted groups selected from: alkyl, alkenyl, alkynyl, or aryl.

In certain embodiments, the compound defined by Formula I is not Benzenesulfonamide, 4-hydroxy-N-(2-methyl- 8-quinolinyl); 2-Thiophenesulfonamide, 4-bromo-N-(2-methyl-8-quinolinyl); Benzenesulfonamide, 4-(1-methylethoxy)-N-(2-methyl-8-quinolinyl); Ethanesulfonamide, N-[2-[(1-ethyl-6,7-dimethoxy-4-isoquinolinyl)methyl]-8-quinolinyl]; Methanesulfonamide, N-[2-[(1-ethyl-6,7-dimethoxy-4-isoquinolinyl)methyl]-8-quinolinyl]; Methanesulfonamide, N-(2-formyl-8-quinolinyl); Benzenesulfonamide, 3-fluoro-N-(2-methyl-8-quinolinyl); Benzenesulfonamide, 2-fluoro-N-(2-methyl-8-quinolinyl); Benzenesulfonamide, 3-bromo-N-(2-methyl-8-quinolinyl); Benzenesulfonamide, 3-chloro-N-(2-methyl-8-quinolinyl); Benzenesulfonamide, 2-chloro-N-(2-methyl-8-quinolinyl); Benzenesulfonamide, 2-bromo-N-(2-methyl-8-quinolinyl); 3-Pyridinesulfonamide, N-(2-methyl-8-quinolinyl); 2-Thiophenesulfonamide, 5-methyl-N-(2-methyl-8-quinolinyl); 2-Thiophenesulfonamide, 3-methyl-N-(2-methyl-8-quinolinyl); 2-Thiophenesulfonamide, 5-ethyl-N-(2-methyl-8-quinolinyl); 3-Thiophenesulfonamide, 2,5-dichloro-N-(2-methyl-8-quinolinyl); 2-Thiophenesulfonamide, 4-bromo-5-chloro-N-(2-methyl-8-quinolinyl); 2-Furansulfonamide, N-(2-methyl-8-quinolinyl); 2-Thiophenesulfonamide, 4,5-dibromo-N-(2-methyl-8-quinolinyl); 2-Thiophenesulfonamide, 5-chloro-N-(2-methyl-8-quinolinyl)-4-nitro; 2-Thiophenesulfonamide, 4,5-dichloro-N-(2-methyl-8-quinolinyl); Benzenesulfonamide, 4-amino-2-fluoro-N-(2-methyl-8-quinolinyl); Benzenesulfonamide, 4-amino-2-methoxy-N-[2-(2-pyridinyl)-8-quinolinyl]; Methanesulfonamide, N-[2-(2-pyridinyl)-8-quinolinyl]; Benzenesulfonamide, 2-methoxy-4-nitro-N-[2-(2-pyridinyl)-8-quinolinyl]; 2-Thiophenesulfonamide, 5-bromo-N-[2-(2-pyridinyl)-8-quinolinyl]; Benzenesulfonamide, 4-cyano-N-[2-(2-pyridinyl)-8-quinolinyl]; Benzoic acid, 3-[[[2-(2-pyridinyl)-8-quinolinyl]amino]sulfonyl]; Benzenesulfonamide, 3,5-difluoro-N-[2-(2-pyridinyl)-8-quinolinyl]; Benzoic acid, 2-[[[2-(2-pyridinyl)-8-quinolinyl]amino]sulfonyl]-, methyl ester; Benzenesulfonamide, N-[2-(2-pyridinyl)-8-quinolinyl]-4-(trifluoromethyl); Benzenesulfonamide, N-[2-(2-pyridinyl)-8-quinolinyl]; Benzenesulfonamide, 4-chloro-N-[2-(2-pyridinyl)-8-quinolinyl]; Benzenesulfonamide, 4-methyl-N-[2-(2-pyridinyl)-8-quinolinyl]; 2-Pyridinesulfonamide, N-[2-[3-(trifluoromethyl)phenyl]-8-quinolinyl]; 1-Piperazinesulfonamide, N-[2-[3-(trifluoromethoxy)phenyl]-8-quinolinyl]; 1-Pyrrolidinesulfonamide, N-[2-[3-(trifluoromethoxy)phenyl]-8-quinolinyl]; Benzenesulfonamide, 3,5-dichloro-N-(2-methyl-8-quinolinyl); Benzenesulfonamide, 2-amino-4-fluoro-N-(2-methyl-8-quinolinyl); Benzenesulfonamide, 4-fluoro-N-(2-methyl-8-quinolinyl)-2-nitro; 2-Thiophenesulfonamide, 5-bromo-N-(2-methyl-8-quinolinyl); Benzenesulfonamide, 2-amino-N-(2-methyl-8-quinolinyl)-4-(trifluoromethyl); Benzenesulfonamide, 2-amino-4-methoxy-N-(2-methyl-8-quinolinyl); Benzenesulfonamide, 4-hydroxy-N-(2-methyl-8-quinolinyl)-2-nitro; 2-Thiophenesulfonamide, 5-chloro-N-(2-methyl-8-quinolinyl); Benzenesulfonamide, 2-amino-N-(2-methyl-8-quinolinyl); Benzenesulfonamide, 2-methyl-N-(2-methyl-8-quinolinyl)-5-nitro; Benzenesulfonamide, 4-methoxy-N-(2-methyl-8-quinolinyl)-2-nitro; Benzenesulfonamide, N-(2-methyl-8-quinolinyl)-2-nitro-4-(trifluoromethyl); Benzenesulfonamide, N-(2-methyl-8-quinolinyl)-3-nitro; Benzenesulfonamide, 2-methoxy-5-methyl-N-(2-methyl-8-quinolinyl); Benzenesulfonamide, 4-amino-N-(2-methyl-8-quinolinyl); 8-Quinolinesulfonamide, N-(2-methyl-8-quinolinyl); Benzenesulfonamide, N-(2-methyl-8-quinolinyl)-2-nitro; Benzenesulfonamide, 4-fluoro-N-(2-methyl-8-quinolinyl); Benzenesulfonamide, 4-chloro-N-(2-methyl-8-quinolinyl); Acetamide, N-[4-[[(2-methyl-8-quinolinyl)amino]sulfonyl]phenyl]; Acetamide, N-[4-[[[2-[2-(diethylamino)ethyl]-8-quinolinyl]amino]sulfonyl] phenyl]; Benzenesulfonamide, N-(2-formyl-8-quinolinyl); Methanesulfonamide, N-[2-(3,5-dimethyl-1Hpyrazol-1-yl)-8-quinolinyl]; Benzenesulfonamide, N-[2-(3,5-dimethyl-1Hpyrazol-1-yl)-8-quinolinyl]-4-methyl; Methanesulfonamide, 1,1,1-trifluoro-N-(2-methyl-8-quinolinyl); Benzenesulfonamide, 4-methoxy-N-(2-methyl-8-quinolinyl); Methanesulfonamide, N-(2-methyl-8-quinolinyl); Benzenesulfonamide, 2,4,6-trimethyl-N-(2-methyl-8-quinolinyl); Benzenesulfonamide, N-(2-methyl-8-quinolinyl) and Benzenesulfonamide, 4-methyl-N-(2-methyl-8-quinolinyl).

In certain embodiments, the compounds defined by Formula I are not ZDR030, ZDR035, ZDR046, ZDR090, ZDR102, ZDR111, ZDR112, ZDR113, ZDR114, ZDR115, ZDR116, ZDR117, ZDR119, ZDR120, ZDR121, ZDR122, ZDR124, ZDR125, ZDR143, ZDR167, ZDR170, ZDR171, ZDR187, ZDR261, ZDR262, ZDR266, ZDR268 and ZDR269, as disclosed herein.

In certain embodiments according to the compounds defined by Formula I, $R_1$ is alkyl, aryl, alkylaryl, alkoxyaryl or heteroaryl substituted with halogen.

In certain embodiments $R_1$ is aryl, alkylaryl or alkoxyaryl substituted with halogen.

In certain embodiments $R_1$ is alkylaryl or alkoxyaryl substituted with halogen.

In certain embodiments $R_1$ is alkylaryl substituted with halogen. For example, $R_1$ may be (trifluoromethyl)phenyl.

In certain embodiments $R_2$ is $(C_1-C_6$ alkyl$)NR_7R_8$.

In certain embodiments $R_1$ is alkyl, aryl, alkylaryl, alkoxyaryl or heteroaryl substituted with halogen and $R_2$ is $(C_1-C_6$ alkyl$)NR_7R_8$.

In certain embodiments $R_1$ is aryl, alkylaryl or alkoxyaryl substituted with halogen and $R_2$ is $(C_1-C_6$ alkyl$)NR_7R_8$.

In certain embodiments $R_1$ is alkylaryl or alkoxyaryl substituted with halogen and $R_2$ is $(C_1-C_6$ alkyl$)NR_7R_8$ In certain embodiments $R_1$ is alkylaryl substituted with halogen and $R_2$ is $(C_1-C_6$ alkyl$)NR_7R_8$.

In certain embodiments $R_1$ is (trifluoromethyl)phenyl and $R_2$ is $(C_1-C_6$ alkyl$)NR_7R_8$.

In certain embodiments $R_2$ is $(C_1-C_6$ alkyl$)NR_7(C_1-C_6$ alkyl$)NR_8R_9$.

In certain embodiments $R_1$ is alkyl, aryl, alkylaryl, alkoxyaryl or heteroaryl substituted with halogen and $R_2$ is $(C_1-C_6$ alkyl$)NR_7(C_1-C_6$ alkyl$)NR_8R_9$.

In certain embodiments $R_1$ is aryl, alkylaryl or alkoxyaryl substituted with halogen and $R_2$ is $(C_1-C_6$ alkyl$)NR_7(C_1-C_6$ alkyl$)NR_8R_9$.

In certain embodiments $R_1$ is alkylaryl or alkoxyaryl substituted with halogen and $R_2$ is $(C_1-C_6$ alkyl$)NR(C_1-C_6$ alkyl$)NR_8R_9$.

In certain embodiments $R_1$ is alkylaryl substituted with halogen and $R_2$ is $(C_1-C_6$ alkyl$)NR_7(C_1-C_6$ alkyl$)NR_8R_9$.

In certain embodiments $R_1$ is (trifluoromethyl)phenyl and $R_2$ is $(C_1-C_6$ alkyl$)NR_7(C_1-C_6$ alkyl$)NR_8R_9$.

In certain embodiments $R_2$ is $(C_0-C_3$ alkyl$)CH=NOR_7$.

In certain embodiments $R_1$ is alkyl, aryl, alkylaryl, alkoxyaryl or heteroaryl substituted with halogen and $R_2$ is $(C_0-C_3$ alkyl$)CH=NOR_7$.

In certain embodiments $R_1$ is aryl, alkylaryl or alkoxyaryl substituted with halogen and $R_2$ is $(C_0-C_3$ alkyl$)CH=NOR_7$.

In certain embodiments $R_1$ is alkylaryl or alkoxyaryl substituted with halogen and $R_2$ is $(C_0-C_3$ alkyl$)CH=NOR_7$.

In certain embodiments $R_1$ is alkylaryl substituted with halogen and $R_2$ is $(C_0-C_3$ alkyl$)CH=NOR_7$.

In certain embodiments $R_1$ is (trifluoromethyl)phenyl and $R_2$ is $(C_0-C_3$ alkyl$)CH=NOR_7$.

In certain embodiments $R_2$ is $(C_0$-$C_3$ alkyl)CH=NNR$_7$R$_8$.

In certain embodiments $R_1$ is alkyl, aryl, alkylaryl, alkoxyaryl or heteroaryl substituted with halogen and $R_2$ is $(C_0$-$C_3$ alkyl)CH=NNR$_7$R$_8$.

In certain embodiments $R_1$ is aryl, alkylaryl or alkoxyaryl substituted with halogen and $R_2$ is $(C_0$-$C_3$ alkyl)CH=NNR$_7$R$_8$.

In certain embodiments $R_1$ is alkylaryl or alkoxyaryl substituted with halogen and $R_2$ is $(C_0$-$C_3$ alkyl)CH=NNR$_7$R$_8$.

In certain embodiments $R_1$ is alkylaryl substituted with halogen and $R_2$ is $(C_0$-$C_3$ alkyl)CH=NNR$_7$R$_8$.

In certain embodiments $R_1$ is (trifluoromethyl)phenyl and $R_2$ is $(C_0$-$C_3$ alkyl)CH=NNR$_7$R$_8$.

In certain embodiments $R_2$ is $(C_0$-$C_3$ alkyl)CH=NNR$_3$C(=O)R$_7$.

In certain embodiments $R_1$ is alkyl, aryl, alkylaryl, alkoxyaryl or heteroaryl substituted with halogen and $R_2$ is $(C_0$-$C_3$ alkyl)CH=NNR$_3$C(=O)R$_7$.

In certain embodiments $R_1$ is aryl, alkylaryl or alkoxyaryl substituted with halogen and $R_2$ is $(C_0$-$C_3$ alkyl)CH=NNR$_3$C(=O)R$_7$.

In certain embodiments $R_1$ is alkylaryl or alkoxyaryl substituted with halogen and $R_2$ is $(C_0$-$C_3$ alkyl)CH=NNR$_3$C(=O)R$_7$.

In certain embodiments $R_1$ is alkylaryl substituted with halogen and $R_2$ is $(C_0$-$C_3$ alkyl)CH=NNR$_3$C(=O)R$_7$.

In certain embodiments $R_1$ is (trifluoromethyl)phenyl and $R_2$ is $(C_0$-$C_3$ alkyl)CH=NNR$_3$C(=O)R$_7$.

In certain embodiments $R_2$ is $(C_0$-$C_3$ alkyl)CH=NNR$_3$C(=O)NR$_7$R$_8$.

In certain embodiments $R_1$ is alkyl, aryl, alkylaryl, alkoxyaryl or heteroaryl substituted with halogen and $R_2$ is $(C_0$-$C_3$ alkyl)CH=NNR$_3$C(=O)NR$_7$R$_8$.

In certain embodiments $R_1$ is aryl, alkylaryl or alkoxyaryl substituted with halogen and $R_2$ is $(C_0$-$C_3$ alkyl)CH=NNR$_3$C(=O)NR$_7$R$_8$.

In certain embodiments $R_1$ is alkylaryl or alkoxyaryl substituted with halogen and $R_2$ is $(C_0$-$C_3$ alkyl)CH=NNR$_3$C(=O)NR$_7$R$_8$.

In certain embodiments $R_1$ is alkylaryl substituted with halogen and $R_2$ is $(C_0$-$C_3$ alkyl)CH=NNR$_3$C(=O)NR$_7$R$_8$.

In certain embodiments $R_1$ is (trifluoromethyl)phenyl and $R_2$ is $(C_0$-$C_3$ alkyl)CH=NNR$_3$C(=O)NR$_7$R$_8$.

In certain embodiments $R_2$ is $(C_0$-$C_3$ alkyl)CH=NNR$_3$C(=S)NR$_7$R$_8$.

In certain embodiments $R_1$ is alkyl, aryl, alkylaryl, alkoxyaryl or heteroaryl substituted with halogen and $R_2$ is $(C_0$-$C_3$ alkyl)CH=NNR$_3$C(=S)NR$_7$R$_8$.

In certain embodiments $R_1$ is aryl, alkylaryl or alkoxyaryl substituted with halogen and $R_2$ is $(C_0$-$C_3$ alkyl)CH=NNR$_3$C(=S)NR$_7$R$_8$.

In certain embodiments $R_1$ is alkylaryl or alkoxyaryl substituted with halogen and $R_2$ is $(C_0$-$C_3$ alkyl)CH=NNR$_3$C(=S)NR$_7$R$_8$.

In certain embodiments $R_1$ is alkylaryl substituted with halogen and $R_2$ is $(C_0$-$C_3$ alkyl)CH=NNR$_3$C(=S)NR$_7$R$_8$.

In certain embodiments $R_1$ is (trifluoromethyl)phenyl and $R_2$ is $(C_0$-$C_3$ alkyl)CH=NNR$_3$C(=S)NR$_7$R$_8$.

Exemplary compounds of the invention include:

ZDR018

$R_1$ = alkylaryl substituted with halogen;
$R_2$ = alkyl

ZDR019

$R_1$ = alkylaryl substituted with halogen;
$R_2$ = formyl

ZDR022

$R_1$ = alkylaryl substituted with halogen;
$R_2$ = $(C_1$-$C_6$ alkyl)NR$_7$R$_8$;
$R_7$ = $R_8$ = alkyl -continued

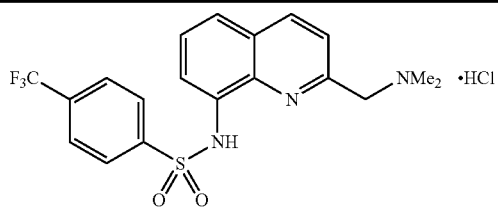

ZDR022-HCl

R$_1$ = alkylaryl substituted with halogen;
R$_2$ = (C$_1$-C$_6$ alkyl)NR$_7$R$_8$;
R$_7$ = R$_8$ = alkyl

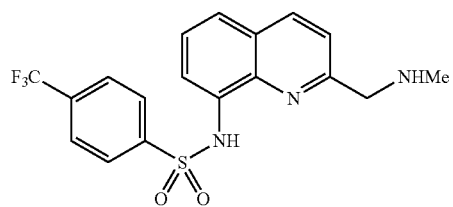

ZDR024

R$_1$ = alkylaryl substituted with halogen;
R$_2$ = (C$_1$-C$_6$ alkyl)NR$_7$R$_8$;
R$_7$ = hydrogen
R$_8$ = alkyl

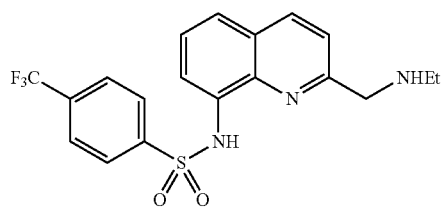

ZDR025

R$_1$ = alkylaryl substituted with halogen;
R$_2$ = (C$_1$-C$_6$ alkyl)NR$_7$R$_8$;
R$_7$ = hydrogen
R$_8$ = alkyl

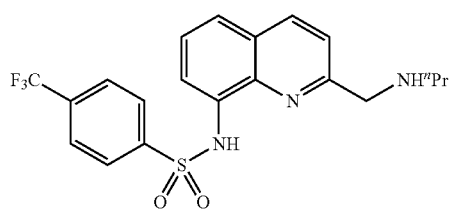

ZDR026

R$_1$ = alkylaryl substituted with halogen;
R$_2$ = (C$_1$-C$_6$ alkyl)NR$_7$R$_8$;
R$_7$ = hydrogen
R$_8$ = alkyl

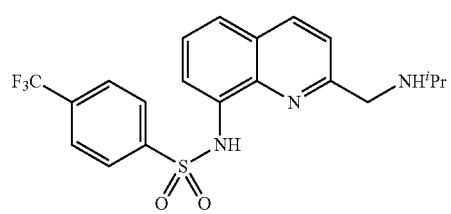

ZDR027

R$_1$ = alkylaryl substituted with halogen;
R$_2$ = (C$_1$-C$_6$ alkyl)NR$_7$R$_8$;
R$_7$ = hydrogen
R$_8$ = alkyl

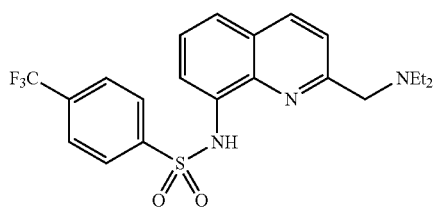

ZDR028

R₁ = alkylaryl substituted with halogen;
R₂ = (C₁-C₆ alkyl)NR₇R₈;
R₇ = R₈ = alkyl

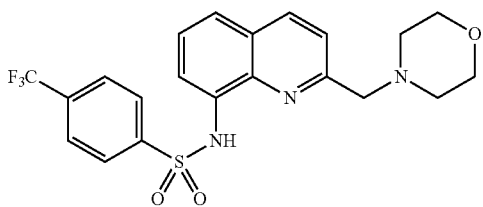

ZDR029

R₁ = alkylaryl substituted with halogen;
R₂ = C₁-C₆ alkyl(heterocycyl)

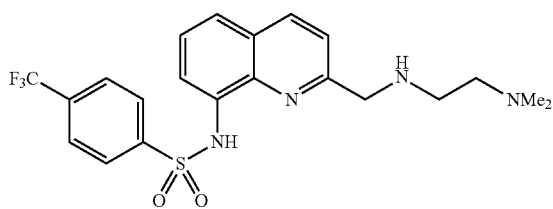

ZDR030

R₁ = alkylaryl substituted with halogen
R₂ = (C₁-C₆ alkyl)NR₇(C₁-C₆ alkyl)NR₈R₉;
R₇ = hydrogen;
R₈ = R₉ = alkyl

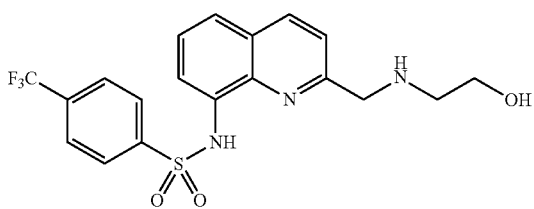

ZDR031

R₁ = alkylaryl substituted with halogen
R₂ = (C₁-C₆ alkyl)NR₇R₈;
R₇ = hydrogen;
R₈ = alkyl substituted with OR₃;
R₃ = hydrogen

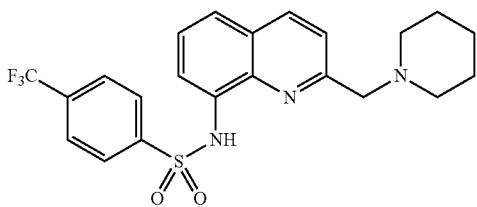

ZDR033

R₁ = alkylaryl substituted with halogen
R₂ = C₁-C₆ alkyl(heterocyclyl)

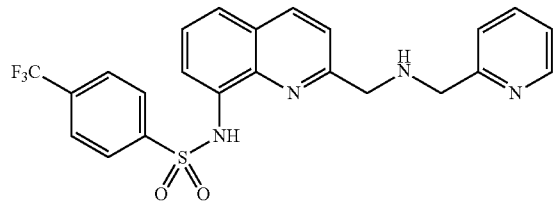

ZDR035

R₁ = alkylaryl substituted with halogen
R₂ = (C₁-C₆ alkyl)NR₇R₈;
R₇ = hydrogen;
R₈ = C₁-C₆ alkyl(heteroaryl)

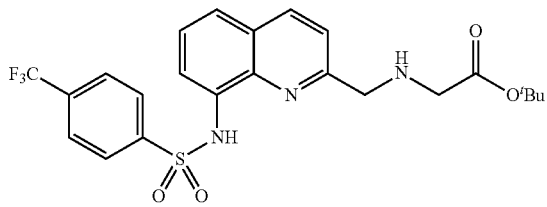

ZDR041

R₁ = alkylaryl substituted with halogen
R₂ = (C₁-C₆ alkyl)NR₇R₈;
R₇ = hydrogen;
R₈ = alkyl substituted with CO₂R₃;
R₃ = alkyl

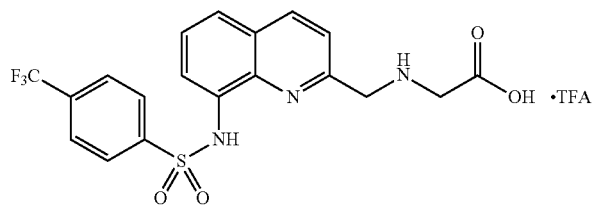

ZDR043

R₁ = alkylaryl substituted with halogen
R₂ = (C₁-C₆ alkyl)NR₇R₈;
R₇ = hydrogen;
R₈ = alkyl substituted with CO₂H

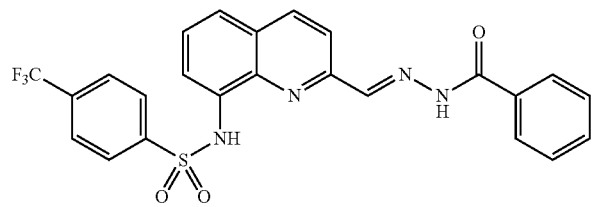

ZDR045

R₁ = alkylaryl substituted with halogen
R₂ = (C₀-C₃ alkyl)CH=NNR₃C(=O)R₇;
R₃ = hydrogen;
R₇ = aryl

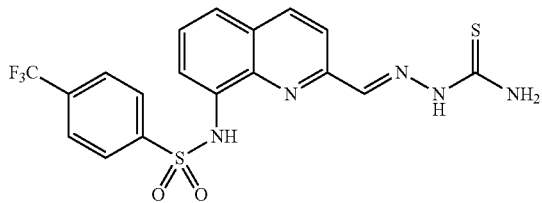
ZDR046
R₁ = alkylaryl substituted with halogen
R₂ = (C₀-C₃ alkyl)CH═NNR₃C(═S)NR₇R₈;
R₃ = R₇ = R₈ = hydrogen
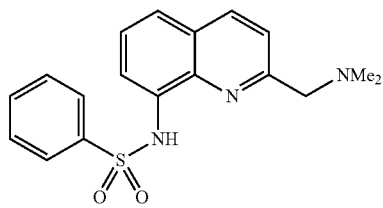
ZDR061
R₁ = aryl
R₂ = (C₁-C₆ alkyl)NR₇R₈;
R₇ = R₈ = alkyl
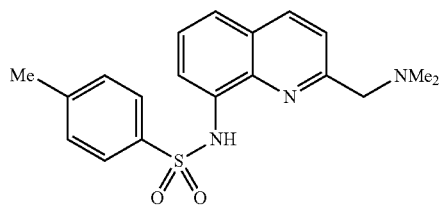
ZDR062
R₁ = alkylaryl
R₂ = (C₁-C₆ alkyl)NR₇R₈;
R₇ = R₈ = alkyl
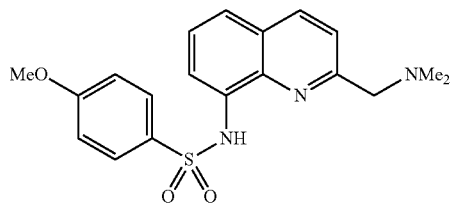
ZDR063
R₁ = alkoxyaryl
R₂ = (C₁-C₆ alkyl)NR₇R₈;
R₇ = R₈ = alkyl
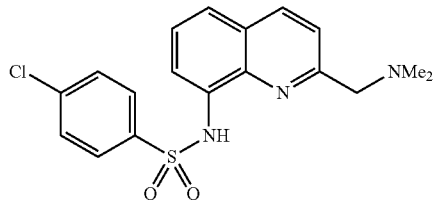
ZDR064
R₁ = aryl substituted with halogen
R₂ = (C₁-C₆ alkyl)NR₇R₈;
R₇ = R₈ = alkyl

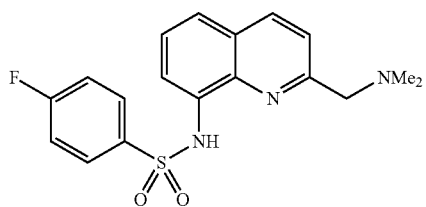

ZDR065

R₁ = aryl substituted with halogen
R₂ = (C₁-C₆ alkyl)NR₇R₈;
R₇ = R₈ = alkyl

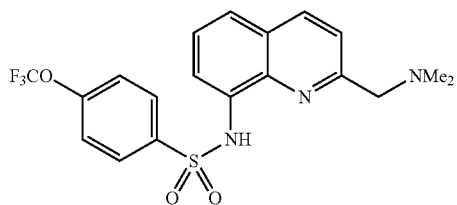

ZDR066

R₁ = alkoxyaryl substituted with halogen
R₂ = (C₁-C₆ alkyl)NR₇R₈;
R₇ = R₈ = alkyl

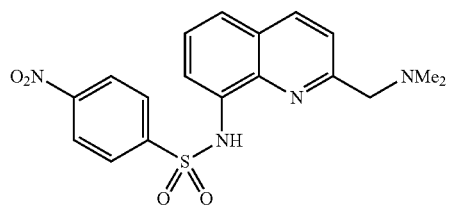

ZDR067

R₁ = aryl substituted with NO₂
R₂ = (C₁-C₆ alkyl)NR₇R₈;
R₇ = R₈ = alkyl

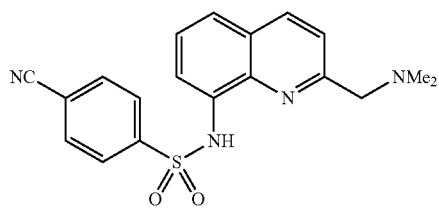

ZDR068

R₁ = aryl substituted with CN
R₂ = (C₁-C₆ alkyl)NR₇R₈;
R₇ = R₈ = alkyl

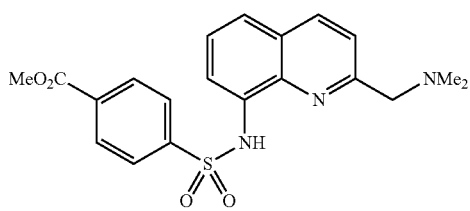

ZDR069

R₁ = aryl substituted with CO₂R₃;
R₃ = alkyl
R₂ = (C₁-C₆ alkyl)NR₇R₈;
R₇ = R₈ = alkyl

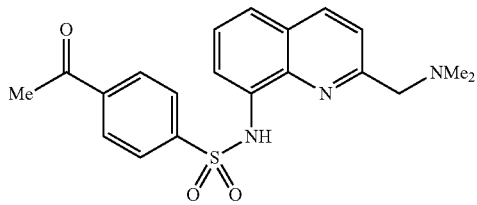

ZDR070

R₁ = aryl substituted with COR$_3$;
R$_3$ = alkyl
R$_2$ = (C$_1$-C$_6$ alkyl)NR$_7$R$_8$;
R$_7$ = R$_8$ = alkyl

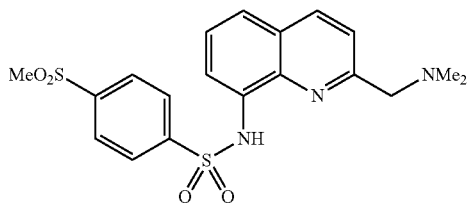

ZDR071

R₁ = aryl substituted with SO$_2$R$_3$;
R$_3$ = alkyl
R$_2$ = (C$_1$-C$_6$ alkyl)NR$_7$R$_8$;
R$_7$ = R$_8$ = alkyl

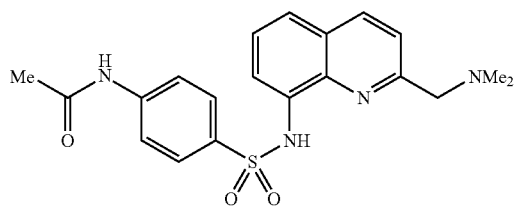

ZDR072

R₁ = aryl substituted with NR$_3$COR$_4$;
R$_3$ = hydrogen;
R$_4$ = alkyl
R$_2$ = (C$_1$-C$_6$ alkyl)NR$_7$R$_8$;
R$_7$ = R$_8$ = alkyl

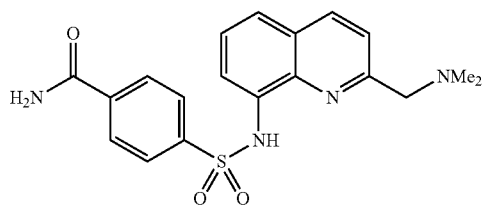

ZDR073

R₁ = aryl substituted with CONR$_3$R$_4$;
R$_3$ = R$_4$ = hydrogen
R$_2$ = (C$_1$-C$_6$ alkyl)NR$_7$R$_8$;
R$_7$ = R$_8$ = alkyl -continued
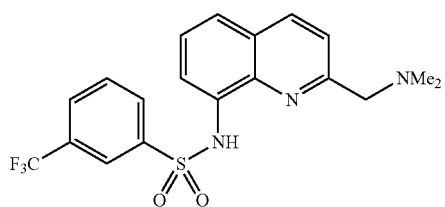
ZDR074
R₁ = alkylaryl substituted with halogen
R₂ = (C₁-C₆ alkyl)NR₇R₈;
R₇ = R₈ = alkyl
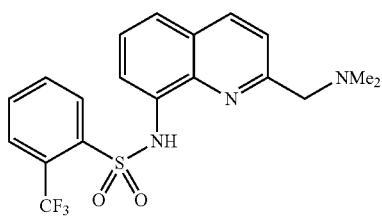
ZDR075
R₁ = alkylaryl substituted with halogen
R₂ = (C₁-C₆ alkyl)NR₇R₈;
R₇ = R₈ = alkyl
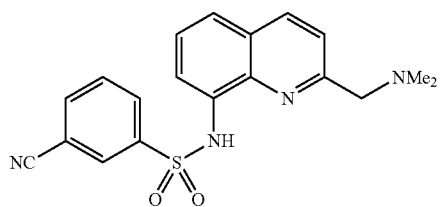
ZDR076
R₁ = aryl substituted with CN
R₂ = (C₁-C₆ alkyl)NR₇R₈;
R₇ = R₈ = alkyl
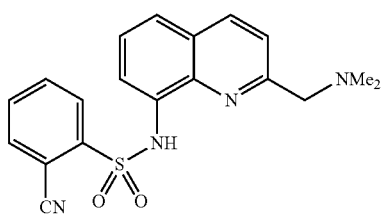
ZDR077
R₁ = aryl substituted with CN
R₂ = (C₁-C₆ alkyl)NR₇R₈;
R₇ = R₈ = alkyl
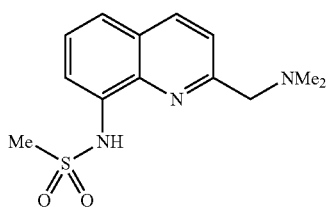
ZDR078
R₁ = alkyl
R₂ = (C₁-C₆ alkyl)NR₇R₈;
R₇ = R₈ = alkyl

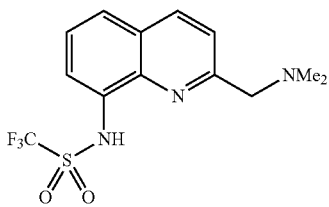
ZDR079
R₁ = alkyl substituted with halogen
R₂ = (C₁-C₆ alkyl)NR₇R₈;
R₇ = R₈ = alkyl
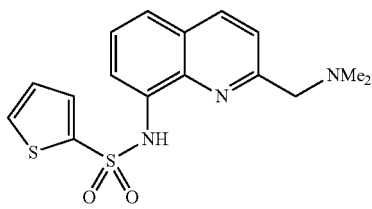
ZDR080
R₁ = heteroaryl
R₂ = (C₁-C₆ alkyl)NR₇R₈;
R₇ = R₈ = alkyl
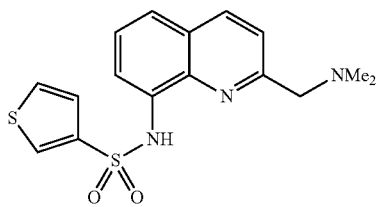
ZDR081
R₁ = heteroaryl
R₂ = (C₁-C₆ alkyl)NR₇R₈;
R₇ = R₈ = alkyl
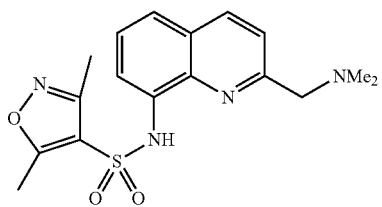
ZDR082
R₁ = heteroaryl
R₂ = (C₁-C₆ alkyl)NR₇R₈;
R₇ = R₈ = alkyl
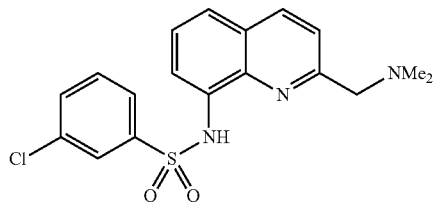
ZDR084
R₁ = aryl substituted with halogen
R₂ = (C₁-C₆ alkyl)NR₇R₈;
R₇ = R₈ = alkyl

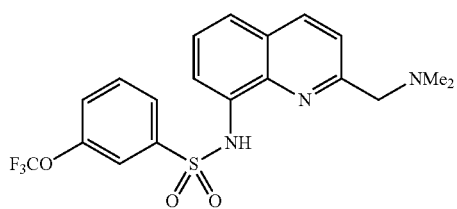

ZDR085

R₁ = alkoxyaryl substituted with halogen
R₂ = (C₁-C₆ alkyl)NR₇R₈;
R₇ = R₈ = alkyl

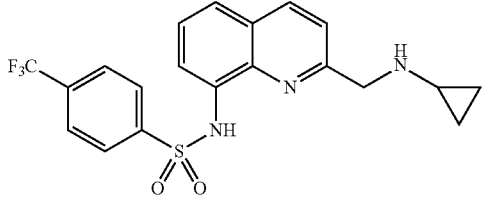

ZDR086

R₁ = alkylaryl substituted with halogen
R₂ = (C₁-C₆ alkyl)NR₇R₈;
R₇ = hydrogen;
R₈ = cycloalkyl

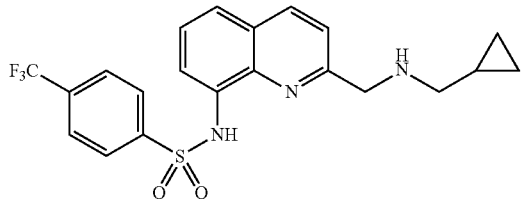

ZDR087

R₁ = alkylaryl substituted with halogen
R₂ = (C₁-C₆ alkyl)NR₇R₈;
R₇ = hydrogen;
R₈ = C₁-C₆ alkyl(cycloalkyl)

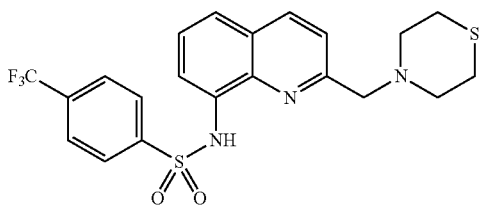

ZDR088

R₁ = alkylaryl substituted with halogen
R₂ = C₁-C₆ alkyl(heterocyclyl)

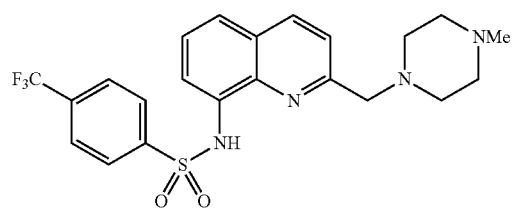

ZDR089

R₁ = alkylaryl substituted with halogen
R₂ = C₁-C₆ alkyl(heterocyclyl)

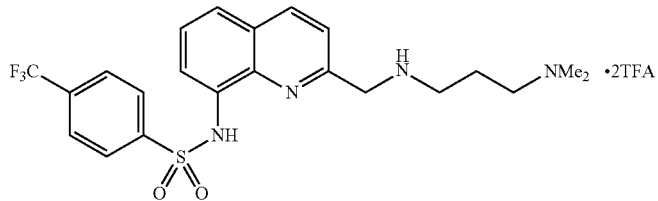

ZDR090

R₁ = alkylaryl substituted with halogen
R₂ = (C₁-C₆ alkyl)NR₇(C₁-C₆ alkyl)NR₈R₉;
R₇ = hydrogen;
R₈ = R₉ = alkyl

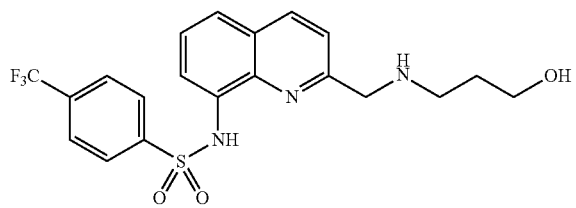

ZDR091

R₁ = alkylaryl substituted with halogen
R₂ = (C₁-C₆ alkyl)NR₇R₈;
R₇ = hydrogen;
R₈ = alkyl substituted with OR₃;
R₃ = hydrogen

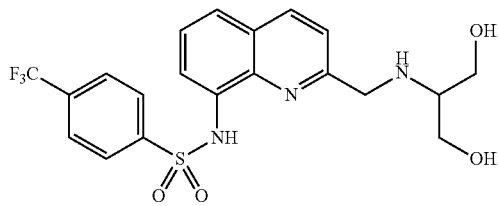

ZDR092

R₁ = alkylaryl substituted with halogen
R₂ = (C₁-C₆ alkyl)NR₇R₈;
R₇ = hydrogen;
R₈ = alkyl substituted with OR₃;
R₃ = hydrogen

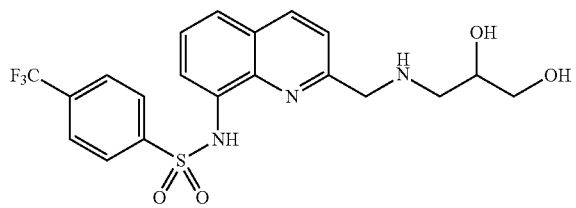

ZDR093

R₁ = alkylaryl substituted with halogen
R₂ = (C₁-C₆ alkyl)NR₇R₈;
R₇ = hydrogen;
R₈ = alkyl substituted with OR₃;
R₃ = hydrogen

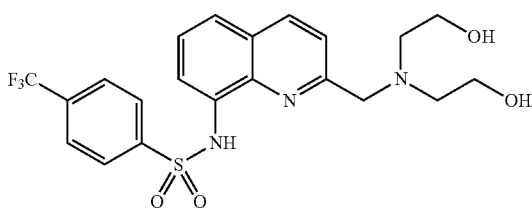

ZDR094

R₁ = alkylaryl substituted with halogen
R₂ = (C₁-C₆ alkyl)NR₇R₈;
R₇ = alkyl substituted with OR₃;
R₈ = alkyl substituted with OR₃;
R₃ = hydrogen

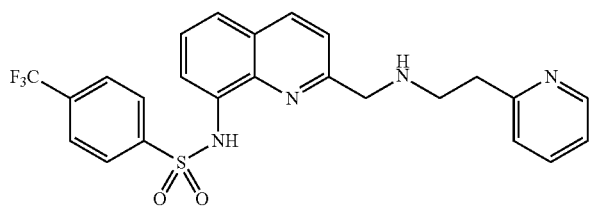

ZDR095

R₁ = alkylaryl substituted with halogen
R₂ = (C₁-C₆ alkyl)NR₇R₈;
R₇ = hydrogen;
R₈ = C₁-C₆ alkyl(heteroaryl)

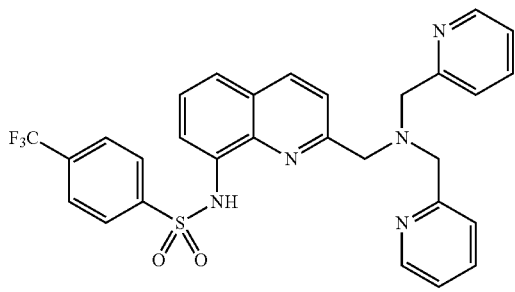

ZDR096

R₁ = alkylaryl substituted with halogen
R₂ = (C₁-C₆ alkyl)NR₇R₈;
R₇ = R₈ = C₁-C₆ alkyl(heteroaryl)

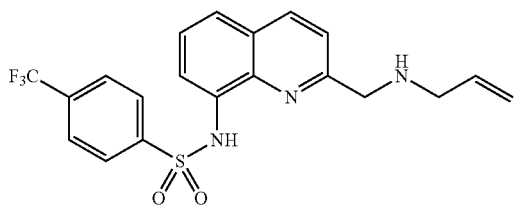

ZDR097

R₁ = alkylaryl substituted with halogen
R₂ = (C₁-C₆ alkyl)NR₇R₈;
R₇ = hydrogen;
R₈ = alkenyl -continued

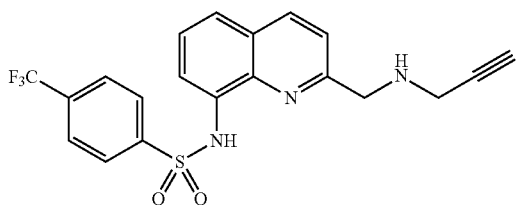

ZDR098

R₁ = alkylaryl substituted with halogen
R₂ = (C₁-C₆ alkyl)NR₇R₈;
R₇ = hydrogen;
R₈ = alkynyl

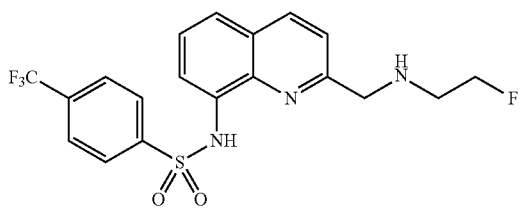

ZDR099

R₁ = alkylaryl substituted with halogen
R₂ = (C₁-C₆ alkyl)NR₇R₈;
R₇ = hydrogen;
R₈ = alkyl substituted with halogen

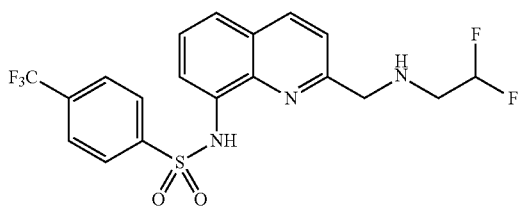

ZDR100

R₁ = alkylaryl substituted with halogen
R₂ = (C₁-C₆ alkyl)NR₇R₈;
R₇ = hydrogen;
R₈ = alkyl substituted with halogen

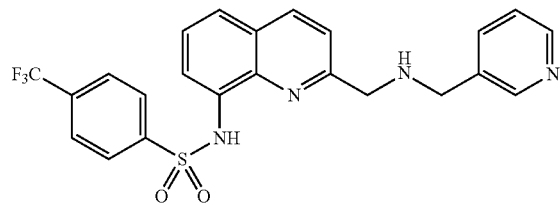

ZDR101

R₁ = alkylaryl substituted with halogen
R₂ = (C₁-C₆ alkyl)NR₇R₈;
R₇ = hydrogen;
R₈ = C₁-C₆ alkyl(heteroaryl)

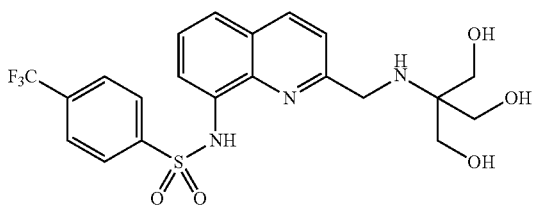

ZDR102

R₁ = alkylaryl substituted with halogen
R₂ = (C₁-C₆ alkyl)NR₇R₈;
R₇ = hydrogen;
R₈ = alkyl substituted with OR₃;
R₃ = hydrogen

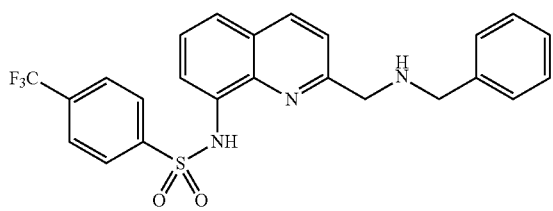

ZDR103

R₁ = alkylaryl substituted with halogen
R₂ = (C₁-C₆ alkyl)NR₇R₈;
R₇ = hydrogen;
R₈ = aralkyl

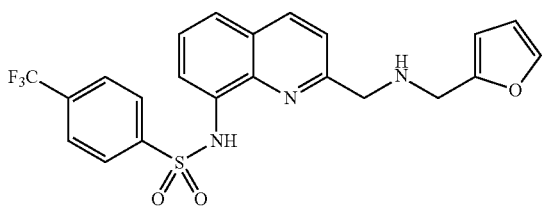

ZDR106

R₁ = alkylaryl substituted with halogen
R₂ = (C₁-C₆ alkyl)NR₇R₈;
R₇ = hydrogen;
R₈ = C₁-C₆ alkyl(heteroaryl)

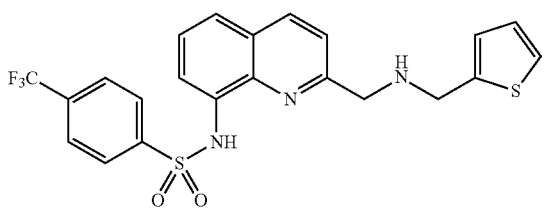

ZDR107

R₁ = alkylaryl substituted with halogen
R₂ = (C₁-C₆ alkyl)NR₇R₈;
R₇ = hydrogen;
R₈ = C₁-C₆ alkyl(heteroaryl)

-continued

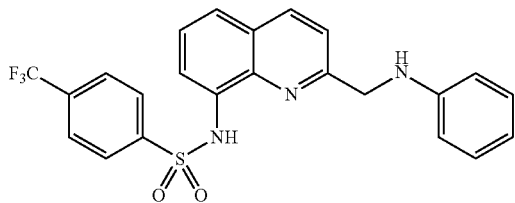

ZDR108

R$_1$ = alkylaryl substituted with halogen
R$_2$ = (C$_1$-C$_6$ alkyl)NR$_7$R$_8$;
R$_7$ = hydrogen;
R$_8$ = aryl

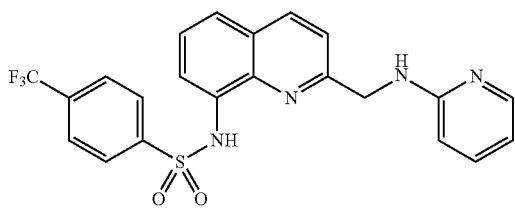

ZDR109

R$_1$ = alkylaryl substituted with halogen
R$_2$ = (C$_1$-C$_6$ alkyl)NR$_7$R$_8$;
R$_7$ = hydrogen;
R$_8$ = heteroaryl

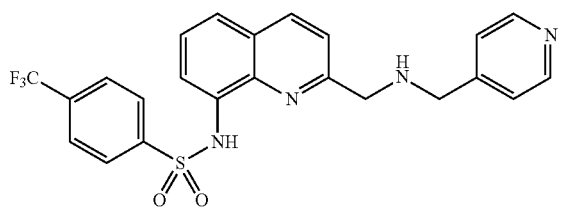

ZDR110

R$_1$ = alkylaryl substituted with halogen
R$_2$ = (C$_1$-C$_6$ alkyl)NR$_7$R$_8$;
R$_7$ = hydrogen;
R$_8$ = C$_1$-C$_6$ alkyl(heteroaryl)

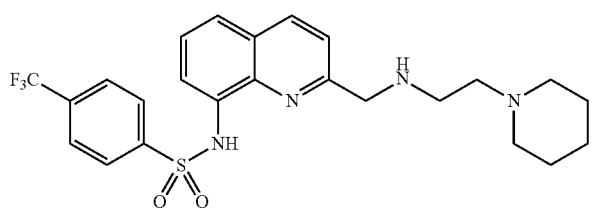

ZDR111

R$_1$ = alkylaryl substituted with halogen
R$_2$ = (C$_1$-C$_6$ alkyl)NR$_7$R$_8$;
R$_7$ = hydrogen;
R$_8$ = C$_1$-C$_6$ alkyl(heterocyclyl)

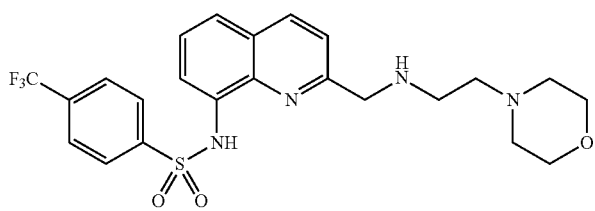

ZDR112

R$_1$ = alkylaryl substituted with halogen
R$_2$ = (C$_1$-C$_6$ alkyl)NR$_7$R$_8$;
R$_7$ = hydrogen;
R$_8$ = C$_1$-C$_6$ alkyl(heterocyclyl)

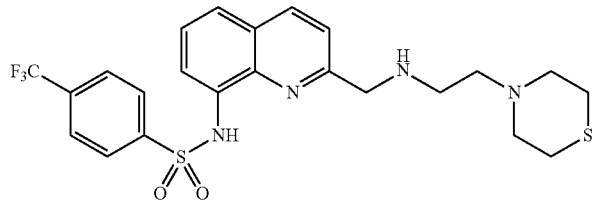

ZDR113

R₁ = alkylaryl substituted with halogen
R₂ = (C₁-C₆ alkyl)NR₇R₈;
R₇ = hydrogen;
R₈ = C₁-C₆ alkyl(heterocyclyl)

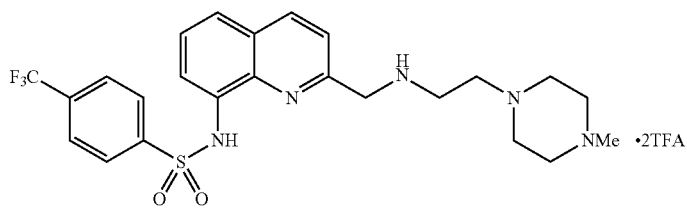

ZDR114

R₁ = alkylaryl substituted with halogen
R₂ = (C₁-C₆ alkyl)NR₇R₈;
R₇ = hydrogen;
R₈ = C₁-C₆ alkyl(heterocyclyl)

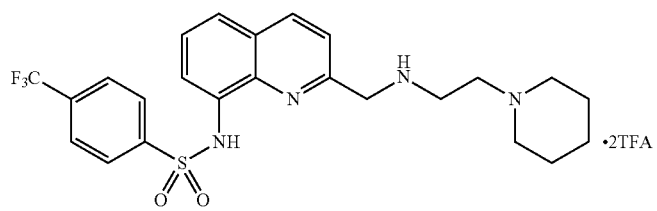

ZDR115

R₁ = alkylaryl substituted with halogen
R₂ = (C₁-C₆ alkyl)NR₇R₈;
R₇ = hydrogen;
R₈ = C₁-C₆ alkyl(heterocyclyl)

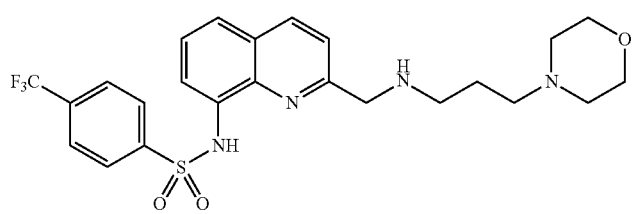

ZDR116

R₁ = alkylaryl substituted with halogen
R₂ = (C₁-C₆ alkyl)NR₇R₈;
R₇ = hydrogen;
R₈ = C₁-C₆ alkyl(heterocyclyl)

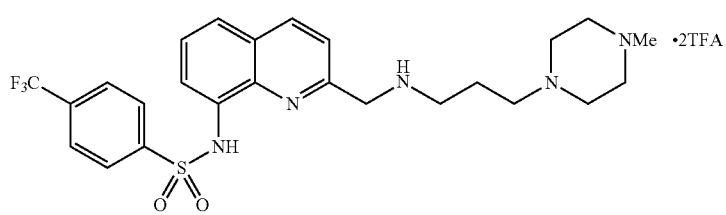

ZDR117

R₁ = alkylaryl substituted with halogen
R₂ = (C₁-C₆ alkyl)NR₇R₈;
R₇ = hydrogen;
R₈ = C₁-C₆ alkyl(heterocyclyl)

-continued

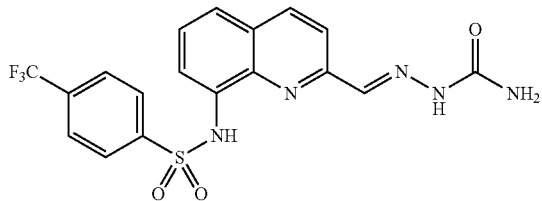

ZDR118

R₁ = alkylaryl substituted with halogen
R₂ = (C₀-C₃ alkyl)CH=NNR₃C(=O)NR₇R₈;
R₃ = R₇ = R₈ = hydrogen

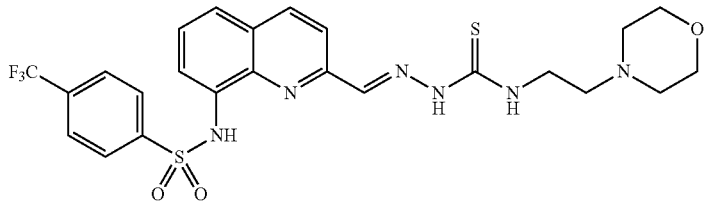

ZDR119

R₁ = alkylaryl substituted with halogen
R₂ = (C₀-C₃ alkyl)CH=NNR₃C(=S)NR₇R₈;
R₃ = R₇ = hydrogen;
R₈ = C₁C₆ alkyl(heterocyclyl

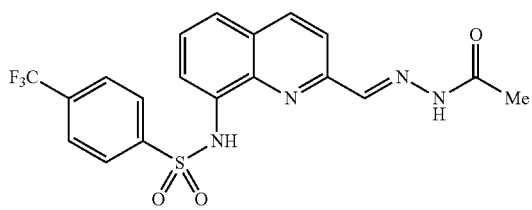

ZDR120

R₁ = alkylaryl substituted with halogen
R₂ = (C₀-C₃ alkyl)CH=NNR₃C(=O)R₇;
R₃ = hydrogen;
R₇ = alkyl

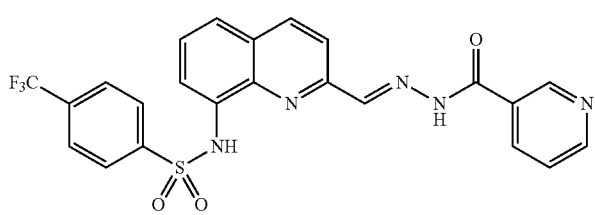

ZDR121

R₁ = alkylaryl substituted with halogen
R₂ = (C₀-C₃ alkyl)CH=NNR₃C(=O)R₇;
R₃ = hydrogen;
R₇ = heteroaryl

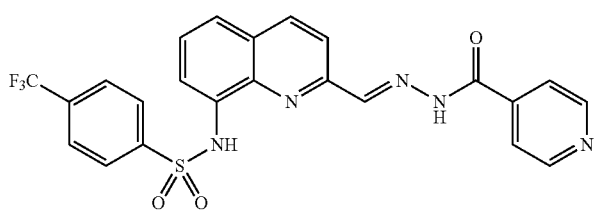

ZDR122

R₁ = alkylaryl substituted with halogen
R₂ = (C₀-C₃ alkyl)CH=NNR₃C(=O)R₇;
R₃ = hydrogen;
R₇ = heteroaryl -continued

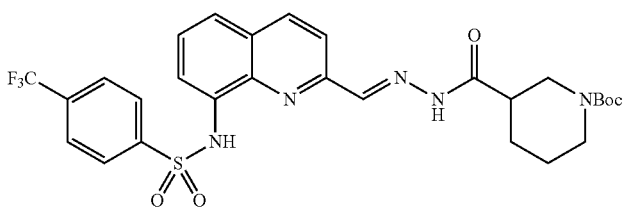

ZDR123

R₁ = alkylaryl substituted with halogen
R₂ = (C₀-C₃ alkyl)CH=NNR₃C(=O)R₇;
R₃ = hydrogen;
R₇ = heterocyclyl

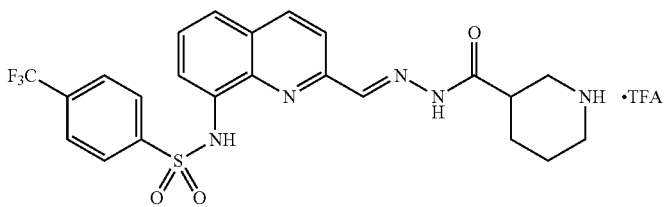

ZDR124

R₁ = alkylaryl substituted with halogen
R₂ = (C₀-C₃ alkyl)CH=NNR₃C(=O)R₇;
R₃ = hydrogen;
R₇ = heterocyclyl

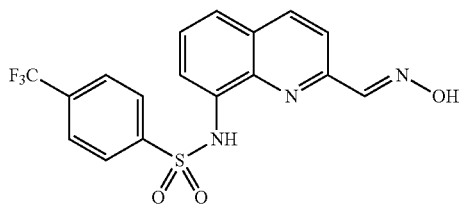

ZDR125

R₁ = alkylaryl substituted with halogen
R₂ = (C₀-C₃ alkyl)CH=NOR₇;
R₇ = hydrogen

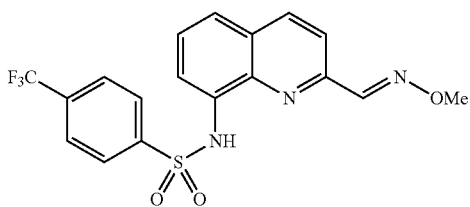

ZDR126

R₁ = alkylaryl substituted with halogen
R₂ = (C₀-C₃ alkyl)CH=NOR₇;
R₇ = alkyl

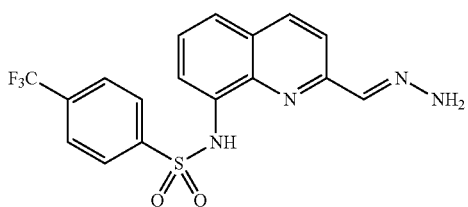

ZDR127

R₁ = alkylaryl substituted with halogen
R₂ = (C₀-C₃ alkyl)CH=NNR₇R₈;
R₇ = R₈ = hydrogen

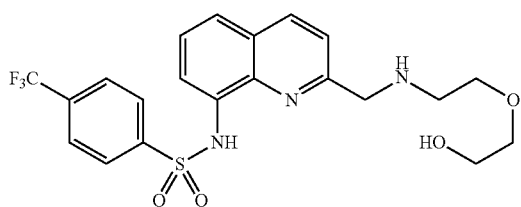

ZDR129

R₁ = alkylaryl substituted with halogen
R₂ = (C₁-C₆ alkyl)NR₇(C₁-C₆ alkyl)OR₈;
R₇ = hydrogen;
R₈ = alkyl subtituted with OR₃;
R₃ = hydrogen

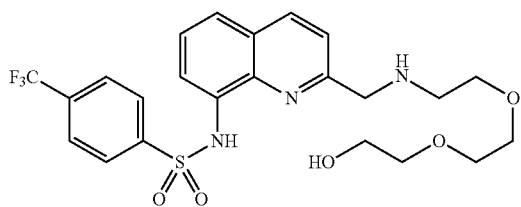

ZDR130

R₁ = alkylaryl substituted with halogen
R₂ = (C₁-C₆ alkyl)NR₇(C₁-C₆ alkyl)O(C₁-C₆ alkyl)OR₈;
R₇ = hydrogen;
R₈ = alkyl subtituted with OR₃;
R₃ = hydrogen

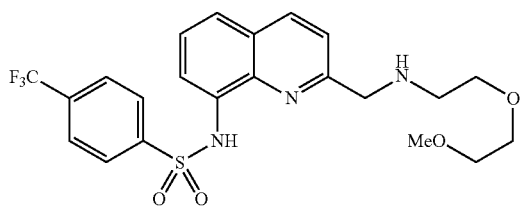

ZDR131

R₁ = alkylaryl substituted with halogen
R₂ = (C₁-C₆ alkyl)NR₇(C₁-C₆ alkyl)OR₈;
R₇ = hydrogen;
R₈ = alkyl subtituted with OR₃;
R₃ = alkyl

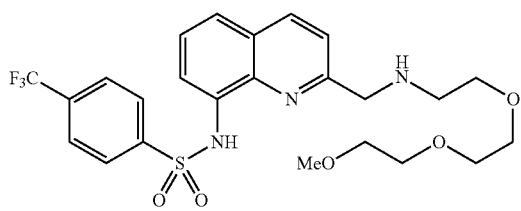

ZDR132

R₁ = alkylaryl substituted with halogen
R₂ = (C₁-C₆ alkyl)NR₇(C₁-C₆ alkyl)O(C₁-C₆ alkyl)OR₈;
R₇ = hydrogen;
R₈ = alkyl subtituted with OR₃;
R₃ = alkyl -continued

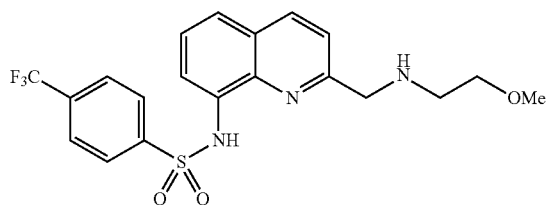

ZDR133

R₁ = alkylaryl substituted with halogen
R₂ = (C₁-C₆ alkyl)NR₇R₈;
R₇ = hydrogen;
R₈ = alkyl subtituted with OR₃;
R₃ = alkyl

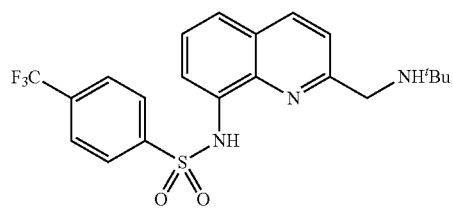

ZDR135

R₁ = alkylaryl substituted with halogen
R₂ = (C₁-C₆ alkyl)NR₇R₈;
R₇ = hydrogen;
R₈ = alkyl

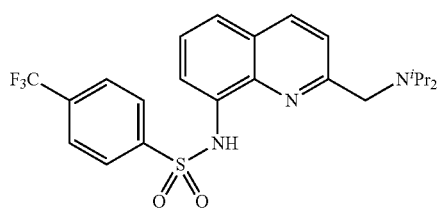

ZDR136

R₁ = alkylaryl substituted with halogen
R₂ = (C₁-C₆ alkyl)NR₇R₈;
R₇ = R₈ = alkyl

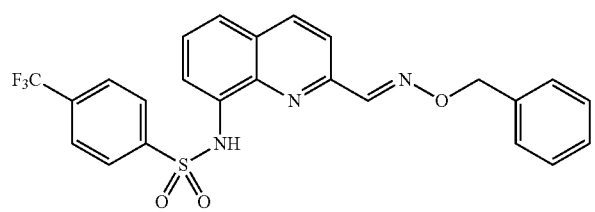

ZDR137

R₁ = alkylaryl substituted with halogen
R₂ = (C₀-C₃ alkyl)CH=NOR₇;
R₇ = aralkyl

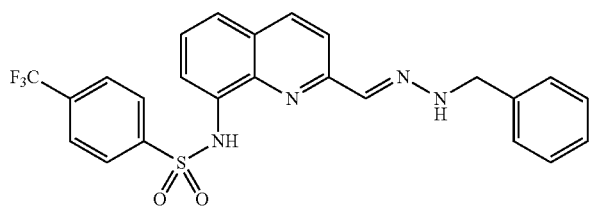

ZDR138

R₁ = alkylaryl substituted with halogen
R₂ = (C₀-C₃ alkyl)CH=NNR₇R₈;
R₇ = hydrogen;
R₈ = aralkyl

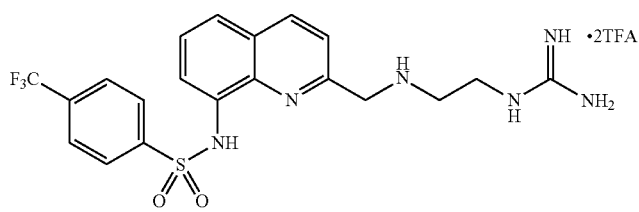

ZDR143

R₁ = alkylaryl substituted with halogen
R₂ = (C₁-C₆ alkyl)NR₇R₈;
R₇ = hydrogen;
R₈ = alkyl substituted with NR₃C(=NR₄)NR₅R₆;
R₃ = R₄ = R₅ = R₆ = hydrogen

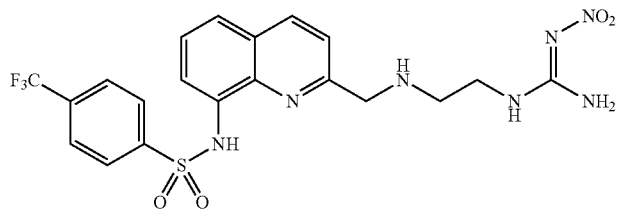

ZDR145

R₁ = alkylaryl substituted with halogen
R₂ = (C₁-C₆ alkyl)NR₇R₈;
R₇ = hydrogen;
R₈ = alkyl substituted with NR₃C(=NNO₂)NR₄R₅;
R₃ = R₄ = R₅ = hydrogen

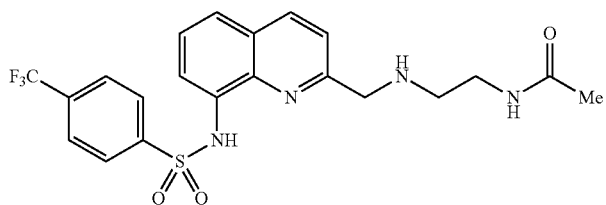

ZDR148

R₁ = alkylaryl substituted with halogen
R₂ = (C₁-C₆ alkyl)NR₇R₈;
R₇ = hydrogen;
R₈ = alkyl substituted with NR₃COR₄;
R₃ = hydrogen;
R₄ = alkyl

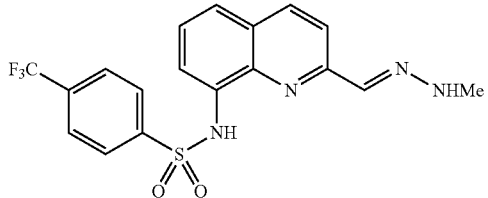
ZDR153
R₁ = alkylaryl substituted with halogen
R₂ = (C₀-C₃ alkyl)CH=NNR₇R₈;
R₇ = hydrogen;
R₈ = alkyl
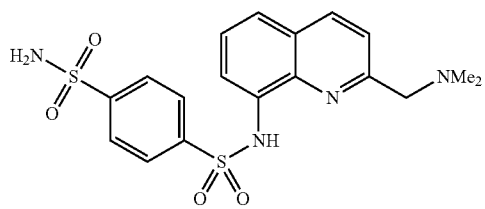
ZDR154
R₁ = aryl substituted with SO₂NR₃R₄;
R₃ = R₄ = hydrogen
R₂ = (C₁-C₆ alkyl)NR₇R₈;
R₇ = R₈ = alkyl
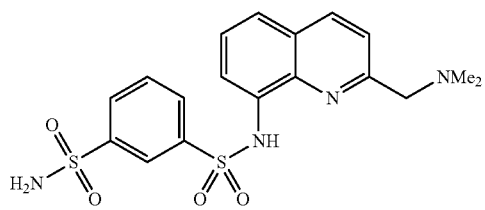
ZDR155
R₁ = aryl substituted with SO₂NR₃R₄;
R₃ = R₄ = hydrogen
R₂ = (C₁-C₆ alkyl)NR₇R₈;
R₇ = R₈ = alkyl
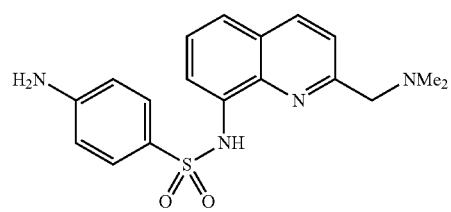
ZDR160
R₁ = aryl substituted with NR₃R₄;
R₃ = R₄ = hydrogen
R₂ = (C₁-C₆ alkyl)NR₇R₈;
R₇ = R₈ = alkyl

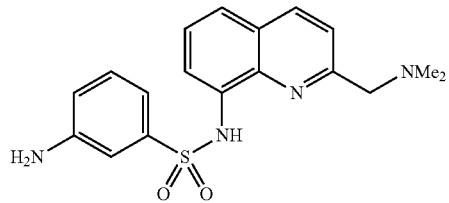

ZDR162

R₁ = aryl substituted with NR₃R₄;
R₃ = R₄ = hydrogen
R₂ = (C₁-C₆ alkyl)NR₇R₈;
R₇ = R₈ = alkyl

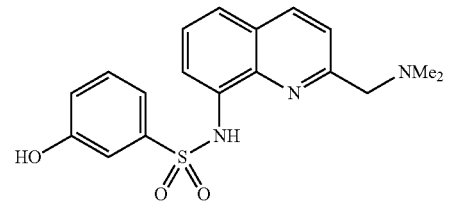

ZDR163

R₁ = aryl substituted with OR₃;
R₃ = hydrogen
R₂ = (C₁-C₆ alkyl)NR₇R₈;
R₇ = R₈ = alkyl

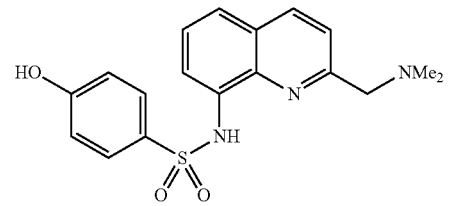

ZDR164

R₁ = aryl substituted with OR₃;
R₃ = hydrogen
R₂ = (C₁-C₆ alkyl)NR₇R₈;
R₇ = R₈ = alkyl

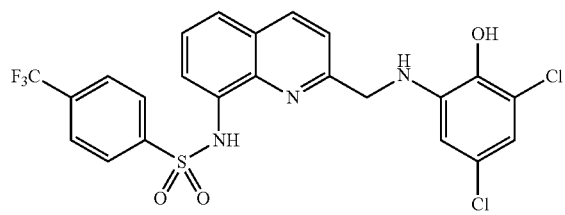

ZDR167

R₁ = alkylaryl substituted with halogen
R₂ = (C₁-C₆ alkyl)NR₇R₈;
R₇ = hydrogen;
R₈ = aryl substituted with halogen and OR₃;
R₃ = hydrogen -continued

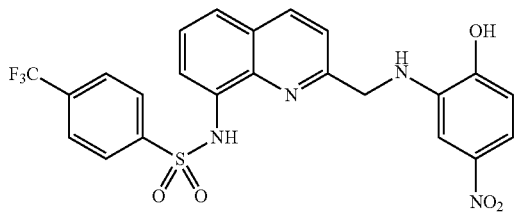
ZDR170

R$_1$ = alkylaryl substituted with halogen
R$_2$ = (C$_1$-C$_6$ alkyl)NR$_7$R$_8$;
R$_7$ = hydrogen;
R$_8$ = aryl substituted with NO$_2$ and OR$_3$;
R$_3$ = hydrogen

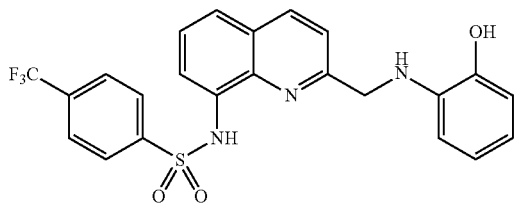
ZDR171

R$_1$ = alkylaryl substituted with halogen
R$_2$ = (C$_1$-C$_6$ alkyl)NR$_7$R$_8$;
R$_7$ = hydrogen;
R$_8$ = aryl substituted with OR$_3$;
R$_3$ = hydrogen

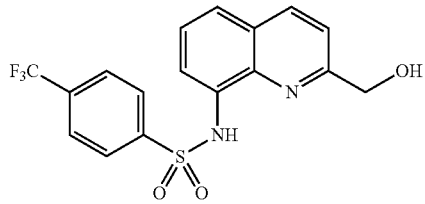
ZDR176

R$_1$ = alkylaryl substituted with halogen
R$_2$ = alkyl substituted with OR$_3$;
R$_3$ = hydrogen

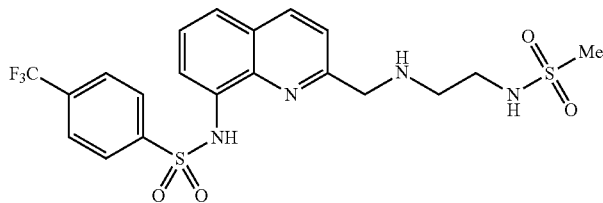
ZDR180

R$_1$ = alkylaryl substituted with halogen
R$_2$ = (C$_1$-C$_6$ alkyl)NR$_7$R$_8$;
R$_7$ = hydrogen;
R$_8$ = alkyl substituted with NR$_3$SO$_2$R$_4$;
R$_3$ = hydrogen;
R$_4$ = alkyl

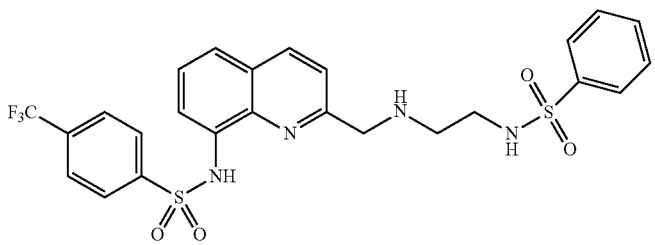

ZDR181

R₁ = alkylaryl substituted with halogen
R₂ = (C₁-C₆ alkyl)NR₇R₈;
R₇ = hydrogen;
R₈ = alkyl substituted with NR₃SO₂R₄;
R₃ = hydrogen;
R₄ = aryl

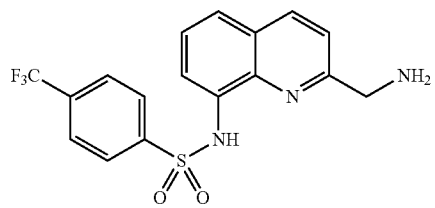

ZDR184

R₁ = alkylaryl substituted with halogen
R₂ = alkyl substituted with NR₃R₄;
R₃ = R₄ = hydrogen

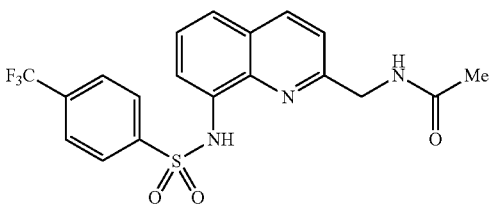

ZDR185

R₁ = alkylaryl substituted with halogen
R₂ = alkyl substituted with NR₃COR₄;
R₃ = hydrogen;
R₄ = alkyl

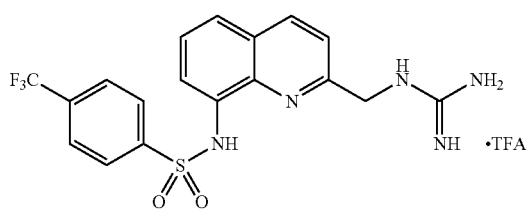

ZDR187

R₁ = alkylaryl substituted with halogen
R₂ = alkyl substituted with NR₃C(=NR₄)NR₅R₆;
R₃ = R₄ = R₅ = R₆ = hydrogen

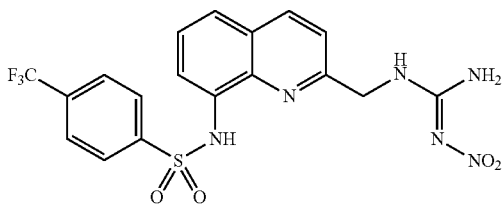

ZDR188

R₁ = alkylaryl substituted with halogen
R₂ = alkyl substituted with NR₃C(=NNO₂)NR₄R₅;
R₃ = R₄ = R₅ = hydrogen

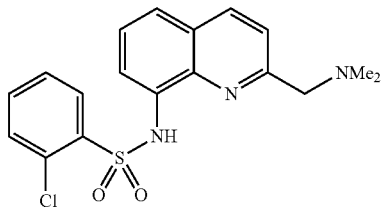

ZDR190

R₁ = aryl substituted with halogen
R₂ = (C₁-C₆ alkyl)NR₇R₈;
R₇ = R₈ = alkyl

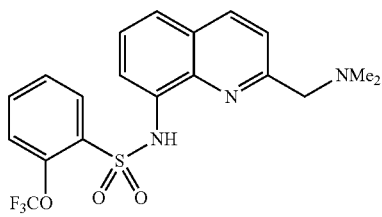

ZDR191

R₁ = alkoxyaryl substituted with halogen
R₂ = (C₁-C₆ alkyl)NR₇R₈;
R₇ = R₈ = alkyl

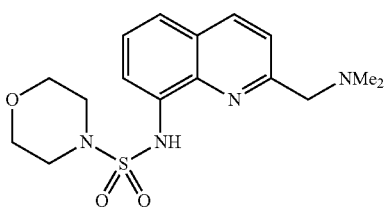

ZDR192

R₁ = heterocyclyl
R₂ = (C₁-C₆ alkyl)NR₇R₈;
R₇ = R₈ = alkyl

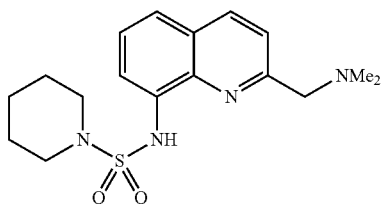

ZDR193

R₁ = heterocyclyl
R₂ = (C₁-C₆ alkyl)NR₇R₈;
R₇ = R₈ = alkyl

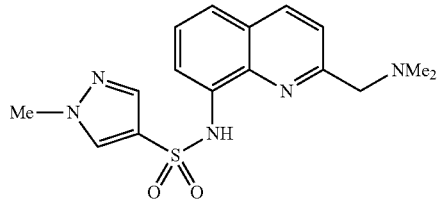
ZDR194
R₁ = alkylheteroaryl
R₂ = (C₁-C₆ alkyl)NR₇R₈;
R₇ = R₈ = alkyl
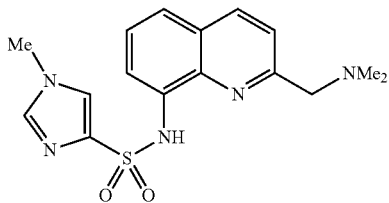
ZDR195
R₁ = alkylheteroaryl
R₂ = (C₁-C₆ alkyl)NR₇R₈;
R₇ = R₈ = alkyl
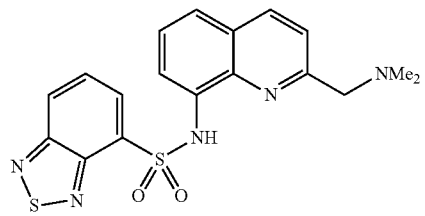
ZDR196
R₁ = heteroaryl
R₂ = (C₁-C₆ alkyl)NR₇R₈;
R₇ = R₈ = alkyl
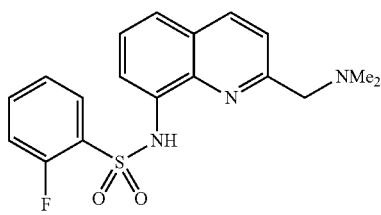
ZDR201
R₁ = aryl substituted
with halogen
R₂ = (C₁-C₆ alkyl)NR₇R₈;
R₇ = R₈ = alkyl
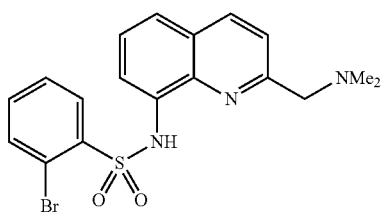
ZDR202
R₁ = aryl substituted with
halogen
R₂ = (C₁-C₆ alkyl)NR₇R₈;
R₇ = R₈ = alkyl

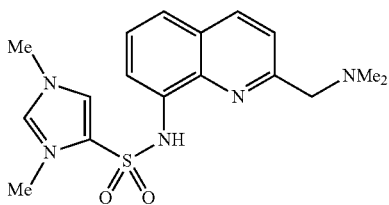
ZDR203
R₁ = alkylheteroaryl
R₂ = (C₁-C₆ alkyl)NR₇R₈;
R₇ = R₈ = alkyl
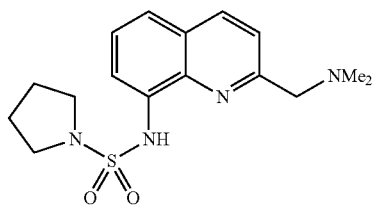
ZDR204
R₁ = heterocyclyl
R₂ = (C₁-C₆ alkyl)NR₇R₈;
R₇ = R₈ = alkyl
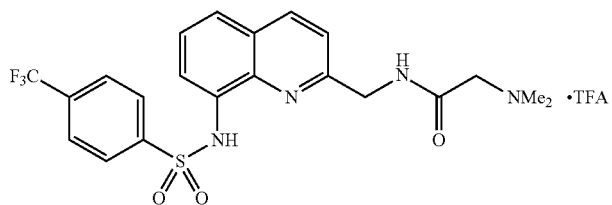
ZDR205
R₁ = alkylaryl substituted with halogen
R₂ = (C₁-C₆ alkyl)NR₇C(═O)R₈;
R₇ = hydrogen;
R₈ = alkyl substituted with NR₃R₄;
R₃ = R₄ = alkyl
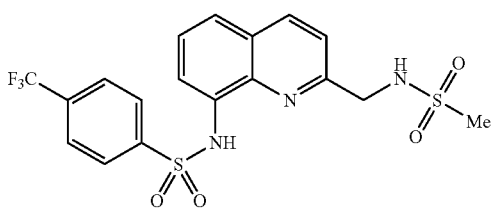
ZDR209
R₁ = alkylaryl substituted with halogen
R₂ = alkyl substituted with NR₃SO₂R₄;
R₃ = hydrogen;
R₄ = alkyl

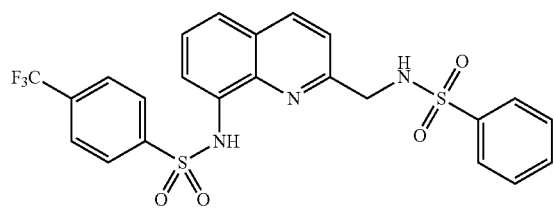

ZDR210

R₁ = alkylaryl substituted with halogen
R₂ = alkyl substituted with NR₃SO₂R₄;
R₃ = hydrogen;
R₄ = aryl

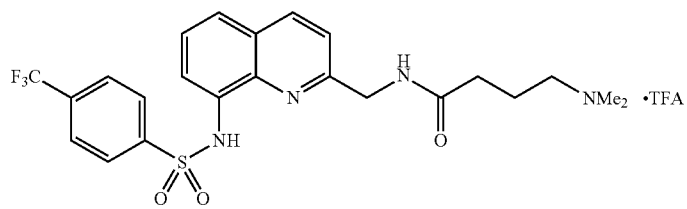

ZDR211

R₁ = alkylaryl substituted with halogen
R₂ = (C₁-C₆ alkyl)NR₇C(═O)R₈;
R₇ = hydrogen;
R₈ = alkyl substituted with NR₃R₄;
R₃ = R₄ = alkyl

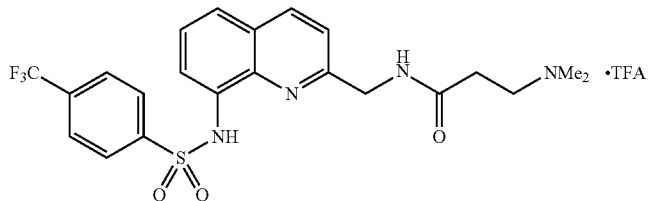

ZDR224

R₁ = alkylaryl substituted with halogen
R₂ = (C₀-C₃ alkyl)C(═O)NR₇R₈;
R₇ = hydrogen;
R₈ = alkyl substituted with NR₃R₄;
R₃ = R₄ = alkyl

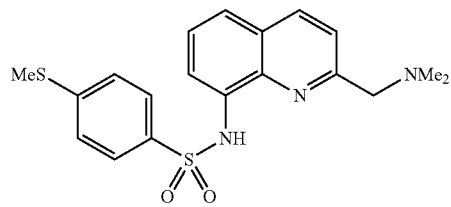

ZDR257

R₁ = aryl substituted with SR₃;
R₃ = alkyl
R₂ = (C₁-C₆ alkyl)NR₇R₈;
R₇ = R₈ = alkyl

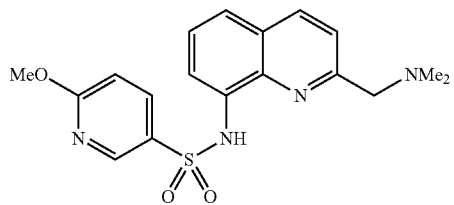

ZDR258

R₁ = alkoxyheteroaryl
R₂ = (C₁-C₆ alkyl)NR₇R₈;
R₇ = R₈ = alkyl

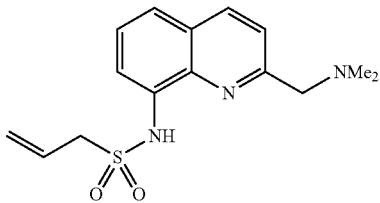

ZDR259

R₁ = alkenyl
R₂ = (C₁-C₆ alkyl)NR₇R₈;
R₇ = R₈ = alkyl

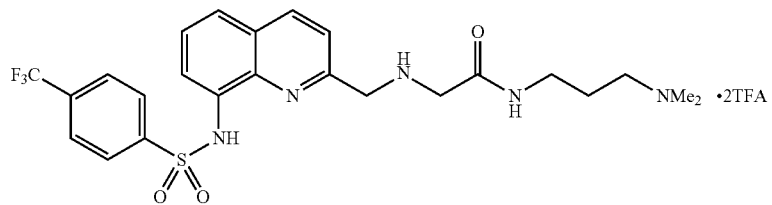

ZDR261

R₁ = alkylaryl substituted with halogen
R₂ = (C₁-C₆ alkyl)NR₇(C₁-C₆ alkyl)C(═O)NR₈R₉;
R₇ = R₈ = hydrogen;
R₉ = alkyl substituted with NR₃R₄;
R₃ = R₄ = alkyl

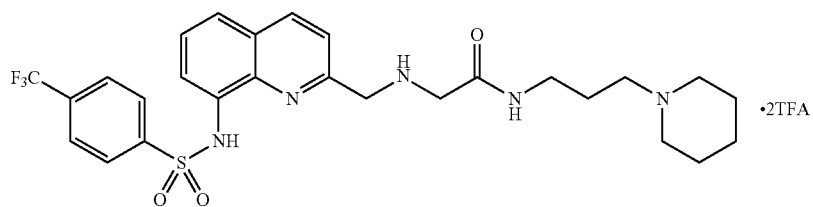

ZDR262

R₁ = alkylaryl substituted with halogen
R₂ = (C₁-C₆ alkyl)NR₇(C₁-C₆ alkyl)C(═O)NR₈R₉;
R₇ = R₈ = hydrogen;
R₉ = C₁-C₆ alkyl(heterocyclyl)

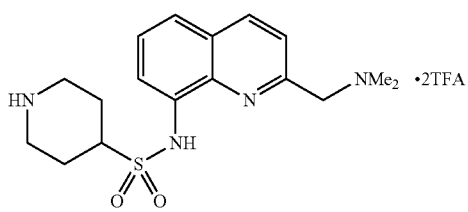

ZDR263

R₁ = heterocyclyl
R₂ = (C₁-C₆ alkyl)NR₇R₈;
R₇ = R₈ = alkyl

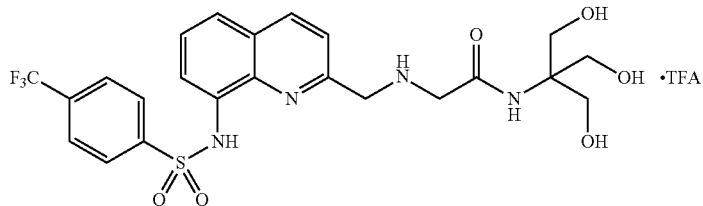

ZDR265

R₁ = alkylaryl substituted with halogen
R₂ = (C₁-C₆ alkyl)NR₇(C₁-C₆ alkyl)C(═O)NR₈R₉;
R₇ = R₈ = hydrogen;
R₉ = alkyl substituted with OR₃;
R₃ = hydrogen

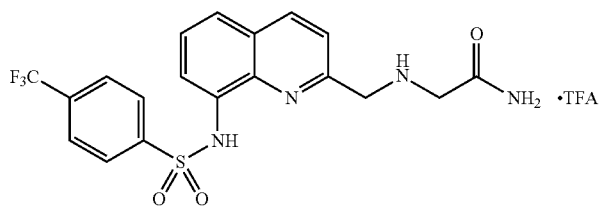

ZDR266

R₁ = alkylaryl substituted with halogen
R₂ = (C₁-C₆ alkyl)NR₇(C₁-C₆ alkyl)C(═O)NR₈R₉;
R₇ = R₈ = R₉ = hydrogen

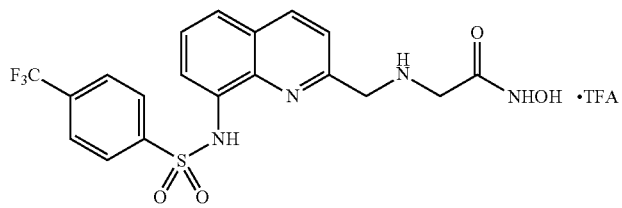

ZDR267

R₁ = alkylaryl substituted with halogen
R₂ = (C₁-C₆ alkyl)NR₇(C₁-C₆ alkyl)C(═O)NR₈R₉;
R₇ = R₈ = hydrogen;
R₉ = OH

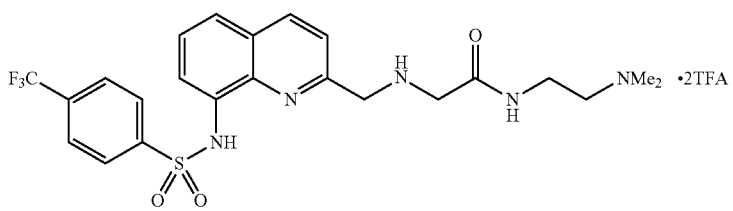

ZDR268

R₁ = alkylaryl substituted with halogen
R₂ = (C₁-C₆ alkyl)NR₇(C₁-C₆ alkyl)C(═O)NR₈R₉;
R₇ = R₈ = hydrogen;
R₉ = alkyl substituted with NR₃R₄;
R₃ = R₄ = alkyl

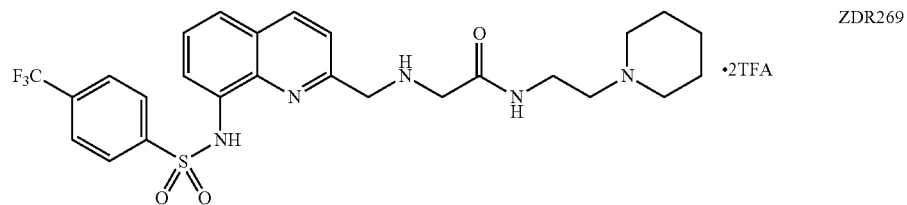

ZDR269

R₁ = alkylaryl substituted with halogen
R₂ = $(C_1-C_6$ alkyl$)NR_7(C_1-C_6$ alkyl$)C(=O)NR_8R_9$;
$R_7 = R_8$ = hydrogen;
$R_9 = C_1-C_6$ alkyl(heterocyclyl)

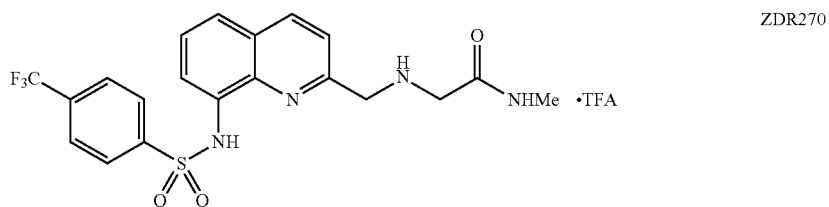

ZDR270

R₁ = alkylaryl substituted with halogen
R₂ = $(C_1-C_6$ alkyl$)NR_7(C_1-C_6$ alkyl$)C(=O)NR_8R_9$;
$R_7 = R_8$ = hydrogen;
$R_9$ = alkyl

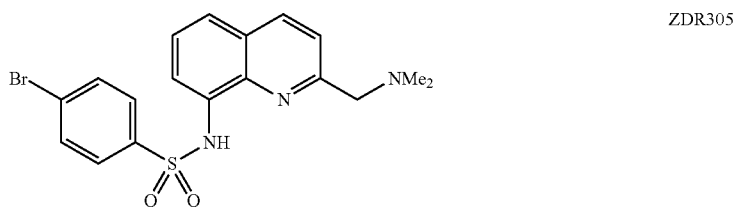

ZDR305

R₁ = aryl substituted with halogen
R₂ = $(C_1-C_6$ alkyl$)NR_7R_8$;
$R_7 = R_8$ = hydrogen;

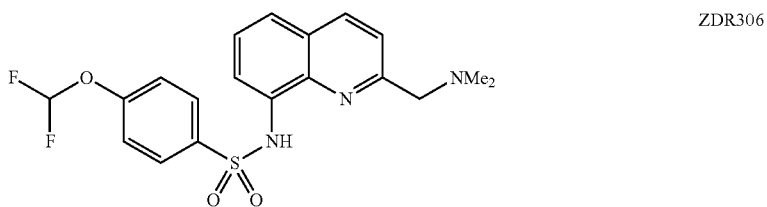

ZDR306

R₁ = alkoxyaryl substituted with halogen
R₂ = $(C_1-C_6$ alkyl$)NR_7R_8$;
$R_7 = R_8$ = alkyl

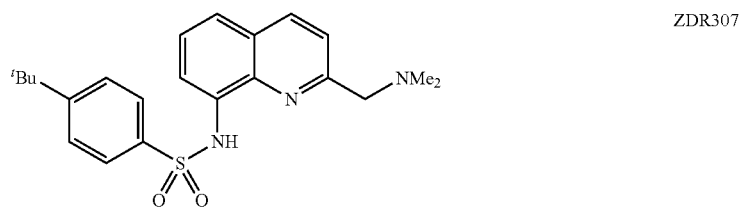

ZDR307

R₁ = alkylaryl
R₂ = $(C_1-C_6$ alkyl$)NR_7R_8$;
$R_7 = R_8$ = alkyl

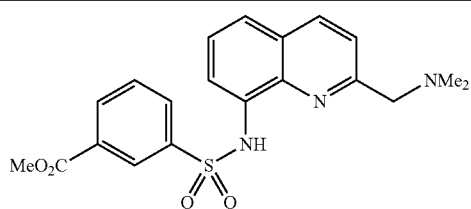
ZDR308
R₁ = aryl substituted with CO₂R₃;
R₃ = alkyl
R₂ = (C₁-C₆ alkyl)NR₇R₈;
R₇ = R₈ = alkyl
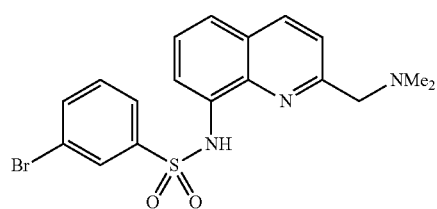
ZDR309
R₁ = aryl substituted with halogen
R₂ = (C₁-C₆ alkyl)NR₇R₈;
R₇ = R₈ = alkyl
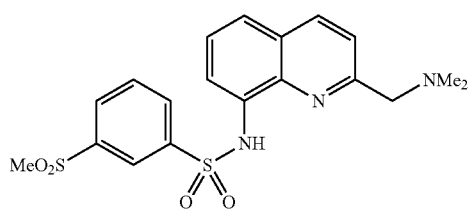
ZDR310
R₁ = aryl substituted with SO₂R₃;
R₃ = alkyl
R₂ = (C₁-C₆ alkyl)NR₇R₈;
R₇ = R₈ = alkyl
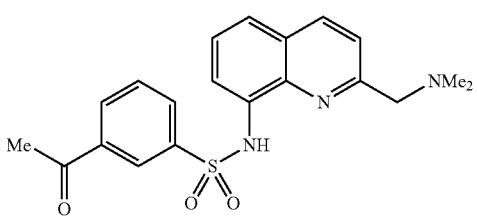
ZDR311
R₁ = aryl substituted with COR₃;
R₃ = alkyl
R₂ = (C₁-C₆ alkyl)NR₇R₈;
R₇ = R₈ = alkyl

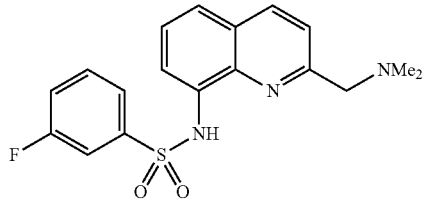
ZDR312
R₁ = aryl substituted with halogen
R₂ = (C₁-C₆ alkyl)NR₇R₈;
R₇ = R₈ = alkyl
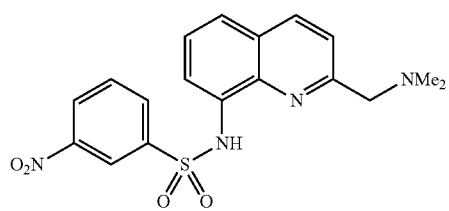
ZDR313
R₁ = aryl substituted with NO₂
R₂ = (C₁-C₆ alkyl)NR₇R₈;
R₇ = R₈ = alkyl
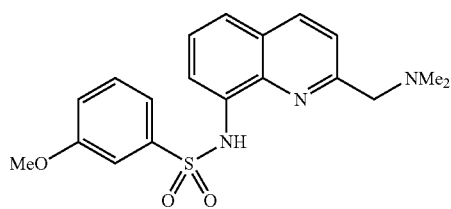
ZDR314
R₁ = alkoxyaryl
R₂ = (C₁-C₆ alkyl)NR₇R₈;
R₇ = R₈ = alkyl
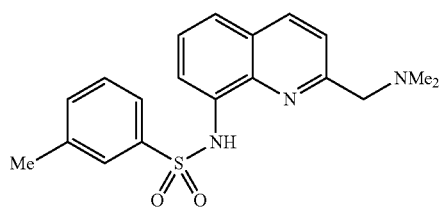
ZDR315
R₁ = alkylaryl
R₂ = (C₁-C₆ alkyl)NR₇R₈;
R₇ = R₈ = alkyl
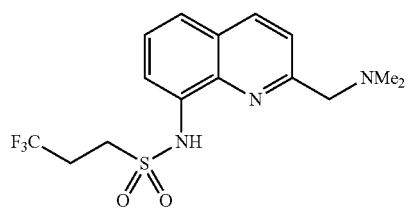
ZDR316
R₁ = alkyl substituted with halogen
R₂ = (C₁-C₆ alkyl)NR₇R₈;
R₇ = R₈ = alkyl

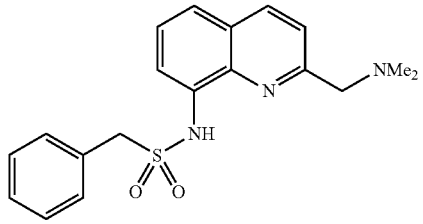
ZDR317
R₁ = aralkyl
R₂ = (C₁-C₆ alkyl)NR₇R₈;
R₇ = R₈ = alkyl
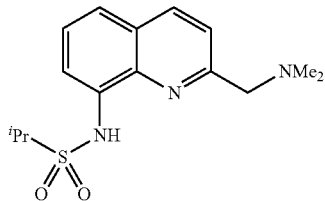
ZDR318
R₁ = alkyl
R₂ = (C₁-C₆ alkyl)NR₇R₈;
R₇ = R₈ = alkyl
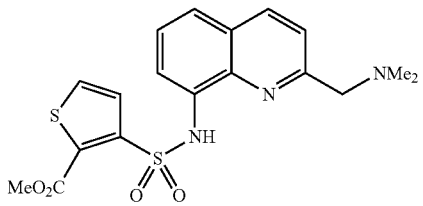
ZDR319
R₁ = heteroaryl substituted with CO₂R₃;
R₃ = alkyl
R₂ = (C₁-C₆ alkyl)NR₇R₈;
R₇ = R₈ = alkyl
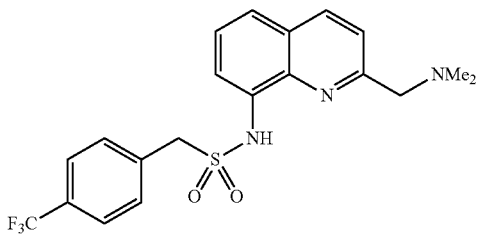
ZDR320
R₁ = C₁-C₆ alkyl(alkylaryl) substituted with halogen
R₂ = (C₁-C₆ alkyl)NR₇R₈;
R₇ = R₈ = alkyl
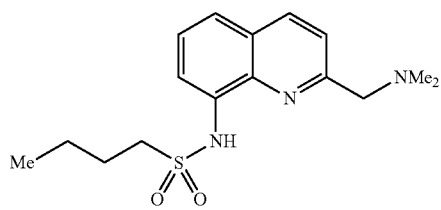
ZDR321
R₁ = alkyl
R₂ = (C₁-C₆ alkyl)NR₇R₈;
R₇ = R₈ = alkyl -continued

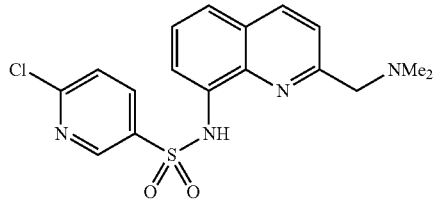

ZDR322

R₁ = heteroaryl substituted with halogen
R₂ = (C₁-C₆ alkyl)NR₇R₈;
R₇ = R₈ = alkyl

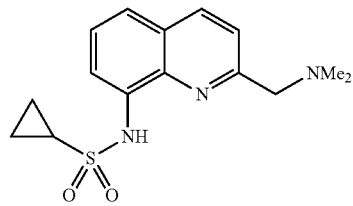

ZDR323

R₁ = cycloalkyl
R₂ = (C₁-C₆ alkyl)NR₇R₈;
R₇ = R₈ = alkyl

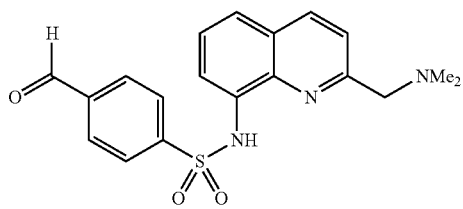

ZDR324

R₁ = aryl substituted with CHO
R₂ = (C₁-C₆ alkyl)NR₇R₈;
R₇ = R₈ = alkyl

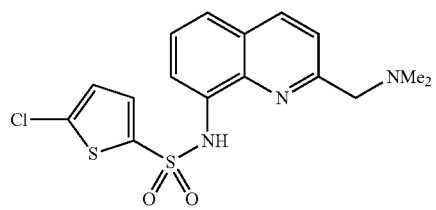

ZDR326

R₁ = heteroaryl substituted with halogen
R₂ = (C₁-C₆ alkyl)NR₇R₈;
R₇ = R₈ = alkyl

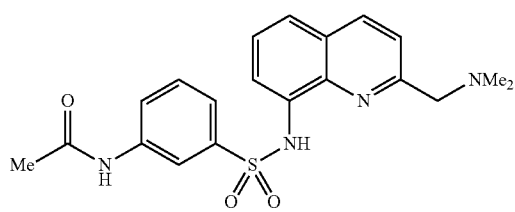

ZDR327

R₁ = aryl substituted with NR₃COR₄;
R₃ = hydrogen;
R₄ = alkyl
R₂ = (C₁-C₆ alkyl)NR₇R₈;
R₇ = R₈ = alkyl

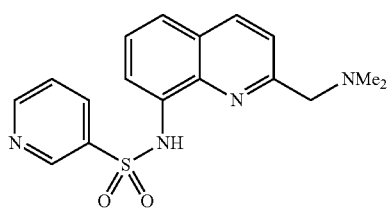
ZDR328
R₁ = heteroaryl
R₂ = (C₁-C₆ alkyl)NR₇R₈;
R₇ = R₈ = alkyl
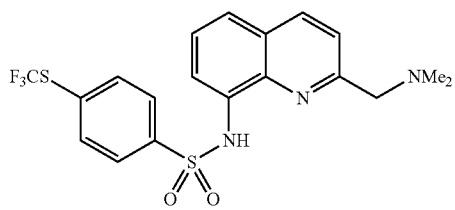
ZDR330
R₁ = aryl substituted with SCF₃
R₂ = (C₁-C₆ alkyl)NR₇R₈;
R₇ = R₈ = alkyl
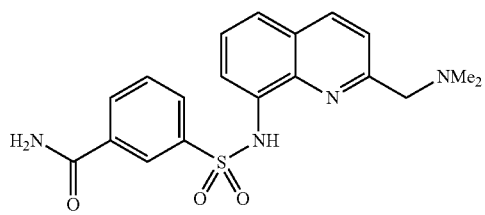
ZDR331
R₁ = aryl substituted with CONR₃R₄;
R₃ = R₄ = hydrogen
R₂ = (C₁-C₆ alkyl)NR₇R₈;
R₇ = R₈ = alkyl
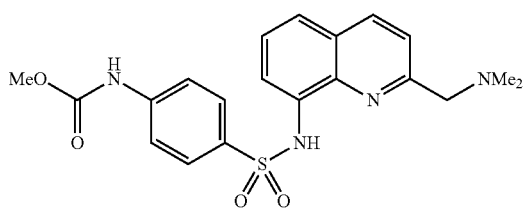
ZDR332
R₁ = aryl substituted with NR₃CO₂R₄;
R₃ = hydrogen;
R₄ = alkyl
R₂ = (C₁-C₆ alkyl)NR₇R₈;
R₇ = R₈ = alkyl

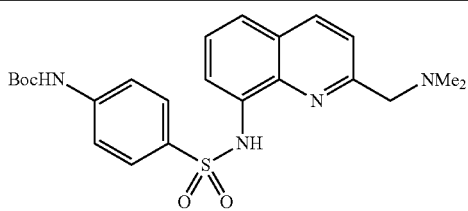

ZDR333

$R_1$ = aryl substituted with $NR_3CO_2R_4$;
$R_3$ = hydrogen;
$R_4$ = alkyl
$R_2$ = $(C_1-C_6$ alkyl$)NR_7R_8$;
$R_7$ = $R_8$ = alkyl

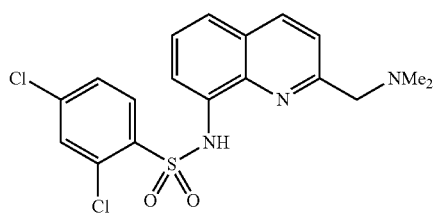

ZDR335

$R_1$ = aryl substituted with halogen
$R_2$ = $(C_1-C_6$ alkyl$)NR_7R_8$;
$R_7$ = $R_8$ = alkyl

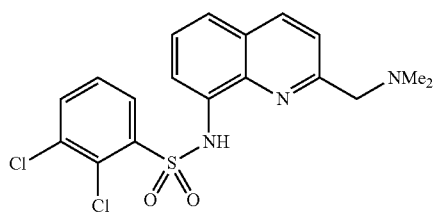

ZDR336

$R_1$ = aryl substituted with halogen
$R_2$ = $(C_1-C_6$ alkyl$)NR_7R_8$;
$R_7$ = $R_8$ = alkyl

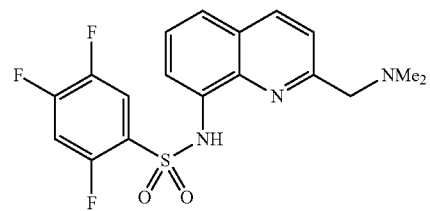

ZDR337

$R_1$ = aryl substituted with halogen
$R_2$ = $(C_1-C_6$ alkyl$)NR_7R_8$;
$R_7$ = $R_8$ = alkyl

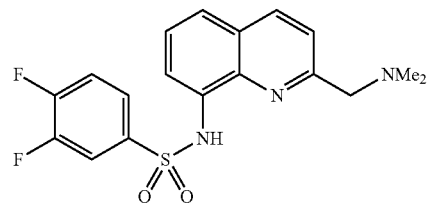

ZDR338

$R_1$ = aryl substituted with halogen
$R_2$ = $(C_1-C_6$ alkyl$)NR_7R_8$;
$R_7$ = $R_8$ = alkyl

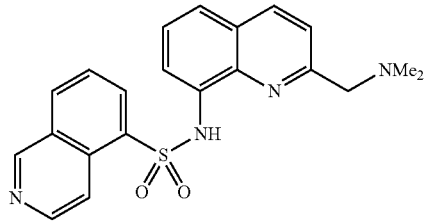

ZDR339

R₁ = heteroaryl
R₂ = (C₁-C₆ alkyl)NR₇R₈;
R₇ = R₈ = alkyl

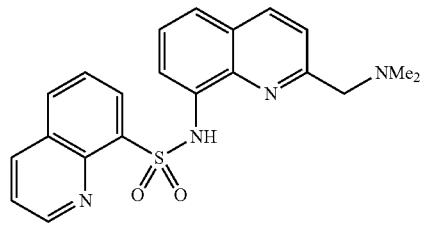

ZDR340

R₁ = heteroaryl
R₂ = (C₁-C₆ alkyl)NR₇R₈;
R₇ = R₈ = alkyl

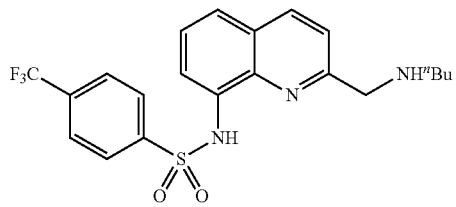

ZDR401

R₁ = alkylaryl substituted with halogen
R₂ = (C₁-C₆ alkyl)NR₇R₈;
R₇ = hydrogen;
R₈ = alkyl

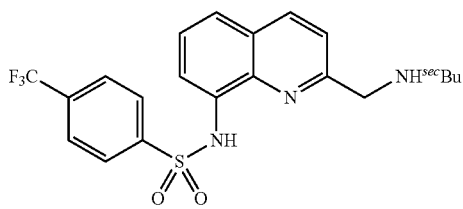

ZDR402

R₁ = alkylaryl substituted with halogen
R₂ = (C₁-C₆ alkyl)NR₇R₈;
R₇ = hydrogen;
R₈ = alkyl

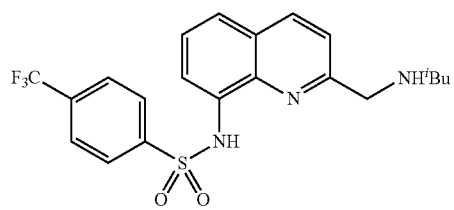

ZDR403

R₁ = alkylaryl substituted with halogen
R₂ = (C₁-C₆ alkyl)NR₇R₈;
R₇ = hydrogen;
R₈ = alkyl

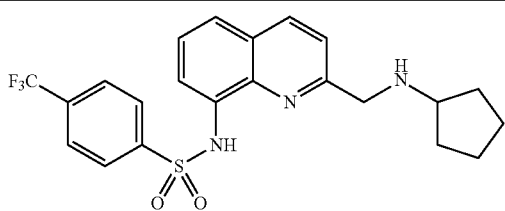

ZDR404

R₁ = alkylaryl substituted with halogen
R₂ = (C₁-C₆ alkyl)NR₇R₈;
R₇ = hydrogen;
R₈ = cycloalkyl

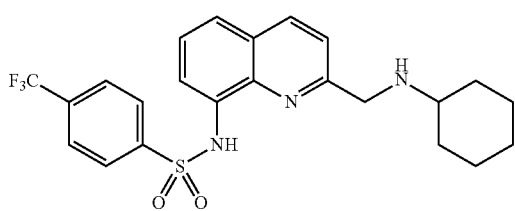

ZDR405

R₁ = alkylaryl substituted with halogen
R₂ = (C₁-C₆ alkyl)NR₇R₈;
R₇ = hydrogen;
R₈ = cycloalkyl

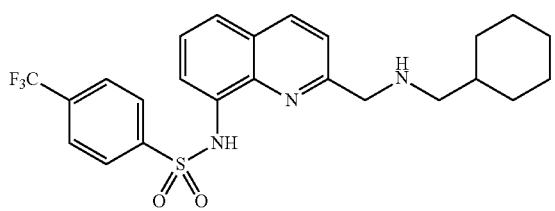

ZDR406

R₁ = alkylaryl substituted with halogen
R₂ = (C₁-C₆ alkyl)NR₇R₈;
R₇ = hydrogen;
R₈ = C₁-C₆ alkyl(cycloalkyl)

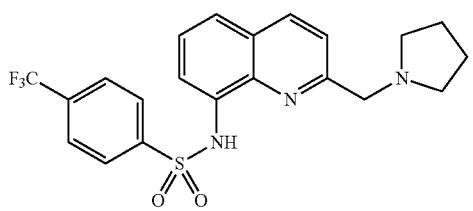

ZDR407

R₁ = alkylaryl substituted with halogen
R₂ = C₁-C₆ alkyl(heterocyclyl)

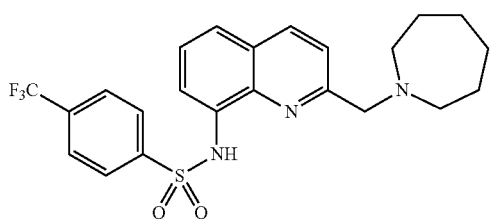

ZDR408

R₁ = alkylaryl substituted with halogen
R₂ = C₁-C₆ alkyl(heterocyclyl)

-continued
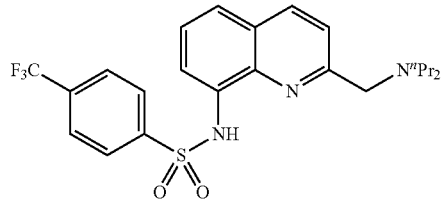
ZDR409
R₁ = alkylaryl substituted with halogen
R₂ = (C₁-C₆ alkyl)NR₇R₈;
R₇ = R₈ = alkyl
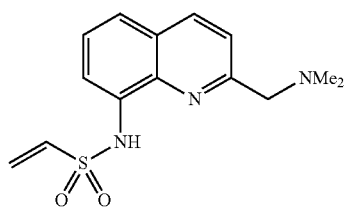
ZDR500
R₁ = alkenyl
R₂ = (C₁-C₆ alkyl)NR₇R₈;
R₇ = R₈ = alkyl
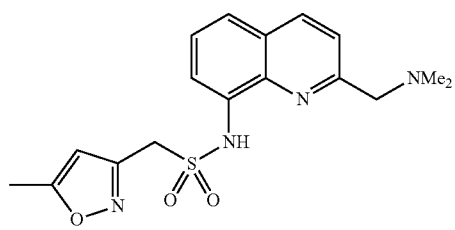
ZDR501
R₁ = C₁-C₆ alkyl(alkylheteroaryl)
R₂ = (C₁-C₆ alkyl)NR₇R₈;
R₇ = R₈ = alkyl
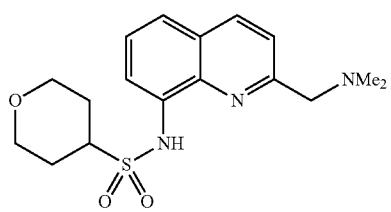
ZDR502
R₁ = heterocyclyl
R₂ = (C₁-C₆ alkyl)NR₇R₈;
R₇ = R₈ = alkyl
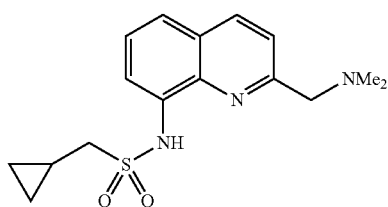
ZDR503
R₁ = C₁-C₆ alkyl(cycloalkyl)
R₂ = (C₁-C₆ alkyl)NR₇R₈;
R₇ = R₈ = alkyl -continued

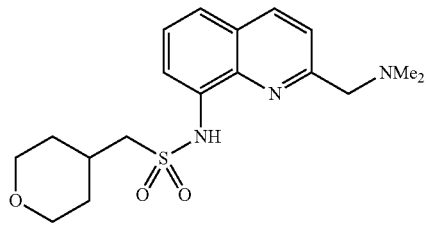

ZDR504

R₁ = $C_1$-$C_6$ alkyl(heterocyclyl)
R₂ = ($C_1$-$C_6$ alkyl)NR₇R₈;
R₇ = R₈ = alkyl

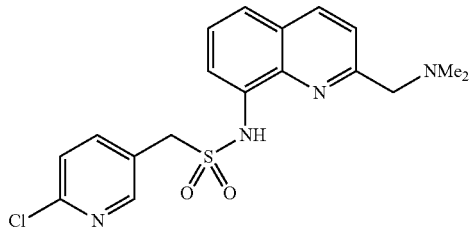

ZDR505

R₁ = $C_1$-$C_6$ alkyl(heteroaryl) substituted with halogen
R₂ = ($C_1$-$C_6$ alkyl)NR₇R₈;
R₇ = R₈ = alkyl

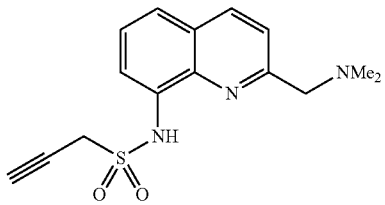

ZDR506

R₁ = alkynyl
R₂ = ($C_1$-$C_6$ alkyl)NR₇R₈;
R₇ = R₈ = alkyl

Advantageously, e compounds described and claimed herein possess antibacterial activity against both Gram positive and Gram negative bacteria. Data to support these observations is presented in Tables 1 & 2 of Example 214, which follows. Specifically, exemplary compounds of the invention demonstrated both growth inhibitory and bactericidal activity against *Streptococcus uberis*, *Staphylococcus aureus* and *Escherichia coli*, as measured using MIC and MBC assays, respectively. In certain examples, the exemplary compounds advantageously demonstrate antibacterial activity in the absence of zinc (i.e. added exogenously to the assay medium).

Accordingly, in yet a further aspect of the invention of the invention there is provided a compound of Formula Ia:

Formula Ia

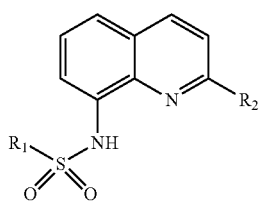

wherein $R_1$ is selected from the group comprising alkyl, cycloalkyl, alkenyl, alkynyl, aryl, alkylaryl, alkoxyaryl, heterocyclyl, alkylheterocyclyl, alkoxyheterocyclyl, heteroaryl, alkylheteroaryl, alkoxyheteroaryl, $C_1$-$C_6$ alkyl(cycloalkyl), aralkyl, $C_1$-$C_6$ alkyl(alkylaryl), $C_1$-$C_6$ alkyl(alkoxyaryl), $C_1$-$C_6$ alkyl(heterocyclyl), $C_1$-$C_6$ alkyl(alkylheterocyclyl), $C_1$-$C_6$ alkyl(alkoxyheterocyclyl), $C_1$-$C_6$ alkyl(heteroaryl), $C_1$-$C_6$ alkyl(alkylheteroaryl), and $C_1$-$C_6$ alkyl(alkoxyheteroaryl), each of which is optionally substituted with one or more of halogen, OR₃, OCHO, OC(=O)R₃, SR₃, SCF₃, SC(=O)R₃, S(=O)R₃, S₂R₃, SO₃H, SO₂NR₃R₄, NR₃R₄, NR₃CHO, NR₃COR₄, NR₃CO₂R₄, NR₃SO₂R₄, NO₂, CN, CHO, COR₃, CO₂H, CO₂R₃, and CONR₃R₄;

$R_2$ is selected from the group comprising ($C_1$-$C_6$ alkyl)NR₇($C_1$-$C_6$ alkyl)NR₇R₈, ($C_1$-$C_6$ alkyl)NR₇($C_0$-$C_6$ alkyl)(pyridinyl), ($C_1$-$C_6$ alkyl)NR₇($C_0$-$C_6$ alkyl)(hydroxyaryl), ($C_1$-$C_6$ alkyl)NR₇($C_1$-$C_6$ hydroxyalkyl), ($C_1$-$C_6$ alkyl)NR₇($C_1$-$C_6$ alkyl)heterocyclyl, ($C_1$-$C_6$ alkyl)NR₇($C_1$-$C_6$ alkyl)NR₃C(=NR₃)NR₇R₈, ($C_1$-$C_6$ alkyl)NR₃C(=NR₃)NR₇R₈, ($C_1$-$C_6$ alkyl)NR₇($C_1$-$C_6$ alkyl)C(=O)NR₇($C_1$-$C_6$ alkyl), ($C_1$-$C_6$ alkyl)NR₇($C_1$-$C_6$ alkyl)C(=O)NR₇R₈, ($C_0$-$C_3$ alkyl)C=NNR₃C(=S)NR₇R₈, ($C_0$-$C_3$ alkyl)C=NNR₃C(=O)R₇ or ($C_0$-$C_3$ alkyl)C=NOR₃; each of which is optionally substituted with one or more of each of alkyl, halogen, $OR_3$, OCHO, $OC(=O)R_3$, $SR_3$, $SC(=O)R_3$, $S(=O)R_3$, $S_2R_3$, $SO_3H$, $SO_2NR_3R_4$, $NR_3R_4$, $NR_3CHO$, $NR_3COR_4$, $NR_3CO_2R_4$, $NR_3C(=O)NR_4R_5$, $NR_3C(=S)NR_4R_5$, $NR_3C(=NR_4)NR_5R_6$, $NR_3C(=NNO_2)NR_4R_5$, $NR_3C(=NCN)NR_4R_5$, $NR_3C(=CHNO_2)NR_4R_5$, $NR_3C(=NR_4)R_5$, $NR_3S_2R_4$, $NO_2$, CN, CHO, $COR_3$, $CO_2H$, $CO_2R_3$, $CONR_3R_4$, $C(=O)NR_3OR_3$, $C(=O)NR_3NR_4R_5$, $C(=O)NR_3CN$;

$R_3$, $R_4$, $R_5$ and $R_6$ are each selected from the group comprising hydrogen, alkyl, aryl and aralkyl; and $R_7$, $R_8$ and $R_9$ are each selected from the group comprising hydrogen, hydroxyl, alkyl, cycloalkyl, alkenyl, alkynyl, aryl, alkylaryl, alkoxyaryl, heterocyclyl, alkylheterocyclyl, alkoxyheterocyclyl, heteroaryl, alkylheteroaryl, alkoxyheteroaryl, $C_1$-$C_6$ alkyl(cycloalkyl), aralkyl, $C_1$-$C_6$ alkyl(alkylaryl), $C_1$-$C_6$ alkyl(alkoxyaryl), $C_1$-$C_6$ alkyl(heterocyclyl), $C_1$-$C_6$ alkyl(alkylheterocyclyl), $C_1$-$C_6$ alkyl(alkoxyheterocyclyl), $C_1$-$C_6$ alkyl(heteroaryl), $C_1$-$C_6$ alkyl(alkylheteroaryl), $C_1$-$C_6$ alkyl(alkoxyheteroaryl), monosaccharide, disaccharide, each of which is optionally substituted with one or more of halogen, $OR_3$, OCHO, $OC(=O)R_3$, $SR_3$, $SC(=O)R_3$, $S(=O)R_3$, $SO_2R_3$, $SO_3H$, $SO_2NR_3R_4$, $NR_3R_4$, $NR_3CHO$, $NR_3COR_4$, $NR_3CO_2R_4$, $NR_3C(=O)NR_4R_5$, $NR_3C(=S)NR_4R_5$, $NR_3C(=NR_4)NR_5R_6$, $NR_3C(=NNO_2)NR_4R_5$, $NR_3C(=NCN)NR_4R_5$, $NR_3C(=CHNO_2)NR_4R_5$, $NR_3C(=NR_4)R_5$, $NR_3S_2R_4$, $NO_2$, CN, CHO, $COR_3$, $CO_2H$, $CO_2R_3$, $CONR_3R_4$, $C(=O)NR_3OR_3$, $C(=O)NR_3NR_4R_5$, $C(=O)NR_3CN$;

or a pharmaceutically acceptable salt or hydrate thereof.

In certain embodiments, the compound defined by Formula Ia is selected from ZDR030, ZDR035, ZDR046, ZDR090, ZDR102, ZDR111, ZDR112, ZDR113, ZDR114, ZDR115, ZDR116, ZDR117, ZDR119, ZDR120, ZDR121, ZDR122, ZDR124, ZDR125, ZDR143, ZDR167, ZDR170, ZDR171, ZDR187, ZDR261, ZDR262ZDR266, ZDR268 and ZDR269.

In another aspect the present invention provides a compound defined as ZDR022.HCl.

In another aspect the present invention provides a compound defined as ZDR090.

In another aspect the present invention provides a compound defined as ZDR091.

In another aspect the present invention provides a compound defined as ZDR092.

In another aspect the present invention provides a compound defined as ZDR095.

In another aspect the present invention provides a compound defined as ZDR102.

In another aspect the present invention provides a compound defined as ZDR111.

In another aspect the present invention provides a compound defined as ZDR112.

In another aspect the present invention provides a compound defined as ZDR114.

In another aspect the present invention provides a compound defined as ZDR115.

In another aspect the present invention provides a compound defined as ZDR116.

In another aspect the present invention provides a compound defined as ZDR117.

In another aspect the present invention provides a compound defined as ZDR119.

In another aspect the present invention provides a compound defined as ZDR120.

In another aspect the present invention provides a compound defined as ZDR121.

In another aspect the present invention provides a compound defined as ZDR122.

In another aspect the present invention provides a compound defined as ZDR124.

In another aspect the present invention provides a compound defined as ZDR125.

In another aspect the present invention provides a compound defined as ZDR127.

In another aspect the present invention provides a compound defined as ZDR143.

In another aspect the present invention provides a compound defined as ZDR167.

In another aspect the present invention provides a compound defined as ZDR170.

In another aspect the present invention provides a compound defined as ZDR171.

In another aspect the present invention provides a compound defined as ZDR187.

In another aspect the present invention provides a compound defined as ZDR224.

In another aspect the present invention provides a compound defined as ZDR261.

In another aspect the present invention provides a compound defined as ZDR269.

In another aspect the present invention provides a compound defined as ZDR335.

In yet another aspect of the invention there is provided a pharmaceutical composition comprising a compound of the invention and a pharmaceutically acceptable carrier.

In certain embodiments the composition is a veterinary pharmaceutical composition.

In certain embodiments the composition further comprises an antibacterial compound selected from the group comprising chlorhexidine, iodine, lactic acid, cetrimide, BZK (benzylalkonium chloride), amoxicillin, erythromycin, cloxacillin, pirlimycin, cephapirin, hetacillin, penicillin, nicin and lacticin.

In certain embodiments the composition is formulated as a tablet, capsule or powder, or as a solution, suspension or dispersion for oral, injectable or sprayable administration.

In another aspect of the invention there is provided a method of treating or preventing a bacterial infection in an animal comprising administering to an animal a pharmaceutically effective amount of a compound of the invention.

In certain embodiments according to this aspect of the invention the compound is selected from ZDR022.HCl, ZDR090, ZDR091, ZDR092, ZDR095, ZDR102, ZDR111, ZDR112, ZDR114, ZDR115, ZDR116, ZDR117, ZDR119, ZDR120, ZDR121, ZDR122, ZDR124, ZDR125, ZDR127, ZDR143, ZDR167, ZDR170, ZDR171, ZDR187, ZDR224, ZDR261, ZDR269 and ZDR335.

In certain embodiments the bacterial infection is caused by one or more bacteria from the Enterobactericeae, Staphylococcaceae, and Streptococcaceae families. By way of non-limiting example, this includes *Streptococcus uberis, Staphylococcus aureus, Staphylococcus agalactiae,* and *Escherichia coli.*

In certain embodiments the bacterial infection is mastitis.

In certain embodiments the animal is a bovine cow.

BRIEF DESCRIPTION OF THE FIGURE

FIG. 1 shows a general mechanism of metal translocation by a compound of the invention.

DETAILED DESCRIPTION

Definitions

The term "alkyl" means any saturated hydrocarbon radical and is intended to include both straight-chain and branched-chain alkyl groups. Examples of alkyl groups include, but are not limited to, methyl, ethyl, n-propyl, iso-propyl, n-butyl, iso-butyl, sec-butyl, t-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, and 1-methyl-2-ethylpropyl. The term "C1-C6 alkyl" means any alkyl radical having up to 6 carbon atoms.

The term "alkenyl" means any hydrocarbon radical having at least one double bond, and is intended to include both straight- and branched-chain alkenyl groups. Examples of alkenyl groups include, but are not limited to, ethenyl, n-propenyl, iso-propenyl, n-butenyl, sec-butenyl, n-pentenyl, 1,1-dimethylpropenyl, 1,2-dimethylpropenyl, 2,2-dimethylpropenyl, 1-ethylpropenyl, 2-ethylpropenyl, n-hexenyl, and 1-methyl-2-ethylpropenyl.

The term "alkynyl" means any hydrocarbon radical having at least one triple bond, and is intended to include both straight- and branched-chain alkynyl groups. Examples of alkynyl groups include, but are not limited to, ethynyl, n-propynyl, n-butynyl, iso-butynyl, sec-butynyl, t-butynyl, n-pentynyl, 1,1-dimethylpropynyl, 2,2-dimethylpropynyl, 1-ethylpropynyl, 2-ethylpropynyl, n-hexynyl, and 1-methyl-2-ethylpropynyl.

The term "alkylene" means a diradical corresponding to an alkyl group. Examples of alkylene groups include, but are not limited to, methylene and ethylene.

The term "cycloalkyl" means a saturated or partially saturated non-aromatic carbocyclic group, having preferably from 3 to 8 ring carbon atoms. Examples of cycloalkyl groups include, but are not limited to, cyclopropyl, cyclobutyl, cyclopentyl, cyclohexyl, cycloheptyl, and cyclooctyl.

The term "heterocyclyl" means a cycloalkyl group where one or more of the ring carbon atoms is replaced with one or more heteroatoms, e.g. nitrogen, oxygen or sulfur. Examples of heterocyclyl groups include, but are not limited to, pyrrolidinyl, pyrrolinyl, pyrazolidinyl, aziridinyl, thiiranyl, 1,2-dithietanyl, morpholinyl, furanyl, pyranyl, thiophenyl, isoxazolyl, furazanyl, tetrahydrofuranyl, thietanyl, piperidinyl, azetidinyl, oxiranyl, epoxide, and thiacyclohexyl.

The term "alkoxy" means an alkyl group singular bonded to an oxygen atom. Examples of alkoxy groups include, but are not limited to, methoxy, ethoxy, propoxy, iso-propoxy, n-butoxy, iso-butoxy, sec-butoxy, and t-butoxy, The term "aryl" means an aromatic radical. Examples include monocyclic groups as well as fused groups such as bicyclic groups and tricyclic groups. Examples include, but are not limited to, phenyl, indenyl, 1-naphthyl, 2-naphthyl, azulenyl, heptalenyl, biphenyl, indacenyl, acenaphthyl, fluorenyl, phenalenyl, phenanthrenyl, anthracenyl, cyclopentacyclooctenyl, and benzocyclooctenyl.

The term "heteroaryl" means a heterocyclic aromatic (heteroaromatic) radical. Examples include monocyclic groups as well as fused groups such as bicyclic groups and tricyclic groups. Examples include, but are not limited to, pyridyl, pyrrolyl, pyridazinyl, pyrimidinyl, pyrazinyl, triazolyl, tetrazolyl, benzotriazolyl, pyrazolyl, imidazolyl, benzimidazolyl, indolyl, isoindolyl, indolizinyl, purinyl, indazolyl, furyl, pyranyl, benzofuryl, isobenzofuryl, thienyl, thiazolyl, isothiazolyl, benzothiazolyl, oxazolyl, and isoxazolyl.

The term "aralkyl" means an aryl group which is attached to an alkylene moiety, where "aryl" and "alkylene" are as defined above. Examples include benzyl.

The term "alkylaryl" means an alkyl group which is attached to an aryl group, where "alkyl" and "aryl" are defined above. Examples include methylphenyl.

The term "alkoxyaryl" means an alkoxy group which is attached to an aryl group, where "alkoxy" and "aryl" are defined above. Examples include methoxyphenyl.

The term "alkylheteroaryl" means an alkyl group which is attached to heteroaryl group, where "alkyl" and "heteroaryl" are defined above. Examples include methylpyridinyl.

The term "alkoxyheteroaryl" means alkoxy group which is attached to heteroaryl group, where "alkoxy" and "heteroaryl" are defined above. Examples includes methoxypyridinyl.

The term "prodrug" as used herein refers to a drug substance that is inactive or weakly active in the intended pharmacological actions and is converted into the pharmacologically active or more active agent by metabolic or physico-chemical transformation.

The term "pharmaceutical composition" as used herein refers to a mixture of one or more of the compounds of formula (I), or pharmaceutically acceptable salts, or hydrates thereof, with other chemical components, such as physiologically acceptable carriers and excipients. The purpose of a pharmaceutical composition is to facilitate administration of a compound to an organism.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carrier may also be saline, gum acacia, gelatin, starch paste, talc, keratin, colloidal silica, urea, and the like. In addition, auxiliary, stabilizing, thickening, lubricating and colouring agents may be used. Other examples of suitable pharmaceutical carriers are described in "Remington's Pharmaceutical Sciences" by E. W. Martin, herein incorporated by reference.

The term "effective amount" means an amount of a compound that, when administered to a subject for treating a disease, is sufficient to effect such treatment for the disease. The "effective amount" will vary depending on the disease to be treated, the compound to be administered, the severity of the disease treated, the age and relative health of the subject, the route and form of administration, whether the treatment is monotherapy or combination therapy, the judgement of the attending clinician, and other factors.

The term "pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "pharmaceutically acceptable salt" as used herein refers to any salt of a compound provided herein which retains its biological properties and which is not toxic or otherwise undesirable for pharmaceutical use and is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids. Pharmaceutically acceptable salt forms may also include forms wherein the ratio of molecules comprising the salt is not 1:1. For example, the salt may comprise more than one inorganic or organic acid molecule per molecule of base, such as two hydrochloric acid molecules per molecule of compound of formula (I).

Compounds of the Invention

The compounds of the invention are defined according to formula (I) above. The applicants have found that the compounds of the invention are effective inhibitors of several bacterial strains. As will be appreciated, there is an expectation that the compounds will be inhibitors of a larger group of bacteria.

The compounds are characterised as having a substituted sulfonamide group at the 8-position of the quinoline ring structure and a substituent at the 2-position. Without being bound by theory, it is considered that the $pK_a$ of the sulfonamide hydrogen plays a role in the ability of the compound to act as an ionophore and therefore that an electron withdrawing group on the sulfonamide substituent is preferable. Examples of electron withdrawing groups include halogen, haloalkyl, haloalkoxy, alkyl carbonyl, alkyl ester, carboxylic acid, nitrile, and nitro.

The substituent at the 2-position may be chosen from a large variety of different types of groups. Some preferred groups are those that incorporate a nitrogen functionality. Again without being bound by theory, it is thought that those compounds having an amino group one carbon removed from the quinoline ring at the 2-position may beneficially interact, in combination with the quinoline nitrogen and the sulfonamide nitrogen, with a zinc cation.

Preparation of Compounds of the Invention

The compounds of the invention may be prepared by any known or standard synthetic procedures. Some compounds may be prepared according to scheme 1 from 8-amino-2-methylquinoline by reaction firstly with a substituted sulfonyl chloride, followed by oxidation of the 2-methyl group to an aldehyde (to give a 2-formyl derivative), and then reductive amination.

Scheme 1

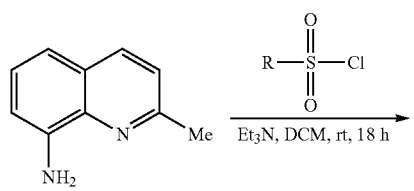

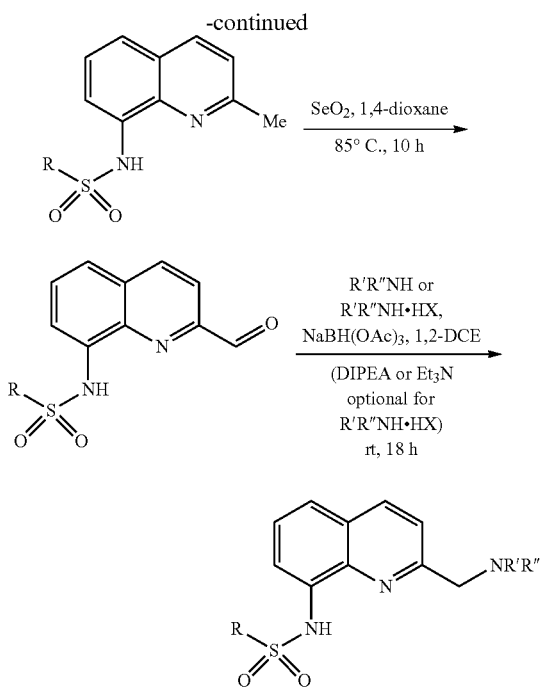

Alternatively, some compounds may be prepared according to scheme 2 from 8-amino-2-methylquinoline (which is first protected as a carbamate) via oxidation of the 2-methyl group to an aldehyde (to give a 2-formyl derivative), reductive amination (followed by deprotection) and then reaction with a substituted sulfonyl chloride.

Scheme 2

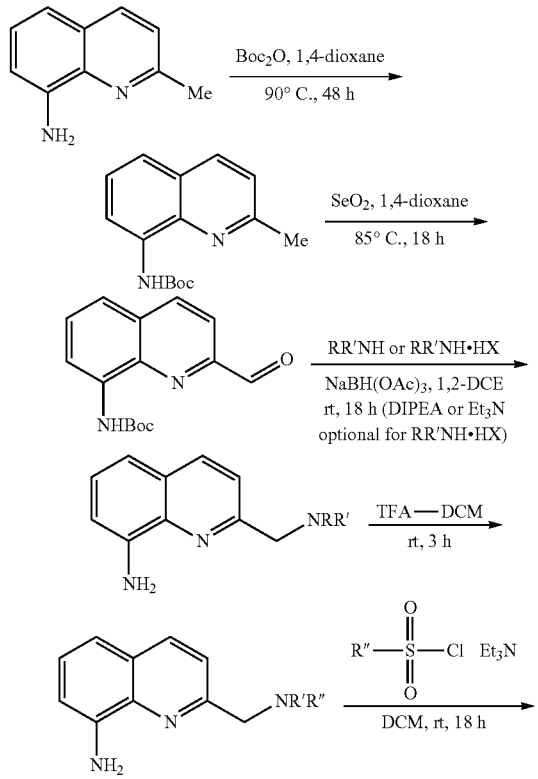

-continued

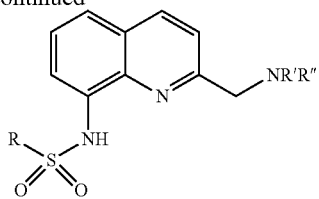

Acyhydrazones and semicarbazones/thiosemicarbazones may be prepared from a common 2-formyl pre-cursor according to schemes 3 and 4, respectively.

Scheme 3

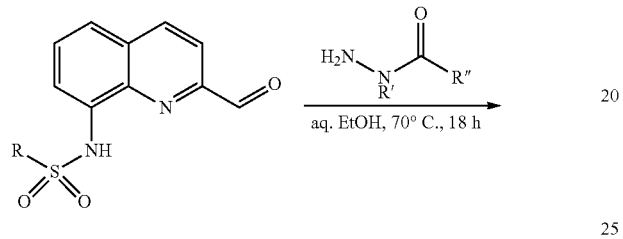

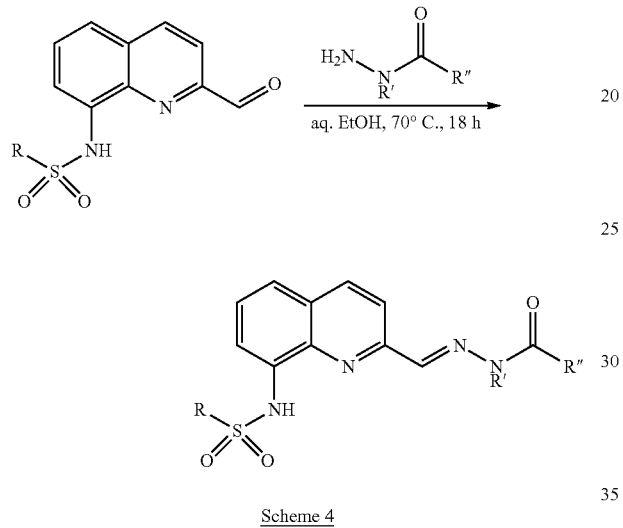

X = O or S

Oximes and hydrazones may be prepared from a common 2-formyl pre-cursor according to schemes 5 and 6, respectively.

Scheme 5

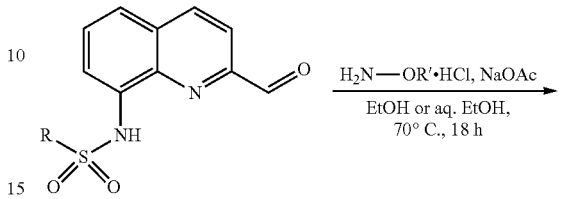

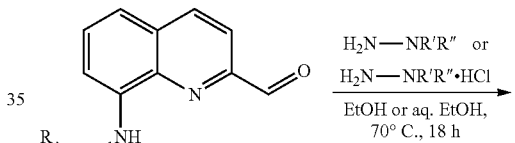

Scheme 6

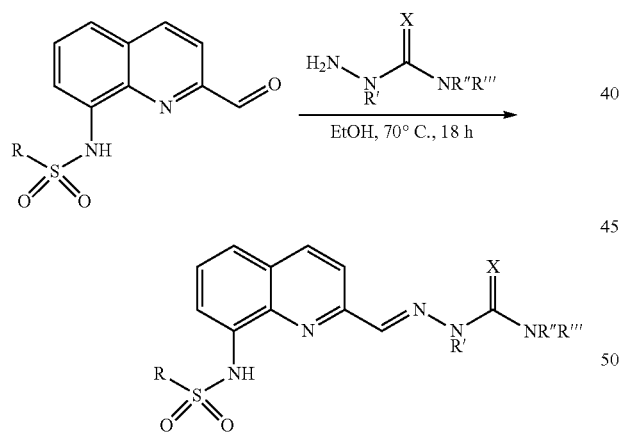

Aminomethyl derivatives (including amides, guanidines, nitro-guanidines and sulfonamides) may be prepared from a common 2-aminomethyl precursor (via an oxime, scheme 5) according to scheme 7.

Scheme 7

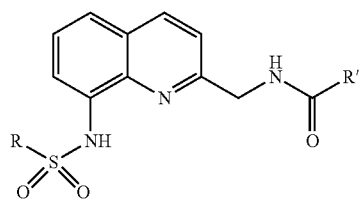
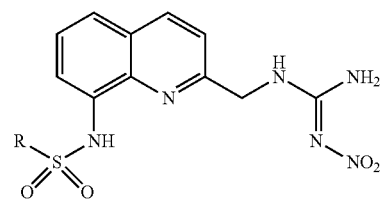

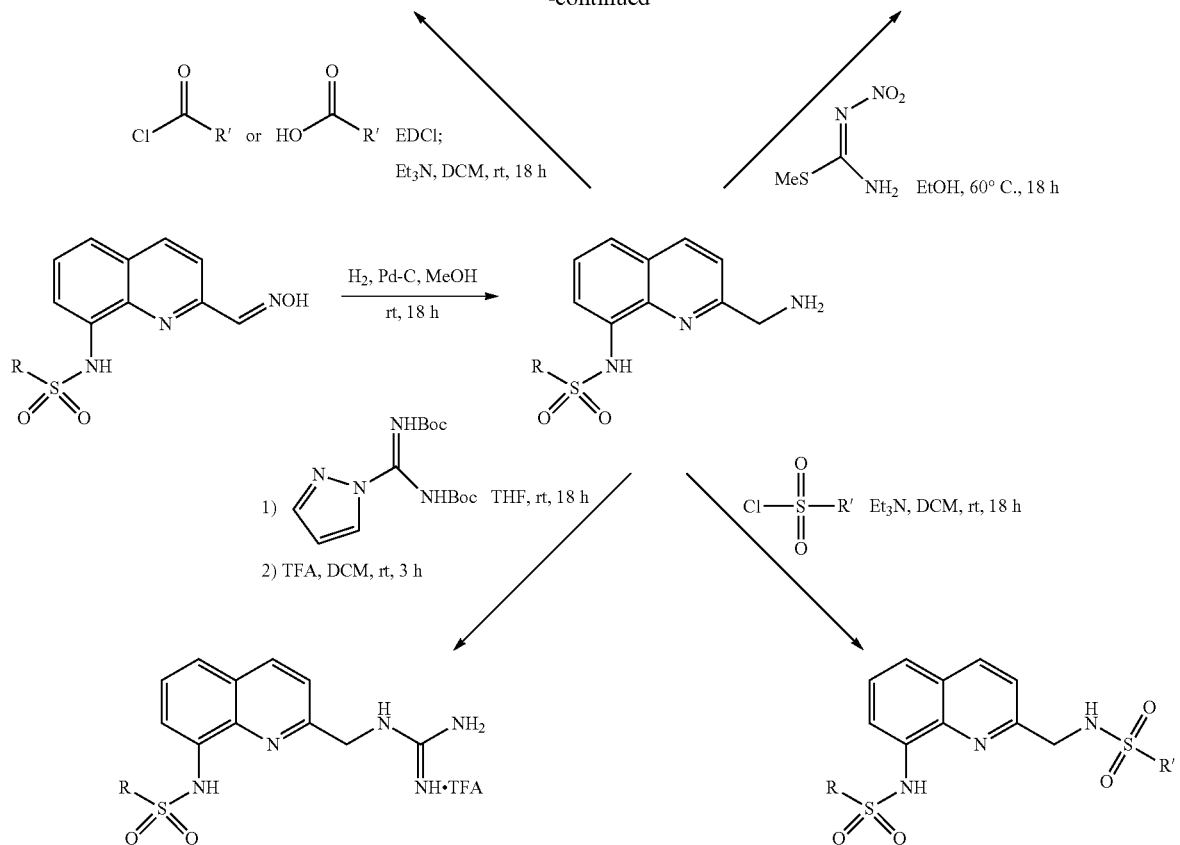
Amino amide derivatives may be prepared from a common N-boc-protected amino acid precursor (via an N-hydroxysuccinimide ester) according to scheme 8.
Scheme 8
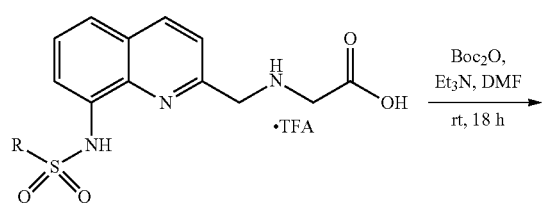
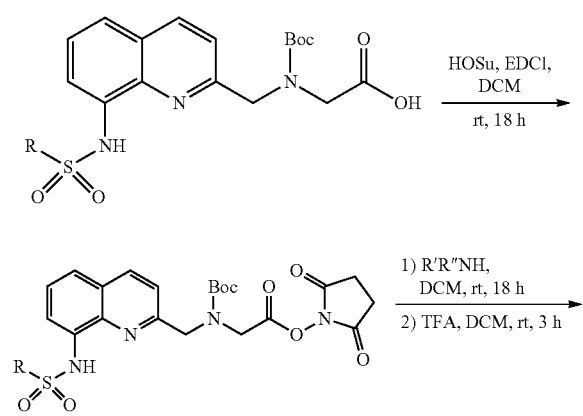
-continued
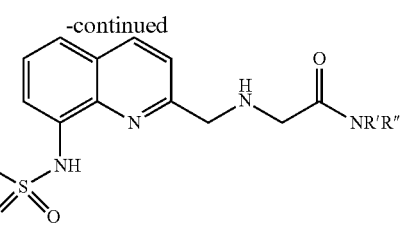
Amide derivatives may be prepared from a common carboxylic acid precursor (itself accessed through the oxidation of a 2-formyl precursor, scheme 1) according to scheme 9.
Scheme 9
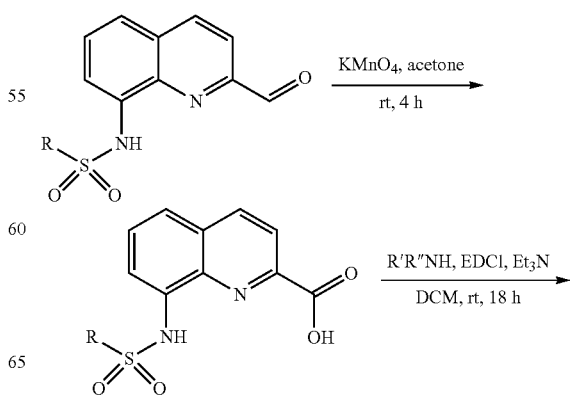

-continued

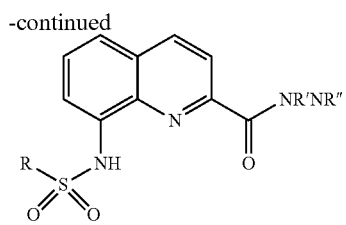

Pharmaceutical Formulations and Administration

The compounds of the invention may be administered to a human or animal patient by a variety of mutes, including orally, parenterally, by inhalation spray, topically, rectally, nasally, buccally, intravenously, intra-muscularly, intra-dermally, subcutaneously or via an implanted reservoir, preferably intravenously. The amount of compound to be administered will vary widely according to the nature of the patient and the nature and extent of the disorder to be treated. Typically the dosage for an adult human will be in the range 50-4800 µg/m² or µg/kg. The specific dosage required for any particular patient will depend upon a variety of factors, including the patient's age, body weight, general health, sex, etc.

For oral administration, the compounds of the invention can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried corn-starch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant. In one preferred embodiment, the compounds are administered by intravenous injection, where the diluent comprises an aqueous solution of sucrose, L-histidine and a pharmaceutically acceptable surfactant, e.g. Tween 20.

The compounds may also be administered topically, including as a spray particularly for some animal indications such as mastitis. Carriers for topical administration of the compounds include mineral oil, liquid petrolatum, white petrolatum, propylene glycol, polyoxyethylene, polyoxypropylene compound, emulsifying wax and water. Some teat spray formulations for treating mastitis may include glycerol and one or more surfactants in addition to other carriers. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

The compounds of the invention may also be administered in combination with other antimicrobial compounds such as chlorhexidine, iodine, lactic acid, cetrimide, BZK (benzylalkonium chloride), amoxicillin, erythromycin, cloxacillin, pirlimycin, cephapirin, hetacillin and penicillin, and bacteriocins such as nisin and lacticin. Such combinations may administered in any form including teat sprays for bovine cows and other animals.

Further, the compounds of the invention may be used alone or in combination with other active ingredients in external or internal teat seal formulations. Teat seals provide a physical barrier to prevent bacteria accessing the teat or udder of a cow. External teat seals provide a barrier across the entrance to the teat canal. The end of each teat is dipped in a teat seal formulation after milking has ended. The seal then dries to provide a film that prevents entry of bacteria to the teat canal. Internal teat seals are typically pastes that are infused into each quarter of a cow's udder at the start of the drying off period. The paste forms an internal physical barrier to bacteria entering the teat canal. Many internal teat seal formulations comprise bismuth sub-nitrate and a heavy metal salt such as barium sulfate, often formulated as gels which solidify after administration. One example is TEAT-SEAL™.

Proposed Mechanism of Action

The applicant does not wish to be bound by theory, but proposes that mechanism of killing of bacteria by a compound of the invention is three-fold. Firstly, the compound is able to translocate zinc into the bacterial cytoplasm (inside the bacterial cell). Accumulation of zinc overcomes the zinc homeostatic apparatus of the bacterial cells, leading to cell death through zinc toxicity. Secondly, the compounds exert their effect in a bacterial-specific manner as an ionophore by depolarising the proton motive force (pmf). Finally, zinc-chelation by the compound in the external media limits the amount of bio-available zinc, leading to extracellular zinc starvation of the bacterium.

It is thought that zinc ionophores translocate protons ($H^+$) in exchange for metal ions ($M^+$) across cell membranes (FIG. 1). When the external pH is higher than the acid dissociation constant ($pK_a$) of the ionophore, the ionophore is predominately deprotonated, and able to form an ionophore-metal complex (MI). When the pH is lower than the $pK_a$ of the ionophore, the metal ion is released as the ionophore becomes protonated (HI). Depending on the properties of the ionophore, they can accumulate in the membrane as shown in FIG. 1, or are able to diffuse through the membrane into extracellular or intracellular spaces.

Summary of Biological Data

All quinoline sulfonamide compounds synthesised to date have been examined for their inhibitory properties against the three-major mastitis-causing microorganisms in New Zealand, these being *S. uberis, S. aureus,* or *E. coli*. Minimum inhibitory concentrations were determined, initially in the absence of any additional zinc (above that contained in the media), and with an additional 50 µM zinc (zinc sulfate). MIC data is summarised in Table 1. In addition to the inhibitory activity of the quinoline sulfonamide compounds, specific compounds were assessed for their ability to kill mastitis-causing microorganisms as shown in Table 2. It is anticipated that the bacterial strains potentially inhibited by compounds of the invention include other members of the Enterobactericeae, Staphylococcaceae, and Streptococcaceae families.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

Example 1: N-(2-Methylquinolin-8-yl)-4-(trifluoromethyl)benzenesulfonamide—Compound (ZDR018)

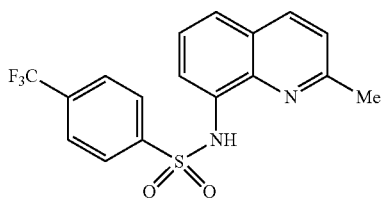 [SMILES: Cc1ccc2cccc(NS(=O)(=O)c3ccc(C(F)(F)F)cc3)c2n1]

A solution of 8-amino-2-methylquinoline (10.0 g, 63.2 mmol), 4-(trifluoromethyl)benzenesulfonyl chloride (17.0 g, 69.5 mmol) and triethylamine (10.5 mL, 75.8 mmol) in dichloromethane (100 mL) was stirred at room temperature for 18 h. The mixture was then diluted with water (100 mL), the pH adjusted to pH 6-7 using aqueous phosphate buffer solution (0.5 M, pH 7) and the separated aqueous layer further extracted with dichloromethane (2×50 mL). The combined organic layers were further washed with aqueous phosphate buffer solution (0.5 M, pH 7) (50 mL), dried over anhydrous magnesium sulfate, filtered and the filtrate concentrated in vacuo to afford compound (ZDR018) as a pale grey solid (22.40 g), which was used without further purification. $^1$H NMR (300 MHz, CDCl$_3$) δ 2.68 (3H, s), 7.28 (1H, d, J=8.4 Hz), 7.37 (1H, t, J=7.4 Hz), 7.45 (1H, dd, J=7.4 and 1.4 Hz), 7.61 (2H, d, J=8.2 Hz), 7.79 (1H, dd, J=7.4 and 1.4 Hz), 7.98 (1H, d, J=8.4 Hz), 8.01 (2H, d, J=8.2 Hz); ESI-MS: m/z calcd for C$_{17}$H$_{13}$F$_3$N$_2$O$_2$S: 366.1; found [M+H]$^+$: 367.1.

Example 2: N-(2-Formylquinolin-8-yl)-4-(trifluoromethyl)benzenesulfonamide—Compound (ZDR019)

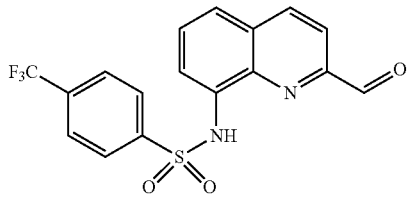 [SMILES: O=Cc1ccc2cccc(NS(=O)(=O)c3ccc(C(F)(F)F)cc3)c2n1]

A solution of compound (ZDR018) (22.40 g) and selenium dioxide (7.45 g, 67.2 mmol) In 1,4-dioxane (400 mL) was heated at 85° C. for 10 h. The mixture was allowed to cool to room temperature then filtered through Celite®, and the filtrate concentrated in vacuo. Purification by flash chromatography (petroleum ether/ethyl acetate, 4:1→2:1→1:1) afforded compound (ZDR019) as an off-white solid (18.50 g, 48.6 mmol, 77% over 2 steps). $^1$H NMR (300 MHz, CDCl$_3$) δ 7.58-7.63 (2H, m), 7.68 (2H, d, J=8.4 Hz), 7.93-7.96 (1H, m), 8.06 (1H, d, J=8.4 Hz), 8.09 (2H, d, J=8.4 Hz), 8.31 (1H, d, J=8.4 Hz), 9.21 (1H, br s), 10.20 (1H, s); ESI-MS: m/z calcd for C$_{17}$H$_{11}$F$_3$N$_2$O$_3$S: 380.0; found [M+H]$^+$: 381.1.

Example 3: N-(2-((Dimethylamino)methyl)quinolin-8-yl)-4-(trifluoromethyl)-benzenesulfonamide—Compound (ZDR022)

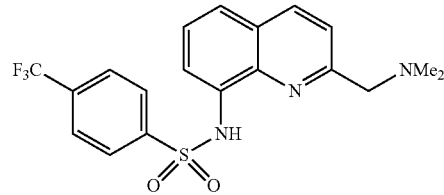 [SMILES: CN(C)Cc1ccc2cccc(NS(=O)(=O)c3ccc(C(F)(F)F)cc3)c2n1]

A solution of compound (ZDR019) (3.0 g, 7.88 mmol), dimethylamine hydrochloride (1.92 g, 23.6 mmol), sodium triacetoxyborohydride (3.32 g, 15.7 mmol) and N,N-diisopropylethylamine (4.8 mL, 27.5 mmol) in 1,2-dichloroethane (150 mL) was stirred at room temperature for 18 h. The reaction was quenched through the addition of water (100 mL) and the pH adjusted to pH 6-7 using aqueous phosphate buffer solution (0.5 M, pH 7). The mixture was then diluted with dichloromethane (100 mL) and the separated aqueous layer further extracted with dichloromethane (2×50 mL). The combined organic layers were washed with aqueous phosphate buffer solution (0.5 M, pH 7) (100 mL), dried over anhydrous magnesium sulfate, filtered and the filtrate concentrated in vacuo. Purification by flash chromatography (dichloromethane/methanol, 20:1→10:1→7:1) afforded compound (ZDR022) as a white solid (2.40 g, 5.86 mmol, 74%). $^1$H NMR (300 MHz, CDCl$_3$) δ 2.32 (6H, s), 3.77 (2H, s), 7.40-7.48 (2H, m), 7.52 (1H, d, J=8.4 Hz), 7.57 (2H, d, J=8.3 Hz), 7.86 (1H, dd, J=7.3 and 1.6 Hz), 8.00 (2H, d, J=8.3 Hz), 8.07 (1H, d, 8.4 Hz); $^{13}$C NMR (75 MHz, CDCl$_3$) δ 45.3 (CH$_3$), 65.5 (CH$_2$), 116.7 (CH), 122.1 (CH), 122.9 (CH), 123.2 (C, q, J=273 Hz), 126.0 (CH, q, J=3.6 Hz), 126.6 (CH), 127.4 (C), 127.7 (CH), 133.2 (C), 134.4 (C, q, J=33 Hz), 137.0 (CH), 138.2 (C), 143.2 (C), 157.8 (C). $^1$H NMR (400 MHz, d$_6$-DMSO) δ 2.14 (6H, s), 3.59 (2H, s), 7.50 (1H, t, J=7.8 Hz), 7.57 (1H, d, J=8.5 Hz), 7.67-7.71 (2H, m), 7.80 (2H, d, J=8.2 Hz), 8.02 (2H, d, J=8.2 Hz), 8.25 (1H, d, J=8.5 Hz); $^{13}$C NMR (100 MHz, d$_6$-DMSO) δ 45.1 (CH$_3$), 65.1 (CH$_2$), 120.2 (CH), 121.5 (CH), 123.2 (C, q, J=273 Hz), 124.1 (CH), 126.0 (CH), 127.2 (C), 127.7 (CH), 132.3 (C, q, J=32 Hz), 132.9 (C), 136.6 (CH), 139.0 (C), 143.9 (C), 159.2 (C); ESI-MS: m/z calcd for C$_{19}$H$_{18}$F$_3$N$_3$O$_2$S: 409.1; found [M+H]$^+$: 410.2.

Example 4: N-(2-((Dimethylamino)methyl)quinolin-8-yl)-4-(trifluoromethyl)-benzenesulfonamide HCl—Compound (ZDR022 Hydrochloride)

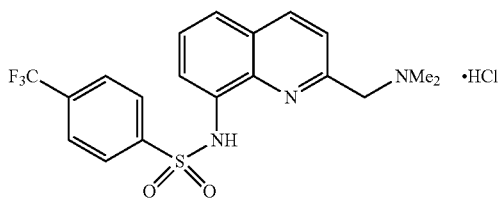 [SMILES: CN(C)Cc1ccc2cccc(NS(=O)(=O)c3ccc(C(F)(F)F)cc3)c2n1 ; Cl]

To a solution of compound (ZDR022) (1.00 g, 2.44 mmol) in 1,4-dioxane (10 mL) was added aqueous hydrochloric acid (20 mL, 0.1 M), and the mixture lyophilized to dryness to afford compound (ZDR022 HCl) as a white solid (1.08 g, 2.44 mmol, quant.). $^1$H NMR (400 MHz, $d_6$-DMSO) δ 2.83 (6H, s), 4.70 (2H, s), 7.56-7.61 (2H, m), 7.73 (1H, dd, J=8.4 and 1.0 Hz), 7.85-7.89 (3H, m), 8.13 (2H, d, J=8.2 Hz), 8.43 (1H, d, J=8.4 Hz), 10.82 (1H, s), 11.16 (1H, s); $^{13}$C NMR (100 MHz, $d_6$-DMSO) δ 42.7 ($CH_3$), 60.0 ($CH_2$), 118.8 (CH), 121.3 (CH), 123.2 (C, q, J=273 Hz), 123.5 (CH), 126.3 (CH, q, J=3.5 Hz), 127.2 (CH), 127.4 (C), 127.8 (CH), 132.5 (C, q, J=32 Hz), 133.2 (C), 138.0 (CH), 143.5 (C), 150.8 (C); ESI-MS: m/z calcd for $C_{19}H_{18}F_3N_3O_2S$: 409.1; found $[M+H]^+$: 410.1.

Example 5: N-(2-((Methylamino)methyl)quinolin-8-yl)-4-(trifluoromethyl)-benzenesulfonamide—Compound (ZDR024)

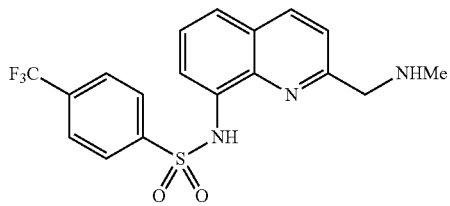 [SMILES: CNCc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), methylamine (72 mg, 0.78 mmol, 33 wt. % In absolute ethanol) and sodium triacetoxyborohydride (111 mg, 0.52 mmol) in 1,2-dichloroethane (5 mL). Purification by flash chromatography (dichloromethane/methanol, 20:1) afforded compound (ZDR024) as a pale yellow solid (65 mg, 0.16 mmol, 62%). $^1$H NMR (300 MHz, $d_6$-DMSO) δ 2.54 (3H, s), 4.29 (2H, s), 7.40-7.58 (5H, m), 7.67 (1H, d, J=7.3 Hz), 7.84 (2H, d, J=8.1 Hz), 8.25 (1H, d, J=8.4 Hz); ESI-MS: m/z calcd for $C_{18}H_{16}F_3N_3O_2S$: 395.1; found $[M+H]^+$: 396.1.

Example 6: N-(2-((Ethylamino)methyl)quinolin-8-yl)-4-(trifluoromethyl)-benzenesulfonamide—Compound (ZDR025)

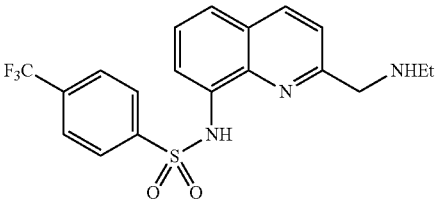

A similar procedure to that described for the preparation of compound (ZDR022) was followed using compound (ZDR019) (100 mg, 0.26 mmol), ethylamine (51 μL, 0.78 mmol) and sodium triacetoxyborohydride (111 mg, 0.52 mmol) in 1,2-dichloroethane (5 mL). Purification by flash chromatography (dichloromethane/methanol, 20:1) afforded compound (ZDR025) as a pale yellow solid (71 mg, 0.17 mmol, 65%). $^1$H NMR (300 MHz, $d_6$-DMSO) δ 1.24 (3H, t, J=7.2 Hz), 2.89 (2H, q, J=7.2 Hz), 4.37 (2H, s), 7.51 (1H, t, J=7.9 Hz), 7.56 (1H, d, J=8.4 Hz), 7.65 (1H, d, J=7.9 Hz), 7.76-7.81 (3H, m), 8.02 (2H, d, J=8.1 Hz), 8.34 (1H, d, J=8.4 Hz); ESI-MS: m/z calcd for $C_{19}H_{18}F_3N_3O_2S$: 409.1; found $[M+H]^+$: 410.1.

Example 7: N-(2-((Propylamino)methyl)quinolin-8-yl)-4-(trifluoromethyl)-benzenesulfonamide—Compound (ZDR026)

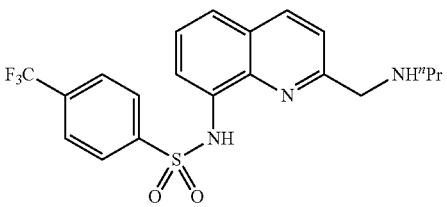

A similar procedure to that described for the preparation of compound (ZDR022) was followed using compound (ZDR019) (100 mg, 0.26 mmol), n-propylamine (64 μL, 0.78 mmol) and sodium triacetoxyborohydride (111 mg, 0.52 mmol) in 1,2-dichloroethane (5 mL). Purification by flash chromatography (dichloromethane/methanol, 20:1) afforded compound (ZDR026) as a pale yellow solid (79 mg, 0.19 mmol, 73%). $^1$H NMR (300 MHz, $d_6$-DMSO) δ 0.89 (3H, t, J=7.2 Hz), 1.55-1.62 (2H, m), 2.67 (2H, t, J=7.2 Hz), 4.17 (2H, s), 7.42-7.70 (6H, m), 7.94 (2H, d, J=8.1 Hz), 8.25 (1H, d, J=8.4 Hz); ESI-MS: m/z calcd for $C_{20}H_{20}F_3N_3O_2S$: 423.1; found $[M+H]^+$: 424.1.

Example 8: N-(2-((Isopropylamino)methyl)quinolin-8-yl)-4-(trifluoromethyl)-benzenesulfonamide—Compound (ZDR027)

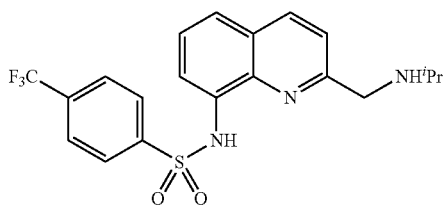

A similar procedure to that described for the preparation of compound (ZDR022) was followed using compound (ZDR019) (100 mg, 0.26 mmol), isopropylamine (64 μL, 0.78 mmol) and sodium triacetoxyborohydride (111 mg, 0.52 mmol) in 1,2-dichloroethane (5 mL). Purification by flash chromatography (dichloromethane/methanol, 20:1) afforded compound (ZDR027) as a pale yellow solid (67 mg, 0.16 mmol, 62%). $^1$H NMR (300 MHz, d$_6$-DMSO) δ 1.11 (6H, d, J=6.3 Hz), 2.89-2.94 (1H, m), 4.10 (2H, s), 7.47 (1H, t, J=7.8 Hz), 7.55 (1H, d, J=8.4 Hz), 7.62 (1H, d, J=7.8 Hz), 7.70 (1H, dd, J=7.8 and 1.2 Hz), 7.74 (2H, d, J=8.2 Hz), 7.97 (2H, d, J=8.2 Hz), 8.26 (1H, d, J=8.4 Hz); ESI-MS: m/z calcd for $C_{20}H_{20}F_3N_3O_2S$: 423.1; found [M+H]$^+$: 424.1.

Example 9: N-(2-((Diethylamino)methyl)quinolin-8-yl)-4-(trifluoromethyl)-benzenesulfonamide—Compound (ZDR028)

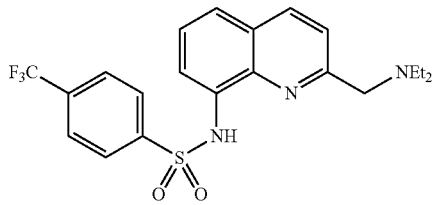

A similar procedure to that described for the preparation of compound (ZDR022) was followed using compound (ZDR019) (100 mg, 0.26 mmol), diethylamine (81 μL, 0.78 mmol) and sodium triacetoxyborohydride (111 mg, 0.52 mmol) in 1,2-dichloroethane (5 mL). Purification by flash chromatography (dichloromethane/methanol, 20:1) afforded compound (ZDR028) as a pale yellow solid (89 mg, 0.20 mmol, 77%). $^1$H NMR (300 MHz, d$_6$-DMSO) δ 0.97 (6H, t, J=7.1 Hz), 2.48-2.51 (4H, m), 3.74 (2H, s), 7.51 (1H, t, J=7.7 Hz), 7.63 (1H, d, J=8.5 Hz), 7.69-7.71 (2H, m), 7.82 (2H, d, J=8.3 Hz), 8.01 (2H, d, J=8.3 Hz), 8.27 (1H, d, J=8.5 Hz); ESI-MS: m/z calcd for $C_{21}H_{22}F_3N_3O_2S$: 437.1; found [M+H]$^+$: 438.1.

Example 10: N-(2-((Morpholin-4-yl)methyl)quinolin-8-yl)-4-(trifluoromethyl)-benzenesulfonamide—Compound (ZDR029)

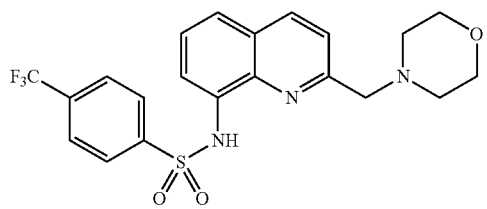

A similar procedure to that described for the preparation of compound (ZDR022) was followed using compound (ZDR019) (100 mg, 0.26 mmol), morpholine (68 μL, 0.78 mmol) and sodium triacetoxyborohydride (111 mg, 0.52 mmol) in 1,2-dichloroethane (5 mL). Purification by flash chromatography (dichloromethane/methanol, 30:1) afforded compound (ZDR029) as a white solid (82 mg, 0.18 mmol, 69%). $^1$H NMR (300 MHz, CDCl$_3$) δ 2.47-2.50 (4H, m), 3.71-3.75 (4H, m), 3.76 (2H, s), 7.40-7.51 (2H, m), 7.59 (2H, d, J=8.2 Hz), 7.64 (1H, d, J=8.4 Hz), 7.83 (1H, dd, J=7.4 and 1.5 Hz), 8.00 (2H, d, J=8.2 Hz), 8.07 (1H, d, J=8.4 Hz); ESI-MS: m/z calcd for $C_{21}H_{20}F_3N_3O_3S$: 451.1; found [M+H]$^+$: 452.0.

Example 11: N-(2-(((2-(Dimethylamino)ethyl)amino)methyl)quinolin-8-yl)-4-(trifluoromethyl)benzenesulfonamide—Compound (ZDR030)

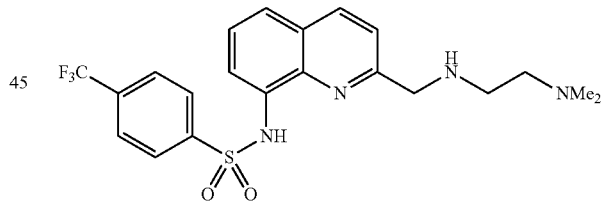

A similar procedure to that described for the preparation of compound (ZDR022) was followed using compound (ZDR019) (100 mg, 0.26 mmol), N,N-dimethylethylenediamine (86 μL, 0.78 mmol) and sodium triacetoxyborohydride (111 mg, 0.52 mmol) in 1,2-dichloroethane (5 mL). Purification by flash chromatography (dichloromethane/methanol, 20:1→10:1) afforded compound (ZDR030) as a pale brown solid (61 mg, 0.13 mmol, 50%). $^1$H NMR (300 MHz, CDCl$_3$) δ 2.41 (6H, s), 2.76 (2H, t, J=5.8 Hz), 2.88 (2H, t, J=5.8 Hz), 4.12 (2H, s), 7.32-7.44 (3H, m), 7.57 (2H, d, J=8.2 Hz), 7.71-7.74 (1H, m), 7.98-8.04 (3H, m); ESI-MS: m/z calcd for $C_{21}H_{23}F_3N_4O_2S$: 452.1; found [M+H]$^+$: 453.0.

Example 12: N-(2-(((2-Hydroxyethyl)amino) methyl)quinolin-8-yl)-4-(trifluoromethyl)benzene- sulfonamide—Compound (ZDR031)

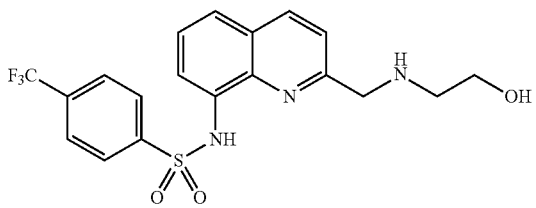 [SMILES: O=S(=O)(Nc1cccc2ccc(CNCCO)nc12)c1ccc(C(F)(F)F)cc1]

A similar procedure to that described for the preparation of compound (ZDR022) was followed using compound (ZDR019) (100 mg, 0.26 mmol), ethanolamine (47 μL, 0.78 mmol) and sodium triacetoxyborohydride (111 mg, 0.52 mmol) in 1,2-dichloroethane (5 mL). Purification by flash chromatography (dichloromethane/methanol, 20:1→10:1) afforded compound (ZDR031) as a pale yellow solid (64 mg, 0.15 mmol, 58%). $^1$H NMR (300 MHz, d$_6$-DMSO) δ 2.82 (2H, t, J=5.6 Hz), 3.64 (2H, t, J=5.6 Hz), 4.20 (2H, s), 7.40-7.68 (6H, m), 7.90 (2H, d, J=8.2 Hz), 8.23 (1H, d, J=8.4 Hz); ESI-MS: m/z calcd for $C_{19}H_{18}F_3N_3O_3S$: 425.1; found [M+H]$^+$: 426.0.

Example 13: N-(2-((Piperidin-1-yl)methyl)quinolin-8-yl)-4-(trifluoromethyl)-benzenesulfonamide—Compound (ZDR033)

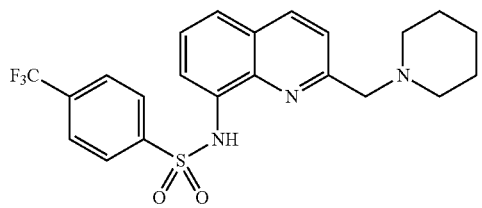 [SMILES: O=S(=O)(Nc1cccc2ccc(CN3CCCCC3)nc12)c1ccc(C(F)(F)F)cc1]

A similar procedure to that described for the preparation of compound (ZDR022) was followed using compound (ZDR019) (100 mg, 0.26 mmol), piperidine (77 μL, 0.78 mmol) and sodium triacetoxyborohydride (111 mg, 0.52 mmol) in 1,2-dichloroethane (5 mL). Purification by flash chromatography (dichloromethane/methanol, 20:1→10:1) afforded compound (ZDR033) as a white solid (88 mg, 0.19 mmol, 73%). $^1$H NMR (300 MHz, CDCl$_3$) δ 1.46-1.54 (2H, m), 1.59-1.69 (4H, m), 2.44-2.52 (4H, m), 3.76 (2H, s), 7.49-7.50 (2H, m), 7.58-7.63 (3H, m), 7.83 (1H, dd, J=7.3 and 1.4 Hz), 8.01 (2H, d, J=8.2 Hz), 8.05 (1H, d, J=8.4 Hz); ESI-MS: m/z calcd for $C_{22}H_{22}F_3N_3O_2S$: 449.1; found [M+H]$^+$: 450.1.

Example 14: N-(2-((((Pyridin-2-yl)methyl)amino) methyl)quinolin-8-yl)-4-(trifluoromethyl)benzene- sulfonamide—Compound (ZDR035)

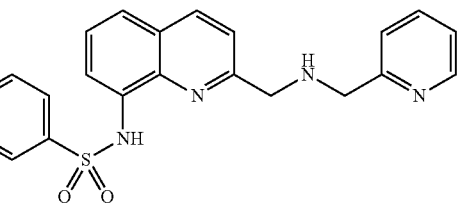

A similar procedure to that described for the preparation of compound (ZDR022) was followed using compound (ZDR019) (100 mg, 0.26 mmol), 2-(aminomethyl)pyridine (81 μL, 0.78 mmol) and sodium triacetoxyborohydride (111 mg, 0.52 mmol) in 1,2-dichloroethane (5 mL). Purification by flash chromatography (petroleum ether/ethyl acetate, 1:1) afforded compound (ZDR035) as a pale yellow solid (85 mg, 0.18 mmol, 69%). $^1$H NMR (300 MHz, CDCl$_3$) δ 3.95 (2H, s), 4.11 (2H, s), 7.20-7.26 (1H, m), 7.31 (1H, d, J=7.5 Hz), 7.40-7.51 (3H, m), 7.54 (2H, d, J=8.2 Hz), 7.65-7.70 (1H, m), 7.86 (1H, dd, J=7.5 and 1.4 Hz), 7.97 (2H, d, J=8.2 Hz), 8.05 (1H, d, J=8.4 Hz), 8.71-8.51 (1H, m); ESI-MS: m/z calcd for $C_{23}H_{19}F_3N_4O_2S$: 472.1; found [M+H]$^+$: 473.0.

Example 15: N,N'-(((Ethane-1,2-diylbis(methyl- azanediyl))bis(methylene))-bis(quinoline-2,8-diyl)) bis(4-(trifluoromethyl)benzenesulfonamide)—Compound (ZDR036)

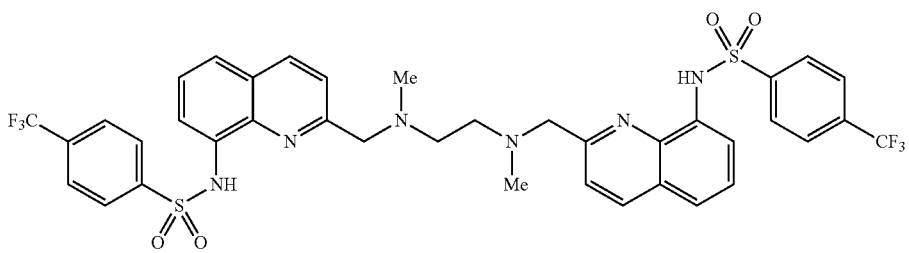 [SMILES: CN(CCN(C)Cc1ccc2cccc(NS(=O)(=O)c3ccc(C(F)(F)F)cc3)c2n1)Cc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), N,N'-dimethylethylenediamine (14 μL, 0.13 mmol) and sodium triacetoxyborohydride (111 mg, 0.52 mmol) in 1,2-dichloroethane (5 mL). Purification by flash chromatography (dichloromethane/methanol, 20:1) afforded compound (ZDR036) as a pale yellow solid (40 mg, 0.05 mmol, 38%). $^1$H NMR (300 MHz, CDCl$_3$) δ 2.25 (2H, d, J=10.5 Hz), 2.31 (6H, s), 2.80 (2H, d, J=10.5 Hz), 3.83 (2H, d, J=15.4 Hz), 4.93 (2H, d, J=15.4 Hz), 7.14-7.30 (10H, m), 7.41 (2H, d, J=8.4 Hz), 7.69 (4H, d, J=8.3 Hz), 8.27 (2H, d, J=8.4 Hz); ESI-MS: m/z calcd for $C_3H_{34}F_6N_6O_4S_2$: 816.2; found [M+H]$^+$: 817.1.

Example 16: N,N'-(((Methylazanediyl)bis(methylene))bis(quinoline-2,8-diyl))bis(4-(trifluoromethyl)benzenesulfonamide)—Compound (ZDR037)

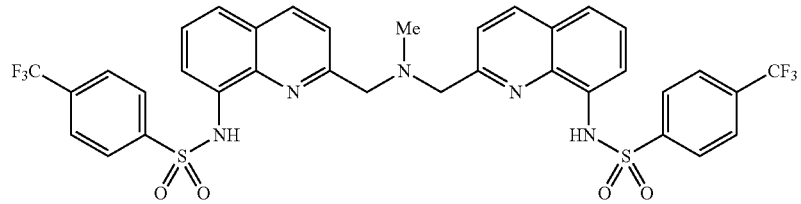 [SMILES: CN(Cc1ccc2cccc(NS(=O)(=O)c3ccc(C(F)(F)F)cc3)c2n1)Cc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), methylamine (12 mg, 0.13 mmol, 33 wt. % in absolute ethanol) and sodium triacetoxyborohydride (111 mg, 0.52 mmol) in 1,2-dichloroethane (5 mL). Purification by flash chromatography (dichloromethane/methanol, 30:1) afforded compound (ZDR037) as a pale yellow solid (45 mg, 0.06 mmol, 46%). $^1$H NMR (400 MHz, CDCl$_3$) δ 2.25 (3H, s), 3.87 (4H, s), 7.43 (2H, t, J=7.8 Hz), 7.49 (2H, dd, J=7.8 and 1.4 Hz), 7.55 (4H, d, J=8.3 Hz), 7.67 (2H, d, J=8.3 Hz), 7.82 (2H, dd, J=7.8 and 1.4 Hz), 7.99 (4H, d, J=8.3 Hz), 8.10 (2H, d, J=8.3 Hz); ESI-MS: m/z calcd for C$_{35}$H$_{27}$F$_6$N$_5$O$_4$S$_2$: 759.1; found [M+H]$^+$: 760.1.

Example 17: N-(2-(((tert-Butoxycarbonylmethyl)amino)methyl)quinolin-8-yl)-4-(trifluoromethyl)benzenesulfonamide—Compound (ZDR041)

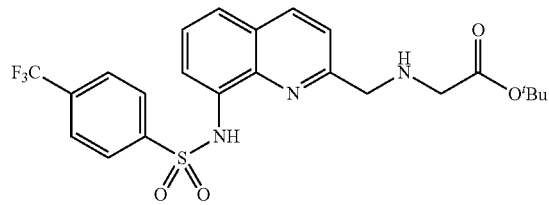 [SMILES: CC(C)(C)OC(=O)CNCc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), glycine tert-butyl ester hydrochloride (132 mg, 0.78 mmol), triethylamine (109 μL, 0.78 mmol) and sodium triacetoxyborohydride (111 mg, 0.52 mmol) in 1,2-dichloroethane (5 mL). Purification by flash chromatography (dichloromethane/methanol, 30:1) afforded compound (ZDR041) as a pale yellow solid (94 mg, 0.19 mmol, 73%). $^1$H NMR (300 MHz, CDCl$_3$) δ 1.49 (9H, s), 3.38 (2H, s), 4.06 (2H, s), 7.41-7.50 (3H, m), 7.61 (2H, d, J=8.2 Hz), 7.83 (1H, dd, J=7.4 and 1.5 Hz), 7.01-8.07 (3H, m); ESI-MS: m/z calcd for C$_{23}$H$_{24}$F$_3$N$_3$O$_4$S: 495.1; found [M+H]$^+$: 496.0.

Example 18: N-(2-(((Carboxymethyl)amino)methyl)quinolin-8-yl)-4-(trifluoromethyl)benzenesulfonamide trifluoroacetate—Compound (ZDR043)

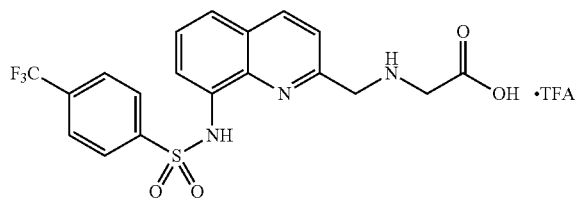 [SMILES: O=C(O)CNCc1ccc2cccc(NS(=O)(=O)c3ccc(C(F)(F)F)cc3)c2n1]

A solution of compound (ZDR041) (50 mg, 0.10 mmol) in trifluoroacetic acid-dichloromethane (3 mL, 50% v/v) was stirred at room temperature for 36 h. The solvent was removed in vacuo to afford compound (ZDR043) as a pale brown solid (53 mg, 0.10 mmol, quant.), which was used without further purification. $^1$H NMR (300 MHz, d$_6$-DMSO) δ 4.01 (2H, s), 4.62 (2H, s), 7.55-7.60 (1H, m), 7.58 (1H, d, J=8.4 Hz), 7.72 (1H, dd, J=7.9 and 1.0 Hz), 7.85 (2H, d, J=8.2 Hz), 7.89 (1H, dd, J=7.9 and 1.0 Hz), 8.07 (2H, d, J=8.2 Hz), 8.42 (1H, d, J=8.4 Hz), 9.78 (2H, br s), 10.62 (1H, s); ESI-MS: m/z calcd for C$_{19}$H$_{16}$F$_3$N$_3$O$_4$S: 439.1; found [M+H]$^+$: 440.0.

Example 19: (E)-N-(2-((2-Benzoylhydrazono)methyl)quinolin-8-yl)-4-(trifluoromethyl)benzenesulfonamide—Compound (ZDR045)

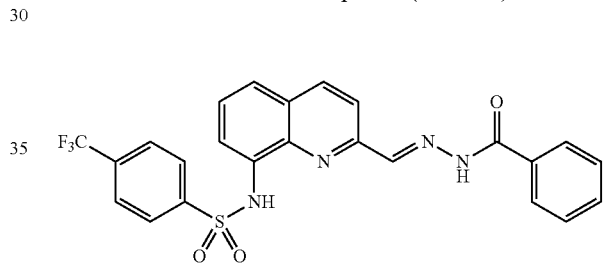

A solution of compound (ZDR019) (0.25 mg, 0.65 mmol) and benzhydrazide (89 mg, 0.65 mmol) in aqueous ethanol (20 mL, 90% v/v) was stirred at 70° C. for 18 h. The mixture was allowed to cool to room temperature and the precipitated product was collected by filtration and washed with ice-cold ethanol (2×2 mL) to afford compound (ZDR045) as a white solid (250 mg, 0.50 mmol, 77%), which was used without further purification. $^1$H NMR (300 MHz, d$_6$-DMSO) δ 7.55-7.64 (4H, m), 7.71 (1H, dd, J=7.8 and 1.1 Hz), 7.78 (1H, d, J=7.8 Hz), 7.84 (2H, d, J=8.3 Hz), 7.90-8.10 (5H, m), 8.37 (1H, d, J=8.5 Hz), 8.51 (1H, s), 10.40 (1H, s), 12.23 (1H, s); ESI-MS: m/z calcd for C$_{24}$H$_{17}$F$_3$N$_4$O$_3$S: 498.1; found [M+H]$^+$: 499.0.

Example 20: (E)-2-((8-((4-(Trifluoromethyl)phenyl)sulfonamido)quinolin-2-yl)methylene)hydrazine-1-carbothioamide—Compound (ZDR046)

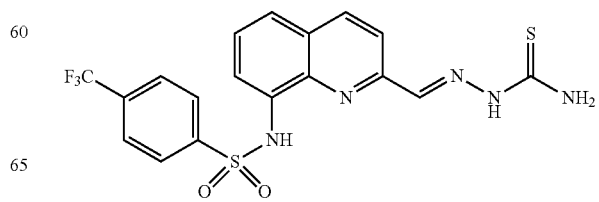

A similar procedure to that described for the preparation of compound (ZDR045) was followed using compound (ZDR019) (0.25 mg, 0.65 mmol) and thiosemicarbazide (59 mg, 0.65 mmol) in ethanol (30 mL) to afford compound (ZDR046) as a white solid (210 mg, 0.46 mmol, 71%), which was used without further purification. $^1$H NMR (300 MHz, d$_6$-DMSO) δ 7.52 (1H, t, J=7.8 Hz), 7.64 (1H, d, J=7.8 Hz), 7.71 (1H, d, J=7.8 Hz), 7.84 (2H, d, J=8.3 Hz), 8.03-8.10 (3H, m), 8.39-8.43 (2H, m), 10.43 (1H, s), 11.87 (1H, s); ESI-MS: m/z calcd for $C_{18}H_{14}F_3N_5O_2S_2$: 453.1; found [M+H]$^+$: 454.0.

Example 21: tert-Butyl (2-methylquinolin-8-yl)carbamate—Compound (ZDR056)

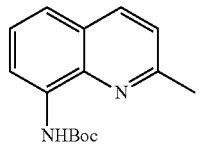 [SMILES: Cc1ccc2cccc(NC(=O)OC(C)(C)C)c2n1]

A solution of 8-amino-2-methylquinoline (11.66 g, 73.6 mmol) and di-tert-butyl dicarbonate (32.2 g, 147.3 mmol) in 1,4-dioxane (200 mL) was heated at 90° C. for 48 h, and the solvent then removed in vacuo. Purification by flash chromatography (petroleum ether/ethyl acetate, 100:1→20:1), followed by crystallisation from petroleum ether/ethanol (10:1 v/v), afforded compound (ZDR056) as a yellow solid (14.62 g, 56.6 mmol, 76%). $^1$H NMR (400 MHz, CDCl$_3$) δ 1.59 (9H, s), 2.74 (3H, s), 7.29 (1H, d, J=8.4 Hz), 7.35-7.38 (1H, m), 7.43 (1H, t, J=7.5 Hz), 8.00 (1H, d, J=8.4 Hz), 8.37 (1H, d, J=7.5 Hz), 9.05 (1H, brs).

Example 22: tert-Butyl (2-formylquinolin-8-yl)carbamate—Compound (ZDR057)

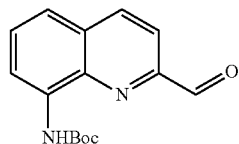 [SMILES: CC(C)(C)OC(=O)Nc1cccc2ccc(C=O)nc12]

A solution of compound (ZDR056) (4.34 g, 16.8 mmol) and selenium dioxide (3.36 g, 30.2 mmol) in 1,4-dioxane (200 mL) was heated at 85° C. for 18 h. The mixture was then filtered through a pad of Celite® and the solvent removed in vacuo. Purification by flash chromatography (dichloromethane) afforded compound (ZDR057) as a yellow solid (3.43 g, 12.5 mmol, 74%). $^1$H NMR (400 MHz, CDCl$_3$) δ 1.61 (9H, s), 7.50 (1H, dd, J=7.9 and 1.7 Hz), 7.66 (1H, t, J=7.9 Hz), 8.05 (1H, d, J=8.4 Hz), 8.29 (1H, d, J=8.4 Hz), 8.52 (1H, d, J=7.9 Hz), 8.99 (1H, brs), 10.25 (1H, s).

Example 23: tert-Butyl (2-((dimethylamino)methyl)quinolin-8-yl)carbamate—Compound (ZDR058)

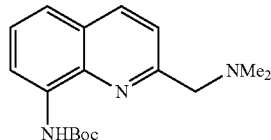 [SMILES: CN(C)Cc1ccc2cccc(NC(=O)OC(C)(C)C)c2n1]

A similar procedure to that described for the preparation of compound (ZDR022) was followed using compound (ZDR057) (7.0 g, 25.7 mmol), dimethylamine hydrochloride (4.19 g, 51.4 mmol), sodium triacetoxyborohydride (10.90 g, 51.4 mmol) and N,N-diisopropylethylamine (9.0 mL, 51.4 mmol) in 1,2-dichloroethane (350 mL). Purification by flash chromatography (dichloromethane/methanol, 10:1) afforded compound (ZDR058) as a yellow oil (6.70 g, 22.2 mmol, 86%). $^1$H NMR (400 MHz, CDCl$_3$) δ 1.59 (9H, s), 2.49 (6H, s), 4.00 (2H, s), 7.41 (1H, dd, J=7.8 and 1.5 Hz), 7.49 (1H, t, J=7.8 Hz), 7.66 (1H, d, J=8.4 Hz), 8.14 (1H, d, J=8.4 Hz), 8.41 (1H, d, J=7.8 Hz), 9.03 (1H, brs).

Example 24: 2-((Dimethylamino)methyl)quinolin-8-amine—Compound (ZDR059)

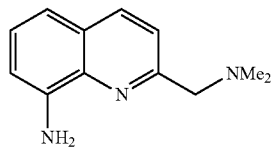 [SMILES: CN(C)Cc1ccc2cccc(N)c2n1]

A solution of compound (ZDR058) (1.50 g, 4.98 mmol) in trifluoroacetic acid-dichloromethane (3 mL, 50% v/v) was stirred at room temperature for 3 h, and the solvent then removed in vacuo. The resulting residue was taken up in dichloromethane (100 mL) and washed with aqueous sodium bicarbonate (2×100 mL), and the separated aqueous layers then further extracted with dichloromethane (50 mL). The combined organic layers were dried over anhydrous magnesium sulfate, filtered and the filtrate concentrated in vacuo. Purification by flash chromatography (dichloromethane/methanol, 50:1→10:1) afforded compound (ZDR059) as a yellow solid (477 mg, 2.36 mmol, 47%). $^1$H NMR (300 MHz, d$_4$-MeOH) δ 2.31 (6H, s), 3.73 (2H, s), 6.94 (1H, d, J=7.8 Hz), 7.08 (1H, d, J=7.8 Hz), 7.26 (1H, t, J=7.8 Hz), 7.36 (1H, d, J=8.4 Hz), 8.03 (1H, d, J=8.4 Hz).

Example 25: N-(2-((Dimethylamino)methyl)quinolin-8-yl)benzenesulfonamide—Compound (ZDR061)

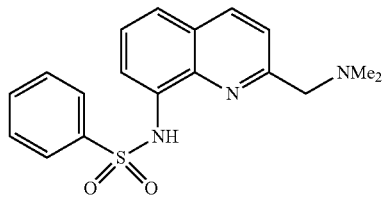 [SMILES: CN(C)Cc1ccc2cccc(NS(=O)(=O)c3ccccc3)c2n1]

A similar procedure to that described for the preparation of compound (ZDR018) was followed using compound (ZDR059) (90 mg, 0.44 mmol), benzenesulfonyl chloride (62 µL, 0.49 mmol) and triethylamine (68 µL, 0.49 mmol) in dichloromethane (5 mL). Purification by flash chromatography (dichloromethane/methanol, 40:1) afforded compound (ZDR061) as a tan solid (104 mg, 0.30 mmol, 68%). $^1$H NMR (300 MHz, CDCl$_3$) δ 2.28 (6H, s), 3.70 (2H, s), 7.29-7.45 (5H, m), 7.57 (1H, d, J=8.4 Hz), 7.80 (1H, dd, J=7.0 and 1.8 Hz), 7.86-7.90 (2H, m), 8.04 (1H, d, J=8.4 Hz); ESI-MS: m/z calcd for C$_{18}$H$_{19}$N$_3$O$_2$S: 341.1; found [M+H]$^+$: 342.1.

Example 26: N-(2-((Dimethylamino)methyl)quinolin-8-yl)-4-methylbenzenesulfonamide—Compound (ZDR062)

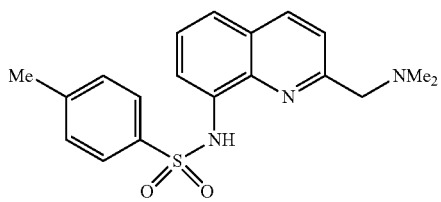

A similar procedure to that described for the preparation of compound (ZDR018) was followed using compound (ZDR059) (90 mg, 0.44 mmol), 4-toluenesulfonyl chloride (93 mg, 0.49 mmol) and triethylamine (68 µL, 0.49 mmol) in dichloromethane (5 mL). Purification by flash chromatography (dichloromethane/methanol, 40:1) afforded compound (ZDR062) as a tan solid (101 mg, 0.28 mmol, 63%). $^1$H NMR (300 MHz, CDCl$_3$) δ 2.26 (3H, s), 2.29 (6H, s), 3.70 (2H, s), 7.11 (2H, d, J=8.0 Hz), 7.35-7.45 (2H, m), 7.57 (1H, d, J=8.4 Hz), 7.74-7.80 (3H, m), 8.04 (1H, d, J=8.4 Hz); ESI-MS: m/z calcd for C$_{19}$H$_{21}$N$_3$O$_2$S: 355.1; found [M+H]$^+$:356.1.

Example 27: N-(2-((Dimethylamino)methyl)quinolin-8-yl)-4-methoxybenzenesulfonamide—Compound (ZDR063)

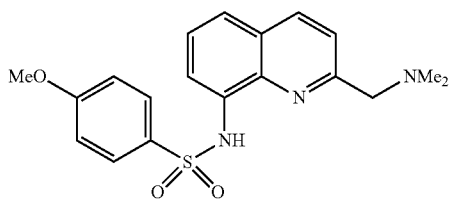 [SMILES: COc1ccc(S(=O)(=O)Nc2cccc3ccc(CN(C)C)nc23)cc1]

A similar procedure to that described for the preparation of compound (ZDR018) was followed using compound (ZDR059) (90 mg, 0.44 mmol), 4-methoxybenzenesulfonyl chloride (101 mg, 0.49 mmol) and triethylamine (68 µL, 0.49 mmol) in dichloromethane (5 mL). Purification by flash chromatography (dichloromethane/methanol, 40:1) afforded compound (ZDR063) as an off-white solid (77 mg, 0.20 mmol, 45%). $^1$H NMR (300 MHz, CDCl$_3$) δ 2.28 (6H, s), 3.70 (2H, s), 3.72 (3H, s), 6.76 (2H, d, J=8.9 Hz), 7.35-7.44 (2H, m), 7.57 (1H, d, J=8.4 Hz), 7.75-7.83 (3H, m), 8.03 (1H, d, J=8.4 Hz); ESI-MS: m/z calcd for C$_{19}$H$_{21}$N$_3$O$_3$S: 371.1; found [M+H]$^+$: 372.1.

Example 28: 4-Chloro-N-(2-((dimethylamino)methyl)quinolin-8-yl)benzenesulfonamide—Compound (ZDR064)

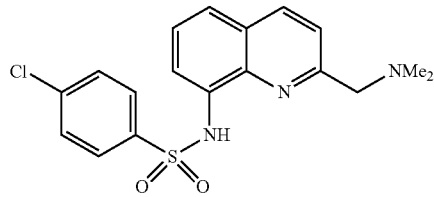 [SMILES: CN(C)Cc1ccc2cccc(NS(=O)(=O)c3ccc(Cl)cc3)c2n1]

A similar procedure to that described for the preparation of compound (ZDR018) was followed using compound (ZDR059) (90 mg, 0.44 mmol), 4-chlorobenzenesulfonyl chloride (103 mg, 0.49 mmol) and triethylamine (68 µL, 0.49 mmol) in dichloromethane (5 mL). Purification by flash chromatography (dichloromethane/methanol, 40:1) afforded compound (ZDR064) as a beige solid (96 mg, 0.25 mmol, 56%). $^1$H NMR (300 MHz, CDCl$_3$) δ 2.30 (6H, s), 3.71 (2H, s), 7.27-7.31 (2H, m), 7.39-7.50 (2H, m), 7.60 (1H, d, J=8.4 Hz), 7.79-7.83 (3H, m), 8.08 (1H, d, J=8.4 Hz); ESI-MS: m/z calcd for C$_{18}$H$_{18}$ClN$_3$O$_2$S: 375.1; found [M+H]$^+$: 376.1.

Example 29: N-(2-((Dimethylamino)methyl)quinolin-8-yl)-4-fluorobenzenesulfonamide—Compound (ZDR065)

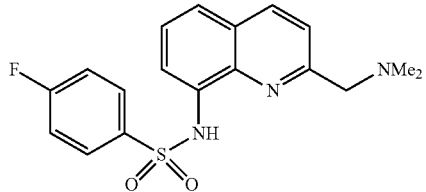 [SMILES: CN(C)Cc1ccc2cccc(NS(=O)(=O)c3ccc(F)cc3)c2n1]

A similar procedure to that described for the preparation of compound (ZDR018) was followed using compound (ZDR059) (90 mg, 0.44 mmol), 4-fluorobenzenesulfonyl chloride (95 mg, 0.49 mmol) and triethylamine (68 µL, 0.49 mmol) in dichloromethane (5 mL). Purification by flash chromatography (dichloromethane/methanol, 40:1) afforded compound (ZDR065) as a tan solid (100 mg, 0.27 mmol, 61%). $^1$H NMR (300 MHz, CDCl$_3$) δ 2.28 (6H, s), 3.70 (2H, s), 6.94-7.00 (2H, m), 7.37-7.47 (2H, m), 7.57 (1H, d, J=8.4 Hz), 7.80 (1H, dd, J=7.2 and 1.5 Hz), 7.86-7.91 (2H, m), 8.05 (1H, d, J=8.4 Hz); ESI-MS: m/z calcd for C$_{18}$H$_{18}$FN$_3$O$_2$S: 359.1; found [M+H]$^+$: 360.1.

Example 30: N-(2-((Dimethylamino)methyl)quinolin-8-yl)-4-(trifluoromethoxy)benzenesulfonamide—Compound (ZDR066)

A similar procedure to that described for the preparation of compound (ZDR018) was followed using compound (ZDR059) (90 mg, 0.44 mmol), 4-(trifluoromethoxy)benzenesulfonyl chloride (127 mg, 0.49 mmol) and triethylamine (68 µL, 0.49 mmol) in dichloromethane (5 mL). Purification by flash chromatography (dichloromethane/methanol, 40:1) afforded compound (ZDR066) as a beige solid (96 mg, 0.22 mmol, 50%). $^1$H NMR (300 MHz, CDCl$_3$) δ 2.28 (6H, s), 3.70 (2H, s), 7.10-7.14 (2H, m), 7.38-7.49 (2H, m), 7.56 (1H, d, J=8.4 Hz), 7.82 (1H, dd, J=7.3 and 1.5 Hz), 7.89-7.94 (2H, m), 8.06 (1H, d, J=8.4 Hz); ESI-MS: m/z calcd for C$_{19}$H$_{18}$F$_3$N$_3$O$_3$S: 425.1; found [M+H]$^+$: 426.1.

Example 31: N-(2-((Dimethylamino)methyl)quinolin-8-yl)-4-nitrobenzenesulfonamide—Compound (ZDR067)

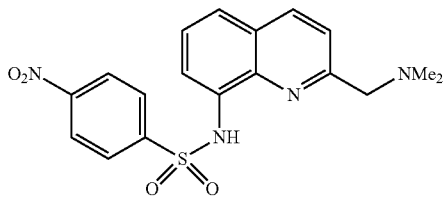

A similar procedure to that described for the preparation of compound (ZDR018) was followed using compound (ZDR059) (90 mg, 0.44 mmol), 4-nitrobenzenesulfonyl chloride (108 mg, 0.49 mmol) and triethylamine (68 µL, 0.49 mmol) in dichloromethane (5 mL). Purification by flash chromatography (dichloromethane/methanol, 40:1) afforded compound (ZDR067) as an orange solid (80 mg, 0.20 mmol, 45%). $^1$H NMR (300 MHz, CDCl$_3$) δ 2.30 (6H, s), 3.72 (2H, s), 7.41-7.53 (2H, m), 7.57 (1H, d, J=8.4 Hz), 7.86 (1H, dd, J=7.4 and 1.4 Hz), 8.05-8.09 (3H, m), 8.13-8.17 (2H, m); ESI-MS: m/z calcd for C$_{18}$H$_{18}$N$_4$O$_4$S: 386.1; found [M+H]$^+$: 387.1.

Example 32: 4-Cyano-N-(2-((dimethylamino)methyl)quinolin-8-yl)benzenesulfonamide—Compound (ZDR068)

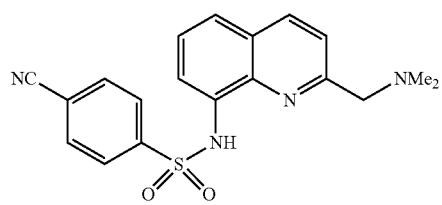

A similar procedure to that described for the preparation of compound (ZDR018) was followed using compound (ZDR059) (90 mg, 0.44 mmol), 4-cyanobenzenesulfonyl chloride (98 mg, 0.49 mmol) and triethylamine (68 µL, 0.49 mmol) in dichloromethane (5 mL). Purification by flash chromatography (dichloromethane/methanol, 40:1) afforded compound (ZDR068) as a pale orange solid (107 mg, 0.29 mmol, 65%). $^1$H NMR (300 MHz, CDCl$_3$) δ 2.30 (6H, s), 3.71 (2H, s), 7.39-7.62 (5H, m), 7.82 (1H, dd, J=7.4 and 1.4 Hz), 7.97-8.01 (2H, m), 8.07 (1H, d, J=8.4 Hz); ESI-MS: m/z calcd for C$_{19}$H$_{18}$N$_4$O$_2$S: 366.1; found [M+H]$^+$: 367.1.

Example 33: Methyl 4-(N-(2-((dimethylamino)methyl)quinolin-8-yl)sulfamoyl)benzoate—Compound (ZDR069)

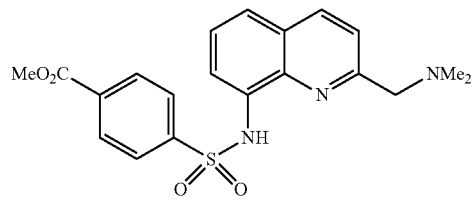

A similar procedure to that described for the preparation of compound (ZDR018) was followed using compound (ZDR059) (90 mg, 0.44 mmol), 4-chlorosulfonylbenzoic acid methyl ester (114 mg, 0.49 mmol) and triethylamine (68 µL, 0.49 mmol) in dichloromethane (5 mL). Purification by flash chromatography (dichloromethane/methanol, 40:1) afforded compound (ZDR069) as a beige solid (88 mg, 0.22 mmol, 50%). $^1$H NMR (300 MHz, CDCl$_3$) δ 2.28 (6H, s), 3.70 (2H, s), 3.85 (3H, s), 7.37-7.47 (2H, m), 7.56 (1H, d, J=8.4 Hz), 7.82 (1H, dd, J=7.4 and 1.5 Hz), 7.91-7.98 (4H, m), 8.05 (1H, d, J=8.4 Hz); ESI-MS: m/z calcd for C$_{20}$H$_{21}$N$_3$O$_4$S: 399.1; found [M+H]$^+$: 400.1.

Example 34: 4-Acetyl-N-(2-((dimethylamino)methyl)quinolin-8-yl)benzenesulfonamide—Compound (ZDR070)

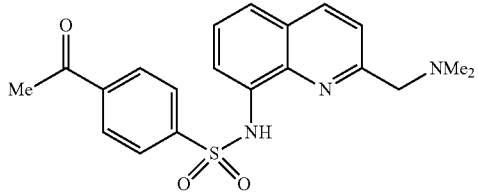 [SMILES: CC(=O)c1ccc(S(=O)(=O)Nc2cccc3ccc(CN(C)C)nc23)cc1]

A similar procedure to that described for the preparation of compound (ZDR018) was followed using compound (ZDR059) (90 mg, 0.44 mmol), 4-acetylbenzenesulfonyl chloride (107 mg, 0.49 mmol) and triethylamine (68 µL, 0.49 mmol) in dichloromethane (5 mL). Purification by flash chromatography (dichloromethane/methanol, 40:1) afforded compound (ZDR070) as a tan solid (66 mg, 0.17 mmol, 38%). $^1$H NMR (300 MHz, CDCl$_3$) δ 2.28 (6H, s), 2.51 (3H, s), 3.70 (2H, s), 7.37-7.47 (2H, m), 7.56 (1H, d, J=8.4 Hz), 7.80-7.87 (3H, m), 7.94-7.99 (2H, m), 8.05 (1H, d, J=8.4 Hz); ESI-MS: m/z calcd for C$_{20}$H$_{21}$N$_3$O$_3$S: 383.1; found [M+H]$^+$: 384.1.

Example 35: N-(2-((Dimethylamino)methyl)quinolin-8-yl)-4-(methylsulfonyl)benzenesulfonamide—Compound (ZDR071)

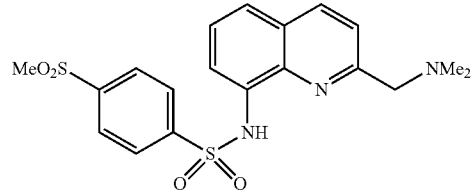 [SMILES: CN(C)Cc1ccc2cccc(NS(=O)(=O)c3ccc(S(C)(=O)=O)cc3)c2n1]

A similar procedure to that described for the preparation of compound (ZDR018) was followed using compound (ZDR059) (90 mg, 0.44 mmol), 4-(methylsulfonyl)benzenesulfonyl chloride (124 mg, 0.49 mmol) and triethylamine (68 µL, 0.49 mmol) in dichloromethane (5 mL). Purification by flash chromatography (dichloromethane/methanol, 40:1) afforded compound (ZDR071) as an off-white solid (83 mg, 0.19 mmol, 43%). $^1$H NMR (300 MHz, CDCl$_3$) δ 2.29 (6H, s), 2.97 (3H, s), 3.70 (2H, s), 7.39-7.51 (2H, m), 7.58 (1H, d, J=8.4 Hz), 7.83 (1H, dd, J=7.4 and 1.5 Hz), 7.86-7.91 (2H, m), 8.06-8.09 (3H, m); ESI-MS: m/z calcd for C$_{19}$H$_{21}$N$_3$O$_4$S$_2$: 419.1; found [M+H]$^+$: 420.1.

Example 36: N-(4-(N-(2-((Dimethylamino)methyl) quinolin-8-yl)sulfamoyl)phenyl)acetamide—Compound (ZDR072)

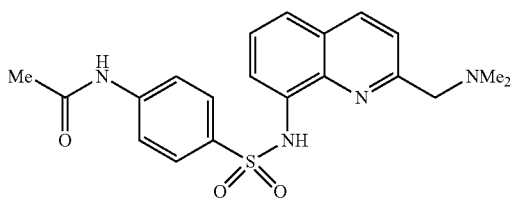 [SMILES: CC(=O)Nc1ccc(S(=O)(=O)Nc2cccc3ccc(CN(C)C)nc23)cc1]

A similar procedure to that described for the preparation of compound (ZDR018) was followed using compound (ZDR059) (90 mg, 0.44 mmol), 4-acetamidobenzenesulfonyl chloride (114 mg, 0.49 mmol) and triethylamine (68 µL, 0.49 mmol) in dichloromethane (5 mL). Purification by flash chromatography (dichloromethane/methanol, 20:1) afforded compound (ZDR072) as a pale yellow solid (60 mg, 0.15 mmol, 34%). $^1$H NMR (300 MHz, CDCl$_3$) δ 2.10 (3H, s), 2.28 (6H, s), 3.70 (2H, s), 7.34-7.48 (4I, m), 7.56 (1H, d, J=8.4 Hz), 7.73-7.80 (3H, m), 8.04 (1H, d, J=8.4 Hz); ESI-MS: m/z calcd for C$_{20}$H$_{22}$N$_4$O$_3$S: 398.1; found [M+H]$^+$: 399.1.

Example 37: 4-(N-(2-((Dimethylamino)methyl)quinolin-8-yl)sulfamoyl)benzamide—Compound (ZDR073)

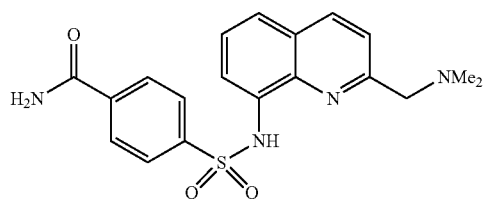 [SMILES: CN(C)Cc1ccc2cccc(NS(=O)(=O)c3ccc(C(N)=O)cc3)c2n1]

A similar procedure to that described for the preparation of compound (ZDR018) was followed using compound (ZDR059) (90 mg, 0.44 mmol), 4-(chlorosulfonyl)benzamide (107 mg, 0.49 mmol) and triethylamine (68 µL, 0.49 mmol) in dichloromethane (5 mL). Purification by flash chromatography (dichloromethane/methanol, 20:1) afforded compound (ZDR073) as a beige solid (70 mg, 0.18 mmol, 40%). $^1$H NMR (300 MHz, CDCl$_3$) δ 2.30 (6H, s), 3.72 (2H, s), 7.37-7.48 (2H, m), 7.56 (1H, d, J=8.4 Hz), 7.70-7.74 (2H, m), 7.81 (1H, dd, J=7.4 and 1.4 Hz), 7.91-7.95 (2H, m), 8.06 (1H, d, J=8.4 Hz); ESI-MS: m/z calcd for C$_{19}$H$_{20}$N$_4$O$_3$S: 384.1; found [M+H]$^+$: 385.1.

Example 38: N-(2-((Dimethylamino)methyl)quinolin-8-yl)-3-(trifluoromethyl)benzenesulfonamide—Compound (ZDR074)

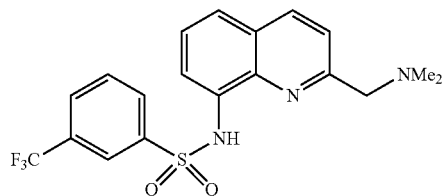 [SMILES: CN(C)Cc1ccc2cccc(NS(=O)(=O)c3cccc(C(F)(F)F)c3)c2n1]

A similar procedure to that described for the preparation of compound (ZDR018) was followed using compound (ZDR059) (100 mg, 0.49 mmol), 3-(trifluoromethyl)benzenesulfonyl chloride (87 µL, 0.54 mmol) and triethylamine (76 µL, 0.54 mmol) in dichloromethane (5 mL). Purification by flash chromatography (dichloromethane/methanol, 20:1) afforded compound (ZDR074) as a pale orange solid (97 mg, 0.23 mmol, 46%). $^1$H NMR (300 MHZ, CDCl$_3$) δ 2.27 (6H, s), 3.68 (2H, s), 7.40-7.50 (3H, m), 7.55-7.64 (2H, m), 7.84 (1H, dd, J=7.3 and 1.5 Hz), 8.00-8.13 (3H, m); ESI-MS: m/z calcd for C$_{19}$H$_{18}$F$_3$N$_3$O$_2$S: 409.1; found [M+H]$^+$: 410.1.

Example 39: N-(2-((Dimethylamino)methyl)quinolin-8-yl)-2-(trifluoromethyl)benzenesulfonamide—Compound (ZDR075)

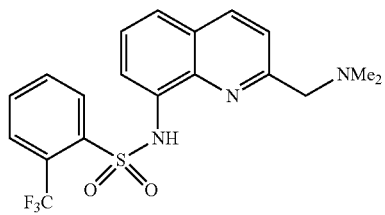 [SMILES: CN(C)Cc1ccc2cccc(NS(=O)(=O)c3ccccc3C(F)(F)F)c2n1]

A similar procedure to that described for the preparation of compound (ZDR018) was followed using compound (ZDR059) (100 mg, 0.49 mmol), 2-(trifluoromethyl)benzenesulfonyl chloride (84 µL, 0.54 mmol) and triethylamine (76 µL, 0.54 mmol) in dichloromethane (5 mL). Purification by flash chromatography (dichloromethane/methanol, 20:1) afforded compound (ZDR075) as a pale orange solid (70 mg, 0.17 mmol, 34%). $^1$H NMR (300 MHz, CDCl$_3$) δ 2.29 (6H, s), 3.70 (2H, s), 7.37-7.46 (2H, m), 7.52-7.56 (2H, m), 7.61 (1H, d, J=8.5 Hz), 7.75-7.78 (1H, m), 7.85 (1H, dd, J=7.2 and 1.7 Hz), 8.05 (1H, d, J=8.5 Hz), 8.18-8.21 (1H, m); ESI-MS: m/z calcd for C$_{19}$H$_{18}$F$_3$N$_3$O$_2$S: 409.1; found [M+H]$^+$: 410.1.

Example 40: 3-cyano-N-(2-((dimethylamino) methyl)quinolin-8-yl)benzenesulfonamide—Compound (ZDR076)

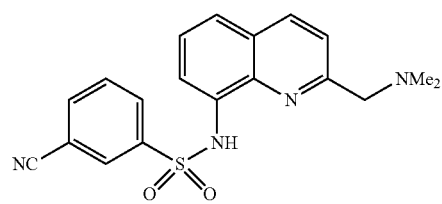 [SMILES: CN(C)Cc1ccc2cccc(NS(=O)(=O)c3cccc(C#N)c3)c2n1]

A similar procedure to that described for the preparation of compound (ZDR018) was followed using compound (ZDR059) (100 mg, 0.49 mmol), 3-cyanobenzenesulfonyl chloride (110 mg, 0.54 mmol) and triethylamine (76 μL, 0.54 mmol) in dichloromethane (5 mL). Purification by flash chromatography (dichloromethane/methanol, 20:1) afforded compound (ZDR076) as a pale orange solid (93 mg, 0.25 mmol, 51%). $^1$H NMR (300 MHz, CDCl$_3$) δ 2.21 (6H, s), 3.72 (2H, s), 7.41-7.52 (3H, m), 7.59 (1H, d, J=8.4 Hz) 7.65-7.68 (1H, m), 7.82 (1H, dd, J=7.4 and 1.4 Hz), 8.06-8.09 (2H, m), 8.17-8.18 (1H, m); ESI-MS: m/z calcd for C$_{19}$H$_{18}$N$_4$O$_2$S: 366.1; found [M+H]$^+$: 367.1.

Example 41: N-(2-((Dimethylamino)methyl)quinolin-8-yl)-2-cyanobenzenesulfonamide—Compound (ZDR077)

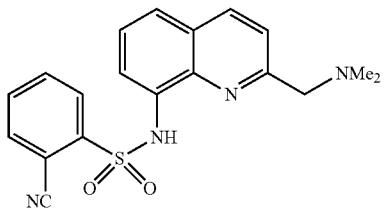 [SMILES: CN(C)Cc1ccc2cccc(NS(=O)(=O)c3ccccc3C#N)c2n1]

A similar procedure to that described for the preparation of compound (ZDR018) was followed using compound (ZDR059) (100 mg, 0.49 mmol), 2-cyanobenzenesulfonyl chloride (110 mg, 0.54 mmol) and triethylamine (76 μL, 0.54 mmol) in dichloromethane (5 mL). Purification by flash chromatography (dichloromethane/methanol, 20:1→10:1) afforded compound (ZDR077) as a pale orange solid (117 mg, 0.31 mmol, 63%). $^1$H NMR (300 MHz, CDCl$_3$) δ 2.32 (6H, s), 3.80 (2H, s), 7.34-7.70 (6H, m), 7.74 (1H, dd, J=7.6 and 1.3 Hz), 8.05 (1H, d, J=8.4 Hz), 8.14 (1H, dd, J=7.6 and 1.3 Hz); ESI-MS: m/z calcd for C$_{19}$H$_{18}$N$_4$O$_2$S: 366.1; found [M+H]$^+$: 367.1.

Example 42: N-(2-((Dimethylamino)methyl)quinolin-8-yl)methanesulfonamide—Compound (ZDR078)

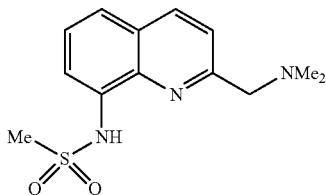 [SMILES: CN(C)Cc1ccc2cccc(NS(C)(=O)=O)c2n1]

A similar procedure to that described for the preparation of compound (ZDR018) was followed using compound (ZDR059) (100 mg, 0.49 mmol), methanesulfonyl chloride (42 μL, 0.54 mmol) and triethylamine (76 μL, 0.54 mmol) in dichloromethane (5 mL). Purification by flash chromatography (dichloromethane/methanol, 40:1) afforded compound (ZDR078) as a pale yellow solid (99 mg, 0.35 mmol, 71%). $^1$H NMR (300 MHz, CDCl$_3$) δ 2.34 (6H, s), 3.03 (3H, s), 3.77 (2H, s), 7.47-7.54 (2H, s), 7.62 (1H, d, J=8.4 Hz), 7.81 (1H, dd, J=7.2 and 1.6 Hz), 8.13 (1H, d, J=8.4 Hz); ESI-MS: m/z calcd for C$_{13}$H$_{17}$N$_3$O$_2$S: 279.1; found [M+H]$^+$: 280.1.

Example 43: N-(2-((Dimethylamino)methyl)quinolin-8-yl)-1,1,1-trifluoromethanesulfonamide—Compound (ZDR079)

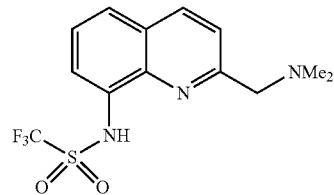 [SMILES: CN(C)Cc1ccc2cccc(NS(=O)(=O)C(F)(F)F)c2n1]

A similar procedure to that described for the preparation of compound (ZDR018) was followed using compound (ZDR059) (100 mg, 0.49 mmol), trifluoromethanesulfonyl chloride (58 μL, 0.54 mmol) and triethylamine (76 μL, 0.54 mmol) in dichloromethane (5 mL). Purification by flash chromatography (dichloromethane/methanol, 20:1) afforded compound (ZDR079) as a beige solid (82 mg, 0.24 mmol, 48%). $^1$H NMR (300 MHz, d$_4$-MeOH) δ 2.98 (6H, s), 4.57 (2H, s), 7.33 (1H, d, J=8.4 Hz), 7.42-7.46 (2H, m), 7.76-7.81 (1H, m), 8.22 (1H, d, J=8.4 Hz); ESI-MS: m/z calcd for C$_{13}$H$_{14}$F$_3$N$_3$O$_2$S: 333.1; found [M+H]$^+$: 334.1.

Example 44: N-(2-((Dimethylamino)methyl)quinolin-8-yl)thiophene-2-sulfonamide—Compound (ZDR080)

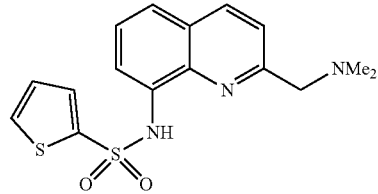 [SMILES: CN(C)Cc1ccc2cccc(NS(=O)(=O)c3cccs3)c2n1]

A similar procedure to that described for the preparation of compound (ZDR018) was followed using compound (ZDR059) (100 mg, 0.49 mmol), 2-thiophenesulfonyl chloride (99 mg, 0.54 mmol) and triethylamine (76 μL, 0.54 mmol) in dichloromethane (5 mL). Purification by flash chromatography (dichloromethane/methanol, 40:1) afforded compound (ZDR080) as a beige solid (93 mg, 0.26 mmol, 53%). $^1$H NMR (300 MHz, CDCl$_3$) δ 2.28 (6H, s), 3.70 (2H, s), 6.85-6.88 (1H, m), 7.36-7.47 (3H, m), 7.56-7.59 (2H, m), 7.87 (1H, dd, J=7.1 and 1.8 Hz), 8.06 (1H, d, J=8.4 Hz); ESI-MS: m/z calcd for C$_{16}$H$_{17}$N$_3$O$_2$S$_2$: 347.1; found [M+H]$^+$: 348.1.

Example 45: N-(2-((Dimethylamino)methyl)quinolin-8-yl)thiophene-3-sulfonamide—Compound (ZDR081)

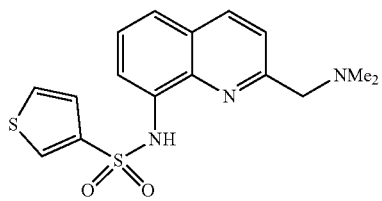 [SMILES: CN(C)Cc1ccc2cccc(NS(=O)(=O)c3ccsc3)c2n1]

A similar procedure to that described for the preparation of compound (ZDR018) was followed using compound (ZDR059) (100 mg, 0.49 mmol), 3-thiophenesulfonyl chloride (99 mg, 0.54 mmol) and triethylamine (76 μL, 0.54 mmol) in dichloromethane (5 mL). Purification by flash chromatography (dichloromethane/methanol, 40:1) afforded compound (ZDR081) as a tan solid (87 mg, 0.25 mmol, 51%). $^1$H NMR (300 MHz, CDCl$_3$) δ 2.30 (6H, s), 3.71 (2H, s), 7.18 (1H, dd, J=5.1 and 3.0 Hz), 7.28 (1H, dd, J=5.1 and 1.2 Hz), 7.39-7.49 (2H, m), 7.59 (1H, d, J=8.4 Hz), 7.83 (1H, dd, J=7.1 and 1.7 Hz), 7.97 (1H, d, J=3.0 and 1.2 Hz), 8.07 (1H, d, J=8.4 Hz); ESI-MS: m/z calcd for C$_{16}$H$_{17}$N$_3$O$_2$S$_2$: 347.1; found [M+H]$^+$: 348.1.

Example 46: N-(2-((Dimethylamino)methyl)quinolin-8-yl)-3,5-dimethylisoxazole-4-sulfonamide—Compound (ZDR082)

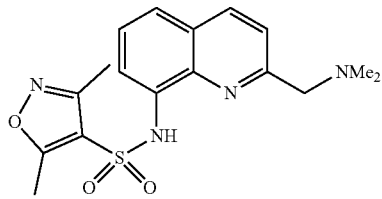 [SMILES: Cc1noc(C)c1S(=O)(=O)Nc1cccc2ccc(CN(C)C)nc12]

A similar procedure to that described for the preparation of compound (ZDR018) was followed using compound (ZDR059) (100 mg, 0.49 mmol), 3,5-dimethylisoxazole-4-sulfonyl chloride (105 mg, 0.54 mmol) and triethylamine (76 μL, 0.54 mmol) in dichloromethane (5 mL). Purification by flash chromatography (dichloromethane/methanol, 40:1) afforded compound (ZDR082) as a pale orange solid (95 mg, 0.26 mmol, 53%). $^1$H NMR (300 MHz, CDCl$_3$) δ 2.29 (6H, s), 2.38 (3H, s), 2.53 (3H, s), 3.70 (2H, s), 7.42 (1H, t, J=7.8 Hz), 7.53 (1H, dd, J=7.8 and 1.3 Hz), 7.62 (1H, d, J=8.4 Hz), 7.77 (1H, dd, J=7.8 and 1.3 Hz), 8.10 (1H, d, J=8.4 Hz); ESI-MS: m/z calcd for C$_{17}$H$_{20}$N$_4$O$_3$S: 360.1; found [M+H]$^+$: 361.1.

Example 47: 3-Chloro-N-(2-((dimethylamino)methyl)quinolin-8-yl)benzenesulfonamide—Compound (ZDR084)

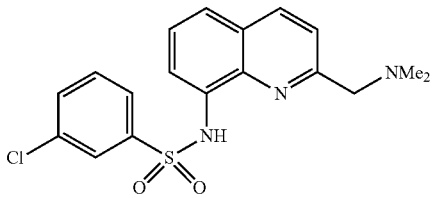 [SMILES: CN(C)Cc1ccc2cccc(NS(=O)(=O)c3cccc(Cl)c3)c2n1]

A similar procedure to that described for the preparation of compound (ZDR018) was followed using compound (ZDR059) (90 mg, 0.44 mmol), 3-chlorobenzenesulfonyl chloride (68 μL, 0.49 mmol) and triethylamine (68 μL, 0.49 mmol) in dichloromethane (5 mL). Purification by flash chromatography (dichloromethane/methanol, 40:1) afforded compound (ZDR084) as a pale yellow solid (109 mg, 0.28 mmol, 63%). $^1$H NMR (300 MHz, CDCl$_3$) δ 2.31 (6H, s), 3.74 (2H, s), 7.25 (1H, t, J=7.8 Hz), 7.35-7.50 (3H, m), 7.57 (1H, d, J=8.4 Hz), 7.73-7.76 (1H, m), 7.82 (1H, dd, J=7.2 and 1.6 Hz), 7.90-7.92 (1H, m), 8.07 (1H, d, J=8.4 Hz); ESI-MS: m/z calcd for C$_{18}$H$_{18}$ClN$_3$O$_2$S: 375.1; found [M+H]$^+$: 376.1.

Example 48: N-(2-((Dimethylamino)methyl)quinolin-8-yl)-3-(trifluoromethoxy)benzenesulfonamide—Compound (ZDR085)

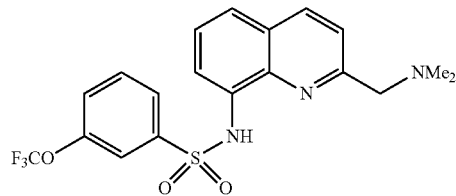 [SMILES: CN(C)Cc1ccc2cccc(NS(=O)(=O)c3cccc(OC(F)(F)F)c3)c2n1]

A similar procedure to that described for the preparation of compound (ZDR018) was followed using compound (ZDR059) (90 mg, 0.44 mmol), 3-(trifluoromethoxy)benzenesulfonyl chloride (83 μL, 0.49 mmol) and triethylamine (68 μL, 0.49 mmol) in dichloromethane (5 mL). Purification by flash chromatography (dichloromethane/methanol, 40:1) afforded compound (ZDR085) as a pale orange solid (101 mg, 0.23 mmol, 52%). $^1$H NMR (300 MHz, CDCl$_3$) δ 2.28 (6H, s), 3.70 (2H, s), 7.20-7.27 (1H, m), 7.33-7.51 (3H, m), 7.58 (1H, d, J=8.4 Hz), 7.69-7.73 (1H, m), 7.79-7.85 (2H, m), 8.06 (1H, d, J=8.4 Hz); ESI-MS: m/z calcd for C$_{19}$H$_{18}$F$_3$N$_3$O$_3$S: 425.1; found [M+H]$^+$: 426.1.

Example 49: N-(2-((Cyclopropylamino)methyl)quinolin-8-yl)-4-(trifluoromethyl)benzenesulfonamide—Compound (ZDR086)

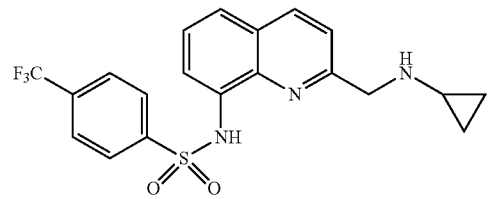 [SMILES: O=S(=O)(Nc1cccc2ccc(CNC3CC3)nc12)c1ccc(C(F)(F)F)cc1]

A similar procedure to that described for the preparation of compound (ZDR022) was followed using compound (ZDR019) (100 mg, 0.26 mmol), cyclopropylamine (54 μL, 0.78 mmol) and sodium triacetoxyborohydride (111 mg, 0.52 mmol) in 1,2-dichloroethane (5 mL). Purification by flash chromatography (dichloromethane/methanol, 50:1) afforded compound (ZDR086) as a pale yellow solid (70 mg, 0.16 mmol, 61%). $^1$H NMR (300 MHz, CDCl$_3$) δ 0.43-0.47 (4H, m), 2.15-2.19 (1H, m), 4.10 (2H, s), 7.38-7.50 (3H, m), 7.59 (2H, d, J=8.2 Hz), 7.82 (1H, dd, J=7.3 and 1.4 Hz), 8.00 (2H, d, J=8.2 Hz), 8.04 (1H, d, J=8.4 Hz); ESI-MS: m/z calcd for C$_{20}$H$_{18}$F$_3$N$_3$O$_2$S: 421.1; found [M+H]$^+$: 422.1.

Example 50: N-(2-(((Cyclopropylmethyl)amino)methyl)quinolin-8-yl)-4-(trifluoromethyl)benzenesulfonamide—Compound (ZDR087)

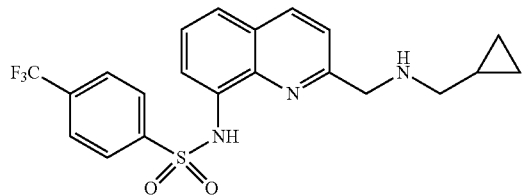 [SMILES: O=S(=O)(Nc1cccc2ccc(CNCC3CC3)nc12)c1ccc(C(F)(F)F)cc1]

A similar procedure to that described for the preparation of compound (ZDR022) was followed using compound (ZDR019) (100 mg, 0.26 mmol), cyclopropylmethylamine (68 μL, 0.78 mmol) and sodium triacetoxyborohydride (111 mg, 0.52 mmol) in 1,2-dichloroethane (5 mL). Purification by flash chromatography (dichloromethane/methanol, 50:1→10:1) afforded compound (ZDR087) as a pale yellow solid (83 mg, 19 mmol, 73%). $^1$H NMR (300 MHz, CDCl$_3$) δ 0.18-0.22 (2H, m), 0.48-0.54 (2H, m), 1.01-1.14 (1H, m), 2.77 (2H, d, J=7.0 Hz), 4.35 (2H, s), 7.33-7.44 (5H, m), 7.70 (1H, dd, J=7.0 and 1.9 Hz), 7.86 (2H, d, J=8.2 Hz), 8.03 (1H, d, J=8.4 Hz); ESI-MS: m/z calcd for $C_{21}H_{20}F_3N_3O_2S$: 435.1; found [M+H]$^+$: 436.1.

Example 51: N-(2-(Thiomorpholinomethyl)quinolin-8-yl)-4-(trifluoromethyl)benzenesulfonamide—Compound (ZDR088)

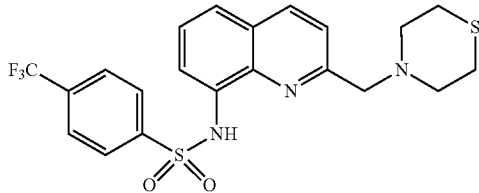 [SMILES: O=S(=O)(Nc1cccc2ccc(CN3CCSCC3)nc12)c1ccc(C(F)(F)F)cc1]

A similar procedure to that described for the preparation of compound (ZDR022) was followed using compound (ZDR019) (100 mg, 0.26 mmol), thiomorpholine (79 μL, 0.78 mmol) and sodium triacetoxyborohydride (111 mg, 0.52 mmol) in 1,2-dichloroethane (5 mL). Purification by flash chromatography (dichloromethane/methanol, 50:1) afforded compound (ZDR088) as a pale yellow solid (55 mg, 0.11 mmol, 42%). $^1$H NMR (300 MHz, CDCl$_3$) δ 2.65-2.78 (8H, m), 3.76 (2H, s), 7.39-7.50 (2H, m), 7.57-7.62 (3H, m), 7.82 (1H, dd, J=7.3 and 1.5 Hz), 8.00 (2H, d, J=8.1 Hz), 8.05 (1H, d, J=8.4 Hz); ESI-MS: m/z calcd for $C_{21}H_{20}F_3N_3O_2S_2$: 467.1; found [M+H]$^+$: 468.1.

Example 52: N-(2-((4-Methylpiperazin-1-yl)methyl)quinolin-8-yl)-4-(trifluoromethyl)benzenesulfonamide—Compound (ZDR089)

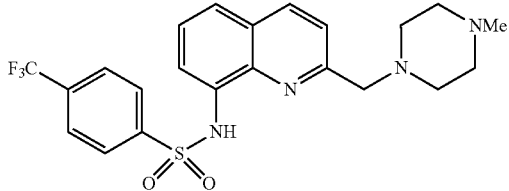 [SMILES: CN1CCN(Cc2ccc3cccc(NS(=O)(=O)c4ccc(C(F)(F)F)cc4)c3n2)CC1]

A similar procedure to that described for the preparation of compound (ZDR022) was followed using compound (ZDR019) (100 mg, 0.26 mmol), 1-methylpiperazine (87 μL, 0.78 mmol) and sodium triacetoxyborohydride (111 mg, 0.52 mmol) in 1,2-dichloroethane (5 mL). Purification by flash chromatography (dichloromethane/methanol, 50:1→20:1→10:1) afforded compound (ZDR089) as a white solid (77 mg, 0.16 mmol, 61%). $^1$H NMR (300 MHz, CDCl$_3$) δ 2.31 (3H, s), 2.40-2.60 (8H, m), 3.76 (2H, s), 7.39-7.50 (2H, m), 7.57-7.63 (3H, in), 7.82 (1H, dd, J=7.3 and 1.5 Hz), 7.99 (2H, d, J=8.1 Hz), 8.05 (1H, d, J=8.4 Hz); ESI-MS: m/z calcd for $C_{22}H_{23}F_3N_4O_2S$: 464.1; found [M+H]$^+$:465.1.

Example 53: N-(2-(((3-(Dimethylamino)propyl)amino)methyl)quinolin-8-yl)-4-(trifluoromethyl)benzenesulfonamide di-trifluoroacetate—Compound (ZDR090)

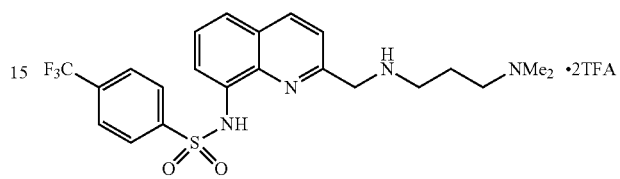

A solution of (ZDR019) (100 mg, 0.26 mmol), 3-(dimethylamino)-1-propylamine (99 μL, 0.78 mmol) and sodium triacetoxyborohydride (111 mg, 0.52 mmol) in 1,2-dichloroethane (5 mL) was stirred at room temperature for 18 h, and the solvent removed in vacuo. Purification by RP-HLPC (10% to 20% A/B gradient over 20 min, where A=water+0.1% trifluoroacetic acid and B=acetonitrile+0.1% trifluoroacetic acid) afforded compound (ZDR090) as a white solid (36 mg, 0.05 mmol, 19%). $^1$H NMR (300 MHz, CDCl$_3$) δ 1.79 (2H, t, J=7.0 Hz), 2.27 (6H, s), 2.43 (2H, t, J=7.0 Hz), 2.81 (2H, t, J=7.0 Hz), 4.10 (2H, s), 7.37-7.47 (3H, m), 7.56 (2H, d, J=8.2 Hz), 7.77 (1H, dd, J=7.3 and 1.5 Hz), 8.00 (2H, d, J=8.2 Hz), 8.05 (1H, d, J=8.4 Hz); ESI-MS: m/z calcd for $C_{22}H_{25}F_3N_4O_2S$: 466.2; found [M+H]$^+$: N/A.

Example 54: N-(2-(((3-Hydroxypropyl)amino)methyl)quinolin-8-yl)-4-(trifluoromethyl)benzenesulfonamide—Compound (ZDR091)

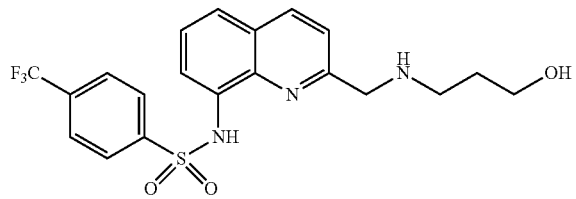 [SMILES: O=S(=O)(Nc1cccc2ccc(CNCCCO)nc12)c1ccc(C(F)(F)F)cc1]

A similar procedure to that described for the preparation of compound (ZDR022) was followed using compound (ZDR019) (100 mg, 0.26 mmol), 3-amino-1-propanol (60 μL, 0.78 mmol) and sodium triacetoxyborohydride (111 mg, 0.52 mmol) in 1,2-dichloroethane (5 mL). Purification by flash chromatography (dichloromethane/methanol, 20:1→15:1→10:1) afforded compound (ZDR091) as a white solid (60 mg, 0.13 mmol, 50%). $^1$H NMR (300 MHz, d$_6$-DMSO) δ 1.76-1.83 (2H, m), 2.87 (2H, t, J=6.5 Hz), 3.53 (2H, t, J=6.5 Hz), 4.25 (2H, s), 7.38 (1H, t, J=7.7 Hz), 7.44-7.58 (4H, m), 7.63 (1H, dd, J=7.4 and 1.1 Hz), 7.83 (2H, d, J=8.0 Hz), 8.19 (1H, d, J=8.4 Hz); ESI-MS: m/z calcd for $C_{20}H_{20}F_3N_3O_3S$: 439.1; found [M+H]$^+$:440.1.

Example 55: N-(2-(((1,3-Dihydroxypropan-2-yl)amino)methyl)quinolin-8-yl)-4-(trifluoromethyl)benzenesulfonamide—Compound (ZDR092)

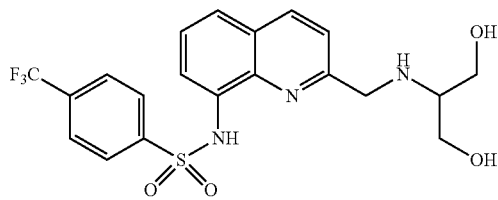 [SMILES: O=S(=O)(Nc1cccc2ccc(CNC(CO)CO)nc12)c1ccc(C(F)(F)F)cc1]

A similar procedure to that described for the preparation of compound (ZDR022) was followed using compound (ZDR019) (100 mg, 0.26 mmol), serinol (71 mg, 0.78 mmol) and sodium triacetoxyborohydride (111 mg, 0.52 mmol) in 1,2-dichloroethane (5 mL). Purification by flash chromatography (dichloromethane/methanol, 20:1→10:1→8:1) afforded compound (ZDR092) as a pale yellow solid (50 mg, 0.10 mmol, 38%). $^1$H NMR (300 MHz, CDCl$_3$) δ 3.06-3.18 (1H, m), 3.79-3.99 (4H, m), 4.32 (2H, s), 7.24-7.41 (3H, m), 7.55 (2H, d, J=8.2 Hz), 7.75 (1H, dd, J=7.0 and 1.8 Hz), 7.97 (1H, d, J=8.4 Hz), 8.02 (2H, d, J=8.2 Hz); ESI-MS: m/z calcd for C$_{20}$H$_{20}$F$_3$N$_3$O$_4$S: 455.1; found [M+H]$^+$: 456.1.

Example 57: N-(2-((Bis(2-hydroxyethyl)amino)methyl)quinolin-8-yl)-4-(trifluoromethyl)benzenesulfonamide—Compound (ZDR094)

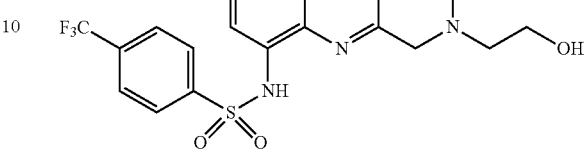

A similar procedure to that described for the preparation of compound (ZDR022) was followed using compound (ZDR019) (100 mg, 0.26 mmol), diethanolamine (78 mg, 0.78 mmol) and sodium triacetoxyborohydride (111 mg, 0.52 mmol) in 1,2-dichloroethane (5 mL). Purification by flash chromatography (dichloromethane/methanol, 30:1→20:1→15:1) afforded compound (ZDR094) as a white solid (30 mg, 0.06 mmol, 23%). $^1$H NMR (300 MHz, CDCl$_3$) δ 2.87 (4H, t, J=5.0 Hz), 3.69 (4H, t, J=5.0 Hz), 4.04 (2H, s), 7.39-7.49 (3H, m), 7.62 (2H, d, J=8.3 Hz), 7.85 (1H, dd, J=7.2 and 1.5 Hz), 8.03-8.09 (3H, m); ESI-MS: m/z calcd for C$_{21}$H$_{22}$F$_3$N$_3$O$_4$S: 469.1; found [M+H]$^+$: 470.1.

Example 56: N-(2-(((2,3-Dihydroxypropyl)amino)methyl)quinolin-8-yl)-4-(trifluoromethyl)benzenesulfonamide—Compound (ZDR093

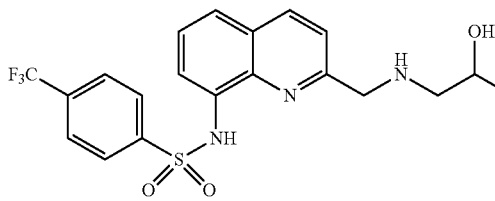

A similar procedure to that described for the preparation of compound (ZDR022) was followed using compound (ZDR019) (100 mg, 0.26 mmol), (±)-3-amino-1,2-propanediol (71 mg, 0.78 mmol) and sodium triacetoxyborohydride (111 mg, 0.52 mmol) in 1,2-dichloroethane (5 mL). Purification by flash chromatography (dichloromethane/methanol, 20:1→10:1→48:1) afforded compound (ZDR093) as a pale yellow solid (60 mg, 0.13 mmol, 50%). $^1$H NMR (300 MHz, CDCl$_3$) δ 2.85-3.00 (2H, m), 3.65-3.82 (2H, m), 4.06-4.20 (3H, m), 7.20 (1H, d, J=8.4 Hz), 7.29-7.37 (2H, m), 7.46 (2H, d, J=8.2 Hz), 7.71 (1H, dd, J=7.0 and 1.9 Hz), 7.90 (1H, d, J=8.4 Hz), 7.98 (2H, d, J=8.2 Hz); ESI-MS: m/z calcd for C$_{20}$H$_{20}$F$_3$N$_3$O$_4$S: 455.1; found [M+H]$^+$: 456.1.

Example 58: N-(2-(((2-(Pyridin-2-yl)ethyl)amino)methyl)quinolin-8-yl)-4-(trifluoromethyl)benzenesulfonamide—Compound (ZDR095)

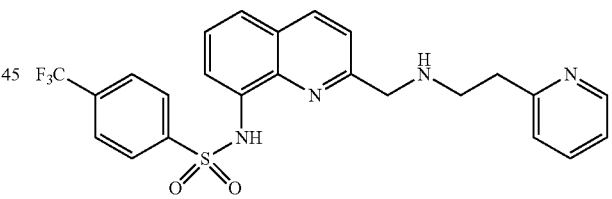

A similar procedure to that described for the preparation of compound (ZDR022) was followed using compound (ZDR019) (100 mg, 0.26 mmol), 2-(2-pyridyl)ethylamine (94 µL, 0.78 mmol) and sodium triacetoxyborohydride (111 mg, 0.52 mmol) in 1,2-dichloroethane (5 mL). Purification by flash chromatography (dichloromethane/methanol, 20:1→10:1) afforded compound (ZDR095) as a pale orange solid (77 mg, 0.15 mmol, 57%). $^1$H NMR (300 MHz, CDCl$_3$) δ 3.21 (2H, t, J=6.5 Hz), 3.38 (2H, t, J=6.5 Hz), 4.36 (2H, s), 7.11-7.20 (2H, m), 7.36-7.46 (3H, m), 7.54-7.63 (3H, m), 7.78 (1H, dd, J=7.2 and 1.6 Hz), 8.03-8.07 (3H, m), 8.55-8.57 (1H, m); ESI-MS: m/z calcd for C$_{24}$H$_{21}$F$_3$N$_4$O$_2$S: 486.1; found [M+H]$^+$: 487.1.

Example 59: N-(2-((Bis(pyridin-2-ylmethyl)amino)methyl)quinolin-8-yl)-4-(trifluoromethyl)benzenesulfonamide—Compound (ZDR096)

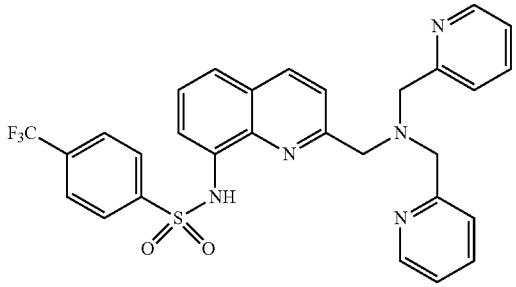 [SMILES: O=S(=O)(Nc1cccc2ccc(CN(Cc3ccccn3)Cc3ccccn3)nc12)c1ccc(C(F)(F)F)cc1]

A similar procedure to that described for the preparation of compound (ZDR022) was followed using compound (ZDR019) (100 mg, 0.26 mmol), di-(2-picoyl)amine (141 μL, 0.78 mmol) and sodium triacetoxyborohydride (111 mg, 0.52 mmol) in 1,2-dichloroethane (5 mL). Purification by flash chromatography (dichloromethane/methanol, 50:1→20:1) afforded compound (ZDR096) as a tan solid (66 mg, 0.11 mmol, 42%). $^1$H NMR (300 MHz, CDCl$_3$) δ 3.86 (4H, s), 3.94 (2H, s), 7.15-7.26 (2H, m), 7.37-7.47 (2H, m), 7.52-7.59 (5H, m), 7.66-7.71 (2H, m), 7.87 (1H, dd, J=7.2 and 1.6 Hz), 8.00-8.05 (3H, m), 8.62-8.64 (2H, m); ESI-MS: m/z calcd for C$_{29}$H$_{24}$F$_3$N$_5$O$_2$S: 563.2; found [M+H]$^+$: 564.2.

Example 60: N-(2-((Allylamino)methyl)quinolin-8-yl)-4-(trifluoromethyl)benzenesulfonamide—Compound (ZDR097)

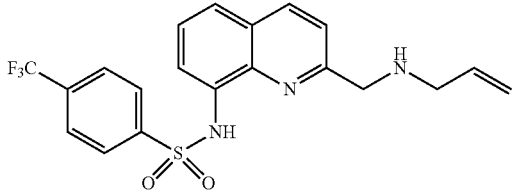 [SMILES: C=CCNCc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), allyamine (59 μL, 0.78 mmol) and sodium triacetoxyborohydride (111 mg, 0.52 mmol) in 1,2-dichloroethane (5 mL). Purification by flash chromatography (dichloromethane/methanol, 50:1→20:1) afforded compound (ZDR097) as a pale yellow solid (62 mg, 0.14 mmol, 53%). $^1$H NMR (300 MHz, CDCl$_3$) δ 3.35-3.38 (2H, m), 4.09 (2H, s), 5.15-5.29 (2H, m), 5.91-5.97 (1H, m), 7.37-7.48 (3H, m), 7.53 (2H, d, J=8.2 Hz), 7.95 (1H, dd, J=7.3 and 1.5 Hz), 7.93 (2H, d, J=8.2 Hz), 8.05 (1H, d, J=8.4 Hz); ESI-MS: m/z calcd for C$_{20}$H$_{18}$F$_3$N$_3$O$_2$S: 421.1; found [M+H]$^+$: 422.1.

Example 61: N-(2-((Prop-2-yn-1-ylamino)methyl)quinolin-8-yl)-4-(trifluoromethyl)benzenesulfonamide—Compound (ZDR098)

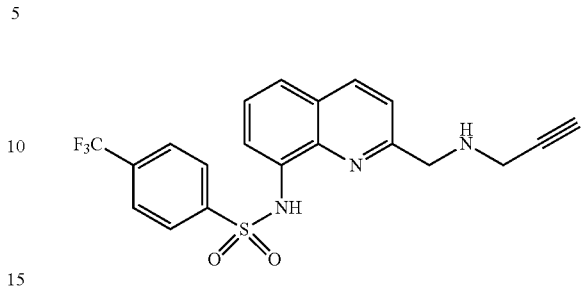

A similar procedure to that described for the preparation of compound (ZDR022) was followed using compound (ZDR019) (100 mg, 0.26 mmol), propargylamine (50 μL, 0.78 mmol) and sodium triacetoxyborohydride (111 mg, 0.52 mmol) in 1,2-dichloroethane (5 mL). Purification by flash chromatography (petroleum ether/ethyl acetate, 1:1→1:2) afforded compound (ZDR098) as a pale yellow solid (66 mg, 0.15 mmol, 57%). $^1$H NMR (300 MHz, CDCl$_3$) δ 2.32 (1H, t, J=2.4 Hz), 3.50 (2H, d, J=2.4 Hz), 4.15 (2H, s), 7.39-7.50 (3H, m), 7.59 (2H, d, J=8.2 Hz), 7.83 (1H, dd, J=7.3 and 1.5 Hz), 8.00 (2H, d, J=8.2 Hz), 8.06 (1H, d, J=8.4 Hz); ESI-MS: m/z calcd for C$_{20}$H$_{16}$F$_3$N$_3$O$_2$S: 419.1; found [M+H]$^+$: 420.1.

Example 62: N-(2-(((2-Fluoroethyl)amino)methyl)quinolin-8-yl)-4-(trifluoromethyl)benzenesulfonamide—Compound (ZDR099)

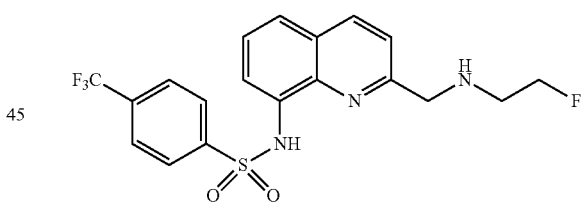

A similar procedure to that described for the preparation of compound (ZDR022) was followed using compound (ZDR019) (100 mg, 0.26 mmol), 2-fluoroethylamine hydrochoride (77 mg, 0.78 mmol), triethylamine (109 μL, 0.78 mmol) and sodium triacetoxyborohydride (111 mg, 0.52 mmol) in 1,2-dichloroethane (5 mL). Purification by flash chromatography (dichloromethane/methanol, 100:1→50:1) afforded compound (ZDR099) as a beige solid (50 mg, 0.11 mmol, 42%). $^1$H NMR (300 MHz, CDCl$_3$) δ 4.10 (2H, s), 2.98 (2H, dt, J=28.5 and 4.7 Hz), 4.62 (2H, dt, J=47.5 and 4.7 Hz), 7.39-7.50 (3H, m), 7.59 (2H, d, J=8.2 Hz), 7.84 (1H, dd, J=7.3 and 1.5 Hz), 7.99 (2H, d, J=8.2 Hz), 8.06 (1H, d, J=8.4 Hz); ESI-MS: m/z calcd for C$_{19}$H$_{17}$F$_4$N$_3$O$_2$S: 427.1; found [M+H]$^+$: 428.1.

Example 63: N-(2-(((2,2-Difluoroethyl)amino)methyl)quinolin-8-yl)-4-(trifluoromethyl)benzenesulfonamide—Compound ZDR100)

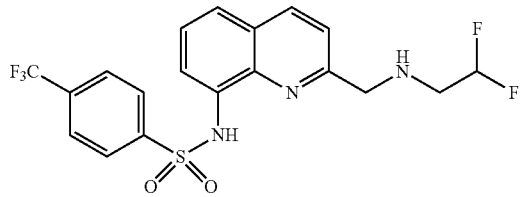 [SMILES: O=S(=O)(Nc1cccc2ccc(CNCC(F)F)nc12)c1ccc(C(F)(F)F)cc1]

A similar procedure to that described for the preparation of compound (ZDR022) was followed using compound (ZDR019) (100 mg, 0.26 mmol), 2,2-difluoroethylamine (63 mg, 0.78 mmol) and sodium triacetoxyborohydride (111 mg, 0.52 mmol) in 1,2-dichloroethane (5 mL). Purification by flash chromatography (dichloromethane/methanol, 100:1→50:1) afforded compound (ZDR100) as a beige solid (49 mg, 0.11 mmol, 42%). $^1$H NMR (300 MHz, CDCl$_3$) δ 3.03 (2H, td, J=15.1 and 4.2 Hz), 4.11 (2H, s), 5.91 (1H, tt, J=56.3 and 4.2 Hz), 7.41-7.51 (3H, m), 7.61 (2H, d, J=8.2 Hz), 7.86 (1H, dd, J=7.3 and 1.5 Hz), 8.01 (2H, d, J=8.2 Hz), 8.08 (1H, d, J=8.4 Hz); ESI-MS: m/z calcd for C$_{19}$H$_{16}$F$_5$N$_3$O$_2$S: 445.1; found [M+H]$^+$: 446.1.

Example 64: N-(2-(((Pyridin-3-ylmethyl)amino)methyl)quinolin-8-yl)-4-(trifluoromethyl)benzenesulfonamide—Compound (ZDR101)

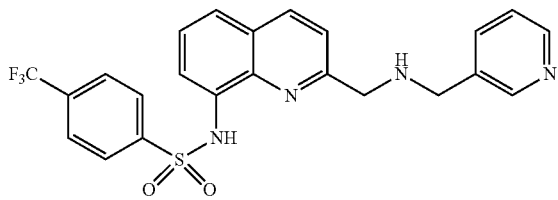

A similar procedure to that described for the preparation of compound (ZDR022) was followed using compound (ZDR019) (100 mg, 0.26 mmol), 3-picolylamine (80 μL, 0.78 mmol) and sodium triacetoxyborohydride (111 mg, 0.52 mmol) in 1,2-dichloroethane (5 mL).

Purification by flash chromatography (dichloromethane/methanol, 100:1→50:1) afforded compound (ZDR101) as a pale yellow solid (59 mg, 0.12 mmol, 46%). $^1$H NMR (300 MHz, CDCl$_3$) δ 3.89 (2H, s), 4.06 (2H, s), 7.25-7.29 (1H, m), 7.38-7.50 (3H, m), 7.58 (2H, d, J=8.2 Hz), 7.70-7.75 (1H, m), 7.80 (1H, dd, J=7.3 and 1.5 Hz), 7.99 (2H, d, J=8.2 Hz), 8.06 (1H, d, J=8.5 Hz), 8.50-8.52 (1H, m), 8.59 (1H, d, J=1.8 Hz); ESI-MS: m/z calcd for C$_{23}$H$_{19}$F$_3$N$_4$O$_2$S: 472.1; found [M+H]$^+$: 473.1.

Example 65: N-(2-(((1,3-Dihydroxy-2-(hydroxymethyl)propan-2-yl)amino)methyl)quinolin-8-yl)-4-(trifluoromethyl)benzenesulfonamide—Compound (ZDR102)

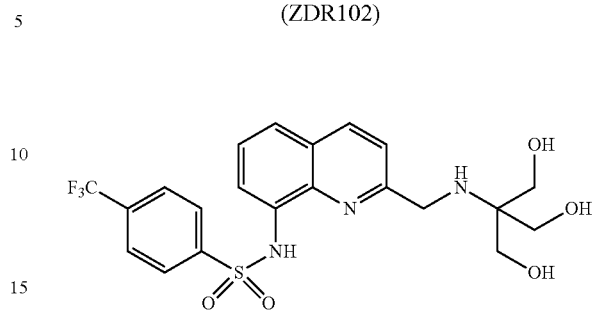

A similar procedure to that described for the preparation of compound (ZDR022) was followed using compound (ZDR019) (100 mg, 0.26 mmol), tris(hydroxymethyl)aminomethane (94 mg, 0.78 mmol) and sodium triacetoxyborohydride (111 mg, 0.52 mmol) in 1,2-dichloroethane (5 mL). Purification by flash chromatography (dichloromethane/methanol, 100:1→50:1) afforded compound (ZDR102) as a pale yellow solid (38 mg, 0.07 mmol, 26%). $^1$H NMR (300 MHz, CDCl$_3$) δ 3.70 (6H, s), 4.18 (2H, s), 7.17-7.30 (3H, m), 7.41 (2H, d, J=8.2 Hz), 7.60 (1H, dd, J=7.2 and 1.8 Hz), 7.82 (1H, d, J=8.4 Hz), 7.93 (2H, d, J=8.2 Hz); ESI-MS: m/z calcd for C$_{21}$H$_{22}$F$_3$N$_3$O$_5$S: 485.1; found [M+H]$^+$: 486.1.

Example 66: N-(2-((Benzylamino)methyl)quinolin-8-yl)-4-(trifluoromethyl)benzenesulfonamide)—Compound (ZDR103)

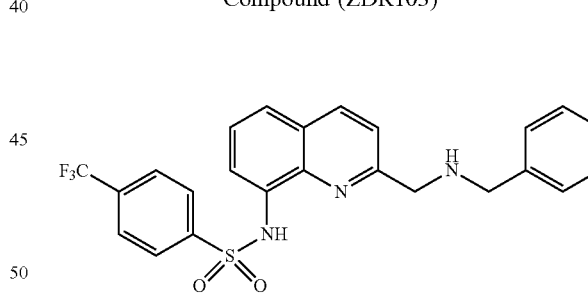

A similar procedure to that described for the preparation of compound (ZDR022) was followed using compound (ZDR019) (100 mg, 0.26 mmol), benzylamine (86 μL, 0.78 mmol) and sodium triacetoxyborohydride (111 mg, 0.52 mmol) in 1,2-dichloroethane (5 mL). Purification by flash chromatography (dichloromethane/methanol, 100:1→50:1) afforded compound (ZDR103) as a pale yellow solid (60 mg, 0.12 mmol, 46%). $^1$H NMR (300 MHz, CDCl$_3$) δ 3.88 (2H, s), 4.07 (2H, s), 7.27-7.54 (10H, m), 7.82 (1H, dd, J=7.3 and 1.5 Hz), 7.94 (2H, d, J=8.3 Hz), 8.06 (1H, d, J=8.4 Hz); ESI-MS: m/z calcd for C$_{24}$H$_{20}$F$_3$N$_3$O$_2$S: 471.1; found [M+H]$^+$: 472.1.

Example 67: N-(2-(((Furan-2-ylmethyl)amino)methyl)quinolin-8-yl)-4-(trifluoromethyl)benzenesulfonamide—Compound (ZDR106)

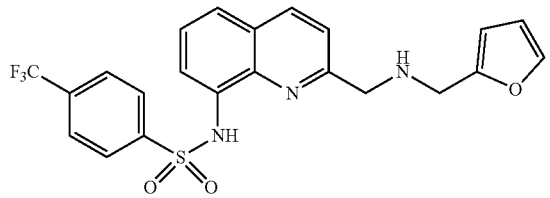 [SMILES: O=S(=O)(Nc1cccc2ccc(CNCc3ccco3)nc12)c1ccc(C(F)(F)F)cc1]

A similar procedure to that described for the preparation of compound (ZDR022) was followed using compound (ZDR019) (100 mg, 0.26 mmol), furfurylamine (69 µL, 0.78 mmol) and sodium triacetoxyborohydride (111 mg, 0.52 mmol) in 1,2-dichloroethane (5 mL). Purification by flash chromatography (dichloromethane→dichloromethane/methanol, 100:1) afforded compound (ZDR106) as a pale orange solid (62 mg, 0.13 mmol, 50%). $^1$H NMR (300 MHz, CDCl$_3$) δ 3.87 (2H, s), 4.08 (2H, s), 6.23-6.25 (1H, m), 6.32-6.35 (1H, m), 7.35-7.49 (4H, m), 7.54 (2H, d, J=8.2 Hz), 7.83 (1H, dd, J=7.3 and 1.4 Hz), 7.94 (2H, d, J=8.2 Hz), 8.05 (1H, d, J=8.4 Hz); ESI-MS: m/z calcd for C$_{22}$H$_{18}$F$_3$N$_3$O$_3$S: 461.1; found [M+H]$^+$: 462.1.

Example 69: N-(2-((Phenylamino)methyl)quinolin-8-yl)-4-(trifluoromethyl)benzenesulfonamide—Compound (ZDR108)

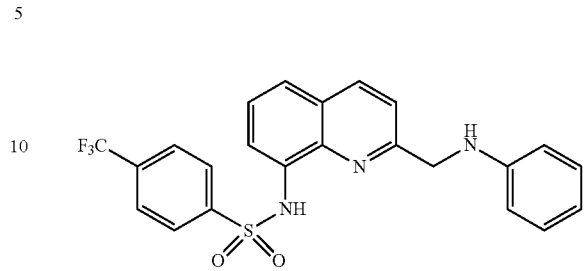

A similar procedure to that described for the preparation of compound (ZDR022) was followed using compound (ZDR019) (100 mg, 0.26 mmol), aniline (72 µL, 0.78 mmol) and sodium triacetoxyborohydride (111 mg, 0.52 mmol) in 1,2-dichloroethane (5 mL). Purification by flash chromatography (dichloromethane) afforded compound (ZDR108) as a beige solid (23 mg, 0.05 mmol, 19%). $^1$H NMR (300 MHz, CDCl$_3$) δ 4.62 (2H, s), 6.75-6.78 (3H, m), 7.18-7.21 (2H, m), 7.41 (1H, t, J=7.9 Hz), 7.46-7.50 (2H, m), 7.54 (2H, d, J=8.2 Hz), 7.83 (1H, dd, J=7.3 and 1.6 Hz), 7.91 (2H, d, J=8.2 Hz), 8.05 (1H, d, J=8.5 Hz); ESI-MS: m/z calcd for C$_{23}$H$_{18}$F$_3$N$_3$O$_2$S: 457.1; found [M+H]$^+$: 458.1.

Example 68: N-(2-(((Thiophen-2-ylmethyl)amino)methyl)quinolin-8-yl)-4-(trifluoromethyl)benzenesulfonamide—Compound (ZDR107)

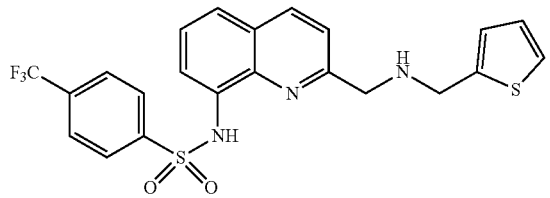 [SMILES: O=S(=O)(Nc1cccc2ccc(CNCc3cccs3)nc12)c1ccc(C(F)(F)F)cc1]

A similar procedure to that described for the preparation of compound (ZDR022) was followed using compound (ZDR019) (100 mg, 0.26 mmol), 2-thiophenemethylamine (80 µL, 0.78 mmol) and sodium triacetoxyborohydride (111 mg, 0.52 mmol) in 1,2-dichloroethane (5 mL). Purification by flash chromatography (dichloromethane→dichloromethane/methanol, 100:1) afforded compound (ZDR107) as a pale orange solid (70 mg, 0.14 mmol, 53%). $^1$H NMR (300 MHz, CDCl$_3$) δ 4.09 (2H, s), 4.11 (2H, s), 6.99-7.01 (2H, m), 7.26-7.28 (1H, m), 7.41-7.52 (3H, m), 7.57 (2H, d, J=8.2 Hz), 7.84 (1H, dd, J=7.4 and 1.4 Hz), 7.99 (2H, d, J=8.2 Hz), 8.07 (1H, d, J=8.4 Hz); ESI-MS: m/z calcd for C$_{22}$H$_{18}$F$_3$N$_3$O$_2$S$_2$: 477.1; found [M+H]$^+$: 478.1.

Example 70: N-(2-((Pyridin-2-ylamino)methyl)quinolin-8-yl)-4-(trifluoromethyl)benzenesulfonamide—Compound (ZDR109)

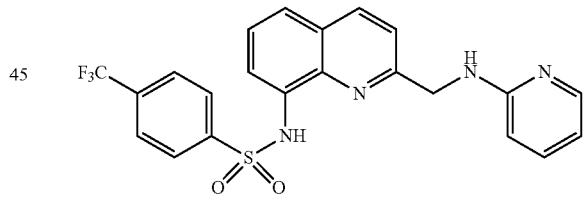

A similar procedure to that described for the preparation of compound (ZDR022) was followed using compound (ZDR019) (100 mg, 0.26 mmol), 2-aminopyridine (73 mg, 0.78 mmol) and sodium triacetoxyborohydride (111 mg, 0.52 mmol) in 1,2-dichloroethane (5 mL). Purification by flash chromatography (petroleum ether/ethyl acetate, 2:1) afforded compound (ZDR109) as a pale yellow solid (20 mg, 0.04 mmol, 15%). $^1$H NMR (300 MHz, CDCl$_3$) δ 4.76 (2H, d, J=5.7 Hz), 5.56-5.64 (1H, m), 6.53 (1H, d, J=8.4 Hz), 6.62-6.66 (1H, m), 7.38-7.56 (6H, m), 7.83 (1H, dd, J=7.3 and 1.4 Hz), 7.94 (2H, d, J=8.2 Hz), 8.04 (1H, d, J=8.4 Hz), 8.11-8.13 (1H, m); ESI-MS: m/z calcd for C$_{22}$H$_{17}$F$_3$N$_4$O$_2$S: 458.1; found [M+H]$^+$: 459.1.

Example 71: N-(2-(((Pyridin-4-ylmethyl)amino)methyl)quinolin-8-yl)-4-(trifluoromethyl)benzenesulfonamide—Compound (ZDR110)

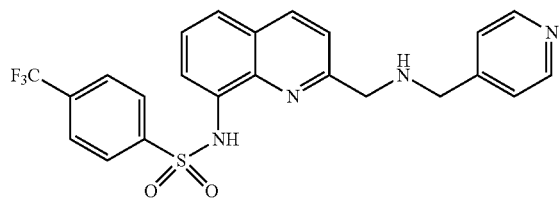 [SMILES: O=S(=O)(Nc1cccc2ccc(CNCc3ccncc3)nc12)c1ccc(C(F)(F)F)cc1]

A similar procedure to that described for the preparation of compound (ZDR022) was followed using compound (ZDR019) (100 mg, 0.26 mmol), 4-(aminomethyl)pyridine (79 µL, 0.78 mmol) and sodium triacetoxyborohydride (111 mg, 0.52 mmol) in 1,2-dichloroethane (5 mL). Purification by flash chromatography (dichloromethane/methanol, 50:1→20:1) afforded compound (ZDR110) as a pale orange solid (44 mg, 0.09 mmol, 34%). $^1$H NMR (300 MHz, CDCl$_3$) δ 3.89 (2H, s), 4.06 (2H, s), 7.30-7.34 (2H, m), 7.39-7.50 (3H, m), 7.58 (2H, d, J=8.2 Hz), 7.81 (1H, dd, J=7.4 and 1.5 Hz), 7.99 (2H, d, J=8.2 Hz), 8.07 (1H, d, J=8.4 Hz), 8.56-8.58 (2H, m); ESI-MS: m/z calcd for C$_{23}$H$_{19}$F$_3$N$_4$O$_2$S: 472.1; found [M+H]$^+$: 473.0.

Example 72: N-(2-(((2-(Piperidin-1-yl)ethyl)amino)methyl)quinolin-8-yl)-4-(trifluoromethyl)benzenesulfonamide—Compound (ZDR111)

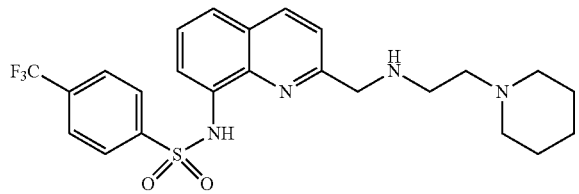 [SMILES: O=S(=O)(Nc1cccc2ccc(CNCCN3CCCCC3)nc12)c1ccc(C(F)(F)F)cc1]

A similar procedure to that described for the preparation of compound (ZDR022) was followed using compound (ZDR019) (100 mg, 0.26 mmol), 1-(2-aminoethyl)piperidine (112 µL, 0.78 mmol) and sodium triacetoxyborohydride (111 mg, 0.52 mmol) in 1,2-dichloroethane (5 mL). Purification by flash chromatography (dichloromethane/methanol, 40:1→20:1→10:1→7:1) afforded compound (ZDR111) as a pale yellow solid (70 mg, 0.14 mmol, 53%). $^1$H NMR (300 MHz, CDCl$_3$) δ 1.44-1.54 (2H, m), 1.64-1.76 (4H, m), 2.66-2.76 (4H, m), 2.90 (2H, t, J=6.2 Hz), 3.03 (2H, t, J=6.2 Hz), 4.19 (2H, s), 7.34-7.43 (3H, m), 7.55 (2H, d, J=8.2 Hz), 7.74 (1H, dd, J=7.2 and 1.5 Hz), 8.01 (1H, d, J=8.4 Hz), 8.06 (2H, d, J=8.2 Hz); ESI-MS: m/z calcd for C$_{24}$H$_{27}$F$_3$N$_4$O$_2$S: 492.2; found [M+Na]$^+$: 515.2.

Example 73: N-(2-(((2-Morpholinoethyl)amino)methyl)quinolin-8-yl)-4-(trifluoromethyl)benzenesulfonamide—Compound (ZDR112)

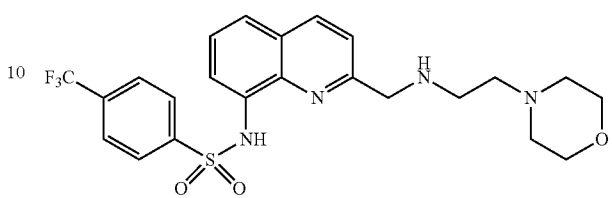

A similar procedure to that described for the preparation of compound (ZDR022) was followed using compound (ZDR019) (100 mg, 0.26 mmol), 4-(2-aminoethyl)morpholine (103 µL, 0.78 mmol) and sodium triacetoxyborohydride (111 mg, 0.52 mmol) in 1,2-dichloroethane (5 mL). Purification by flash chromatography (dichloromethane/methanol, 40:1→20:1) afforded compound (ZDR112) as a pale yellow solid (80 mg, 0.16 mmol, 61%). $^1$H NMR (300 MHz, CDCl$_3$) δ 2.43-2.46 (4H, m), 2.58 (2H, t, J=6.2 Hz), 2.83 (2H, t, J=6.2 Hz), 3.68-3.71 (4H, m), 4.14 (2H, s), 7.37-7.49 (3H, m), 7.58 (2H, d, J=8.2 Hz), 7.78 (1H, dd, J=7.3 and 1.5 Hz), 8.01 (2H, d, J=8.2 Hz), 8.05 (1H, d, J=8.4 Hz); ESI-MS: m/z calcd for C$_{23}$H$_{25}$F$_3$N$_4$O$_3$S: 494.2; found [M+H]$^+$: N/A.

Example 74: N-(2-(((2-Thiomorpholinoethyl)amino)methyl)quinolin-8-yl)-4-(trifluoromethyl)benzenesulfonamide—Compound (ZDR113)

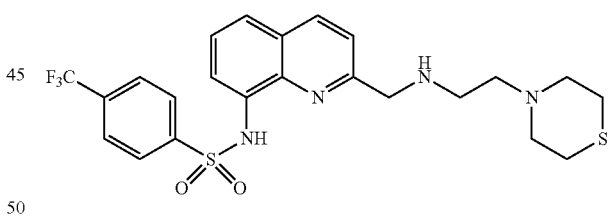

A similar procedure to that described for the preparation of compound (ZDR022) was followed using compound (ZDR019) (100 mg, 0.26 mmol), 4-(2-aminoethyl)thiomorpholine (109 µL, 0.78 mmol) and sodium triacetoxyborohydride (111 mg, 0.52 mmol) in 1,2-dichloroethane (5 mL). Purification by flash chromatography (dichloromethane/methanol, 40:1→20:1) afforded compound (ZDR113) as a pale orange solid (70 mg, 0.13 mmol, 50%). $^1$H NMR (300 MHz, CDCl$_3$) δ 2.59 (2H, t, J=5.9 Hz), 2.63-2.75 (8H, m), 2.80 (2H, t, J=5.9 Hz), 4.12 (2H, s), 7.37-7.48 (3H, m), 7.58 (2H, d, J=8.2 Hz), 7.78 (1H, dd, J=7.3 and 1.4 Hz), 8.02 (2H, d, J=8.2 Hz), 8.06 (1H, d, J=8.4 Hz); ESI-MS: m/z calcd for C$_{23}$H$_{25}$F$_3$N$_4$O$_2$S$_2$: 510.1; found [M+H]$^+$: 511.1.

Example 75: N-(2-(((2-(4-Methylpiperazin-1-yl)ethyl)amino)methyl)quinolin-8-yl)-4-(trifluoromethyl)benzenesulfonamide di-trifluoroacetate—Compound (ZDR114)

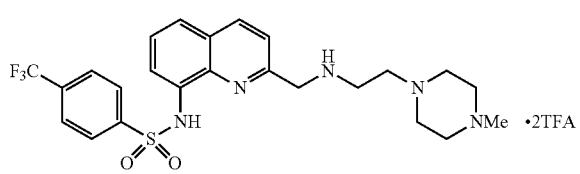 [SMILES: CN1CCN(CCNCc2ccc3cccc(NS(=O)(=O)c4ccc(C(F)(F)F)cc4)c3n2)CC1]

A similar procedure to that described for the preparation of compound (ZDR090) was followed using compound (ZDR019) (100 mg, 0.26 mmol), 1-(2-aminoethyl)-4-methylpiperazine (118 µL, 0.78 mmol) and sodium triacetoxyborohydride (111 mg, 0.52 mmol) in 1,2-dichloroethane (5 mL). Purification by RP-HLPC (10% to 20% A/B gradient over 20 min, where A=water+0.1% trifluoroacetic acid and B=acetonitrile+0.1% trifluoroacetic acid) afforded compound (ZDR114) as a white solid (50 mg, 0.06 mmol, 23%). $^1$H NMR (300 MHz, CDCl$_3$) δ 2.31 (3H, s), 2.47-2.57 (8H, m), 2.58 (2H, t, J=6.9 Hz), 2.78 (2H, t, J=6.9 Hz), 4.07 (2H, s), 7.38-7.49 (3H, m), 7.61 (2H, d, J=8.2 Hz), 7.80 (1H, dd, J=7.4 and 1.4 Hz), 8.0-8.07 (3H, m); ESI-MS: m/z calcd for C$_{24}$H$_{28}$F$_3$N$_5$O$_2$S: 507.2; found [M+H]$^+$: N/A.

Example 76: N-(2-(((3-(Piperidin-1-yl)propyl)amino)methyl)quinolin-8-yl)-4-(trifluoromethyl)benzenesulfonamide di-trifluoroacetate—Compound (ZDR115)

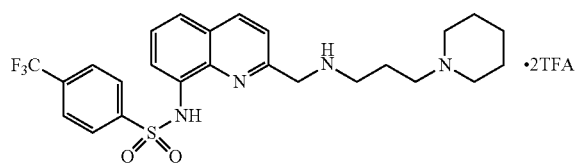 [SMILES: O=S(=O)(Nc1cccc2ccc(CNCCCN3CCCCC3)nc12)c1ccc(C(F)(F)F)cc1]

A similar procedure to that described for the preparation of compound (ZDR090) was followed using compound (ZDR019) (100 mg, 0.26 mmol), N-(3-aminopropyl)piperidine (125 µL, 0.78 mmol) and sodium triacetoxyborohydride (111 mg, 0.52 mmol) in 1,2-dichloroethane (5 mL). Purification by RP-HLPC (10% to 20% A/B gradient over 20 min, where A=water+0.1% trifluoroacetic acid and B=acetonitrile+0.1% trifluoroacetic acid) afforded compound (ZDR115) as a white solid (70 mg, 0.10 mmol, 38%). $^1$H NMR (300 MHz, CDCl$_3$) δ 1.40-1.50 (2H, m), 1.58-1.69 (4H, m), 1.86-1.95 (2H, m), 2.58-2.73 (6H, m), 2.86 (2H, t, J=6.9 Hz), 4.12 (2H, s), 7.36-7.46 (3H, m), 7.56 (2H, d, J=8.2 Hz), 7.74 (1H, dd, J=7.3 and 1.5 Hz), 8.01 (2H, d, J=8.2 Hz), 8.05 (1H, d, J=8.4 Hz); ESI-MS: m/z calcd for C$_{25}$H$_{29}$F$_3$N$_4$O$_2$S: 506.2; found [M+H]$^+$: 507.2.

Example 77: N-(2-(((3-Morpholinopropyl)amino)methyl)quinolin-8-yl)-4-(trifluoromethyl)benzenesulfonamide—Compound (ZDR116)

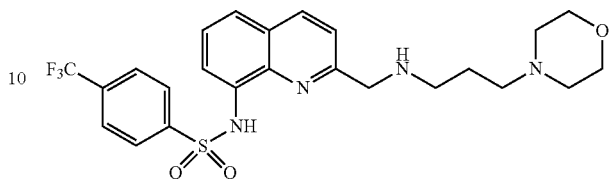

A similar procedure to that described for the preparation of compound (ZDR022) was followed using compound (ZDR019) (100 mg, 0.26 mmol), 3-(4-morpholinyl)-1-propanamine (112 µL, 0.78 mmol) and sodium triacetoxyborohydride (111 mg, 0.52 mmol) in 1,2-dichloroethane (5 mL). Purification by flash chromatography (dichloromethane/methanol, 40:1) afforded compound (ZDR116) as a pale orange solid (92 mg, 0.18 mmol, 69%). $^1$H NMR (300 MHz, CDCl$_3$) δ 1.88 (2H, t, J=6.9 Hz), 2.42-2.48 (6H, m), 2.93 (2H, t, J=6.9 Hz), 3.60-3.64 (4H, m), 4.21 (2H, s), 7.38-7.43 (3H, m), 7.53 (2H, d, J=8.2 Hz), 7.75 (1H, dd, J=7.2 and 1.6 Hz), 8.02-8.06 (3H, m); ESI-MS: m/z calcd for C$_{24}$H$_{27}$F$_3$N$_4$O$_3$S: 508.2; found [M+H]$^+$: 509.2.

Example 78: N-(2-(((3-(4-Methylpiperazin-1-yl)propyl)amino)methyl)quinolin-8-yl)-4-(trifluoromethyl)benzenesulfonamide di-trifluoroacetate—Compound (ZDR117)

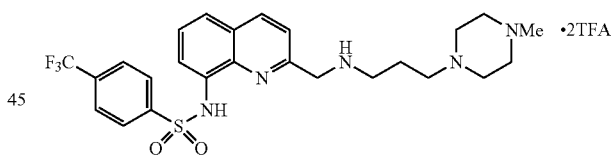

A similar procedure to that described for the preparation of compound (ZDR090) was followed using compound (ZDR019) (100 mg, 0.26 mmol), 1-(3-aminopropyl)-4-methylpiperazine (134 µL, 0.78 mmol) and sodium triacetoxyborohydride (111 mg, 0.52 mmol) in 1,2-dichloroethane (5 mL). Purification by RP-HLPC (10% to 20% A/B gradient over 20 min, where A=water+0.1% trifluoroacetic acid and B=acetonitrile+0.1% trifluoroacetic acid) afforded compound (ZDR117) as a white solid (44 mg, 0.06 mmol, 23%). $^1$H NMR (300 MHz, CDCl$_3$) δ 1.79 (2H, t, J=6.9 Hz), 2.22 (3H, s), 2.35-2.55 (8H, m), 2.45 (2H, t, J=6.9 Hz), 2.80 (2H, t, J=6.9 Hz), 4.10 (2H, s), 7.36-7.46 (3H, m), 7.55 (2H, d, J=8.2 Hz), 7.76 (1H, dd, J=7.3 and 1.5 Hz), 8.01 (2H, d, J=8.2 Hz), 8.04 (1H, d, J=8.4 Hz); ESI-MS: m/z calcd for C$_{25}$H$_{30}$F$_3$N$_5$O$_2$S: 521.2; found [M+H]$^+$: 522.2.

Example 79: (E)-2-((8-((4-(Trifluoromethyl)phenyl)sulfonamido)quinolin-2-yl)methylene)hydrazine-1-carboxamide—Compound (ZDR118)

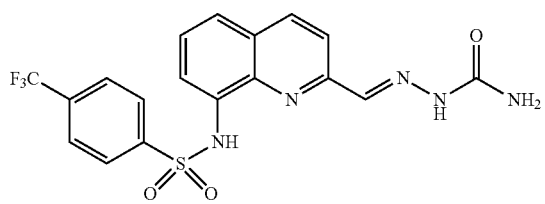

A solution of compound (ZDR019) (100 mg, 0.26 mmol), semicarbazide hydrochloride (29 mg, 0.26 mmol) and sodium acetate (43 mg, 0.52 mmol) in aqueous ethanol (5 mL, 90% v/v) was heated at 70° C. for 18 h. The mixture was then diluted with dichloromethane/methanol (25 mL, 9:1 v/v), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/methanol, 40:1) afforded compound (ZDR118) as a white solid (85 mg, 0.19 mmol, 73%). $^1$H NMR (300 MHz, CDCl$_3$) δ 7.19-7.22 (1H, m), 7.29 (1H, t, J=7.6 Hz), 7.61-7.66 (3H, m), 7.85 (1H, d, J=8.4 Hz), 8.02-8.07 (4H, m), 11.22 (1H, s); ESI-MS: m/z calcd for $C_{18}H_{14}F_3N_5O_3S$: 437.1; found [M+Na]$^+$: 460.1.

Example 80: (E)-N-(2-Morpholinoethyl)-2-((8-((4-(trifluoromethyl)phenyl)sulfonamido)quinolin-2-yl)methylene)hydrazine-1-carbothioamide—Compound (ZDR119)

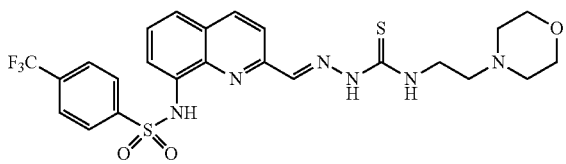 [SMILES: O=S(=O)(Nc1cccc2ccc(/C=N/NC(=S)NCCN3CCOCC3)nc12)c1ccc(C(F)(F)F)cc1]

A similar procedure to that described for the preparation of compound (ZDR118) was followed using compound (ZDR019) (100 mg, 0.26 mmol) and 4-[2-(4-morpholinyl)ethyl]-3-thiosemicarbazide (53 mg, 0.26 mmol) in aqueous ethanol (5 mL, 90% v/v). Purification by flash chromatography (dichloromethane/methanol, 50:1) afforded compound (ZDR119) as a pale yellow solid (95 mg, 0.16 mmol, 61%). $^1$H NMR (400 MHz, CDCl$_3$) δ 2.58 (4H, brs), 2.72 (2H, t, J=5.8 Hz), 3.76-3.80 (4H, m), 3.84 (2H, q, J=5.8 Hz), 7.47-7.52 (2H, m), 7.65 (2H, d, J=8.5 Hz), 7.86 (1H, dd, J=6.7 and 2.3 Hz), 8.01-8.06 (4H, m), 8.13 (1H, d, J=8.5 Hz), 8.30 (1H, brs), 9.15 (1H, brs), 9.78 (1H, brs); ESI-MS: m/z calcd for $C_{24}H_{25}F_3N_6O_3S_2$: 566.1; found [M+H]$^+$: 567.1.

Example 81: (E/Z)—N-(2-((2-Acetylhydrazineylidene)methyl)quinolin-8-yl)-4-(trifluoromethyl)benzenesulfonamide—Compound (ZDR120)

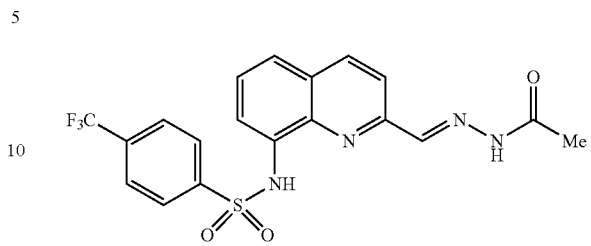

A similar procedure to that described for the preparation of compound (ZDR118) was followed using compound (ZDR019) (100 mg, 0.26 mmol) and acetylhydrazide (19 mg, 0.26 mmol) in aqueous ethanol (5 mL, 90% v/v). Purification by flash chromatography (dichloromethane/methanol, 50:1) afforded compound (ZDR120) as a white solid (90 mg, 0.20 mmol, 76%), as a 1:1 mixture of E/Z isomers. $^1$H NMR (300 MHz, CDCl$_3$/d$_4$-MeOH, 1:1 v/v) δ 2.14 (1.5H, s), 2.36 (1.5H, s), 7.41-7.56 (2H, m), 7.60 (2H, d, J=8.2 Hz), 7.77-7.82 (1H, m), 7.95-8.03 (3H, m), 8.10-8.17 (2H, m); ESI-MS: m/z calcd for $C_{19}H_{15}F_3N_4O_3S$: 436.1; found [M+Na]$^+$: 459.1.

Example 82: (E)-N-(2-((2-Nicotnoylhydrazineylidene)methyl)quinolin-8-yl)-4-(trifluoromethyl)benzenesulfonamide—Compound (ZDR121)

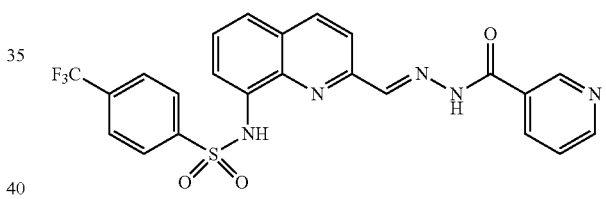

A similar procedure to that described for the preparation of compound (ZDR118) was followed using compound (ZDR019) (100 mg, 0.26 mmol) and nicotinic acid hydrazide (36 mg, 0.26 mmol) in aqueous ethanol (5 mL, 90% v/v). Purification by flash chromatography (dichloromethane/methanol, 50:1) afforded compound (ZDR121) as a white solid (85 mg, 0.17 mmol, 65%). $^1$H NMR (300 MHz, d$_6$-DMSO) δ 7.56-7.85 (6H, m), 7.98-8.08 (3H, m), 8.24-8.42 (2H, m), 8.50 (1H, s), 8.74-8.85 (1H, m), 8.95-9.14 (1H, m), 10.41 (1H, br s), 12.39 (1H, s); ESI-MS: m/z calcd for $C_{23}H_{16}F_3N_5O_3S$: 499.1; found [M+Na]$^+$: 522.1.

Example 83: (E)-N-(2-((2-Isonicotinoylhydrazneylidene)methyl)quinolin-8-yl)-4-(trifluoromethyl)benzenesulfonamide—Compound (ZDR122)

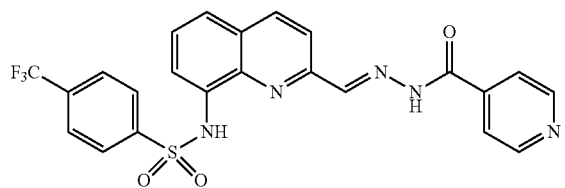 [SMILES: O=C(N/N=C/c1ccc2cccc(NS(=O)(=O)c3ccc(C(F)(F)F)cc3)c2n1)c1ccncc1]

A similar procedure to that described for the preparation of compound (ZDR118) was followed using compound (ZDR019) (100 mg, 0.26 mmol) and isonicotinic acid hydrazide (36 mg, 0.26 mmol) in aqueous ethanol (5 mL, 90% v/v). Purification by flash chromatography (dichloromethane/methanol, 50:1) afforded compound (ZDR122) as a yellow solid (83 mg, 0.16 mmol, 61%). $^1$H NMR (300 MHz, d$_6$-DMSO) δ 7.56-7.88 (7H, m), 8.00-8.07 (3H, m), 8.37 (1H, d, J=8.4 Hz), 8.53 (1H, s), 8.75-8.87 (2H, m), 12.44 (1H, s); ESI-MS: m/z calcd for C$_{23}$H$_{16}$F$_3$N$_5$O$_3$S: 499.1; found [M+Na]$^+$: 522.1.

Example 84: tert-Butyl (E/Z)-3-(2-((8-((4-(trifluoromethyl)phenyl)sulfonamido)quinolin-2-yl)methylene)hydrazine-1-carbonyl)piperidine-1-carboxylate—Compound ZDR123

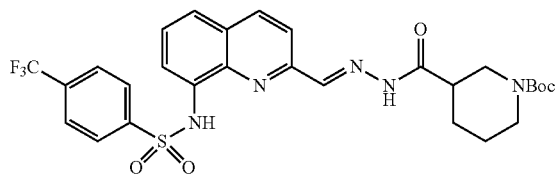 [SMILES: CC(C)(C)OC(=O)N1CCCC(C(=O)N/N=C/c2ccc3cccc(NS(=O)(=O)c4ccc(C(F)(F)F)cc4)c3n2)C1]

A similar procedure to a described for the preparation of compound (ZDR118) was followed using compound (ZDR019) (100 mg, 0.26 mmol) and 1-Boc-nipecotic acid hydrazide (63 mg, 0.26 mmol) in aqueous ethanol (5 mL, 90% v/v). Purification by flash chromatography (dichloromethane/methanol, 50:1) afforded compound (ZDR123) as a white solid (97 mg, 0.16 mmol, 61%). ESI-MS: m/z calcd for C$_{29}$H$_{30}$F$_3$N$_5$O$_5$S: 605.2; found [M+Na]$^+$: 628.2.

Example 85: (E/Z)—N-(2-((2-(Piperidine-3-carbonyl)hydrazineylidene)methyl)quinolin-8-yl)-4-(trifluoromethyl)benzenesulfonamide trifluoroacetate—Compound (ZDR124)

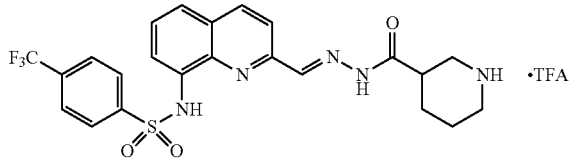 [SMILES: O=C(N/N=C/c1ccc2cccc(NS(=O)(=O)c3ccc(C(F)(F)F)cc3)c2n1)C1CCCNC1]

A solution of compound (ZDR123) (50 mg, 0.08 mmol) in trifluoroacetic acid-dichloromethane (3 mL, 50% v/v) was stirred at room temperature for 3 h. The solvent was removed in vacuo to afford compound (ZDR124) as a white solid (48 mg, 0.08 mmol, quant.), as a 1:1 mixture of E/Z isomers, which was used without further purification. $^1$H NMR (400 MHz, d$_4$-MeOH) δ 1.85-2.06 (3H, m), 2.12-2.20 (1H, m), 2.98 (0.5H, sept, J=4.1 Hz), 3.14-3.21 (1H, m), 3.26-3.31 (1H, m), 3.37-3.44 (2H, m), 3.82 (0.5H, sept, J=4.1 Hz), 7.50-7.56 (1H, m), 7.62-7.66 (3H, m), 7.86 (1H, dt, J=7.5 and 1.3 Hz), 7.95-7.99 (2H, m), 8.01 (0.5H, d, J=8.6 Hz), 8.04 (0.5H, s), 8.10 (0.5H, d, J=8.6 Hz), 8.21 (1H, dd, J=8.6 and 1.6 Hz), 8.25 (0.5H, s); ESI-MS: m/z calcd for C$_{25}$H$_{22}$F$_3$N$_5$O$_4$S: 505.1; found [M+H]$^+$: N/A.

Example 86: (E)-N-(2-((Hydroxyimino)methyl)quinolin-8-yl)-4-(trifluoromethyl)benzenesulfonamide—Compound (ZDR125)

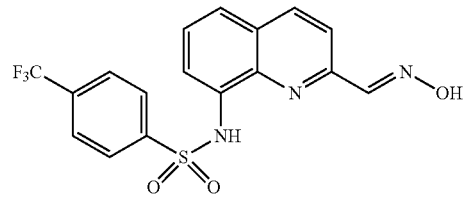 [SMILES: O=S(=O)(Nc1cccc2ccc(/C=N/O)nc12)c1ccc(C(F)(F)F)cc1]

A similar procedure to that described for the preparation of compound (ZDR118) was followed using compound (ZDR019) (100 mg, 0.26 mmol) and hydroxylamine hydrochloride (18 mg, 0.26 mmol) in aqueous ethanol (10 mL, 60% v/v). Purification by flash chromatography (dichloromethane/methanol, 50:1) afforded compound (ZDR125) as a white solid (80 mg, 0.20 mmol, 76%). $^1$H NMR (300 MHz, CDCl$_3$) δ 6.90 (1H, d, J=8.4 Hz), 7.36-7.61 (5H, m), 7.76 (1H, dd, J=7.3 and 1.4 Hz), 7.92 (2H, d, J=8.2 Hz), 8.05 (1H, d, J=8.4 Hz); ESI-MS: m/z calcd for C$_{17}$H$_{12}$F$_3$N$_3$O$_3$S: 395.1; found [M+H]$^+$: N/A.

Example 87: (E)-N-(2-((Methoxyimino)methyl)quinolin-8-yl)-4-(trifluoromethyl)benzenesulfonamide—Compound (ZDR126)

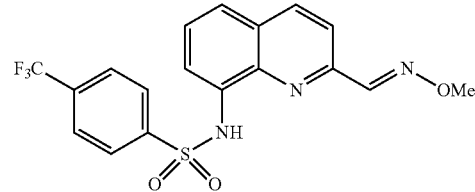 [SMILES: CO/N=C/c1ccc2cccc(NS(=O)(=O)c3ccc(C(F)(F)F)cc3)c2n1]

A similar procedure to that described for the preparation of compound (ZDR118) was followed using compound (ZDR019) (100 mg, 0.26 mmol), methoxyamine hydrochloride (21 mg, 0.26 mmol) and sodium acetate (43 mg, 0.52 mmol) in ethanol (10 mL). Purification by flash chromatography (dichloromethane/methanol, 50:1) afforded compound (ZDR126) as a white solid (75 mg, 0.18 mmol, 69%). $^1$H NMR (300 MHz, CDCl$_3$) δ 4.07 (3H, s), 7.43-7.49 (2H, m), 7.62 (2H, d, J=8.4 Hz), 7.84 (1H, dd, J=7.2 and 1.5 Hz), 7.97-8.07 (4H, m), 8.21 (1H, s), 9.12 (1H, br s); ESI-MS: m/z calcd for C$_{18}$H$_{14}$F$_3$N$_3$O$_3$S: 409.1; found [M+Na]$^+$: 432.1.

Example 88: (E)-N-(2-(Hydrazineylidenemethyl)quinolin-8-yl)-4-(trifluoromethyl)benzenesulfonamide—Compound (ZDR127)

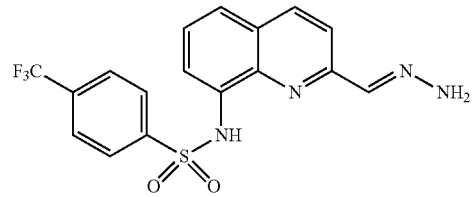 [SMILES: N/N=C/c1ccc2cccc(NS(=O)(=O)c3ccc(C(F)(F)F)cc3)c2n1]

A similar procedure to that described for the preparation of compound (ZDR118) was followed using compound (ZDR019) (100 mg, 0.26 mmol) and aqueous hydrazine (1 mL, 50% w/w in water) in ethanol (10 mL). Purification by flash chromatography (dichloromethane/methanol, 50:1) afforded compound (ZDR127) as a yellow solid (66 mg, 0.16 mmol, 61%). $^1$H NMR (400 MHz, CDCl$_3$) δ 6.00 (2H, s), 7.40 (1H, t, J=8.0 Hz), 7.46 (1H, dd, J=8.2 and 1.4 Hz), 7.62 (2H, d, J=8.4 Hz), 7.80 (1H, dd, J=7.6 and 1.4 Hz), 7.89 (1H, s), 7.96-8.04 (4H, m); ESI-MS: m/z calcd for $C_{17}H_{13}F_3N_4O_2S$: 394.1; found [M+H]$^+$: 395.1.

Example 89: N-(2-(((2-(2-Hydroxyethoxy)ethyl)amino)methyl)quinolin-8-yl)-4-(trifluoromethyl)benzenesulfonamide—Compound (ZDR129)

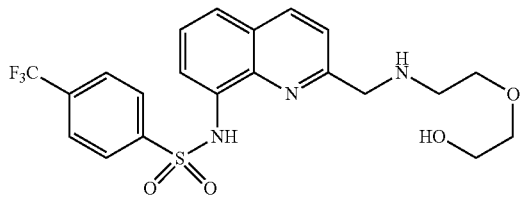 [SMILES: O=S(=O)(Nc1cccc2ccc(CNCCOCCO)nc12)c1ccc(C(F)(F)F)cc1]

A similar procedure to that described for the preparation of compound (ZDR022) was followed using compound (ZDR019) (100 mg, 0.26 mmol), 2-(2-aminoethoxy)ethanol (79 μL, 0.78 mmol) and sodium triacetoxyborohydride (111 mg, 0.52 mmol) in 1,2-dichloroethane (5 mL). Purification by flash chromatography (dichloromethane/methanol, 40:1→20:1→15:1) afforded compound (ZDR129) as a pale orange solid (81 mg, 0.17 mmol, 65%). $^1$H NMR (300 MHz, CDCl$_3$) δ 2.98 (2H, t, J=5.0 Hz), 3.70 (2H, t, J=5.0 Hz), 3.76 (2H, t, J=5.0 Hz), 3.84 (2H, t, J=5.0 Hz), 4.16 (2H, s), 7.29 (1H, d, J=8.4 Hz), 7.34-7.42 (2H, m), 7.56 (2H, d, J=8.3 Hz), 7.79 (1H, dd, J=7.0 and 1.9 Hz), 7.96 (1H, d, J=8.4 Hz), 8.03 (2H, d, J=8.3 Hz); ESI-MS: m/z calcd for $C_{21}H_{22}F_3N_3O_4S$: 469.1; found [M+H]$^+$: 470.1.

Example 90: N-(2-(((2-(2-(2-Hydroxyethoxy)ethoxy)ethyl)amino)methyl)quinolin-8-yl)-4-(trifluoromethyl)benzenesulfonamide—Compound (ZDR130)

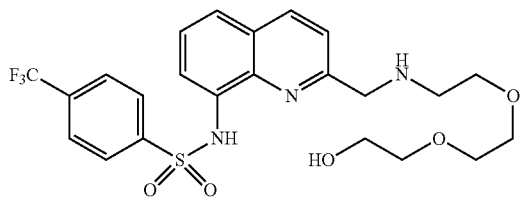 [SMILES: O=S(=O)(Nc1cccc2ccc(CNCCOCCOCCO)nc12)c1ccc(C(F)(F)F)cc1]

A similar procedure to that described for the preparation of compound (ZDR022) was followed using compound (ZDR019) (100 mg, 0.26 mmol), 2-(2-(2-aminoethoxy)ethoxy)ethanol (109 μL, 0.78 mmol) and sodium triacetoxyborohydride (111 mg, 0.52 mmol) in 1,2-dichloroethane (5 mL). Purification by flash chromatography (dichloromethane/methanol, 40:1→20:1→15:1) afforded compound (ZDR130) as a pale orange solid (81 mg, 0.15 mmol, 57%). $^1$H NMR (300 MHz, CDCl$_3$) δ 2.90 (2H, t, J=5.0 Hz), 3.63 (2H, t, J=5.0 Hz), 3.69-3.78 (8H, m), 4.14 (2H, s), 6.44 (1H, br s), 7.33 (1H, d, J=8.4 Hz), 7.37-7.48 (2H, m), 7.54 (2H, d, J=8.3 Hz), 7.85 (1H, dd, J=7.1 and 1.7 Hz), 7.97-8.03 (3H, m); ESI-MS: m/z calcd for $C_{23}H_{26}F_3N_3O_5S$: 513.2; found [M+H]$^+$: 514.2.

Example 91: N-(2-(((2-(2-Methoxyethoxy)ethyl)amino)methyl)quinolin-8-yl)-4-(trifluoromethyl)benzenesulfonamide—Compound (ZDR131)

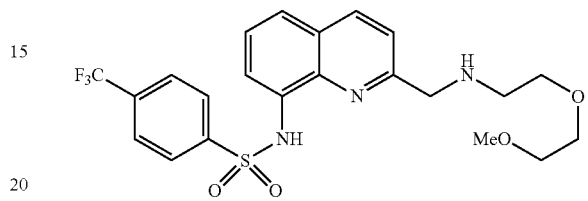

A similar procedure to that described for the preparation of compound (ZDR022) was followed using compound (ZDR019) (100 mg, 0.26 mmol), 2-(2-methoxyethoxy)ethanamine (97 μL, 0.78 mmol) and sodium triacetoxyborohydride (111 mg, 0.52 mmol) in 1,2-dichloroethane (5 mL). Purification by flash chromatography (dichloromethane/methanol, 40:1→30:1→20:1) afforded compound (ZDR131) as a pale yellow solid (80 mg, 0.16 mmol, 61%). $^1$H NMR (300 MHz, CDCl$_3$) δ 2.95 (2H, t, J=5.1 Hz), 3.35 (3H, s), 3.59 (2H, t, J=5.1 Hz), 3.66-3.76 (4H, m), 4.16 (2H, s), 7.37-7.48 (3H, m), 7.56 (2H, d, J=8.3 Hz), 7.83 (1H, dd, J=7.3 and 1.5 Hz), 8.00 (2H, d, J=8.3 Hz), 8.03 (1H, d, J=8.4 Hz); ESI-MS: m/z calcd for $C_{22}H_{24}F_3N_3O_4S$: 483.1; found [M+H]$^+$: 484.2.

Example 92: N-(2-(5,8,11-Trioxa-2-azadodecyl)quinolin-8-yl)-4-(trifluoromethyl)benzenesulfonamide—Compound (ZDR132)

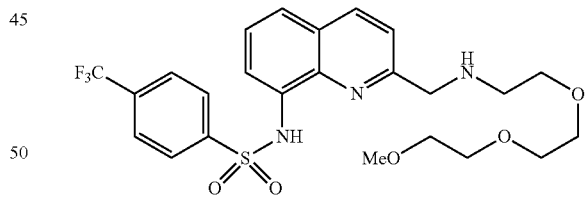

A similar procedure to that described for the preparation of compound (ZDR022) was followed using compound (ZDR019) (100 mg, 0.26 mmol), 2-(2-(2-methoxyethoxy)ethoxy)ethanamine (128 μL, 0.78 mmol) and sodium triacetoxyborohydride (111 mg, 0.52 mmol) in 1,2-dichloroethane (5 mL). Purification by flash chromatography (dichloromethane/methanol, 40:1→30:1→20:1) afforded compound (ZDR132) as a pale orange solid (75 mg, 0.14 mmol, 53%). $^1$H NMR (300 MHz, CDCl$_3$) δ 2.92 (2H, t, J=5.1 Hz), 3.29 (3H, s), 3.48-3.51 (2H, m), 3.62-3.65 (2H, m), 3.69-3.72 (6H, m), 4.13 (2H, s), 7.37-7.48 (3H, m), 7.55 (2H, d, J=8.2 Hz), 7.82 (1H, dd, J=7.2 and 1.5 Hz), 7.97 (2H, d, J=8.2 Hz), 8.03 (1H, d, J=8.4 Hz); ESI-MS: m/z calcd for $C_{24}H_{28}F_3N_3O_5S$: 527.2; found [M+H]$^+$: 528.2.

Example 93: N-(2-(((2-Methoxyethyl)amino) methyl)quinolin-8-yl)-4-(trifluoromethyl)benzenesulfonamide—Compound (ZDR133)

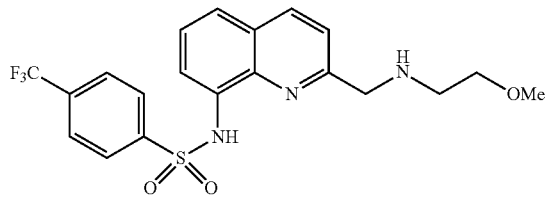 [SMILES: COCCNCc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), 2-methoxyethylamine (67 μL, 0.78 mmol) and sodium triacetoxyborohydride (111 mg, 0.52 mmol) in 1,2-dichloroethane (5 mL). Purification by flash chromatography (dichloromethane/methanol, 40:1→20:1→15:1) afforded compound (ZDR133) as a pale yellow solid (69 mg, 0.15 mmol, 57%). $^1$H NMR (300 MHz, CDCl$_3$) δ 2.91 (2H, t, J=5.1 Hz), 3.46 (3H, s), 3.61 (2H, t, J=5.1 Hz), 4.14 (2H, s), 7.36 (1H, d, J=8.4 Hz), 7.40-7.50 (2H, m), 7.57 (2H, d, J=8.3 Hz), 7.87 (1H, dd, J=7.3 and 1.5 Hz), 7.98 (2H, d, J=8.3 Hz), 8.05 (1H, d, J=8.4 Hz); ESI-MS: m/z calcd for C$_{20}$H$_{20}$F$_3$N$_3$O$_3$S: 439.1; found [M+H]$^+$: 440.1.

Example 94: N-(2-((tert-Butylamino)methyl)quinolin-8-yl)-4-(trifluoromethyl)benzenesulfonamide—Compound (ZDR135)

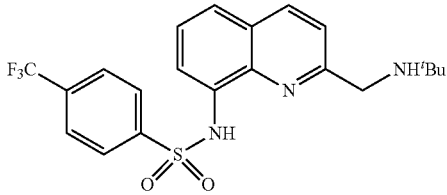

A similar procedure to that described for the preparation of compound (ZDR022) was followed using compound (ZDR019) (100 mg, 0.26 mmol), tert-butylamine (81 μL, 0.78 mmol) and sodium triacetoxyborohydride (111 mg, 0.52 mmol) in 1,2-dichloroethane (5 mL). Purification by flash chromatography (dichloromethane/methanol, 40:1→30:1→20:1) afforded compound (ZDR135) as a pale orange solid (75 mg, 0.17 mmol, 65%). $^1$H NMR (300 MHz, CDCl$_3$) δ 1.24 (9H, s), 4.13 (2H, s), 7.35-7.43 (3H, m), 7.57 (2H, d, J=8.3 Hz), 7.78 (1H, dd, J=7.0 and 1.8 Hz), 7.98 (1H, d, J=8.5 Hz), 8.02 (2H, d, J=8.3 Hz); ESI-MS: m/z calcd for C$_{21}$H$_{22}$F$_3$N$_3$O$_2$S: 437.1; found [M+H]$^+$: 438.1.

Example 95: N-(2-((Diisopropylamino)methyl)quinolin-8-yl)-4-(trifluoromethyl)benzenesulfonamide—Compound (ZDR136)

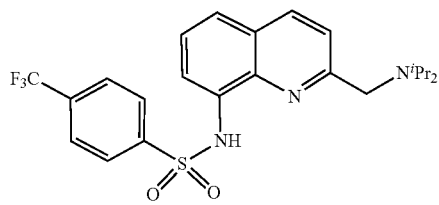

A similar procedure to that described for the preparation of compound (ZDR022) was followed using compound (ZDR019) (100 mg, 0.26 mmol), diisopropylamine (109 μL, 0.78 mmol) and sodium triacetoxyborohydride (111 mg, 0.52 mmol) in 1,2-dichloroethane (5 mL). Purification by flash chromatography (dichloromethane/methanol, 40:1→30:1→20:1) afforded compound (ZDR136) as a white solid (40 mg, 0.08 mmol, 30%). $^1$H NMR (300 MHz, CDCl$_3$) δ 1.03 (12H, d, J=6.5 Hz), 2.96-3.08 (2H, m), 3.86 (2H, s), 7.36-7.49 (2H, m), 7.58 (2H, d, J=8.3 Hz), 7.76-7.82 (2H, m), 7.98-8.03 (3H, m); ESI-MS: m/z calcd for C$_{23}$H$_{26}$F$_3$N$_3$O$_2$S: 465.2; found [M+H]$^+$: 466.2.

Example 96: (E)-N-(2-(((Benzyloxy)imino)methyl) quinolin-8-yl)-4-(trifluoromethyl)benzenesulfonamide—Compound (ZDR137)

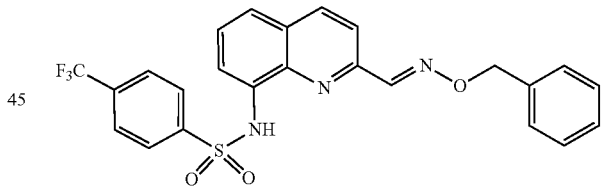

A similar procedure to that described for the preparation of compound (ZDR118) was followed using compound (ZDR019) (100 mg, 0.26 mmol), benzyloxyamine hydrochloride (41 mg, 0.26 mmol) and sodium acetate (43 mg, 0.52 mmol) in ethanol (10 mL). Purification by flash chromatography (dichloromethane/methanol, 50:1) afforded compound (ZDR137) as a white solid (75 mg, 0.15 mmol, 57%). $^1$H NMR (400 MHz, d$_6$-acetone) δ 5.32 (2H, s), 7.34-7.47 (3H, m), 7.49 (2H, d, J=8.4 Hz), 7.57 (1H, t, J=7.9 Hz), 7.67 (1H, dd, J=8.4 and 1.2 Hz), 7.81 (2H, d, J=8.4 Hz), 7.90 (1H, dd, J=7.6 and 1.2 Hz), 7.98 (1H, d, J=7.6 Hz), 8.15 (2H, d, J=8.4 Hz), 8.30 (1H, d, J=8.4 Hz), 8.36 (1H, s), 9.59 (1H, s); ESI-MS: m/z calcd for C$_{24}$H$_{18}$F$_3$N$_3$O$_3$S: 485.1; found [M+Na]$^+$: 508.1.

Example 97: (E)-N-(2-((2-Benzylhydrazineylidene)methyl)quinolin-8-yl)-4-(trifluoromethyl)benzenesulfonamide—Compound (ZDR138)

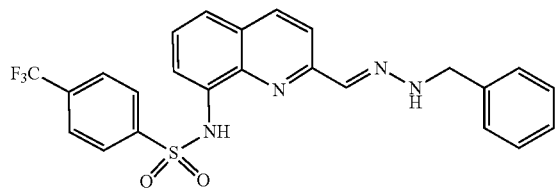 [SMILES: O=S(=O)(Nc1cccc2ccc(/C=N/NCc3ccccc3)nc12)c1ccc(C(F)(F)F)cc1]

A similar procedure to that described for the preparation of compound (ZDR118) was followed using compound (ZDR019) (100 mg, 0.26 mmol), benzylhydrazine dihydrochloride (50 mg, 0.26 mmol) and sodium acetate (43 mg, 0.52 mmol) in ethanol (10 mL). Purification by flash chromatography (dichloromethane/methanol, 50:1) afforded compound (ZDR138) as a yellow solid (70 mg, 0.14 mmol, 53%). $^1$H NMR (400 MHz, CDCl$_3$) δ 4.56 (2H, d, J=4.6 Hz), 6.28 (1H, t, J=4.6 Hz), 7.34-7.45 (7H, m), 7.59 (2H, d, J=8.4 Hz), 7.70 (1H, s), 7.77 (1H, dd, J=7.7 and 1.3 Hz), 7.98-8.00 (4H, m); ESI-MS: m/z calcd for C$_{24}$H$_{19}$F$_3$N$_4$O$_2$S: 484.1; found [M+H]$^+$: 485.1.

Example 98: N-(2-(((N,N'-Bis-Boc-2-Guanidinoethyl)amino)methyl)quinolin-8-yl)-4-(trifluoromethyl)benzenesulfonamide—Compound (ZDR139)

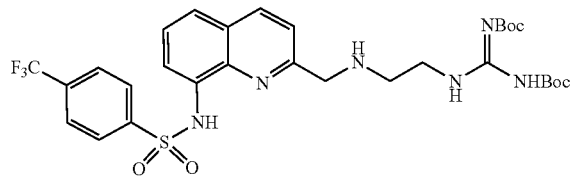

A similar procedure to that described for the preparation of compound (ZDR022) was followed using compound (ZDR019) (100 mg, 0.26 mmol), compound (ZDR140) (235 mg, 0.78 mmol) and sodium triacetoxyborohydride (111 mg, 0.52 mmol) in 1,2-dichloroethane (5 mL). Purification by flash chromatography (dichloromethane/methanol, 40:1→30:1→20:1) afforded compound (ZDR139) as a pale yellow solid (120 mg, 0.17 mmol, 65%). $^1$H NMR (300 MHz, CDCl$_3$) δ 1.45 (9H, s), 1.48 (9H, s), 2.86 (2H, t, J=5.9 Hz), 3.52-3.58 (2H, m), 4.07 (2H, s), 7.35-7.46 (2H, m), 7.55-7.59 (3H, m), 7.79 (1H, dd, J=7.3 and 1.4 Hz), 7.98 (2H, d, J=8.3 Hz), 8.02 (1H, d, J=8.4 Hz), 8.70-8.73 (1H, m), 11.49 (1H, br s).

Example 99: 1-(2-Aminoethyl)-N,N'-Bis-Boc-guanidine—Compound (ZDR140)

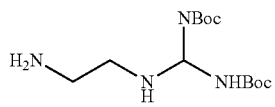

A solution of N,N'-Bis-Boc-1-guanylpyrazol (1.0 g, 3.22 mmol) in dichloromethane (10 mL) was added dropwise to a solution of 1,2-diaminoethane (2.1 mL, 32.2 mmol) in dichloromethane (10 mL), and the mixture stirred at room temperature for 18 h. The mixture was then washed with water (5×20 mL) and the separated organic layer dried over anhydrous magnesium sulfate, filtered and the filtrate concentrated in vacuo. Purification by flash chromatography (ethyl acetate) afforded compound (ZDR140) as an off-white solid (800 mg, 2.64 mmol, 81%). $^1$H NMR (300 MHz, CDCl$_3$) δ 1.48 (18H, s), 2.88 (2H, t, J=5.9 Hz), 3.44-3.50 (2H, m), 8.63 (1H, br s).

Example 100: tert-Butyl (E)-(2-(2-nitroguanidino)ethyl)carbamate—Compound (ZDR141)

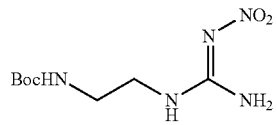 [SMILES: CC(C)(C)OC(=O)NCCN/C(N)=N/[N+](=O)[O-]]

A solution of N-Boc-ethylenediamine (1.0 g, 6.24 mmol) and N-nitro-S-methylisothiourea (0.84 g, 6.24 mmol) in ethanol (30 mL) was heated at 60° C. for 18 h. The solvent was then removed in vacuo to afford compound (ZDR141) as a white solid (1.5 g), which was used without further purification. $^1$H NMR (300 MHz, d$_6$-DMSO) δ 1.37 (9H, s), 3.06-3.10 (2H, m), 3.17-3.21 (2H, m), 6.86-6.88 (1H, m).

Example 101: (E)-1-(2-Aminoethyl)-2-nitroguanidine trifluoroacetate—Compound (ZDR142)

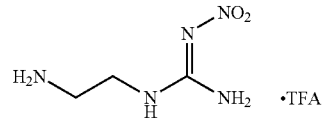

A similar procedure to that described for the preparation of compound (ZDR124) was followed using compound (ZDR141) (192 mg, 0.78 mmol) and trifluoroacetic acid-dichloromethane (3 mL, 50% v/v) to afford compound (ZDR142) as a colourless oil (190 mg, 0.78 mmol, quant.), which was used without further purification.

Example 102: N-(2-(((2-Guanidinoethyl)amino)methyl)quinolin-8-yl)-4-(trifluoromethyl)benzenesulfonamide di-trifluoroacetate—Compound (ZDR143)

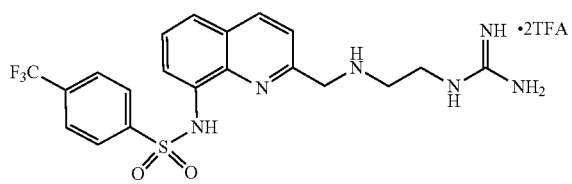 [SMILES: N=C(N)NCCNCc1ccc2cccc(NS(=O)(=O)c3ccc(C(F)(F)F)cc3)c2n1]

A similar procedure to that described for the preparation of compound (ZDR124) was followed using compound (ZDR139) (100 mg, 0.14 mmol) and trifluoroacetic acid-dichloromethane (3 mL, 50% v/v) to afford compound (ZDR143) as a white solid (92 mg, 0.14 mmol, quant.), which was used without further purification. $^1$H NMR (300 MHz, d$_4$-MeOH) δ 3.48 (2H, t, J=6.2 Hz), 3.77 (2H, t, J=6.2 Hz), 4.68 (2H, s), 7.48-7.56 (2H, m), 7.61 (1H, dd, J=8.3 and 1.1 Hz), 7.77 (2H, d, J=8.3 Hz), 7.83 (1H, dd, J=7.7 and 1.1 Hz), 8.15 (2H, d, J=8.3 Hz), 8.33 (1H, d, J=8.4 Hz); ESI-MS: m/z calcd for C$_{20}$H$_{21}$F$_3$N$_6$O$_2$S: 466.1; found [M+H]$^+$: N/A.

Example 103: (E)-N-(2-(((2-(2-Nitroguanidino) ethyl)amino)methyl)quinolin-8-yl)-4-(trifluoromethyl)benzenesulfonamide—Compound (ZDR145)

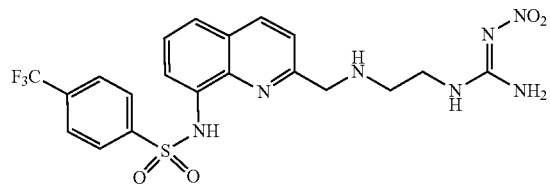 [SMILES: N/C(=N\[N+](=O)[O-])NCCNCc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), compound (ZDR142) (190 mg, ca. 0.78 mmol) and sodium triacetoxyborohydride (111 mg, 0.52 mmol) in 1,2-dichloroethane (5 mL). Purification by flash chromatography (dichloromethane/methanol, 40:1→30:1→20:1) afforded compound (ZDR145) as a white solid (80 mg, 0.15 mmol, 57%). $^1$H NMR (300 MHz, d$_6$-DMSO) δ 2.71 (2H, t, J=5.8 Hz), 3.31 (2H, t, J=5.8 Hz), 3.95 (2H, s), 7.45-7.53 (2H, m), 7.63-7.73 (2H, m), 7.79 (2H, d, J=8.3 Hz), 8.01 (2H, d, J=8.3 Hz), 8.24 (1H, d, J=8.4 Hz); ESI-MS: m/z calcd for C$_{20}$H$_{20}$F$_3$N$_7$O$_4$S: 511.1; found [M+H]$^+$: 512.2.

Example 104: tert-Butyl (2-acetamidoethyl)carbamate—Compound (ZDR146)

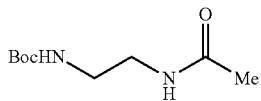 [SMILES: CC(=O)NCCNC(=O)OC(C)(C)C]

A solution of N-Boc-ethylenediamine (1.0 g, 6.24 mmol), acetyl chloride (443 μL, 6.24 mmol) and triethylamine (2.6 mL, 18.7 mmol) in dichloromethane (30 mL) was stirred at room temperature for 18 h. The mixture was then washed with water (2×20 mL) and the separated organic layer dried over anhydrous magnesium sulfate, filtered and the filtrate concentrated in vacuo. Purification by flash chromatography (dichloromethane) afforded compound (ZDR146) as a white solid (900 mg, 4.44 mmol, 71%). $^1$H NMR (300 MHz, CDCl$_3$) δ 1.29 (9H, s) 1.84 (3H, s), 3.07-3.15 (2H, m), 3.16-3.23 (2H, m), 5.57 (1H, t, J=5.3 Hz), 7.11 (1H, t, J=5.3 Hz).

Example 105: N-(2-Aminoethyl)acetamide trifluoroacetate—Compound (ZDR147)

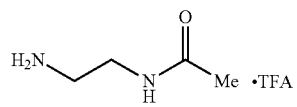

A similar procedure to that described for the preparation of compound (ZDR124) was followed using compound (ZDR146) (157 mg, 0.78 mmol) and trifluoroacetic acid-dichloromethane (3 mL, 50% v/v) to afford compound (ZDR147) as a colourless oil (150 mg, 0.78 mmol, quant.), which was used without further purification.

Example 106: N-(2-(((8-((4-(Trifluoromethyl)phenyl)sulfonamido)quinolin-2-yl)methyl)amino)ethyl) acetamide—Compound (ZDR148)

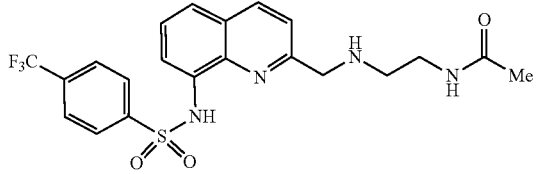 [SMILES: CC(=O)NCCNCc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), compound (ZDR147) (150 mg, ca. 0.78 mmol) and sodium triacetoxyborohydride (111 mg, 0.52 mmol) in 1,2-dichloroethane (5 mL). Purification by flash chromatography (dichloromethane/methanol, 40:1→30:1→20:1) afforded compound (ZDR148) as a pale yellow solid (80 mg, 0.17 mmol, 65%). $^1$H NMR (300 MHz, CDCl$_3$) δ 1.99 (3H, s), 2.92 (2H, t, J=6.1 Hz), 3.44-3.49 (2H, m), 4.11 (2H, s), 7.38-7.47 (3H, m), 7.54 (2H, d, J=8.3 Hz), 7.77 (1H, dd, J=7.5 and 1.4 Hz), 7.98 (2H, d, J=8.3 Hz), 8.04 (1H, d, J=8.4 Hz); ESI-MS: m/z calcd for C$_{21}$H$_{21}$F$_3$N$_4$O$_3$S: 466.1; found [M+H]$^+$: 467.1.

Example 107: (E)-N-(2-((2-Methylhydrazinylidene)methyl)quinolin-8-yl)-4-(trifluoromethyl) benzenesulfonamide—Compound (ZDR153)

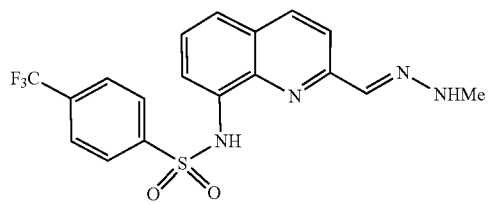 [SMILES: CN/N=C/c1ccc2cccc(NS(=O)(=O)c3ccc(C(F)(F)F)cc3)c2n1]

A similar procedure to that described for the preparation of compound (ZDR118) was followed using compound (ZDR019) (100 mg, 0.26 mmol), methylhydrazine dihydrochloride (21 mg, 0.26 mmol) and sodium acetate (43 mg, 0.52 mmol) in ethanol (10 mL). Purification by flash chromatography (dichloromethane/methanol, 50:1) afforded compound (ZDR153) as a yellow solid (72 mg, 0.17 mmol, 65%). $^1$H NMR (300 MHz, CDCl$_3$) δ 3.10 (3H, s), 7.32-7.43 (2H, m), 7.61-7.63 (3H, m), 7.76 (1H, dd, J=7.6 and 1.3 Hz), 7.92-8.03 (4H, m); ESI-MS: m/z calcd for C$_{18}$H$_{15}$F$_3$N$_4$O$_2$S: 408.1; found [M+H]$^+$: 409.1.

Example 108: N-(2-((Dimethylamino)methyl)quinolin-8-yl)benzene-1,4-disulfonamide—Compound (ZDR154)

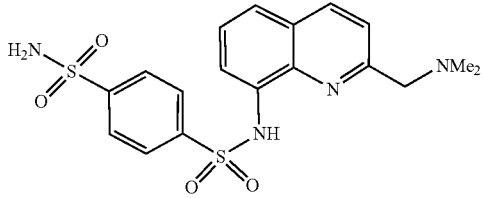 [SMILES: CN(C)Cc1ccc2cccc(NS(=O)(=O)c3ccc(S(N)(=O)=O)cc3)c2n1]

A similar procedure to that described for the preparation of compound (ZDR018) was followed using compound (ZDR059) (90 mg, 0.44 mmol), 4-(aminosulfonyl)benzenesulfonyl chloride (125 mg, 0.49 mmol) and triethylamine (68 μL, 0.49 mmol) in dichloromethane (5 mL). Purification by flash chromatography (dichloromethane/methanol, 20:1→15:1→10:1) afforded compound (ZDR154) as a pale yellow solid (50 mg, 0.11 mmol, 25%). $^1$H NMR (300 MHz, CDCl$_3$/d$_4$-MeOH, 1:1) δ 2.34 (6H, s), 3.75 (2H, s), 4.51 (2H, br s), 7.32 (1H, d, J=8.3 Hz), 7.37-7.41 (1H, m), 7.48 (1H, dd, J=7.4 and 1.2 Hz), 7.83-7.86 (3H, m), 7.99 (2H, 8.5 Hz), 8.07 (1H, d, J=8.3 Hz); ESI-MS: m/z calcd for C$_{18}$H$_{20}$N$_4$O$_4$S$_2$: 420.1; found [M+H]$^+$: 421.1.

Example 109: N-(2-((Dimethylamino)methyl)quinolin-8-yl)benzene-1,3-disulfonamide—Compound (ZDR155)

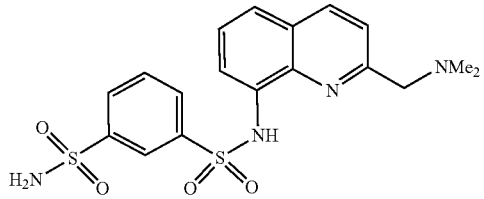 [SMILES: CN(C)Cc1ccc2cccc(NS(=O)(=O)c3cccc(S(N)(=O)=O)c3)c2n1]

A similar procedure to that described for the preparation of compound (ZDR018) was followed using compound (ZDR059) (90 mg, 0.44 mmol), 3-(aminosulfonyl)benzenesulfonyl chloride (125 mg, 0.49 mmol) and triethylamine (68 μL, 0.49 mmol) in dichloromethane (5 mL). Purification by flash chromatography (dichloromethane/methanol, 20:1→15:1→10:1) afforded compound (ZDR155) as a pale yellow solid (57 mg, 0.13 mmol, 29%). $^1$H NMR (300 MHz, CDCl$_3$/d$_4$-MeOH, 1:1) δ 2.38 (6H, s), 3.81 (2H, s), 4.53 (2H, br s), 7.32 (1H, d, J=8.4 Hz), 7.39-7.51 (3H, m), 7.87 (1H, dd, J=7.4 and 1.3 Hz), 7.91-7.94 (1H, m), 7.95-7.99 (1H, m), 8.08 (1H, d, J=8.4 Hz), 8.49-8.50 (1H, m); ESI-MS: m/z calcd for C$_{18}$H$_{20}$N$_4$O$_4$S$_2$: 420.1; found [M+H]$^+$: 421.1.

Example 110: 4-Amino-N-(2-((dimethylamino)methyl)quinolin-8-yl)benzenesulfonamide—Compound (ZDR160)

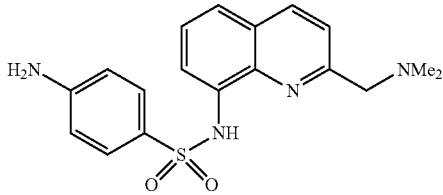

A similar procedure to that described for the preparation of compound (ZDR124) was followed using compound (ZDR333) (60 mg, 0.13 mmol) and trifluoroacetic acid-dichloromethane (3 mL, 50% v/v). The residue was then taken up in dichloromethane (10 mL), diluted with water and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/methanol, 30:1→20:1) afforded compound (ZDR160) as a white solid (40 mg, 0.11 mmol, 84%). $^1$H NMR (300 MHz, CDCl$_3$) δ 2.29 (6H, s), 3.71 (2H, s), 4.02 (2H, br s), 6.47 (2H, d, J=8.6 Hz), 7.34-7.42 (2H, m), 7.56 (1H, d, J=8.4 Hz), 7.64 (2H, d, J=8.6 Hz), 7.74 (1H, dd, J=6.7 and 2.2 Hz), 8.03 (1H, d, J=8.4 Hz); ESI-MS: m/z calcd for C$_{18}$H$_{20}$N$_4$O$_2$S: 356.1; found [M+H]$^+$: 357.1.

Example 111: 3-Amino-N-(2-((dimethylamino)methyl)quinolin-8-yl)benzenesulfonamide—Compound (ZDR162)

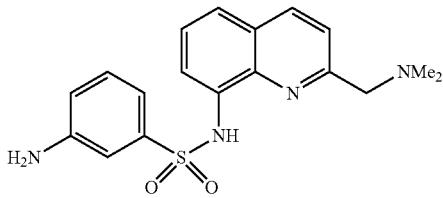

A suspension of compound (ZR313) (60 mg, 0.15 mmol) and palladium-on-carbon (cat., 10% w/w) in methanol (10 mL) was stirred at room temperature under an atmosphere of hydrogen for 18 h. The mixture was then filtered through a pad of Celite® and the solvent removed in vacuo. Purification by flash chromatography (dichloromethane/methanol, 20:1) afforded compound (ZDR162) as a pale yellow solid (45 mg, 0.12 mmol, 80%). $^1$H NMR (300 MHz, CDCl$_3$) δ 2.31 (6H, s), 3.74 (2H, s), 3.78 (2H, br s), 6.64-6.70 (1H, m), 7.07 (1H, t, J=7.8 Hz), 7.18-7.21 (2H, m), 7.36-7.46 (2H, m), 7.56 (1H, d, J=8.4 Hz), 7.77 (1H, dd, J=7.0 and 1.8 Hz), 8.05 (1H, d, J=8.4 Hz); ESI-MS: m/z calcd for C$_{18}$H$_{20}$N$_4$O$_2$S: 356.1; found [M+H]$^+$: 357.1.

Example 112: N-(2-((Dimethylamino)methyl)quinolin-8-yl)-3-hydroxybenzenesulfonamide—Compound (ZDR163)

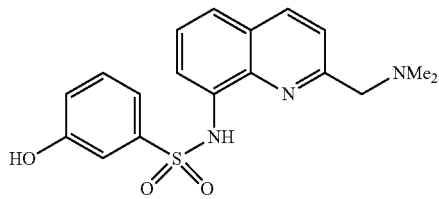 [SMILES: CN(C)Cc1ccc2cccc(NS(=O)(=O)c3cccc(O)c3)c2n1]

A solution of compound (ZDR314) (75 mg, 0.20 mmol) and boron tribromide (400 μL, 0.40 mmol, 1 M in dichloromethane) in dichloromethane (2 mL) was stirred at room temperature for 2 h. The mixture was then diluted with dichloromethane/methanol (25 mL, 9:1 v/v), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/methanol, 30:1→20:1→15:1) afforded compound (ZDR163) as a beige solid (45 mg, 0.12 mmol, 60%). $^1$H NMR (300 MHz, CDCl$_3$/d$_4$-MeOH, 3:1 v/v) δ 2.31 (6H, s), 3.74 (2H, s), 6.80-6.83 (1H, m), 7.08 (1H, t, J=7.9 Hz), 7.27-7.40 (5H, m), 7.76 (1H, dd, J=7.4 and 1.4 Hz), 8.01 (1H, d, J=8.4 Hz); ESI-MS: m/z calcd for C$_{18}$H$_{19}$N$_3$O$_3$S: 357.1; found [M+H]$^+$: 358.1.

Example 113: N-(2-((Dimethylamino)methyl)quinolin-8-yl)-4-hydroxybenzenesulfonamide—Compound (ZDR164)

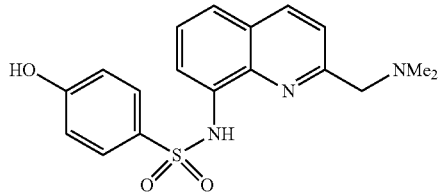

A similar procedure to that described for the preparation of compound (ZDR163) was followed using compound (ZDR063) (75 mg, 0.20 mmol) and boron tribromide (400 μL, 0.40 mmol, 1 M in dichloromethane) in dichloromethane (2 mL). Purification by flash chromatography (dichloromethane/methanol, 20:1→15:1) afforded compound (ZDR164) as a white solid (53 mg, 0.14 mmol, 70%). $^1$H NMR (400 MHz, CDCl$_3$) δ 2.35 (6H, s), 3.76 (2H, s), 6.49 (2H, d, J=8.8 Hz), 7.41-7.42 (2H, m), 7.45 (1H, d, J=8.4 Hz), 7.54 (2H, d, J=8.8 Hz), 7.85 (1H, dd, J=7.4 and 1.4 Hz), 8.01 (1H, d, J=8.4 Hz); ESI-MS: m/z calcd for C$_{18}$H$_{19}$N$_3$O$_3$S: 357.1; found [M+H]$^+$: 358.1.

Example 114: N-(2-(((3,5-Dichloro-2-hydroxyphenyl)amino)methyl)quinolin-8-yl)-4-(trifluoromethyl)benzenesulfonamide—Compound (ZDR167)

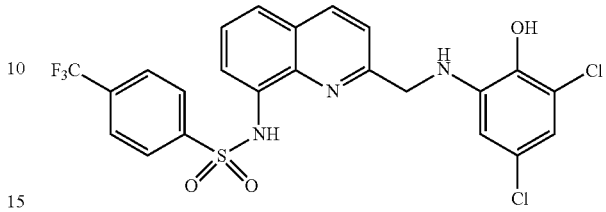

A similar procedure to that described for the preparation of compound (ZDR022) was followed using compound (ZDR019) (100 mg, 0.26 mmol), 2-amino-4,6-dichlorophenol (138 mg, 0.78 mmol) and sodium triacetoxyborohydride (111 mg, 0.52 mmol) in 1,2-dichloroethane (5 mL). Purification by flash chromatography (dichloromethane/methanol, 100:1) afforded compound (ZDR167) as an orange solid (55 mg, 0.10 mmol, 38%). $^1$H NMR (300 MHz, CDCl$_3$) δ 4.63 (2H, s), 5.57 (1H, br s), 6.54 (1H, d, J=2.3 Hz), 6.71 (1H, d, J=2.3 Hz), 7.37-7.49 (3H, m), 7.56 (2H, d, J=8.3 Hz), 7.80 (1H, dd, J=7.3 and 1.4 Hz), 7.94 (2H, d, J=8.3 Hz), 8.07 (1H, d, J=8.4 Hz); ESI-MS: m/z calcd for C$_{23}$H$_{16}$Cl$_2$F$_3$N$_3$O$_3$S: 541.0; found [M+H]$^+$: 541.9.

Example 115: N-(2-(((2-Hydroxy-5-nitrophenyl)amino)methyl)quinolin-8-yl)-4-(trifluoromethyl)benzenesulfonamide—Compound (ZDR170)

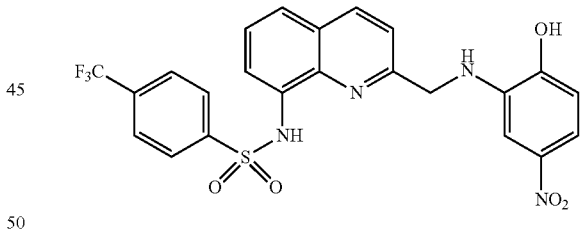

A similar procedure to that described for the preparation of compound (ZDR022) was followed using compound (ZDR019) (100 mg, 0.26 mmol), 2-amino-4-nitrophenol (120 mg, 0.78 mmol) and sodium triacetoxyborohydride (111 mg, 0.52 mmol) in 1,2-dichloroethane (5 mL). Purification by flash chromatography (dichloromethane/methanol, 100:1) afforded compound (ZDR170) as an orange solid (25 mg, 0.04 mmol, 15%). $^1$H NMR (300 MHz, CDCl$_3$) δ 4.77 (2H, s), 6.89-6.93 (1H, m), 7.38-7.43 (2H, m), 7.49 (1H, dd, J=8.2 and 1.3 Hz), 7.56 (2H, d, J=8.3 Hz), 7.59-7.63 (2H, m), 7.73 (1H, dd, J=7.5 and 1.3 Hz), 7.90 (2H, d, J=8.3 Hz), 8.09 (1H, d, J=8.4 Hz); ESI-MS: m/z calcd for C$_{23}$H$_{17}$F$_3$N$_4$O$_5$S: 518.1; found [M+Na]$^+$:541.1.

Example 116: N-(2-(((2-Hydroxyphenyl)amino)methyl)quinolin-8-yl)-4-(trifluoromethyl)benzenesulfonamide—Compound (ZDR171)

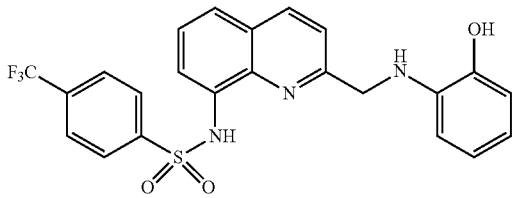 [SMILES: O=S(=O)(Nc1cccc2ccc(CNc3ccccc3O)nc12)c1ccc(C(F)(F)F)cc1]

A similar procedure to that described for the preparation of compound (ZDR022) was followed using compound (ZDR019) (100 mg, 0.26 mmol), 2-aminophenol (85 mg, 0.78 mmol) and sodium triacetoxyborohydride (111 mg, 0.52 mmol) in 1,2-dichloroethane (5 mL). Purification by flash chromatography (dichloromethane/methanol, 100:1) afforded compound (ZDR171) as an orange solid (38 mg, 0.08 mmol, 30%). $^1$H NMR (300 MHz, CDCl$_3$) δ 4.73 (2H, s), 6.61-6.66 (1H, m), 6.74-6.85 (3H, m), 7.37 (2H, d, J=8.3 Hz), 7.44 (1H, dd, J=8.3 and 1.1 Hz), 7.48 (2H, d, J=8.3 Hz), 7.75 (1H, dd, J=7.4 and 1.1 Hz), 7.84 (2H, d, J=8.3 Hz), 8.02 (1H, d, J=8.3 Hz); ESI-MS: m/z calcd for C$_{23}$H$_{18}$F$_3$N$_3$O$_3$S: 473.1; found [M+H]$^+$: 474.1.

Example 117: tert-Butyl (2-(methylsulfonamido)ethyl)carbamate—Compound (ZDR173)

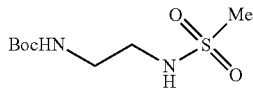

A similar procedure to that described for the preparation of compound (ZDR146) was followed using N-Boc-ethylenediamine (1.0 g, 6.24 mmol), methanesulfonyl chloride (482 µL, 6.24 mmol) and triethylamine (2.6 mL, 18.7 mmol) in dichloromethane (30 mL). Purification by flash chromatography (dichloromethane/methanol, 40:1) afforded compound (ZDR173) as a white solid (1.20 g, 5.03 mmol, 80%). $^1$H NMR (300 MHz, CDCl$_3$/d$_4$-MeOH, 1:1 v/v) δ 1.41 (9H, s), 2.93 (3H, s), 3.11-3.23 (4H, m).

Example 118: tert-Butyl (2-(phenylsulfonamido)ethyl)carbamate—Compound (ZDR174)

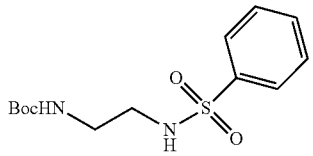

A similar procedure to that described for the preparation of compound (ZDR146) was followed using N-Boc-ethylenediamine (1.0 g, 6.24 mmol), benzenesulfonyl chloride (796 µL, 6.24 mmol) and triethylamine (2.6 mL, 18.7 mmol) in dichloromethane (30 mL). Purification by flash chromatography (dichloromethane/methanol, 40:1) afforded compound (ZDR174) as a white solid (1.70 g, 5.65 mmol, 90%). $^1$H NMR (300 MHz, CDCl$_3$/d$_4$-MeOH, 1:1 v/v) δ 1.38 (9H, s), 2.96 (2H, t, J=6.1 Hz), 3.11-3.18 (2H, m), 7.45-7.57 (3H, m), 7.80-7.85 (2H, m).

Example 119: N-(2-Aminoethyl)benzenesulfonamide trifluoroacetate—Compound (ZDR178)

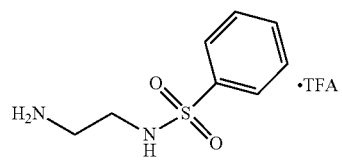

A similar procedure to that described for the preparation of compound (ZDR124) was followed using compound (ZDR174) (234 mg, 0.78 mmol) and trifluoroacetic acid-dichloromethane (3 mL, 50% v/v) to afford compound (ZDR178) as a colourless oil (230 mg, 0.78 mmol, quant.), which was used without further purification.

Example 120: N-(2-Aminoethyl)methanesulfonamide trifluoroacetate—Compound (ZDR179)

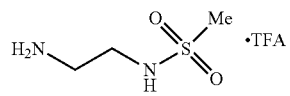

A similar procedure to that described for the preparation of compound (ZDR124) was followed using compound (ZDR173) (157 mg, 0.78 mmol) and trifluoroacetic acid-dichloromethane (3 mL, 50% v/v) to afford compound (ZDR179) as a colourless oil (185 mg, 0.78 mmol, quant.), which was used without further purification.

Example 121: N-(2-(Hydroxymethyl)quinolin-8-yl)-4-(trifluoromethyl)benzenesulfonamide—Compound (ZDR176)

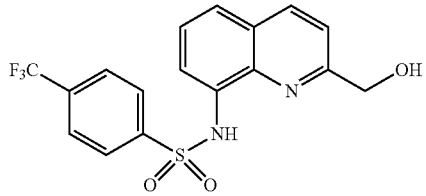 [SMILES: O=S(=O)(Nc1cccc2ccc(CO)nc12)c1ccc(C(F)(F)F)cc1]

A suspension of compound (ZDR019) (100 mg, 0.26 mmol) and sodium borohydride (14 mg, 0.39 mmol) in ethanol (5 mL) was stirred at room temperature for 18 h. The mixture was then diluted with dichloromethane (25 mL), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/

Example 122: N-(2-(((2-(Methylsulfonamido)ethyl)amino)methyl)quinolin-8-yl)-4-(trifluoromethyl)benzenesulfonamide—Compound (ZDR180)

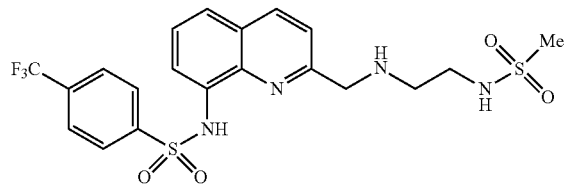 [SMILES: CS(=O)(=O)NCCNCc1ccc2cccc(NS(=O)(=O)c3ccc(C(F)(F)F)cc3)c2n1]

A similar procedure to that described for the preparation of compound (ZDR022) was followed using compound (ZDR019) (100 mg, 0.26 mmol), compound (ZDR179) (180 mg, ca. 0.78 mmol) and sodium triacetoxyborohydride (111 mg, 0.52 mmol) in 1,2-dichloroethane (5 mL). Purification by flash chromatography (dichloromethane/methanol, 20:1) afforded compound (ZDR180) as a pale yellow solid (63 mg, 0.12 mmol, 46%). $^1$H NMR (300 MHz, CDCl$_3$) δ 2.97-3.00 (2H, m), 2.99 (3H, s), 3.34-3.37 (2H, m), 3.98 (2H, s), 7.35 (1H, d, J=8.4 Hz), 7.38 (1H, d, J=7.4 Hz), 7.41 (1H, dd, J=8.3 and 1.4 Hz), 7.48 (2H, d, J=8.3 Hz), 7.74 (1H, dd, J=7.4 and 1.4 Hz), 7.97-8.01 (3H, m); ESI-MS: m/z calcd for C$_{20}$H$_{21}$F$_3$N$_4$O$_4$S$_2$: 502.1; found [M+H]$^+$: 503.1.

Example 123: N-(2-(((2-(Phenylsulfonamido)ethyl)amino)methyl)quinolin-8-yl)-4-(trifluoromethyl)benzenesulfonamide—Compound (ZDR181)

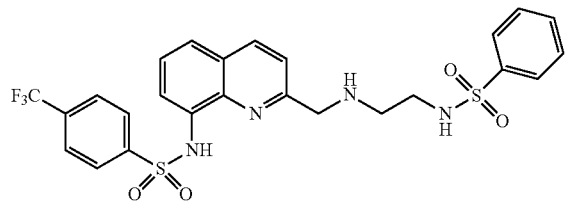 [SMILES: O=S(=O)(NCCNCc1ccc2cccc(NS(=O)(=O)c3ccc(C(F)(F)F)cc3)c2n1)c1ccccc1]

A similar procedure to that described for the preparation of compound (ZDR022) was followed using compound (ZDR019) (100 mg, 0.26 mmol), compound (ZDR178) (230 mg, ca. 0.78 mmol) and sodium triacetoxyborohydride (111 mg, 0.52 mmol) in 1,2-dichloroethane (5 mL). Purification by flash chromatography (dichloromethane/methanol, 20:1) afforded compound (ZDR181) as a pale yellow solid (59 mg, 0.10 mmol, 38%). $^1$H NMR (300 MHz, CDCl$_3$) δ 2.81-2.85 (2H, m), 3.10-3.14 (2H, m), 3.97 (2H, s), 7.36-7.54 (6H, m), 7.57 (2H, d, J=8.3 Hz), 7.77 (1H, dd, J=7.1 and 1.6 Hz), 7.85-7.88 (2H, m), 8.01-8.04 (3H, m); ESI-MS: m/z calcd for C$_{25}$H$_{23}$F$_3$N$_4$O$_4$S$_2$: 564.1; found [M+H]$^+$: 565.1.

Example 124: N-(2-(Aminomethyl)quinolin-8-yl)-4-(trifluoromethyl)benzenesulfonamide—Compound (ZDR184)

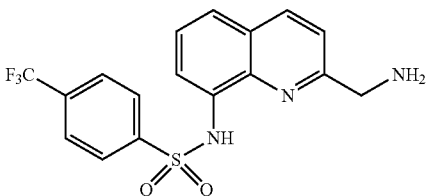 [SMILES: NCc1ccc2cccc(NS(=O)(=O)c3ccc(C(F)(F)F)cc3)c2n1]

A similar procedure to that described for the preparation of compound (ZDR162) was followed using compound (ZDR126) (100 mg, 0.25 mmol) and palladium-on-carbon (cat., 10% w/w) in methanol (20 mL). Purification by flash chromatography (dichloromethane/methanol, 20:1) afforded compound (ZDR184) as a yellow solid (64 mg, 0.16 mmol, 64%). $^1$H NMR (400 MHz, d$_6$-DMSO): δ 4.40 (2H, s), 6.84 (2H, br s), 7.38 (1H, d, J=7.8 Hz), 7.45 (1H, d, J=7.8 Hz), 7.54 (1H, d, J=8.5 Hz), 7.59 (1H, d, J=7.4 Hz), 7.70 (2H, d, J=8.2 Hz), 8.00 (2H, d, J=8.2 Hz), 8.25 (1H, d, J=8.5 Hz); ESI-MS: m/z calcd for C$_{17}$H$_{14}$F$_3$N$_3$O$_2$S: 381.1; found [M+H]$^+$: 382.0.

Example 125: N-((8-((4-(Trifluoromethyl)phenyl)sulfonamido)quinolin-2-yl)methyl)acetamide—Compound (ZDR185)

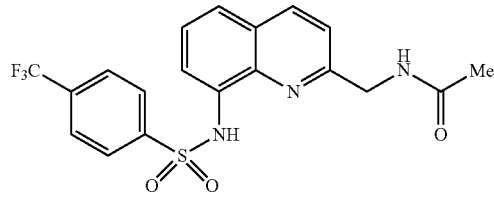 [SMILES: CC(=O)NCc1ccc2cccc(NS(=O)(=O)c3ccc(C(F)(F)F)cc3)c2n1]

A solution of compound (ZDR184) (50 mg, 0.13 mmol) and acetyl chloride (10 μL, 0.14 mmol) in dichloromethane (3 mL) was stirred at room temperature for 18 h. The mixture was then diluted with dichloromethane (25 mL), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/methanol, 20:1) afforded compound (ZDR185) as a colourless solid (30 mg, 0.07 mmol, 53%). $^1$H NMR (400 MHz, CDCl$_3$): δ 2.14 (3H, s), 4.70 (2H, d, J=5.6 Hz), 6.78 (1H, br s), 7.38-7.43 (2H, m), 7.47 (1H, dd, J=8.3 and 1.3 Hz), 7.60 (2H, d, J=8.4 Hz), 7.89 (1H, dd, J=7.5 and 1.3 Hz), 8.01 (2H, d, J=8.4 Hz), 8.05 (1H, d, J=8.5 Hz), 9.29 (1H, br s); ESI-MS: m/z calcd for C$_{19}$H$_{16}$F$_3$N$_3$O$_3$S: 423.1; found [M+Na]$^+$: 446.1.

---

(Page 157 top, continued from previous:)

methanol, 50:1) afforded compound (ZDR176) as a white solid (80 mg, 0.20 mmol, 76%). $^1$H NMR (300 MHz, CDCl$_3$) δ 4.96 (2H, s), 7.37 (1H, d, J=8.4 Hz), 7.43-7.54 (2H, m), 7.58 (2H, d, J=8.3 Hz), 7.89 (1H, dd, J=7.4 and 1.4 Hz), 8.02 (2H, d, J=8.3 Hz), 8.09 (1H, d, J=8.4 Hz); ESI-MS: m/z calcd for C$_{17}$H$_{13}$F$_3$N$_2$O$_3$S: 382.1; found [M+Na]$^+$: 405.0.

Example 126: N-(2-(N,N'-Bis-Boc-Guanidinomethyl)quinolin-8-yl)-4-(trifluoromethyl)benzenesulfonamide—Compound (ZDR186)

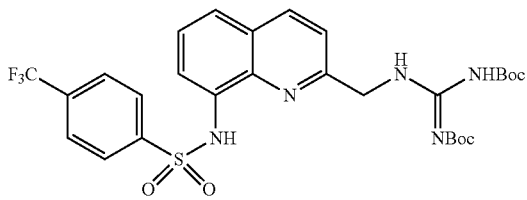

A solution of compound (ZDR184) (55 mg, 0.14 mmol) and N,N'-di-Boc-1H-pyrazole-1-carboxamidine (54 mg, 0.17 mmol) in tetrahydrofuran (2 mL) was stirred at room temperature for 18 h. The mixture was then diluted with ethyl acetate (10 mL), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (petroleum ether/ethyl acetate, 4:1) afforded compound (ZDR186) as a colourless solid (80 mg, 0.12 mmol, 85%). $^1$H NMR (400 MHz, CDCl$_3$): δ 1.54 (9H, s), 1.63 (9H, s), 4.88 (2H, d, J=3.9 Hz), 7.28 (1H, d, J=8.4 Hz), 7.44-7.56 (4H, m), 7.96-8.01 (3H, m), 8.07 (1H, d, J=8.4 Hz), 9.13 (1H, br s), 10.12 (1H, br s), 11.58 (1H, br s).

Example 127: N-(2-(Guanidinomethyl)quinolin-8-yl)-4-(trifluoromethyl)benzenesulfonamide trifluoroacetate—Compound (ZDR187)

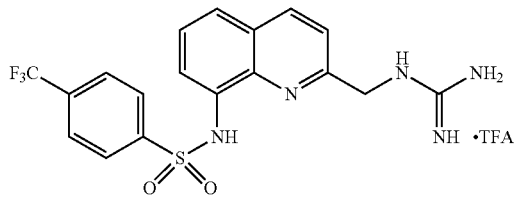 [SMILES: N=C(N)NCc1ccc2cccc(NS(=O)(=O)c3ccc(C(F)(F)F)cc3)c2n1]

A similar procedure to that described for the preparation of compound (ZDR124) was followed using compound (ZDR186) (80 mg, 0.13 mmol) and trifluoroacetic acid-dichloromethane (3 mL, 50% v/v) to afford compound (ZDR187) as a white solid (67 mg, 0.13 mmol, quant.), which was used without further purification. $^1$H NMR (400 MHz, d$_4$-MeOH): δ 4.66 (2H, s), 7.43 (1H, d, J=8.5 Hz), 7.51 (1H, t, J=8.0 Hz), 7.63-7.67 (3H, m), 7.88 (1H, dd, J=7.6 and 1.0 Hz), 7.98 (2H, d, J=8.4 Hz), 8.25 (1H, d, J=8.5 Hz); ESI-MS: m/z calcd for C$_{18}$H$_{16}$F$_3$N$_5$O$_2$S: 423.1; found [M+H]$^+$: 424.0.

Example 128: (E)-N-(2-((2-Nitroguanidino)methyl)quinolin-8-yl)-4-(trifluoromethyl)benzenesulfonamide—Compound (ZDR188)

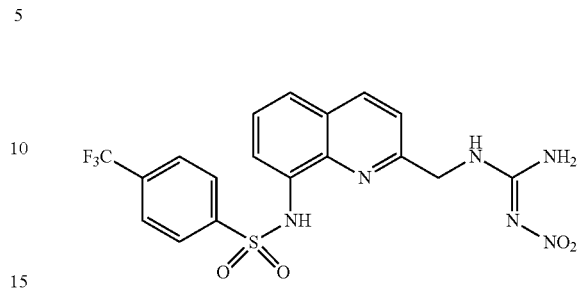

A solution of compound (ZDR184) (50 mg, 0.13 mmol) and N-nitro-S-methylisothiourea (21 mg, 0.16 mmol) in ethanol (2 mL) was stirred at 40° C. for 3 days, and the solvent then removed in vacuo. Purification by flash chromatography (dichloromethane/methanol, 20:1) afforded compound (ZDR188) as a pale yellow solid (43 mg, 0.09 mmol, 69%). $^1$H NMR (400 MHz, d$_6$-DMSO): δ 4.65 (2H, d, J=4.4 Hz), 7.48 (1H, d, J=8.5 Hz), 7.57 (1H, t, J=7.9 Hz), 7.74 (1H, d, J=8.4 Hz), 7.77 (2H, d, J=8.4 Hz), 7.82 (1H, d, J=7.6 Hz), 8.01 (2H, d, J=8.4 Hz), 8.34 (1H, d, J=8.5 Hz), 9.16 (1H, br s); ESI-MS: m/z calcd for C$_{18}$H$_{18}$F$_3$N$_6$O$_4$S: 468.1; found [M+Na]$^+$: 491.1.

Example 129: 2-Chloro-N-(2-((dimethylamino)methyl)quinolin-8-yl)benzenesulfonamide—Compound (ZDR190)

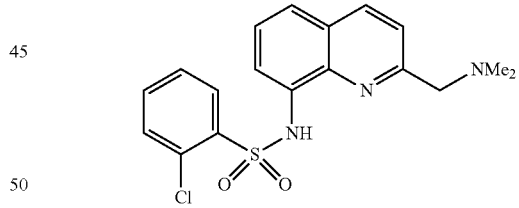

A similar procedure to that described for the preparation of compound (ZDR018) was followed using compound (ZDR059) (90 mg, 0.44 mmol), 2-chlorobenzenesulfonyl chloride (66 μL, 0.49 mmol) and triethylamine (68 μL, 0.49 mmol) in dichloromethane (5 mL). Purification by flash chromatography (dichloromethane/methanol, 50:1→15:1) afforded compound (ZDR190) as a tan solid (80 mg, 0.21 mmol, 47%). $^1$H NMR (400 MHz, CDCl$_3$) δ 2.32 (6H, s), 3.75 (2H, s), 7.29-7.41 (5H, m), 7.63 (1H, d, J=8.5 Hz), 7.71 (1H, d, J=7.4 Hz), 8.05 (1H, d, J=8.5 Hz), 8.18 (1H, d, J=7.8 Hz); ESI-MS: m/z calcd for C$_{18}$H$_{18}$ClN$_3$O$_2$S: 375.1; found [M+H]$^+$: 376.1.

Example 130: N-(2-((Dimethylamino)methyl)quinolin-8-yl)-2-(trifluoromethoxy)benzenesulfonamide—Compound (ZDR191)

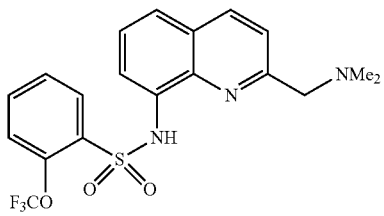

A similar procedure to that described for the preparation of compound (ZDR018) was followed using compound (ZDR059) (90 mg, 0.44 mmol), 2-(trifluoromethoxy)benzenesulfonyl chloride (117 mg, 0.49 mmol) and triethylamine (68 μL, 0.49 mmol) in dichloromethane (5 mL). Purification by flash chromatography (dichloromethane/methanol, 50:1→15:1) afforded compound (ZDR191) as a pale yellow solid (71 mg, 0.17 mmol, 38%). $^1$H NMR (400 MHz, CDCl$_3$) δ 2.32 (6H, s), 3.74 (2H, s), 7.21 (1H, d, J=8.0 Hz), 7.26-7.35 (2H, m), 7.41 (1H, d, J=8.0 Hz), 7.48 (1H, t, J=7.5 Hz), 7.66 (1H, d, J=8.4 Hz), 7.73 (1H, d, J=7.5 Hz), 8.06 (1H, d, J=8.4 Hz), 8.13 (1H, d, J=7.7 Hz); ESI-MS: m/z calcd for C$_{19}$H$_{18}$F$_3$N$_3$O$_3$S: 425.1; found [M+H]$^+$: 426.1.

Example 131: N-(2-((Dimethylamino)methyl)quinolin-8-yl)morpholine-4-sulfonamide—Compound (ZDR192)

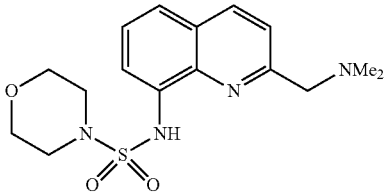

A similar procedure to that described for the preparation of compound (ZDR018) was followed using compound (ZDR059) (90 mg, 0.44 mmol), morpholine-4-sulfonyl chloride (90 mg, 0.49 mmol) and triethylamine (68 μL, 0.49 mmol) in dichloromethane (5 mL). Purification by flash chromatography (dichloromethane/methanol, 50:1→20:1→10:1) afforded compound (ZDR192) as a pale yellow solid (33 mg, 0.09 mmol, 20%). $^1$H NMR (400 MHz, CDCl$_3$) δ 2.32 (6H, s), 3.24 (4H, t, J=4.7 Hz), 3.58 (4H, t, J=4.7 Hz), 3.75 (2H, s), 7.45 (1H, t, J=7.8 Hz), 7.50 (1H, dt, J=8.2 and 1.5 Hz), 7.67 (1H, d, J=8.5 Hz), 7.83 (1H, dd, J=7.3 and 1.5 Hz), 8.14 (1H, d, J=8.5 Hz), 8.98 (1H, brs); ESI-MS: m/z calcd for C$_{16}$H$_{22}$N$_4$O$_3$S: 350.1; found [M+H]$^+$: 351.1.

Example 132: N-(2-((Dimethylamino)methyl)quinolin-8-yl)piperidine-1-sulfonamide—Compound (ZDR193)

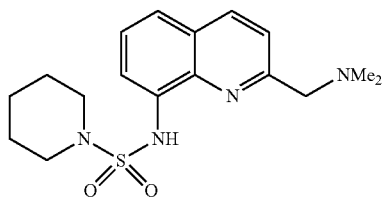 [SMILES: CN(C)Cc1ccc2cccc(NS(=O)(=O)N3CCCCC3)c2n1]

A similar procedure to that described for the preparation of compound (ZDR018) was followed using compound (ZDR059) (90 mg, 0.44 mmol), piperidine-1-sulfonyl chloride (68 μL, 0.49 mmol) and triethylamine (68 μL, 0.49 mmol) in dichloromethane (5 mL). Purification by flash chromatography (dichloromethane/methanol, 50:1→20:1→10:1) afforded compound (ZDR193) as a yellow oil (35 mg, 0.10 mmol, 22%). $^1$H NMR (400 MHz, CDCl$_3$) δ 1.37-1.42 (2H, m), 1.46-1.51 (4H, m), 2.32 (6H, s), 3.25 (4H, t, J=5.5 Hz), 3.74 (2H, s), 7.42-7.48 (2H, m), 7.65 (1H, d, J=8.5 Hz), 7.73 (1H, dd, J=6.8 and 2.0 Hz), 8.12 (1H, d, J=8.5 Hz), 8.95 (1H, brs); ESI-MS: m/z calcd for C$_{17}$H$_{24}$N$_4$O$_2$S: 348.2; found [M+H]$^+$: 349.2.

Example 133: N-(2-((Dimethylamino)methyl)quinolin-8-yl)-1-methyl-1H-pyrazole-4-sulfonamide—Compound (ZDR194)

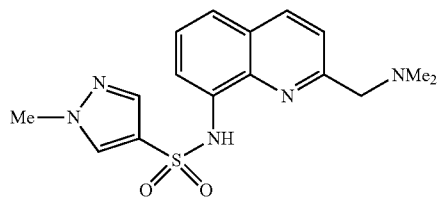 [SMILES: CN(C)Cc1ccc2cccc(NS(=O)(=O)c3cnn(C)c3)c2n1]

A similar procedure to that described for the preparation of compound (ZDR018) was followed using compound (ZDR059) (90 mg, 0.44 mmol), 1-methyl-1H-pyrazole-4-sulfonyl chloride (88 mg, 0.49 mmol) and triethylamine (68 μL, 0.49 mmol) in dichloromethane (5 mL). Purification by flash chromatography (dichloromethane/methanol, 20:1→8:1) afforded compound (ZDR194) as a pale yellow solid (14 mg, 0.04 mmol, 9%). $^1$H NMR (400 MHz, CDCl$_3$) δ 2.31 (6H, s), 3.72 (2H, s), 3.77 (3H, s), 7.42-7.49 (2H, m), 7.61 (1H, d, J=8.5 Hz), 7.70 (1H, s), 7.75 (1H, s), 7.82 (1H, dd, J=7.5 and 1.5 Hz), 8.09 (1H, d, J=8.5 Hz); ESI-MS: m/z calcd for C$_{16}$H$_{19}$N$_5$O$_2$S: 345.1; found [M+Na]$^+$: 368.1.

Example 134: N-(2-((Dimethylamino)methyl)quinolin-8-yl)-1-methyl-1H-imidazole-4-sulfonamide—Compound (ZDR195)

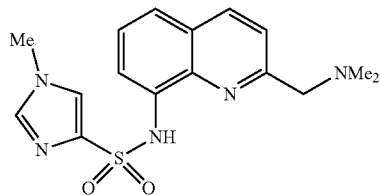 [SMILES: CN(C)Cc1ccc2cccc(NS(=O)(=O)c3cn(C)cn3)c2n1]

A similar procedure to that described for the preparation of compound (ZDR018) was followed using compound (ZDR059) (90 mg, 0.44 mmol), 1-methyl-1H-imidazole-4-sulfonyl chloride (88 mg, 0.49 mmol) and triethylamine (68 µL, 0.49 mmol) in dichloromethane (5 mL). Purification by flash chromatography (dichloromethane/methanol, 20:1→7:1) afforded compound (ZDR195) as a yellow solid (44 mg, 0.12 mmol, 27%). $^1$H NMR (400 MHz, CDCl$_3$) δ 2.33 (6H, s), 3.64 (3H, s), 3.76 (2H, s), 7.32-7.42 (3H, m), 7.54-7.60 (2H, m), 7.78-7.84 (1H, m), 8.05 (1H, d, J=8.5 Hz); ESI-MS: m/z calcd for C$_{16}$H$_{19}$N$_5$O$_2$S: 345.1; found [M+H]$^+$: 346.1.

Example 135: N-(2-((Dimethylamino)methyl)quinolin-8-yl)benzo[c][1,2,5]thiadiazole-4-sulfonamide—Compound (ZDR196)

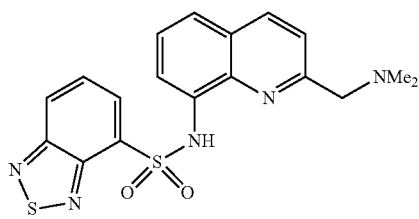 [SMILES: CN(C)Cc1ccc2cccc(NS(=O)(=O)c3cccc4nsnc34)c2n1]

A similar procedure to that described for the preparation of compound (ZDR018) was followed using compound (ZDR059) (90 mg, 0.44 mmol), 2,1,3-benzothiadiazole-4-sulfonyl chloride (114 mg, 0.49 mmol) and triethylamine (68 µL, 0.49 mmol) in dichloromethane (5 mL). Purification by flash chromatography (dichloromethane/methanol, 50:1→15:1) afforded compound (ZDR196) as a pale yellow solid (145 mg, 0.36 mmol, 81%). $^1$H NMR (400 MHz, CDCl$_3$) δ 2.31 (6H, s), 3.70 (2H, s), 7.31-7.37 (2H, m), 7.54 (1H, d, J=8.5 Hz), 7.61 (1H, dd, J=8.9 and 6.9 Hz), 7.84 (1H, dd, J=7.0 and 1.9 Hz), 7.97 (1H, d, J=8.5 Hz), 8.08 (1H, dd, J=8.9 and 0.9 Hz), 8.33 (1H, dd, J=6.9 and 0.9 Hz); ESI-MS: m/z calcd for C$_{18}$H$_{17}$N$_5$O$_2$S$_2$: 399.1; found [M+H]$^+$: 400.1.

Example 136: N-(2-((Dimethylamino)methyl)quinolin-8-yl)-2-fluorobenzenesulfonamide—Compound (ZDR201)

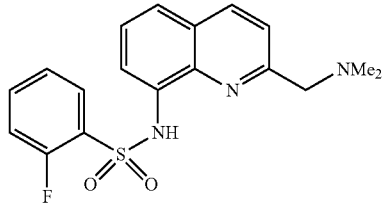

A similar procedure to that described for the preparation of compound (ZDR018) was followed using compound (ZDR059) (90 mg, 0.44 mmol), 2-fluorobenzenesulfonyl chloride (64 µL, 0.49 mmol) and triethylamine (68 µL, 0.49 mmol) in dichloromethane (5 mL). Purification by flash chromatography (dichloromethane/methanol, 50:1→15:1) afforded compound (ZDR201) as a pale yellow solid (72 mg, 0.20 mmol, 45%). $^1$H NMR (400 MHz, CDCl$_3$) δ 2.32 (6H, s), 3.76 (2H, s), 6.97-7.02 (1H, m), 7.13-7.17 (1H, m), 7.35 (1H, t, J=7.7 Hz), 7.39-7.45 (2H, m), 7.61 (1H, d, J=8.5 Hz), 7.75 (1H, dd, J=7.5 and 1.2 Hz), 7.93-7.98 (1H, m), 8.05 (1H, d, J=8.5 Hz); ESI-MS: m/z calcd for C$_{18}$H$_{18}$FN$_3$O$_2$S: 359.1; found [M+H]$^+$: 360.1.

Example 137: 2-Bromo-N-(2-((dimethylamino)methyl)quinolin-8-yl)benzenesulfonamide—Compound (ZDR202)

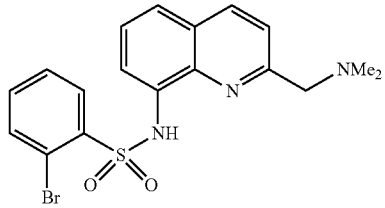 [SMILES: CN(C)Cc1ccc2cccc(NS(=O)(=O)c3ccccc3Br)c2n1]

A similar procedure to that described for the preparation of compound (ZDR018) was followed using compound (ZDR059) (90 mg, 0.44 mmol), 2-bromobenzenesulfonyl chloride (125 mg, 0.49 mmol) and triethylamine (68 µL, 0.49 mmol) in dichloromethane (5 mL). Purification by flash chromatography (dichloromethane/methanol, 50:1→15:1) afforded compound (ZDR202) as a pale yellow solid (57 mg, 0.14 mmol, 31%). $^1$H NMR (400 MHz, CDCl$_3$) δ 2.32 (6H, s), 3.76 (2H, s), 7.25-7.41 (4H, m), 7.55 (1H, d, J=7.8 Hz), 7.63 (1H, d, J=8.5 Hz), 7.71 (1H, d, J=7.4 Hz), 8.05 (1H, d, J=8.5 Hz), 8.24 (1H, d, J=7.5 Hz); ESI-MS: m/z calcd for C$_{18}$H$_{18}$BrN$_3$O$_2$S: 419.0; found [M+H]$^+$: 420.0.

Example 138: N-(2-((Dimethylamino)methyl)quinolin-8-yl)-2,4-dimethylthiazole-5-sulfonamide—Compound (ZDR203)

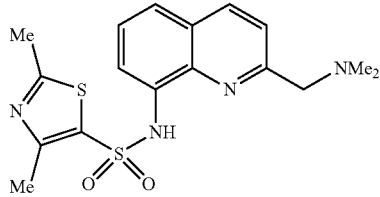 [SMILES: Cc1nc(C)c(S(=O)(=O)Nc2cccc3ccc(CN(C)C)nc23)s1]

A similar procedure to that described for the preparation of compound (ZDR018) was followed using compound (ZDR059) (90 mg, 0.44 mmol), 2,4-dimethyl-1,3-thiazole-5-sulfonyl chloride (103 mg, 0.49 mmol) and triethylamine (68 μL, 0.49 mmol) in dichloromethane (5 mL). Purification by flash chromatography (dichloromethane/methanol, 50:1→15:1) afforded compound (ZDR203) as a pale yellow solid (40 mg, 0.11 mmol, 25%). $^1$H NMR (400 MHz, CDCl$_3$) δ 2.31 (6H, s), 2.51 (3H, s), 2.55 (3H, s), 3.72 (2H, s), 7.44 (1H, t, J=7.7 Hz), 7.52 (1H, d, J=8.0 Hz), 7.64 (1H, d, J=8.5 Hz), 7.85 (1H, d, J=7.4 Hz), 8.10 (1H, d, J=8.5 Hz); ESI-MS: m/z calcd for C$_{17}$H$_{20}$N$_4$O$_2$S$_2$: 376.1; found [M+H]$^+$: 377.1.

Example 139: N-(2-((Dimethylamino)methyl)quinolin-8-yl)pyrrolidine-1-sulfonamide—Compound (ZDR204)

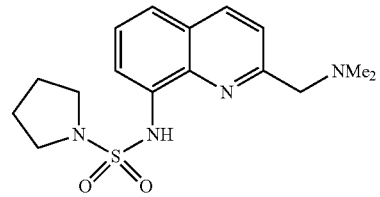 [SMILES: CN(C)Cc1ccc2cccc(NS(=O)(=O)N3CCCC3)c2n1]

A similar procedure to that described for the preparation of compound (ZDR018) was followed using compound (ZDR059) (90 mg, 0.44 mmol), pyrrolidine-1-sulfonyl chloride (83 mg, 0.49 mmol) and triethylamine (68 μL, 0.49 mmol) in dichloromethane (5 mL). Purification by flash chromatography (dichloromethane/methanol, 10:1→5:1) afforded compound (ZDR204) as a pale brown solid (17 mg, 0.05 mmol, 11%). $^1$H NMR (400 MHz, CDCl$_3$) δ 1.72-1.75 (4H, m), 2.32 (6H, s), 3.34-3.37 (4H, m), 3.75 (2H, s), 7.43-7.48 (2H, m), 7.65 (1H, d, J=8.5 Hz), 7.76 (1H, dd, J=7.0 and 2.0 Hz), 8.12 (1H, d, J=8.5 Hz), 8.99 (1H, brs); ESI-MS: m/z calcd for C$_{16}$H$_{22}$N$_4$O$_2$S: 334.1; found [M+H]$^+$: 335.2.

Example 140: 2-(Dimethylamino)-N-((8-((4-(trifluoromethyl)phenyl)sulfonamido)quinolin-2-yl)methyl)acetamide—Compound (ZDR205)

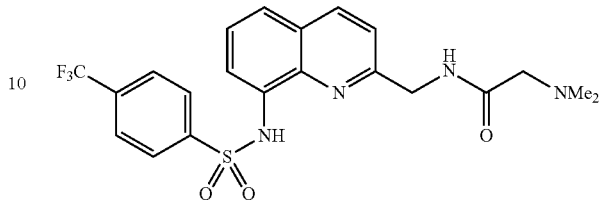

A solution of compound (ZDR184) (50 mg, 0.13 mmol), N,N-dimethylglycine hydrochloride (21 mg, 0.15 mmol), N-(3-dimethylaminopropyl)-N'-ethylcarbodiimide hydrochloride (28 mg, 0.15 mmol) and triethylamine (55 μL, 0.39 mmol) in dimethylformamide (3 mL) was stirred at room temperature for 18 h. The mixture was then diluted with dichloromethane (25 mL), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/methanol, 50:1→30:1→15:1) afforded compound (ZDR205) as a pale yellow solid (30 mg, 0.06 mmol, 46%). $^1$H NMR (300 MHz, CDCl$_3$) δ 2.46 (6H, s), 3.13 (2H, s), 4.77 (2H, d, J=5.4 Hz), 7.39 (1H, d, J=8.4 Hz), 7.45 (1H, d, J=7.3 Hz), 7.50 (1H, dd, J=8.4 and 1.3 Hz), 7.63 (2H, d, J=8.3 Hz), 7.84 (1H, dd, J=7.3 and 1.3 Hz), 8.03 (2H, d, J=8.3 Hz), 8.09 (1H, d, J=8.4 Hz); ESI-MS: m/z calcd for C$_{21}$H$_{21}$F$_3$N$_4$O$_3$S: 466.1; found [M+H]$^+$: 467.1.

Example 141: N-(2-(Methylsulfonamidomethyl)quinolin-8-yl)-4-(trifluoromethyl)benzenesulfonamide—Compound (ZDR209)

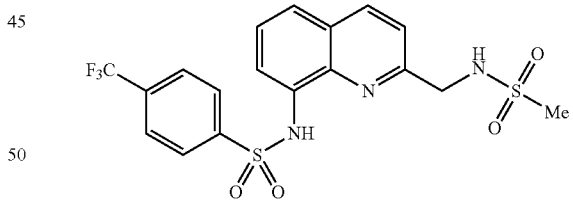

A similar procedure to that described for the preparation of compound (ZDR185) was followed using compound (ZDR184) (50 mg, 0.13 mmol), methanesulfonyl chloride (11 μL, 0.15 mmol) and triethylamine (55 μL, 0.39 mmol) in dichloromethane (3 mL). Purification by flash chromatography (dichloromethane/methanol, 50:1→20:1) afforded compound (ZDR209) as a colourless solid (35 mg, 0.07 mmol, 53%). $^1$H NMR (400 MHz, CDCl$_3$) δ 3.08 (3H, s), 4.65 (2H, d, J=5.8 Hz), 6.24-6.26 (1H, m), 7.38 (1H, d, J=8.5 Hz), 7.43 (1H, d, J=7.6 Hz), 7.48 (1H, dd, J=8.0 and 1.5 Hz), 7.61 (2H, d, J=8.5 Hz), 7.84 (1H, dd, J=7.5 and 1.5 Hz), 8.08 (3H, dd, J=8.5 and 2.1 Hz), 9.51 (1H, br s); ESI-MS: m/z calcd for C$_{18}$H$_{16}$F$_3$N$_3$O$_4$S$_2$: 459.1; found [M+Na]$^+$: 482.0.

Example 142: N-(2-(Phenylsulfonamidomethyl)quinolin-8-yl)-4-(trifluoromethyl)benzenesulfonamide—Compound (ZDR210)

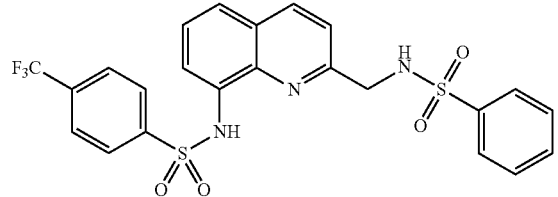 [SMILES: O=S(=O)(NCc1ccc2cccc(NS(=O)(=O)c3ccc(C(F)(F)F)cc3)c2n1)c1ccccc1]

A similar procedure to that described for the preparation or compound (ZDR185) was followed using compound (ZDR184) (50 mg, 0.13 mmol), benzenesulfonyl chloride (26 mg, 0.15 mmol) and triethylamine (55 μL, 0.39 mmol) in dichloromethane (3 mL). Purification by flash chromatography (dichloromethane/methanol, 50:1→20:1) afforded compound (ZDR210) as a pale yellow solid (51 mg, 0.09 mmol, 69%). $^1$H NMR (400 MHz, CDCl$_3$) δ 4.47 (2H, d, J=5.7 Hz), 6.24 (1H, brt, J=5.7 Hz), 7.32 (1H, d, J=8.4 Hz), 7.39-7.49 (5H, m), 7.57 (2H, d, J=8.4 Hz), 7.82 (1H, dd, J=7.1 and 1.7 Hz), 7.90-7.93 (2H, m), 8.00 (1H, d, J=8.4 Hz), 8.03 (2H, d, J=8.4 Hz), 9.28 (1H, brs); ESI-MS: m/z calcd for C$_{23}$H$_{18}$F$_3$N$_3$O$_4$S$_2$: 521.1; found [M+Na]$^+$: 544.1.

Example 143: 4-(Dimethylamino)-N-((8-((4-(trifluoromethyl)phenyl)sulfonamido)quinolin-2-yl)methyl)butanamide trifluoroacetate—Compound (ZDR211)

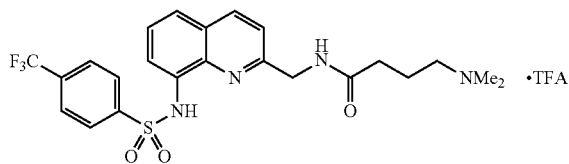 [SMILES: CN(C)CCCC(=O)NCc1ccc2cccc(NS(=O)(=O)c3ccc(C(F)(F)F)cc3)c2n1]

A solution of compound (ZDR184) (50 mg, 0.13 mmol), 4-(dimethylamino)butyric acid hydrochloride (25 mg, 0.15 mmol), N-(3-dimethylaminopropyl)-N'-ethylcarbodiimide hydrochloride (28 mg, 0.15 mmol) and triethylamine (55 μL, 0.39 mmol) in dimethylformamide (3 mL) was stirred at room temperature for 18 h (no work-up). Purification by RP-HLPC (30% to 90% A/B gradient over 60 min, where A=water+0.1% trifluoroacetic acid and B=acetonitrile+0.1% trifluoroacetic acid) afforded compound (ZDR211) as a white solid (30 mg, 0.05 mmol, 38%). $^1$H NMR (400 MHz, d$_6$-acetone) δ 2.18 (2H, quin, J=6.9 Hz), 2.69 (2H, t, J=6.9 Hz), 3.01 (6H, s), 3.36 (2H, t, J=6.9 Hz), 4.71 (2H, d, J=5.5 Hz), 7.50-7.54 (2H, m), 7.65 (1H, dd, J=8.4 and 1.4 Hz), 7.79 (2H, d, J=8.3 Hz), 8.36 (1H, dd, J=7.6 and 1.2 Hz), 8.12 (2H, d, J=8.3 Hz), 8.26 (1H, d, J=8.4 Hz), 8.42 (1H, brs), 9.66 (1H, brs); ESI-MS: m/z calcd for C$_{23}$H$_{25}$F$_3$N$_4$O$_3$S: 494.2; found [M+H]$^+$:495.2.

Example 144: N-(3-(Dimethylamino)propyl)-8-((4-(trifluoromethyl)phenyl)sulfonamido)quinoline-2-carboxamide trifluoroacetate—Compound (ZDR224)

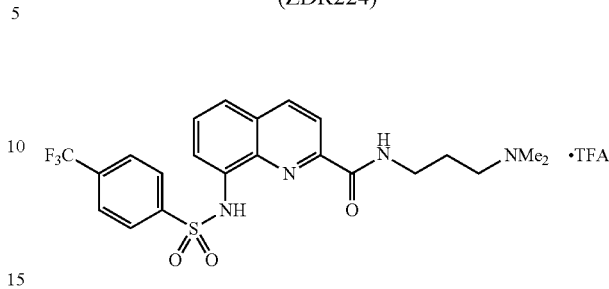

A solution of compound (ZDR271) (79 mg, 0.20 mmol), 3-(dimethylamino)-1-propylamine (27 μL, 0.22 mmol), N-(3-dimethylaminopropyl)-N'-ethylcarbodiimide hydrochloride (42 mg, 0.22 mmol) and triethylamine (84 μL, 0.6 mmol) in dichloromethane (5 mL) was stirred at room temperature for 18 h. Trifluoroacetic acid (5 mL) was added and the solution was stirred at room temperature for a further 3 h, and the solvent removed in vacuo. Purification by RP-HLPC (30% to 90% A/B gradient over 60 min, where A=water+0.1% trifluoroacetic acid and B=acetonitrile+0.1% trifluoroacetic acid) afforded compound (ZDR224) as a white solid (21 mg, 0.03 mmol, 15%). $^1$H NMR (400 MHz, d$_6$-acetone) δ 2.20 (2H, quin, J=6.9 Hz), 3.02 (6H, s), 3.40 (2H, t, J=6.9 Hz), 3.61 (2H, t, J=6.9 Hz), 7.64 (1H, t, J=8.0 Hz), 7.75-7.79 (3H, m), 7.96 (1H, dd, J=7.7 and 1.2 Hz), 8.09 (2H, d, J=8.1 Hz), 8.22 (1H, d, J=8.5 Hz), 8.47 (1H, d, J=8.5 Hz), 9.60 (1H, brs), 10.12 (1H, brs); ESI-MS: m/z calcd for C$_{22}$H$_{23}$F$_3$N$_4$O$_3$S: 480.1; found [M+H]$^+$: N/A.

Example 145: N-(tert-Butoxycarbonyl)-N-((8-((4-(trifluoromethyl)phenyl)sulfonamido)quinolin-2-yl)methyl)glycine—Compound (ZDR227)

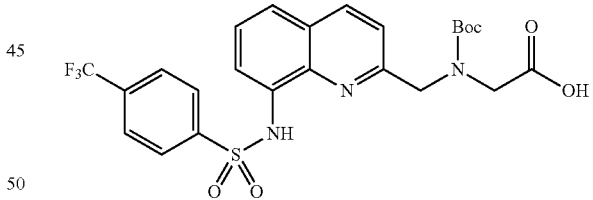

A solution of compound (ZDR043) (500 mg, 0.93 mmol), di-tert-butyl dicarbonate (212 mg, 1.11 mmol) and triethylamine (391 μL, 2.79 mmol) in dimethylformamide (12 mL) was stirred at room temperature for 18 h. The mixture was then diluted with dichloromethane (50 mL), washed with aqueous sodium hydrogen sulfate (50 mL, 1 M) and the separated organic layer dried over anhydrous magnesium sulfate, filtered and the filtrate concentrated in vacuo. Purification by flash chromatography (dichloromethane/methanol, 10:1) afforded compound (ZDR227) as a yellow oil (400 mg, 0.74 mmol, 79%). $^1$H NMR (400 MHz, CDCl$_3$) δ 1.52 (9H, s), 3.95-4.07 (2H, m), 4.71-4.78 (2H, m), 7.39-7.49 (3H, m), 7.61-7.64 (2H, m), 7.82-7.87 (1H, m), 8.01-8.10 (3H, m), 9.23 (1H, brs).

Example 146: tert-Butyl (2-((2-(dimethylamino)ethyl)amino)-2-oxoethyl)((8-((4-(trifluoromethyl)phenyl)sulfonamido)quinolin-2-yl)methyl)carbamate—Compound (ZDR234)

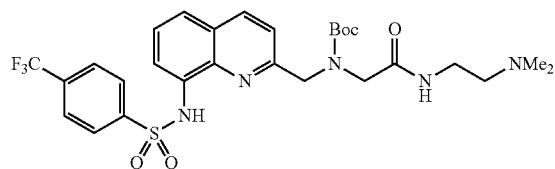 [SMILES: CN(C)CCNC(=O)CN(Cc1ccc2cccc(NS(=O)(=O)c3ccc(C(F)(F)F)cc3)c2n1)C(=O)OC(C)(C)C]

A solution of compound (ZDR246) (100 mg, 0.15 mmol) and N,N-dimethylethylenediamine (49 μL, 0.45 mmol) in dichloromethane (5 mL) was stirred at room temperature for 18 h. The mixture was then diluted with dichloromethane (50 mL), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/methanol, 20:1→10:1→5:1) afforded compound (ZDR234) as a pale yellow solid (28 mg, 0.04 mmol, 26%). $^1$H NMR (400 MHz, $d_6$-acetone) δ 1.32 (4.5H, s), 1.50 (4.5H, s), 2.19 (6H, s), 2.37 (2H, brs), 3.30 (2H, brs), 3.96-4.06 (2H, m), 4.77-4.80 (2H, m), 7.15-7.24 (1H, m), 7.51 (1H, t, J=7.6 Hz), 7.55-7.59 (1H, m), 7.64 (1H, d, J=8.0 Hz), 7.83-7.91 (3H, m), 8.18-8.21 (2H, m), 8.28 (1H, brs).

Example 147: 2,5-Dioxopyrrolidin-1-yl N-(tert-butoxycarbonyl)-N-((8-((4-(trifluoromethyl)phenyl)sulfonamido)quinolin-2-yl)methyl)glycinate—Compound (ZDR246)

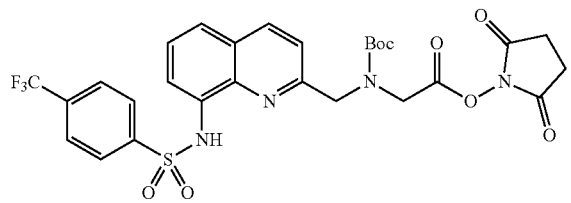 [SMILES: CC(C)(C)OC(=O)N(CC(=O)ON1C(=O)CCC1=O)Cc1ccc2cccc(NS(=O)(=O)c3ccc(C(F)(F)F)cc3)c2n1]

A solution of compound (ZDR227) (750 mg, 1.39 mmol), N-hydroxysuccinimide (191 mg, 1.66 mmol) and N-(3-dimethylaminopropyl)-N'-ethylcarbodiimide hydrochloride (318 mg, 1.66 mmol) in dichloromethane-dimethylformamide (20 mL, 10:1 v/v) was stirred at room temperature for 18 h. The mixture was then diluted with dichloromethane (50 mL), water (25 mL) added and the pH adjusted to pH 6-7 using aqueous phosphate buffer solution (0.5 M, pH 7). The separated organic layer was dried over anhydrous magnesium sulfate, filtered and the filtrate concentrated in vacuo. Purification by flash chromatography (dichloromethane/methanol, 50:1→20:1) afforded compound (ZDR246) as a yellow oil (630 mg, 1.0 mmol, 71%). $^1$H NMR (400 MHz, CDCl$_3$) δ 1.30 (4.5H, s) 1.51 (4.5H, s), 3.46 (4H, s), 4.30-4.43 (2H, m), 4.69-4.78 (2H, m), 7.39-7.48 (4H, m), 7.61 (2H, d, J=7.9 Hz), 7.84-7.86 (1H, m), 8.02-8.08 (2H, m), 9.29 (1H, brs).

Example 148: tert-Butyl(2-oxo-2-((2-(piperidin-1-yl)ethyl)amino)ethyl)((8-((4-(trifluoromethyl)phenyl)sulfonamido)quinolin-2-yl)methyl)carbamate—Compound (ZDR247)

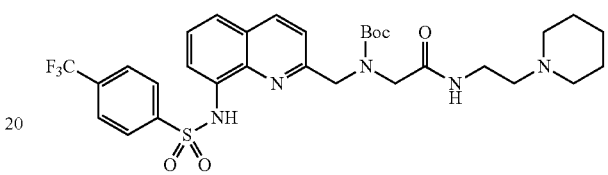

A similar procedure to that described for the preparation of compound (ZDR234) was followed using compound (ZDR246) (100 mg, 0.15 mmol) and 1-(2-aminoethyl)piperidine (64 μL, 0.45 mmol) in dichloromethane (5 mL). Purification by flash chromatography (dichloromethane/methanol, 20:1→10:1→45:1) afforded compound (ZDR247) as a colourless solid (49 mg, 0.07 mmol, 46%). $^1$H NMR (400 MHz, CDCl$_3$) δ 1.37 (4.5H, s), 1.52 (4.5H, s), 1.45 (2H, brs), 1.60 (4H, brs), 2.44 (4H, brs), 2.48 (2H, brs), 3.39 (2H, brq, J=5.4 Hz), 3.89-3.98 (2H, m), 4.71-4.77 (2H, m), 6.91-7.09 (1H, m), 7.39-7.52 (3H, m), 7.65 (2H, d, J=8.4 Hz), 7.83 (1H, brs), 8.04-8.09 (3H, m).

Example 149: 8-((4-(Trifluoromethyl)phenyl)sulfonamido)quinoline-2-carboxylic acid—Compound (ZDR251)

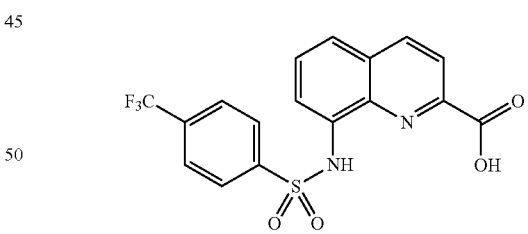

A solution of compound (ZDR019) (500 mg, 1.31 mmol) and potassium permanganate (350 mg, 2.22 mmol) in acetone (10 mL) was stirred at room temperature for 4 h. The mixture was then diluted with dichloromethane (30 mL) and washed with aqueous sodium hydrogen sulfate (30 mL, 1 M). The separated organic layer was dried over anhydrous magnesium sulfate, filtered and the filtrate concentrated in vacuo. Purification by flash chromatography (dichloromethane/methanol, 100:1→420:1) afforded compound (ZDR251) as an off-white solid (280 mg, 0.70 mmol, 53%). $^1$H NMR (300 MHz, $d_6$-DMSO) δ 7.61 (1H, t, J=7.9 Hz), 7.68 (1H, dd, J=7.9 and 1.5 Hz), 7.74 (2H, d, J=8.5 Hz), 7.92 (1H, dd, J=7.9 and 1.5 Hz), 8.09 (2H, d, J=8.5 Hz), 8.19 (1H, d, J=8.5 Hz), 8.44 (1H, d, J=8.5 Hz).

Example 150: tert-Butyl (2-(methylamino)-2-oxoethyl)((8-((4-(trifluoromethyl)phenyl)sulfonamido)quinolin-2-yl)methyl)carbamate—Compound (ZDR253)

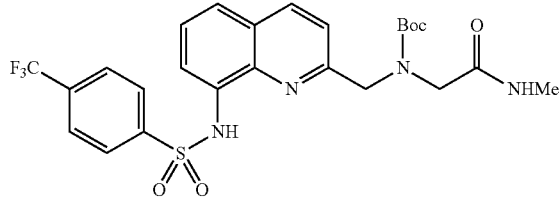 [SMILES: CNC(=O)CN(Cc1ccc2cccc(NS(=O)(=O)c3ccc(C(F)(F)F)cc3)c2n1)C(=O)OC(C)(C)C]

A similar procedure to that described for the preparation of compound (ZDR234) was followed using compound (ZDR246) (100 mg, 0.15 mmol) and methylamine (0.5 mL, 1.0 mmol, 2 M in tetrahydrofuran) in dichloromethane (5 mL). Purification by flash chromatography (dichloromethane/methanol, 20:1→10:1) afforded compound (ZDR253) as a colourless solid (58 mg, 0.10 mmol, 66%). $^1$H NMR (400 MHz, CDCl$_3$) δ 1.37 (4.5H, s), 1.52 (4.5H, s), 2.81-2.82 (3H, m), 3.91-3.95 (2H, m), 4.72-4.78 (2H, m), 6.24-6.37 (1H, m), 7.39-7.50 (3H, m), 7.66 (2H, d, J=8.5 Hz), 7.83 (1H, brs), 8.02-8.06 (2H, m), 8.10 (1H, d, J=8.5 Hz), 9.16 (1H, brs).

Example 151: tert-Butyl 4-(N-(2-((dimethylamino)methyl)quinolin-8-yl)sulfamoyl)piperidine-1-carboxylate—Compound (ZDR256)

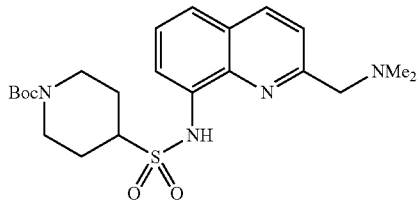 [SMILES: CN(C)Cc1ccc2cccc(NS(=O)(=O)C3CCN(C(=O)OC(C)(C)C)CC3)c2n1]

A similar procedure to that described for the preparation of compound (ZDR018) was followed using compound (ZDR059) (90 mg, 0.44 mmol), 4-chlorosulfonyl-piperidine-1-carboxylic acid tert-butyl ester (139 mg, 0.49 mmol) and triethylamine (68 μL, 0.49 mmol) In dichloromethane (5 mL). Purification by flash chromatography (dichloromethane/methanol, 20:1→10:1) afforded compound (ZDR256) as a yellow oil (60 mg, 0.13 mmol, 29%). $^1$H NMR (400 MHz, CDCl$_3$) δ 1.40 (9H, s), 1.81 (2H, qd, J=12.5 and 4.5 Hz), 2.07-2.11 (2H, m), 2.31 (6H, s), 2.56 (2H, brs), 3.14 (1H, tt, J=11.9 and 3.7 Hz), 3.74 (2H, s), 4.14 (2H, brs), 7.47 (1H, d, J=7.6 Hz), 7.53 (1H, dd, J=8.2 and 1.2 Hz), 7.66 (1H, d, J=8.5 Hz), 8.36 (1H, dd, J=7.6 and 1.2 Hz), 8.15 (1H, d, J=8.5 Hz), 8.93 (1H, brs).

Example 152: N-(2-((Dimethylamino)methyl)quinolin-8-yl)-4-(methylthio)benzenesulfonamide—Compound ZDR257

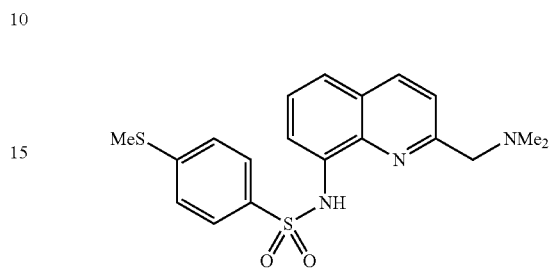

A similar procedure to that described for the preparation of compound (ZDR018) was followed using compound (ZDR059) (90 mg, 0.44 mmol), 4-(thiomethyl)benzenesulfonyl chloride (109 mg, 0.49 mmol) and triethylamine (68 μL, 0.49 mmol) in dichloromethane (5 mL). Purification by flash chromatography (dichloromethane/methanol, 100:1→20:1) afforded compound (ZDR257) as a yellow solid (142 mg, 0.36 mmol, 81%). $^1$H NMR (400 MHz, CDCl$_3$) δ 2.29 (6H, s), 2.40 (3H, s), 3.70 (2H, s), 7.09-7.12 (2H, m), 7.38-7.46 (2H, m), 7.58 (1H, d, J=8.5 Hz), 7.75-7.80 (3H, m), 8.06 (1H, d, J=8.5 Hz); ESI-MS: m/z calcd for $C_{19}H_{21}N_3O_2S_2$: 387.1; found [M+H]$^+$: 388.1.

Example 153: N-(2-((Dimethylamino)methyl)quinolin-8-yl)-6-methoxypyridine-3-sulfonamide—Compound (ZDR258)

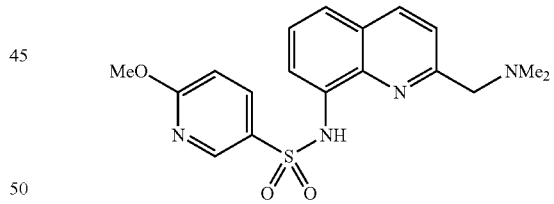

A similar procedure to that described for the preparation of compound (ZDR018) was followed using compound (ZDR059) (90 mg, 0.44 mmol), 6-methoxypyridine-3-sulfonyl chloride (101 mg, 0.49 mmol) and triethylamine (68 μL, 0.49 mmol) in dichloromethane (5 mL). Purification by flash chromatography (dichloromethane/methanol, 100:1→20:1) afforded compound (ZDR258) as a yellow solid (28 mg, 0.08 mmol, 18%). $^1$H NMR (400 MHz, CDCl$_3$) δ 2.29 (6H, s), 3.70 (2H, s), 3.87 (3H, s), 6.60 (1H, d, J=8.8 Hz), 7.40-7.49 (2H, m), 7.59 (1H, d, J=8.5 Hz), 7.82 (1H, dd, J=7.5 and 1.6 Hz), 7.93-7.96 (1H, m), 8.07 (1H, d, J=8.5 Hz), 8.67 (1H, d, J=2.5 Hz); ESI-MS: m/z calcd for $C_{18}H_{20}N_4O_3S$: 372.1; found [M+H]$^+$: 373.1.

Example 154: N-(2-((Dimethylamino)methyl)quinolin-8-yl)prop-2-ene-1-sulfonamide—Compound (ZDR259)

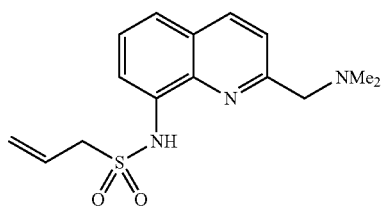 [SMILES: C=CCS(=O)(=O)Nc1cccc2ccc(CN(C)C)nc12]

A similar procedure to that described for the preparation of compound (ZDR018) was followed using compound (ZDR059) (90 mg, 0.44 mmol), propene-1-sulfonyl chloride (68 mg, 0.49 mmol) and triethylamine (68 µL, 0.49 mmol) in dichloromethane (5 mL). Purification by flash chromatography (dichloromethane/methanol, 100:1→20:1) afforded compound (ZDR259) as a yellow oil (55 mg, 0.18 mmol, 40%). $^1$H NMR (400 MHz, CDCl$_3$) δ 2.32 (6H, s), 3.73 (2H, s), 3.84 (2H, d, J=7.3 Hz), 5.03-5.07 (1H, m), 5.25-5.27 (1H, m), 5.81-5.91 (1H, m), 7.45-7.54 (2H, m), 7.67 (1H, d, J=8.5 Hz), 7.87 (1H, dd, J=7.5 and 1.6 Hz), 8.14 (1H, d, J=8.5 Hz); ESI-MS: m/z calcd for C$_{15}$H$_{19}$N$_3$O$_2$S: 305.1; found [M+H]$^+$: 306.1.

Example 155: N-(3-(Dimethylamino)propyl)-2-(((8-((4-(trifluoromethyl)phenyl)sulfonamido)quinolin-2-yl)methyl)amino)acetamide di-trifluoroacetate—Compound (ZDR261)

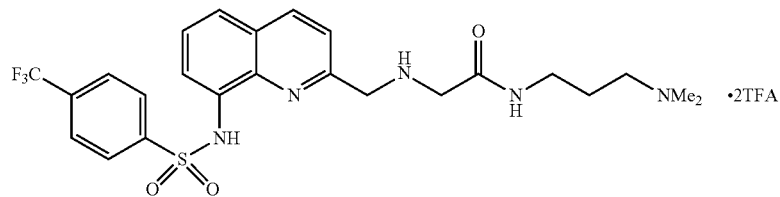 [SMILES: CN(C)CCCNC(=O)CNCc1ccc2cccc(NS(=O)(=O)c3ccc(C(F)(F)F)cc3)c2n1]

A solution of compound (ZDR246) (100 mg, 0.15 mmol) and 3-(dimethylamino)-1-propylamine (56 µL, 0.45 mmol) in dichloromethane (5 mL) was stirred at room temperature for 18 h. Trifluoroacetic acid (5 mL) was added and the solution was stirred at room temperature for a further 3 h, and the solvent then removed in vacuo. Purification by RP-HLPC (30% to 90% A/B gradient over 60 min, where A=water+0.1% trifluoroacetic acid and B=acetonitrile+ 0.1% trifluoroacetic acid) afforded compound (ZDR261) as a white solid (40 mg, 0.05 mmol, 33%). $^1$H NMR (400 MHz, d$_6$-acetone) δ 2.11 (2H, quin, J=7.0 Hz), 2.96 (6H, s), 3.38 (2H, t, J=7.0 Hz), 3.52 (2H, t, J=7.0 Hz), 4.24 (2H, s), 4.85 (2H, s), 7.52 (1H, t, J=8.0 Hz), 7.56 (1H, d, J=8.4 Hz), 7.63 (1H, dd, J=8.4 and 1.2 Hz), 7.81 (2H, d, J=8.3 Hz), 7.91 (1H, dd, J=7.8 and 1.2 Hz), 8.23 (2H, d, J=8.3 Hz), 8.29 (1H, d, J=8.4 Hz), 8.81 (1H, brs), 10.06 (1H, brs), 11.21 (1H, brs); ESI-MS: m/z calcd for C$_{24}$H$_{29}$F$_3$N$_5$O$_3$S: 523.2; found [M+Na]$^+$: 546.1.

Example 156: N-(3-(Piperidin-1-yl)propyl)-2-(((8-((4-(trifluoromethyl)phenyl)sulfonamido)quinolin-2-yl)methyl)amino)acetamide di-trifluoroacetate—Compound (ZDR262)

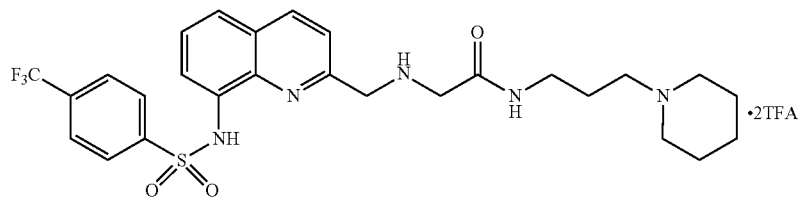 [SMILES: O=C(CNCc1ccc2cccc(NS(=O)(=O)c3ccc(C(F)(F)F)cc3)c2n1)NCCCN1CCCCC1]

A similar procedure to that described for the preparation of compound (ZDR261) was followed using compound (ZDR246) (100 mg, 0.15 mmol) and N-(3-aminopropyl)piperidine (71 µL, 0.45 mmol) in dichloromethane (5 mL), with the subsequent addition of trifluoroacetic acid (5 mL). Purification by RP-HLPC (30% to 90% A/B gradient over 60 min, where A=water+0.1% trifluoroacetic acid and B=acetonitrile+0.1% trifluoroacetic acid) afforded compound (ZDR262) as a white solid (45 mg, 0.06 mmol, 40%). $^1$H NMR (400 MHz, d$_6$-acetone) δ 1.45-1.52 (1H, m), 1.78-1.81 (1H, m), 1.85-1.91 (4H, m), 2.12 (2H, quin, J=7.2 Hz), 2.92-2.99 (2H, m), 3.31 (2H, t, J=7.2 Hz), 3.47-3.51 (2H, m), 3.58-3.62 (2H, m), 4.19 (2H, s), 4.84 (2H, s), 7.56 (1H, t, J=8.1 Hz), 7.61 (1H, d, J=8.5 Hz), 7.68 (1H, dd, J=8.1 and 1.2 Hz), 7.82 (2H, d, J=8.3 Hz), 7.95 (1H, dd, J=7.6 and 1.2 Hz), 8.24 (2H, d, J=8.3 Hz), 8.36 (1H, d, J=8.5 Hz), 8.67 (1H, brs), 10.04 (1H, brs), 10.83 (1H, brs); ESI-MS: m/z calcd for C$_{27}$H$_{32}$F$_3$N$_5$O$_3$S: 563.2; found [M+H]$^+$: N/A.

Example 157: N-(2-((Dimethylamino)methyl)quinolin-8-yl)piperidine-4-sulfonamide di-trifluoroacetate—Compound (ZDR263)

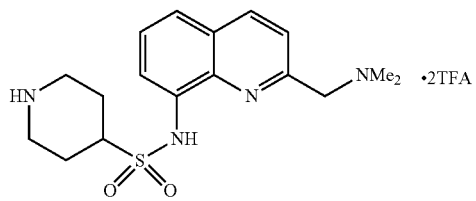 [SMILES: CN(C)Cc1ccc2cccc(NS(=O)(=O)C3CCNCC3)c2n1]

A similar procedure to that described for the preparation of compound (ZDR124) was followed using compound (ZDR256) (50 mg, 0.11 mmol) and trifluoroacetic acid-dichloromethane (3 mL, 50% v/v) to afford compound (ZDR263) as a pale yellow oil (60 mg, 0.11 mmol, quant.), which was used without further purification. $^1$H NMR (400 MHz, d$_6$-acetone) δ 2.22-2.29 (2H, m), 2.39-2.43 (2H, m), 2.78-2.90 (1H, m), 3.23 (2H, s), 3.25 (6H, s), 3.69-3.75 (2H, m), 5.00 (2H, s), 7.53 (1H, t, J=8.0 Hz), 7.69-7.71 (2H, m), 7.85 (1H, d, J=7.5 Hz), 8.48 (1H, d, J=8.4 Hz), 8.67 (1H, brs), 9.42 (1H, s); ESI-MS: m/z calcd for C$_{17}$H$_{24}$N$_4$O$_2$S: 348.2; found [M+H]$^+$: N/A.

Example 158: tert-Butyl (2-amino-2-oxoethyl)((8-((4-(trifluoromethyl)phenyl)sulfonamido)quinolin-2-yl)methyl)carbamate—Compound (ZDR264)

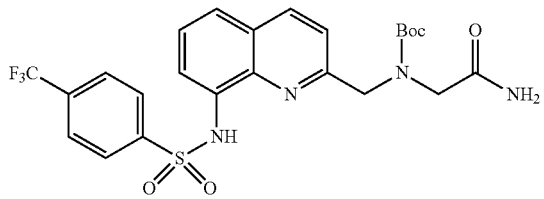 [SMILES: CC(C)(C)OC(=O)N(CC(N)=O)Cc1ccc2cccc(NS(=O)(=O)c3ccc(C(F)(F)F)cc3)c2n1]

A similar procedure to that described for the preparation of compound (ZDR234) was followed using compound (ZDR246) (100 mg, 0.15 mmol) and saturated methanolic ammonia (3 mL) in dichloromethane (3 mL). Purification by flash chromatography (dichloromethane/methanol, 20:1→10:1) afforded compound (ZDR264) as a pale yellow solid (21 mg, 0.04 mmol, 26%). $^1$H NMR (400 MHz, CDCl$_3$) δ 1.25 (4.5H, s), 1.52 (4.5H, s), 3.93-4.04 (2H, m), 4.74-4.78 (2H, m), 6.21-6.27 (1H, m), 6.92 (2H, brs), 7.31-7.33 (1H, m), 7.41 (1H, t, J=7.9 Hz), 7.46 (1H, d, J=7.5 Hz), 7.65 (2H, d, J=8.4 Hz), 7.80 (1H, d, J=7.5 Hz), 8.08 (2H, d, J=8.4 Hz), 8.17-8.19 (1H, m), 9.45 (1H, brs).

Example 159: N-(1,3-Dihydroxy-2-(hydroxymethyl)propan-2-yl)-2-(((8-((4-(trifluoromethyl)phenyl)sulfonamido)quinolin-2-yl)methyl)amino)acetamide trifluoroacetate—Compound (ZDR265)

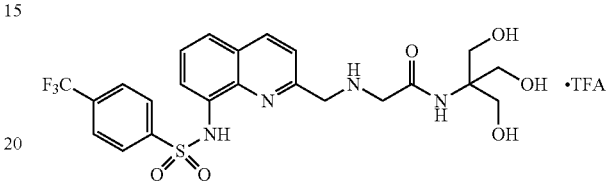

A similar procedure to that described for the preparation of compound (ZDR234) was followed using compound (ZDR246) (100 mg, 0.15 mmol) and tris(hydroxymethyl)aminomethane (54 mg, 0.45 mmol) in dichloromethane/dimethylformamide (5 mL, 9:1 v/v). The resulting residue was then taken up in trifluoroacetic acid-dichloromethane (3 mL, 50% v/v) and the mixture stirred at room temperature for 3 h, and the solvent removed in vacuo. Purification by RP-HLPC (30% to 90% A/B gradient over 60 min, where A=water+0.1% trifluoroacetic acid and B=acetonitrile+0.1% trifluoroacetic acid) afforded compound (ZDR265) as a white solid (15 mg, 0.02 mmol, 13%, over 2 steps). $^1$H NMR (400 MHz, d$_6$-acetone) δ 3.82 (6H, s), 4.23 (2H, s), 4.84 (2H, s), 7.59 (1H, t, J=8.0 Hz), 7.64 (1H, d, J=8.5 Hz), 7.72 (1H, dd, J=8.4 and 1.4 Hz), 7.82 (2H, d, J=8.2 Hz), 7.98 (1H, dd, J=7.7 and 1.3 Hz), 8.22 (2H, d, J=8.2 Hz), 8.41 (1H, d, J=8.5 Hz); ESI-MS: m/z calcd for C$_{23}$H$_{25}$F$_3$N$_4$O$_6$S: 542.1; found [M+H]$^+$: 543.2.

Example 160: 2-(((8-((4-(Trifluoromethyl)phenyl)sulfonamido)quinolin-2-yl)methyl)amino)acetamide trifluoroacetate—Compound (ZDR266)

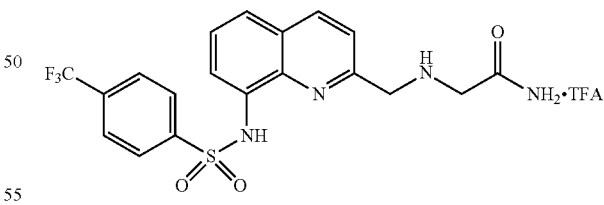

A similar procedure to that described for the preparation of compound (ZDR124) was followed using compound (ZDR264) (20 mg, 0.03 mmol) and trifluoroacetic acid-dichloromethane (3 mL, 50% v/v) to afford compound (ZDR266) as a yellow oil (16 mg, 0.03 mmol, quant.), which was used without further purification. $^1$H NMR (400 MHz, d$_6$-acetone) δ 4.29 (2H, s), 4.93 (2H, s), 7.31 (1H, brs), 7.56 (1H, t, J=8.0 Hz), 7.64 (1H, d, J=8.4 Hz), 7.70 (1H, d, J=8.2 Hz), 7.81 (2H, d, J=8.2 Hz), 7.97-7.99 (1H, m), 8.22 (2H, d, J=8.2 Hz), 8.40 (1H, d, J=8.4 Hz), 9.83 (1H, s); ESI-MS: m/z calcd for C$_{19}$H$_{17}$F$_3$N$_4$O$_3$S: 438.1; found [M+H]$^+$: N/A.

Example 161: N-hydroxy-2-(((8-((4-(trifluoromethyl)phenyl)sulfonamido)quinolin-2-yl)methyl)amino)acetamide trifluoroacetate—Compound (ZDR267)

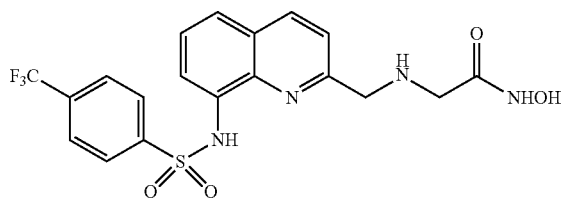

A similar procedure to that described for the preparation of compound (ZDR234) was followed using compound (ZDR246) (100 mg, 0.15 mmol), hydroxylamine hydrochloride (31 mg, 0.45 mmol) and potassium carbonate (70 mg, 0.45 mmol) in aqueous tetrahydrofuran (5 mL, 1:1 v/v). The resulting residue was then taken up in trifluoroacetic acid-dichloromethane (3 mL, 50% v/v) and the mixture stirred at room temperature for 3 h, and the solvent removed in vacuo. Purification by RP-HLPC (30% to 90% A/B gradient over 60 min, where A=water+0.1% trifluoroacetic acid and B=acetonitrile+0.1% trifluoroacetic acid) afforded compound (ZDR267) as a white solid (20 mg, 0.03 mmol, 20%). $^1$H NMR (300 MHz, d$_6$-acetone) δ 4.32 (2H, s), 4.92 (2H, s), 7.56 (1H, t, J=8.0 Hz), 7.62 (1H, d, J=8.5 Hz), 7.68 (1H, dd, J=8.4 and 1.1 Hz), 7.74-7.76 (2H, m), 7.95 (1H, dd, J=7.6 and 1.3 Hz), 8.17-8.20 (2H, m), 8.36 (1H, d, J=8.5 Hz); ESI-MS: m/z calcd for C$_{19}$H$_{17}$F$_3$N$_4$O$_4$S: 454.4; found [M+H]$^+$: N/A.

Example 162: N-(2-(Dimethylamino)ethyl)-2-(((8-((4-(trifluoromethyl)phenyl)sulfonamido)quinolin-2-yl)methyl)amino)acetamide di-trifluoroacetate—Compound ZDR(268)

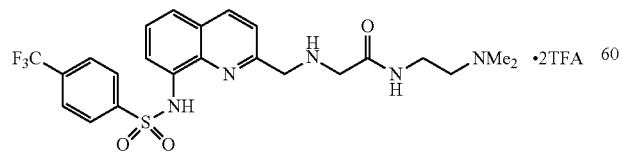

A similar procedure to that described for the preparation of compound (ZDR124) was followed using compound (ZDR234) (28 mg, 0.04 mmol) and trifluoroacetic acid-dichloromethane (3 mL, 50% v/v) to afford compound (ZDR268) as a pale yellow solid (28 mg, 0.04 mmol, quant.), which was used without further purification. $^1$H NMR (400 MHz, d$_6$-acetone) δ 3.15 (6H, s), 3.60-3.62 (2H, m), 3.94-3.97 (2H, m), 4.28 (2H, s), 4.93 (2H, s), 7.59 (1H, t, J=8.0 Hz), 7.64 (1H, d, J=8.5 Hz), 7.72 (1H, d, J=8.3 Hz), 7.82 (2H, d, J=8.2 Hz), 7.97-7.99 (1H, m), 8.22 (2H, d, J=8.2 Hz), 8.42 (1H, d, J=8.5 Hz), 8.62 (1H, t, J=5.6 Hz), 9.65 (1H, brs); ESI-MS: m/z calcd for C$_{23}$H$_{26}$F$_3$N$_5$O$_3$S: 509.2; found [M+H]$^+$: N/A.

Example 163: N-(2-(Piperidin-1-yl)ethyl)-2-(((8-((4-(trifluoromethyl)phenyl)sulfonamido)quinolin-2-yl)methyl)amino)acetamide di-trifluoroacetate—Compound—(ZDR269)

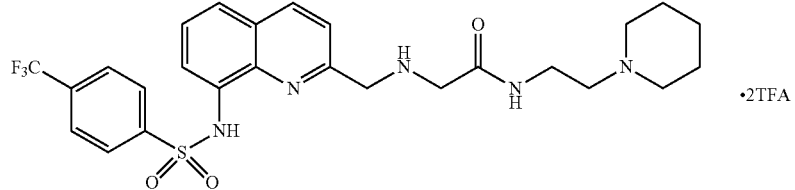 [SMILES: O=C(CNCc1ccc2cccc(NS(=O)(=O)c3ccc(C(F)(F)F)cc3)c2n1)NCCN1CCCCC1]

A similar procedure to that described for the preparation of compound (ZDR124) was followed using compound (ZDR247) (49 mg, 0.07 mmol) and trifluoroacetic acid-dichloromethane (3 mL, 50% v/v) to afford compound (ZDR269) as a pale yellow oil (52 mg, 0.07 mmol, quant.), which was used without further purification. $^1$H NMR (400 MHz, d$_6$-acetone) δ 1.50-1.59 (1H, m), 1.77-1.81 (1H, m), 1.90-1.96 (4H, m), 3.07-3.12 (2H, m), 3.52-3.54 (2H, m), 3.93-3.95 (4H, m), 4.28 (2H, s), 4.92 (2H, s), 7.57 (1H, t, J=8.0 Hz), 7.63 (1H, d, J=8.5 Hz), 7.71 (1H, d, J=8.2 Hz), 7.82 (2H, d, J=8.2 Hz), 7.99 (1H, d, J=7.7 Hz), 8.22 (2H, d, J=8.2 Hz), 8.41 (1H, d, J=8.5 Hz), 8.67 (1H, brt, J=5.6 Hz), 8.89 (1H, brs), 9.99 (1H, s); ESI-MS: m/z calcd for C$_{26}$H$_{30}$F$_3$N$_5$O$_3$S: 549.2; found [M+H]$^+$: N/A.

Example 164: N-Methyl-2-(((8-((4-(trifluoromethyl)phenyl)sulfonamido)quinolin-2-yl)methyl)amino)acetamide trifluoroacetate—Compound (ZDR270)

A similar procedure to that described for the preparation of compound (ZDR124) was followed using compound (ZDR253) (58 mg, 0.10 mmol) and trifluoroacetic acid-dichloromethane (3 mL, 50% v/v) to afford compound (ZDR270) as a beige solid (55 mg, 0.10 mmol, quant.), which was used without further purification. ¹H NMR (400 MHz, d₆-acetone) δ 2.87 (3H, s), 4.26-4.36 (2H, m), 4.92-4.96 (2H, m), 7.56 (1H, t, J=8.0 Hz), 7.41 (1H, d, J=8.4 Hz), 7.67 (1H, d, J=8.0 Hz), 7.80 (2H, d, J=8.2 Hz), 7.95 (1H, d, J=7.4 Hz), 8.21 (2H, d, J=8.2 Hz), 8.37 (1H, d, J=8.4 Hz); ESI-MS: m/z calcd for $C_{20}H_{19}F_3N_4O_3S$: 452.1; found [M+H]⁺: N/A.

Example 165: 4-Bromo-N-(2-((dimethylamino)methyl)quinolin-8-yl)benzenesulfonamide—Compound (ZDR305)

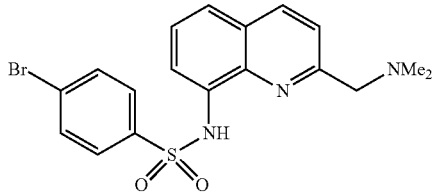

A similar procedure to that described for the preparation of compound (ZDR018) was followed using compound (ZDR059) (95 mg, 0.47 mmol), 4-bromobenzenesulfonyl chloride (133 mg, 0.52 mmol) and triethylamine (73 μL, 0.52 mmol) in dichloromethane (4 mL). Purification by flash chromatography (dichloromethane/methanol, 50:1→20:1) afforded compound (ZDR305) as a pale yellow solid (160 mg, 0.38 mmol, 80%). ¹H NMR (400 MHz, CDCl₃) δ 2.27 (6H, s), 3.68 (2H, s), 7.37-7.46 (4H, m), 7.58 (1H, d, J=8.4 Hz), 7.71 (2H, d, J=8.5 Hz), 7.79 (1H, d, J=7.4 Hz), 8.04 (1H, d, J=8.4 Hz); ESI-MS: m/z calcd for $C_{18}H_{18}BrN_3O_2S$: 419.0; found [M+H]⁺: 420.0.

Example 166: 4-(Difluoromethoxy)-N-(2-((dimethylamino)methyl)quinolin-8-yl)benzenesulfonamide—Compound (ZDR306)

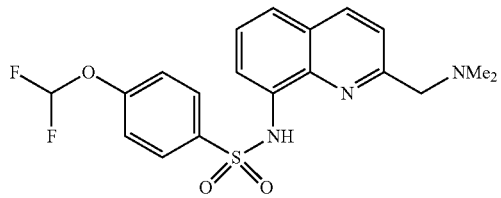 [SMILES: CN(C)Cc1ccc2cccc(NS(=O)(=O)c3ccc(OC(F)F)cc3)c2n1]

A similar procedure to that described for the preparation of compound (ZDR018) was followed using compound (ZDR059) (95 mg, 0.47 mmol), 4-(difluoromethoxy)benzenesulfonyl chloride (126 mg, 0.52 mmol) and triethylamine (73 μL, 0.52 mmol) in dichloromethane (4 mL). Purification by flash chromatography (dichloromethane/methanol, 50:1→20:1) afforded compound (ZDR306) as a yellow solid (178 mg, 0.44 mmol, 92%). ¹H NMR (400 MHz, CDCl₃) δ 2.27 (6H, s), 3.69 (2H, s), 6.46 (1H, t, J=72.7 Hz), 7.00 (2H, d, J=8.8 Hz), 7.37-7.46 (2H, m), 7.56 (1H, d, J=8.5 Hz), 7.79 (1H, dd, J=7.4 and 1.4 Hz), 7.85-7.89 (2H, m), 8.04 (1H, d, J=8.5 Hz); ESI-MS: m/z calcd for $C_{19}H_{19}F_2N_3O_3S$: 407.1; found [M+H]⁺: 408.1.

Example 167: 4-(tert-Butyl)-N-(2-((dimethylamino)methyl)quinolin-8-yl)benzenesulfonamide—Compound (ZDR307)

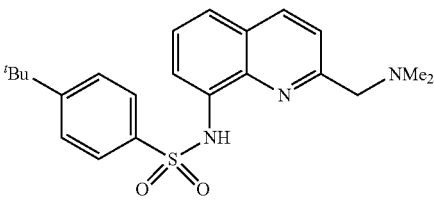

A similar procedure to that described for the preparation of compound (ZDR018) was followed using compound (ZDR059) (95 mg, 0.47 mmol), 4-tert-butylbenzenesulfonyl chloride (121 mg, 0.52 mmol) and triethylamine (73 μL, 0.52 mmol) in dichloromethane (4 mL). Purification by flash chromatography (dichloromethane/methanol, 50:1→20:1) afforded compound (ZDR307) as a white solid (173 mg, 0.44 mmol, 92%). ¹H NMR (400 MHz, CDCl₃) δ 1.20 (9H, s), 2.28 (6H, s), 3.70 (2H, s), 7.31-7.34 (2H, m), 7.36-7.42 (2H, m), 7.57 (1H, d, J=8.5 Hz), 7.79-7.82 (3H, m), 8.03 (1H, d, J=8.5 Hz); ESI-MS: m/z calcd for $C_{22}H_{27}N_3O_2S$: 397.2; found [M+H]⁺: 398.2.

Example 168: Methyl 3-(N-(2-((dimethylamino)methyl)quinolin-8-yl)sulfamoyl)benzoate—Compound (ZDR308)

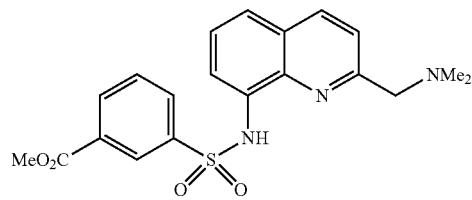 [SMILES: CN(C)Cc1ccc2cccc(NS(=O)(=O)c3cccc(S(C)(=O)=O)c3)c2n1]

A similar procedure to that described for the preparation of compound (ZDR018) was followed using compound (ZDR059) (95 mg, 0.47 mmol), 3-chlorosulfonyl-benzoic acid methyl ester (122 mg, 0.52 mmol) and triethylamine (73 μL, 0.52 mmol) in dichloromethane (4 mL). Purification by flash chromatography (dichloromethane/methanol, 50:1→20:1) afforded compound (ZDR308) as an orange oil (122 mg, 0.31 mmol, 64%). ¹H NMR (400 MHz, CDCl₃) δ 2.25 (6H, s), 3.67 (2H, s), 3.84 (3H, s), 7.34-7.42 (3H, m), 7.53 (1H, d, J=8.4 Hz), 7.79 (1H, d, J=7.0 Hz), 7.99-8.01 (3H, m), 8.53 (1H, s); ESI-MS: m/z calcd for $C_{20}H_{21}N_3O_4S$: 399.1; found [M+H]⁺: 400.1.

Example 169: 3-Bromo-N-(2-((dimethylamino)methyl)quinolin-8-yl)benzenesulfonamide—Compound (ZDR309)

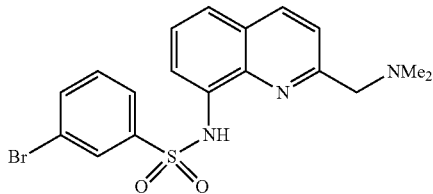

A similar procedure to that described for the preparation of compound (ZDR018) was followed using compound (ZDR059) (95 mg, 0.47 mmol), 3-bromobenzenesulfonyl chloride (133 mg, 0.52 mmol) and triethylamine (73 μL, 0.52 mmol) in dichloromethane (4 mL). Purification by flash chromatography (dichloromethane/methanol, 50:1→20:1) afforded compound (ZDR309) as a yellow solid (160 mg, 0.38 mmol, 80%). $^1$H NMR (400 MHz, CDCl$_3$) δ 2.28 (6H, s), 3.70 (2H, s), 7.14 (1H, t, J=7.9 Hz), 7.38-7.49 (3H, m), 7.56 (1H, d, J=8.4 Hz), 7.75 (1H, d, J=7.9 Hz), 7.80 (1H, dd, J=7.5 and 1.2 Hz), 8.03-8.05 (2H, m); ESI-MS: m/z calcd for C$_{18}$H$_{18}$BrN$_3$O$_2$S: 419.0; found [M+H]$^+$: 420.0.

Example 171: 3-Acetyl-N-(2-((dimethylamino)methyl)quinolin-8-yl)benzenesulfonamide—Compound (ZDR311)

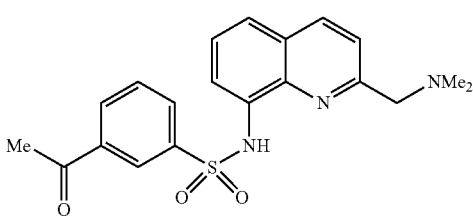 [SMILES: CC(=O)c1cccc(S(=O)(=O)Nc2cccc3ccc(CN(C)C)nc23)c1]

A similar procedure to that described for the preparation of compound (ZDR018) was followed using compound (ZDR059) (130 mg, 0.65 mmol), 3-acetylbenzenesulfonyl chloride (155 mg, 0.71 mmol) and triethylamine (99 μL, 0.71 mmol) in dichloromethane (6 mL). Purification by flash chromatography (dichloromethane/methanol, 50:1→20:1) afforded compound (ZDR311) as a brown oil (201 mg, 0.52 mmol, 81%). $^1$H NMR (400 MHz, CDCl$_3$) δ 2.27 (6H, s), 2.50 (3H, s), 3.69 (2H, s), 7.39-7.47 (3H, m), 7.56 (1H, d, J=8.5 Hz), 7.84 (1H, dd, J=7.5 and 1.5 Hz), 7.96-7.99 (1H, m), 8.03-8.07 (2H, m), 8.41 (1H, t, J=1.7 Hz); ESI-MS: m/z calcd for C$_{20}$H$_{21}$N$_3$O$_3$S: 383.1; found [M+H]$^+$: 384.1.

Example 170: N-(2-((Dimethylamino)methyl)quinolin-8-yl)-3-(methylsulfonyl)benzenesulfonamide—Compound (ZDR310)

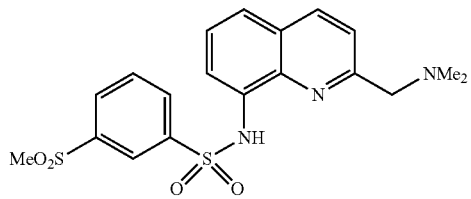

A similar procedure to that described for the preparation of compound (ZDR018) was followed using compound (ZDR059) (88 mg, 0.44 mmol), 3-methylsulfonylbenzenesulfonyl chloride (122 mg, 0.48 mmol) and triethylamine (67 μL, 0.48 mmol) in dichloromethane (4 mL). Purification by flash chromatography (dichloromethane/methanol, 50:1→20:1) afforded compound (ZDR310) as a pale yellow foam (137 mg, 0.33 mmol, 75%). $^1$H NMR (400 MHz, CDCl$_3$) δ 2.30 (6H, s), 2.92 (3H, s), 3.72 (2H, s), 7.42-7.59 (4H, m), 7.85 (1H, dd, J=7.4 and 1.1 Hz), 7.96 (1H, d, J=7.9 Hz), 8.06 (1H, d, J=8.4 Hz), 8.13 (1H, d, J=8.4 Hz), 8.43 (1H, s); ESI-MS: m/z calcd for C$_{19}$H$_{21}$N$_3$O$_4$S$_2$: 419.1; found [M+H]$^+$: 420.1.

Example 172: N-(2-((Dimethylamino)methyl)quinolin-8-yl)-3-fluorobenzenesulfonamide—Compound (ZDR312)

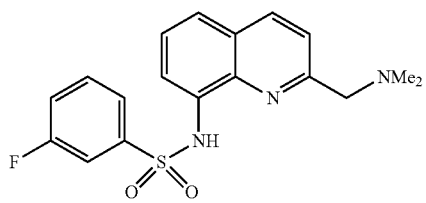 [SMILES: CN(C)Cc1ccc2cccc(NS(=O)(=O)c3cccc(F)c3)c2n1]

A similar procedure to that described for the preparation of compound (ZDR018) was followed using compound (ZDR059) (88 mg, 0.44 mmol), 3-fluorobenzenesulfonyl chloride (94 mg, 0.48 mmol) and triethylamine (67 μL, 0.48 mmol) in dichloromethane (4 mL). Purification by flash chromatography (dichloromethane/methanol, 50:1→20:1) afforded compound (ZDR312) as brown solid (138 mg, 0.38 mmol, 88%). $^1$H NMR (400 MHz, CDCl$_3$) δ 2.30 (6H, s), 3.72 (2H, s), 7.08-7.13 (1H, m), 7.27-7.33 (1H, m), 7.40-7.49 (2H, m), 7.58-7.62 (2H, m), 7.65-7.67 (1H, m), 7.82 (1H, dd, J=7.5 and 1.5 Hz), 8.07 (1H, d, J=8.5 Hz); ESI-MS: m/z calcd for C$_{18}$H$_{18}$FN$_3$O$_2$S: 359.1; found [M+H]$^+$: 360.1.

Example 173: N-(2-((Dimethylamino)methyl)quinolin-8-yl)-3-nitrobenzenesulfonamide—Compound (ZDR313)

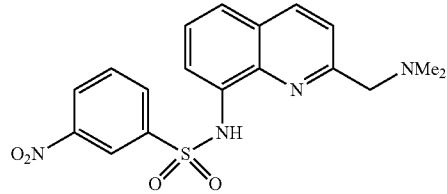 [SMILES: CN(C)Cc1ccc2cccc(NS(=O)(=O)c3cccc([N+](=O)[O-])c3)c2n1]

A similar procedure to that described for the preparation of compound (ZDR018) was followed using compound (ZDR059) (88 mg, 0.44 mmol), 3-nitrobenzenesulfonyl chloride (107 mg, 0.48 mmol) and triethylamine (67 μL, 0.48 mmol) in dichloromethane (4 mL). Purification by flash chromatography (dichloromethane/methanol, 50:1→20:1) afforded compound (ZDR313) as a red/orange oil (67 mg, 0.17 mmol, 40%). $^1$H NMR (400 MHz, CDCl$_3$) δ 2.29 (6H, s), 3.72 (2H, s), 7.41-7.59 (4H, m), 7.85 (1H, dd, J=7.5 and 1.2 Hz), 8.06 (1H, d, J=8.5 Hz), 8.18 (1H, m), 8.24 (1H, m), 8.74 (1H, t, J=1.9 Hz); ESI-MS: m/z calcd for $C_{18}H_{18}N_4O_4S$: 386.1; found [M+H]$^+$: 387.1.

Example 174: N-(2-((Dimethylamino)methyl)quinolin-8-yl)-3-methoxybenzenesulfonamide—Compound (ZDR314)

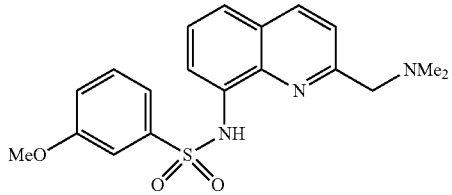 [SMILES: COc1cccc(S(=O)(=O)Nc2cccc3ccc(CN(C)C)nc23)c1]

A similar procedure to that described for the preparation of compound (ZDR018) was followed using compound (ZDR059) (88 mg, 0.44 mmol), 3-methoxybenzene sulfonyl chloride (99 mg, 0.48 mmol) and triethylamine (67 μL, 0.48 mmol) in dichloromethane (4 mL). Purification by flash chromatography (dichloromethane/methanol, 50:1→20:1) afforded compound (ZDR314) as a pale brown solid (139 mg, 0.37 mmol, 86%). $^1$H NMR (400 MHz, CDCl$_3$) δ 2.29 (6H, s), 3.70 (2H, s), 3.70 (3H, s), 6.91-6.94 (1H, m), 7.22 (1H, t, J=8.0 Hz), 7.37-7.47 (4H, m), 7.59 (1H, d, J=8.5 Hz), 7.82 (1H, dd, J=7.5 and 1.5 Hz), 8.06 (1H, d, J=8.5 Hz); ESI-MS: m/z calcd for $C_{19}H_{21}N_3O_3S$: 371.1; found [M+H]$^+$: 372.1.

Example 175: N-(2-((Dimethylamino)methyl)quinolin-8-yl)-3-methylbenzenesulfonamide—Compound (ZDR315)

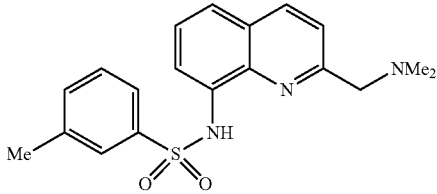

A similar procedure to that described for the preparation of compound (ZDR018) was followed using compound (ZDR059) (88 mg, 0.44 mmol), 3-toluenesulfonyl chloride (92 mg, 0.48 mmol) and triethylamine (67 μL, 0.48 mmol) in dichloromethane (4 mL). Purification by flash chromatography (dichloromethane/methanol, 50:1→20:1) afforded compound (ZDR315) as a pale yellow solid (124 mg, 0.35 mmol, 80%). $^1$H NMR (400 MHz, CDCl$_3$) δ 2.28 (3H, s), 2.35 (6H, s), 3.79 (2H, s), 7.19-7.22 (2H, m), 7.39-7.46 (2H, m), 7.59 (1H, d, J=8.5 Hz), 7.67-7.72 (2H, m), 7.79 (1H, dd, J=7.0 and 1.5 Hz), 8.07 (1H, d, J=8.5 Hz); ESI-MS: m/z calcd for $C_{19}H_{21}N_3O_2S$: 355.1; found [M+H]$^+$: 356.1.

Example 176: N-(2-((Dimethylamino)methyl)quinolin-8-yl)-3,3,3-trifluoropropane-1-sulfonamide—Compound (ZDR316)

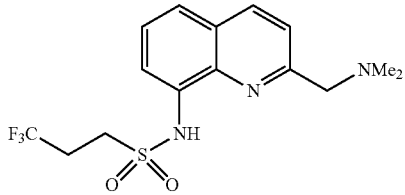 [SMILES: CN(C)Cc1ccc2cccc(NS(=O)(=O)CCC(F)(F)F)c2n1]

A similar procedure to that described for the preparation of compound (ZDR018) was followed using compound (ZDR059) (100 mg, 0.50 mmol), 3,3,3-trifluoropropane-1-sulfonyl chloride (69 μL, 0.55 mmol) and triethylamine (76 μL, 0.55 mmol) in dichloromethane (4 mL). Purification by flash chromatography (dichloromethane/methanol, 50:1→20:1) afforded compound (ZDR316) as an orange solid (144 mg, 0.40 mmol, 80%). $^1$H NMR (400 MHz, CDCl$_3$) δ 2.34 (6H, s), 2.65-2.77 (2H, m), 3.27-3.31 (2H, m), 3.78 (2H, s), 7.51 (1H, t, J=7.9 Hz), 7.59-7.61 (1H, m), 7.68 (1H, d, J=8.4 Hz), 7.85 (1H, dd, J=7.5 and 1.0 Hz), 8.18 (1H, d, J=8.4 Hz); ESI-MS: m/z calcd for $C_{18}H_{18}F_3N_3O_2S$: 361.1; found [M+H]$^+$: 362.1.

Example 177: N-(2-((Dimethylamino)methyl)quinolin-8-yl)-1-phenylmethanesulfonamide—Compound (ZDR317)

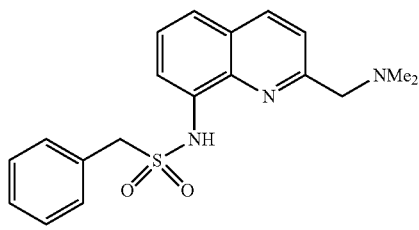 [SMILES: CN(C)Cc1ccc2cccc(NS(=O)(=O)Cc3ccccc3)c2n1]

A similar procedure to that described for the preparation of compound (ZDR018) was followed using compound (ZDR059) (100 mg, 0.50 mmol), phenylmethanesulfonyl chloride (104 mg, 0.55 mmol) and triethylamine (76 μL, 0.55 mmol) in dichloromethane (4 mL). Purification by flash chromatography (dichloromethane/methanol, 50:1→20:1) afforded compound (ZDR317) as a brown oil (44 mg, 0.12 mmol, 25%). $^1$H NMR (400 MHz, CDCl$_3$) δ 2.29 (6H, s), 3.63 (2H, s), 4.41 (2H, s), 7.07-7.09 (2H, m), 7.12-7.16 (2H, m), 7.23-7.26 (1H, m), 7.46 (1H, t, J=7.8 Hz), 7.52 (1H, dd, J=8.0 and 1.5 Hz), 7.66 (1H, d, J=8.4 Hz), 7.81 (1H, dd, J=7.5 and 1.5 Hz), 8.14 (1H, d, J=8.4 Hz); ESI-MS: m/z calcd for $C_{19}H_{21}N_3O_2S$: 355.1; found [M+H]$^+$: 356.1.

Example 178: N-(2-((Dimethylamino)methyl)quinolin-8-yl)propane-2-sulfonamide—Compound (ZDR318)

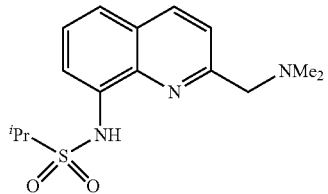 [SMILES: CC(C)S(=O)(=O)Nc1cccc2ccc(CN(C)C)nc12]

A similar procedure to that described for the preparation of compound (ZDR018) was followed using compound (ZDR059) (170 mg, 0.84 mmol), 2-propanesulfonyl chloride (104 μL, 0.93 mmol) and triethylamine (130 μL, 0.93 mmol) in dichloromethane (8 mL). Purification by flash chromatography (dichloromethane/methanol, 50:1→20:1) afforded compound (ZDR318) as a dark brown solid (206 mg, 0.67 mmol, 79%). $^1$H NMR (400 MHz, CDCl$_3$) δ 1.26-1.28 (6H, m), 2.74 (6H, s), 3.34-3.35 (1H, m), 4.24 (2H, s), 6.98-7.01 (1H, m), 7.14-7.18 (1H, m), 7.33-7.43 (2H, m), 8.11-8.15 (1H, m); ESI-MS: m/z calcd for $C_{15}H_{21}N_3O_2S$: 307.1; found [M+H]$^+$: N/A.

Example 179: Methyl 3-(N-(2-((dimethylamino)methyl)quinolin-8-yl)sulfamoyl)thiophene-2-carboxylate—Compound (ZDR319)

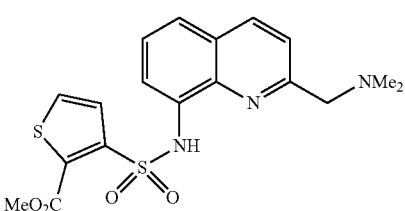

A similar procedure to that described for the preparation of compound (ZDR018) was followed using compound (ZDR059) (100 mg, 0.50 mmol), methyl 3-chlorosulfonyl-thiophene-2-carboxylate (132 mg, 0.55 mmol) and triethylamine (76 μL, 0.55 mmol) in dichloromethane (4 mL). Purification by flash chromatography (dichloromethane/methanol, 50:1→20:1) afforded compound (ZDR319) as an orange solid (78 mg, 0.19 mmol, 39%). $^1$H NMR (400 MHz, CDCl$_3$) δ 2.30 (6H, s), 3.73 (2H, s), 3.97 (3H, s), 7.35-7.45 (3H, m), 7.57-7.62 (2H, m), 7.87 (1H, dd, J=7.8 and 1.5 Hz), 8.05 (1H, d, J=8.5 Hz); ESI-MS: m/z calcd for $C_{18}H_{19}N_3O_4S_2$: 405.1; found [M+H]$^+$: 406.1.

Example 180: N-(2-((Dimethylamino)methyl)quinolin-8-yl)-1-(4-(trifluoromethyl)phenyl)methanesulfonamide—Compound (ZDR320)

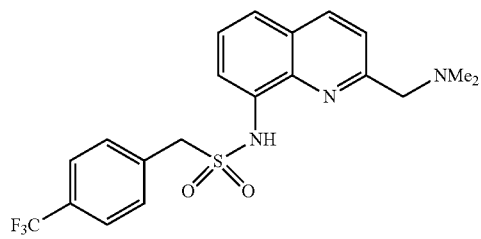 [SMILES: CN(C)Cc1ccc2cccc(NS(=O)(=O)Cc3ccc(C(F)(F)F)cc3)c2n1]

A similar procedure to that described for the preparation of compound (ZDR018) was followed using compound (ZDR059) (100 mg, 0.50 mmol), 4-(trifluoromethyl)benzylsulfonyl chloride (141 mg, 0.55 mmol) and triethylamine (76 μL, 0.55 mmol) in dichloromethane (4 mL). Purification by flash chromatography (dichloromethane/methanol, 50:1→20:1) afforded compound (ZDR320) as a pale brown oil (163 mg, 0.38 mmol, 77%). $^1$H NMR (400 MHz, CDCl$_3$) δ 2.28 (6H, s), 3.61 (2H, s), 4.45 (2H, s), 7.19 (2H, d, J=8.1 Hz), 7.37 (2H, d, J=8.1 Hz), 7.42-7.54 (2H, m), 7.65 (1H, d, J=8.4 Hz), 7.82 (1H, dd, J=7.6 and 1.6 Hz), 8.14 (1H, d, J=8.4 Hz); ESI-MS: m/z calcd for $C_{20}H_{20}F_3N_3O_2S$: 423.1; found [M+H]$^+$: 424.1.

Example 181: N-(2-((Dimethylamino)methyl)quinolin-8-yl)butane-1-sulfonamide—Compound (ZDR321)

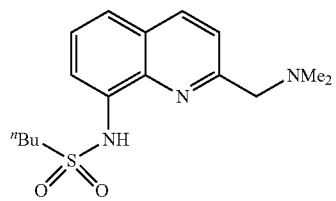

A similar procedure to that described for the preparation of compound (ZDR018) was followed using compound (ZDR059) (100 mg, 0.50 mmol), 1-butane sulfonyl chloride (71 µL, 0.55 mmol) and triethylamine (76 µL, 0.55 mmol) in dichloromethane (4 mL). Purification by flash chromatography (dichloromethane/methanol, 50:1→20:1) afforded compound (ZDR321) as an orange oil (100 mg, 0.31 mmol, 63%). $^1$H NMR (400 MHz, CDCl$_3$) δ 0.78 (3H, t, J=7.4 Hz), 1.26-1.35 (2H, m), 1.74-1.82 (2H, m), 2.31 (6H, s), 3.08-3.12 (2H, m), 3.73 (2H, s), 7.43-7.52 (2H, m), 7.66 (1H, d, J=8.4 Hz), 7.82 (1H, dd, J=7.5 and 1.5 Hz), 8.13 (1H, d, J=8.4 Hz); ESI-MS: m/z calcd for C$_{16}$H$_{23}$N$_3$O$_2$S: 321.2; found [M+H]$^+$: 322.2.

Example 182: 6-Chloro-N-(2-((dimethylamino)methyl)quinolin-8-yl)pyridine-3-sulfonamide—Compound (ZDR322)

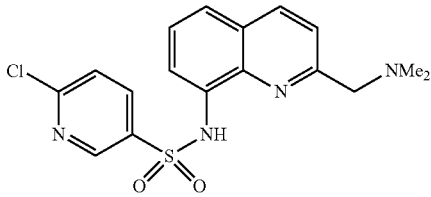 [SMILES: CN(C)Cc1ccc2cccc(NS(=O)(=O)c3ccc(Cl)nc3)c2n1]

A similar procedure to that described for the preparation of compound (ZDR018) was followed using compound (ZDR059) (100 mg, 0.50 mmol), 2-chloropyridine-5-sulfonyl chloride (116 mg, 0.55 mmol) and triethylamine (76 µL, 0.55 mmol) in dichloromethane (4 mL). Purification by flash chromatography (dichloromethane/methanol, 50:1→20:1) afforded compound (ZDR322) as a yellow solid (90 mg, 0.24 mmol, 48%). $^1$H NMR (400 MHz, CDCl$_3$) δ 2.28 (6H, s), 3.69 (2H, s), 7.26-7.28 (1H, m), 7.44 (1H, t, J=7.9 Hz), 7.52 (1H, dd, J=7.9 and 1.5 Hz), 7.58 (1H, d, J=8.5 Hz), 7.85 (1H, dd, J=7.5 and 0.9 Hz), 8.04-8.09 (2H, m), 8.82-8.83 (1H, m); ESI-MS: m/z calcd for C$_{17}$H$_{17}$ClN$_4$O$_2$S: 376.1; found [M+H]$^+$: 377.1.

Example 183: N-(2-((Dimethylamino)methyl)quinolin-8-yl)cyclopropanesulfonamide—Compound (ZDR323)

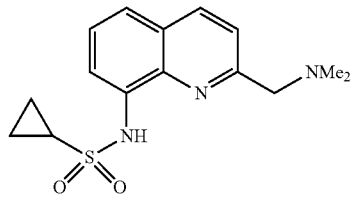 [SMILES: CN(C)Cc1ccc2cccc(NS(=O)(=O)C3CC3)c2n1]

A similar procedure to that described for the preparation of compound (ZDR018) was followed using compound (ZDR059) (100 mg, 0.50 mmol), cyclopropanesulfonyl chloride (56 µL, 0.55 mmol) and triethylamine (76 µL, 0.55 mmol) in dichloromethane (4 mL). Purification by flash chromatography (dichloromethane/methanol, 50:1→20:1) afforded compound (ZDR323) as a brown solid (41 mg, 0.13 mmol, 27%). $^1$H NMR (400 MHz, CDCl$_3$) δ 0.83-0.89 (2H, m), 1.25-1.29 (2H, m), 2.33 (6H, s), 2.49-2.56 (1H, m), 3.75 (2H, s), 7.45-7.54 (2H, m), 7.66 (1H, d, J=8.5 Hz), 7.88 (1H, dd, J=7.5 and 1.5 Hz), 8.14 (1H, d, J=8.5 Hz); ESI-MS: m/z calcd for C$_{15}$H$_{19}$N$_3$O$_2$S: 305.1; found [M+H]$^+$: 306.1.

Example 184: N-(2-((Dimethylamino)methyl)quinolin-8-yl)-4-formylbenzenesulfonamide—Compound (ZDR324)

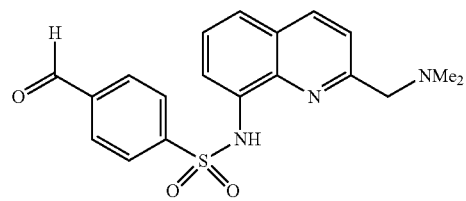 [SMILES: CN(C)Cc1ccc2cccc(NS(=O)(=O)c3ccc(C=O)cc3)c2n1]

A similar procedure to that described for the preparation of compound (ZDR018) was followed using compound (ZDR059) (95 mg, 0.47 mmol), 4-formylbenzene-1-sulfonyl chloride (106 mg, 0.52 mmol) and triethylamine (72 µL, 0.52 mmol) in dichloromethane (4 mL). Purification by flash chromatography (dichloromethane/methanol, 50:1→20:1) afforded compound (ZDR324) as a yellow oil (70 mg, 0.19 mmol, 40%). $^1$H NMR (400 MHz, CDCl$_3$) δ 2.28 (6H, s), 3.70 (2H, s), 7.39-7.48 (2H, m), 7.56 (1H, d, J=8.4 Hz), 7.80-7.85 (3H, m), 8.03-8.06 (3H, m), 9.94 (1H, s); ESI-MS: m/z calcd for C$_{19}$H$_{19}$N$_3$O$_3$S: 369.1; found [M+H]$^+$: N/A.

Example 185: 5-Chloro-N-(2-((dimethylamino)methyl)quinolin-8-yl)thiophene-2-sulfonamide—Compound (ZDR326)

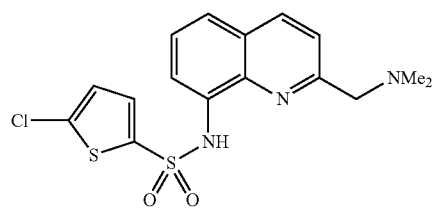

A similar procedure to that described for the preparation of compound (ZDR018) was followed using compound (ZDR059) (95 mg, 0.47 mmol), 5-chlorothiophene-2-sulfonyl chloride (69 µL, 0.52 mmol) and triethylamine (72 µL, 0.52 mmol) in dichloromethane (4 mL). Purification by flash chromatography (dichloromethane/methanol, 50:1→20:1) afforded compound (ZDR326) as a yellow solid (38 mg, 0.10 mmol, 21%). $^1$H NMR (400 MHz, CDCl$_3$) δ 2.29 (6H, s), 3.71 (2H, s), 6.70 (1H, d, J=4.0 Hz), 7.34 (1H, d, J=4.0 Hz), 7.45-7.54 (2H, m), 7.62 (1H, d, J=8.4 Hz), 7.86 (1H, dd, J=7.5 and 1.3 Hz), 8.10 (1H, d, J=8.4 Hz); ESI-MS: m/z calcd for C$_{16}$H$_{16}$ClN$_3$O$_2$S$_2$: 381.0; found [M+H]$^+$: N/A.

Example 186: N-(3-(N-(2-((Dimethylamino)methyl)quinolin-8-yl)sulfamoyl)phenyl)acetamide—Compound (ZDR327)

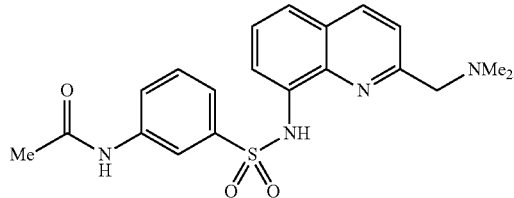 [SMILES: CC(=O)Nc1cccc(S(=O)(=O)Nc2cccc3ccc(CN(C)C)nc23)c1]

A similar procedure to that described for the preparation of compound (ZDR018) was followed using compound (ZDR059) (95 mg, 0.47 mmol), 3-acetamidobenzene-1-sulfonyl chloride (121 mg, 0.52 mmol) and triethylamine (72 µL, 0.52 mmol) in dichloromethane (4 mL). Purification by flash chromatography (dichloromethane/methanol, 50:1→20:1) afforded compound (ZDR327) as a yellow solid (31 mg, 0.08 mmol, 16%). $^1$H NMR (400 MHz, CDCl$_3$) δ 2.12 (3H, s), 2.28 (6H, s), 3.71 (2H, s), 7.22-7.30 (1H, m), 7.37-7.41 (1H, m), 7.43-7.46 (1H, m), 7.50 (1H, d, J=8.4 Hz), 7.54 (1H, d, J=7.9 Hz), 7.83 (1H, dd, J=7.5 Hz and 1.5 Hz), 7.96 (1H, s), 7.99-8.01 (1H, m), 8.04 (1H, d, J=8.4 Hz), 8.10 (1H, br s); ESI-MS: m/z calcd for C$_{20}$H$_{22}$N$_4$O$_3$S: 398.1; found [M+H]$^+$: N/A.

Example 187: N-(2-((Dimethylamino)methyl)quinolin-8-yl)pyridine-3-sulfonamide—Compound (ZDR328)

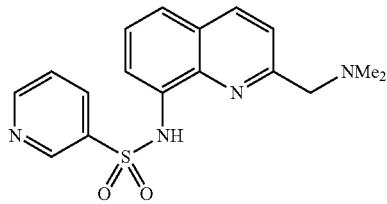 [SMILES: CN(C)Cc1ccc2cccc(NS(=O)(=O)c3cccnc3)c2n1]

A similar procedure to that described for the preparation of compound (ZDR018) was followed using compound (ZDR059) (95 mg, 0.47 mmol), pyridine-3-sulfonyl chloride (63 µL, 0.52 mmol) and triethylamine (72 µL, 0.52 mmol) in dichloromethane (4 mL). Purification by flash chromatography (dichloromethane/methanol, 50:1→20:1) afforded compound (ZDR328) as a yellow solid (123 mg, 0.36 mmol, 76%). $^1$H NMR (400 MHz, CDCl$_3$) δ 2.28 (6H, s), 3.70 (2H, s), 7.24-7.27 (1H, m), 7.41-7.45 (1H, m), 7.48-7.50 (1H, m), 7.59 (1H, d, J=8.4 Hz), 7.85 (1H, dd, J=7.5 and 1.2 Hz), 8.06 (1H, d, J=8.4 Hz), 8.12-8.15 (1H, m), 8.61 (1H, dd, J=5.0 and 1.5 Hz), 9.06-9.07 (1H, m); ESI-MS: m/z calcd for C$_{17}$H$_{18}$N$_4$O$_2$S: 342.1; found [M+H]$^+$: 343.1.

Example 188: N-(2-((Dimethylamino)methyl)quinolin-8-yl)-4-((trifluoromethyl)thio)benzenesulfonamide—Compound (ZDR330)

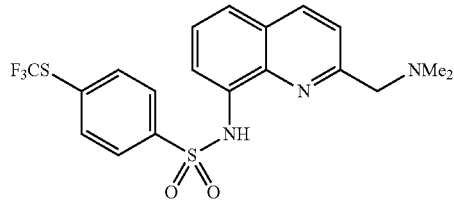

A similar procedure to that described for the preparation of compound (ZDR018) was followed using compound (ZDR059) (84 mg, 0.42 mmol), 4-(trifluoromethylsulfanyl)benzenesulfonyl chloride (127 mg, 0.46 mmol) and triethylamine (64 µL, 0.46 mmol) in dichloromethane (4 mL). Purification by flash chromatography (dichloromethane/methanol, 50:1→20:1) afforded compound (ZDR330) as an orange solid (140 mg, 0.32 mmol, 76%). $^1$H NMR (400 MHz, CDCl$_3$) δ 2.29 (6H, s), 3.69 (2H, s), 7.41-7.50 (2H, m), 7.58-7.60 (3H, m), 7.83 (1H, dd, J=7.5 and 1.7 Hz), 7.90 (2H, d, J=8.4 Hz), 8.06 (1H, d, J=8.4 Hz); ESI-MS: m/z calcd for C$_{19}$H$_{18}$F$_3$N$_3$O$_2$S$_2$: 441.1; found [M+H]$^+$: 442.1.

Example 189: 3-(N-(2-((Dimethylamino)methyl)quinolin-8-yl)sulfamoyl)benzamide—Compound (ZDR331)

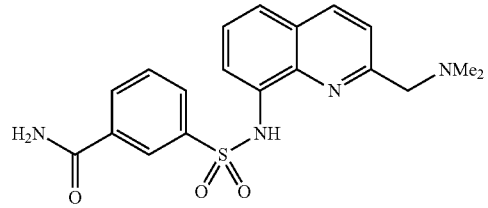 [SMILES: CN(C)Cc1ccc2cccc(NS(=O)(=O)c3cccc(C(N)=O)c3)c2n1]

A similar procedure to that described for the preparation of compound (ZDR018) was followed using compound (ZDR059) (84 mg, 0.42 mmol), 3-carbamoylbenzene-1-sulfonyl chloride (101 mg, 0.46 mmol) and triethylamine (64 µL, 0.46 mmol) in dichloromethane (4 mL). Purification by flash chromatography (dichloromethane/methanol, 50:1→20:1) afforded compound (ZDR331) as a yellow solid (123 mg, 0.32 mmol, 77%). $^1$H NMR (400 MHz, CDCl$_3$) δ 2.26 (6H, s), 3.70 (2H, s), 6.26 (1H, br s), 6.98 (1H, br s), 7.33-7.48 (4H, m), 7.80 (1H, dd, J=7.5 and 1.6 Hz), 7.94 (2H, t, J=6.8 Hz), 8.01 (1H, d, J=8.4 Hz), 8.44 (1H, s); ESI-MS: m/z calcd for C$_{19}$H$_{20}$N$_4$O$_3$S: 384.1; found [M+H]$^+$: 385.1.

Example 190: Methyl (4-(N-(2-((dimethylamino)methyl)quinolin-8-yl)sulfamoyl)phenyl)carbamate—Compound (ZDR332)

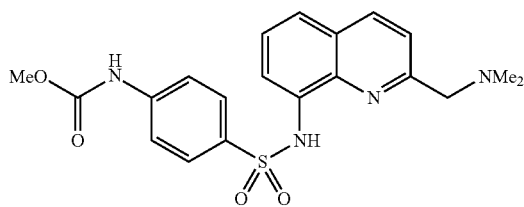 [SMILES: COC(=O)Nc1ccc(S(=O)(=O)Nc2cccc3ccc(CN(C)C)nc23)cc1]

A similar procedure to that described for the preparation of compound (ZDR018) was followed using compound (ZDR059) (84 mg, 0.42 mmol), methyl N-[4-(chlorosulfonyl)phenyl]carbamate (115 mg, 0.46 mmol) and triethylamine (64 μL, 0.46 mmol) in dichloromethane (4 mL). Purification by flash chromatography (dichloromethane/methanol, 50:1→20:1) afforded compound (ZDR332) as a brown oil (153 mg, 0.37 mmol, 88%). $^1$H NMR (400 MHz, CDCl$_3$) δ 2.27 (6H, s), 3.67 (3H, s), 3.69 (2H, s), 7.32-7.42 (4H, m), 7.53 (1H, d, J=8.5 Hz), 7.74-7.77 (3H, m), 8.01 (1H, d, J=8.5 Hz); ESI-MS: m/z calcd for C$_{20}$H$_{21}$N$_4$O$_4$S: 414.1; found [M+H]$^+$: 415.1.

Example 191: tert-Butyl (4-(N-(2-((dimethylamino)methyl)quinolin-8-yl)sulfamoyl)phenyl)carbamate—Compound (ZDR333)

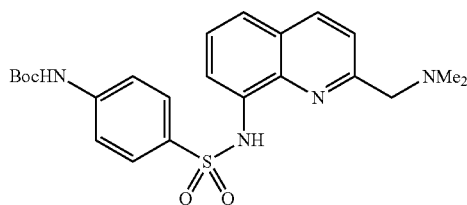 [SMILES: CN(C)Cc1ccc2cccc(NS(=O)(=O)c3ccc(NC(=O)OC(C)(C)C)cc3)c2n1]

A similar procedure to that described for the preparation of compound (ZDR018) was followed using compound (ZDR059) (113 mg, 0.56 mmol), tert-butyl[4-(chlorosulfonyl)phenyl]carbamate (180 mg, 0.62 mmol) and triethylamine (86 μL, 0.62 mmol) in dichloromethane (5 mL). Purification by flash chromatography (dichloromethane/methanol, 50:1→20:1) afforded compound (ZDR333) as a white foam (209 mg, 0.46 mmol, 82%). $^1$H NMR (400 MHz, CDCl$_3$) δ 1.46 (9H, s), 2.29 (6H, s), 3.71 (2H, s), 6.58 (1H, br s), 7.30-7.33 (2H, m), 7.36-7.44 (2H, m), 7.58 (1H, d, J=8.5 Hz), 7.76-7.81 (3H, m), 8.05 (1H, d, J=8.5 Hz); ESI-MS: m/z calcd for C$_{23}$H$_{28}$N$_4$O$_4$S: 456.2; found [M+H]$^+$: 457.2.

Example 192: 2,4-Dichloro-N-(2-((dimethylamino)methyl)quinolin-8-yl)benzenesulfonamide—Compound (ZDR335)

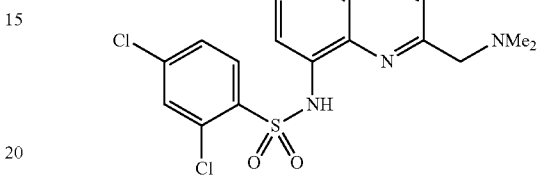

A similar procedure to that described for the preparation of compound (ZDR018) was followed using compound (ZDR059) (100 mg, 0.50 mmol), 2,4-dichlorobenzenesulfonyl chloride (134 mg, 0.55 mmol) and triethylamine (76 μL, 0.55 mmol) in dichloromethane (4 mL). Purification by flash chromatography (dichloromethane/methanol, 50:1→20:1) afforded compound (ZDR335) as a pale yellow solid (156 mg, 0.38 mmol, 77%). $^1$H NMR (400 MHz, CDCl$_3$) δ 2.32 (6H, s), 3.74 (2H, s), 7.27 (1H, dd, J=8.5 and 2.0 Hz), 7.32 (1H, d, J=2.0 Hz), 7.35 (1H, d, J=7.8 Hz), 7.42 (1H, dd, J=8.4 and 1.1 Hz), 7.64 (1H, d, J=8.5 Hz), 7.71 (1H, dd, J=7.6 and 1.3 Hz), 8.06 (1H, d, J=8.4 Hz), 8.10 (1H, d, J=8.4 Hz); ESI-MS: m/z calcd for C$_{18}$H$_{17}$Cl$_2$N$_3$O$_2$S: 409.0; found [M+H]$^+$: 410.0.

Example 193: 2,3-Dichloro-N-(2-((dimethylamino)methyl)quinolin-8-yl)benzenesulfonamide—Compound (ZDR336)

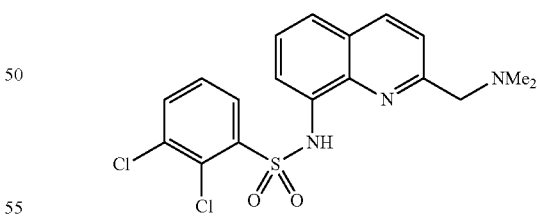

A similar procedure to that described for the preparation of compound (ZDR018) was followed using compound (ZDR059) (100 mg, 0.50 mmol), 2,3-dichlorobenzenesulfonyl chloride (134 mg, 0.55 mmol) and triethylamine (76 μL, 0.55 mmol) in dichloromethane (4 mL). Purification by flash chromatography (dichloromethane/methanol, 50:1→20:1) afforded compound (ZDR336) as a tan solid (169 mg, 0.41 mmol, 83%). $^1$H NMR (400 MHz, CDCl$_3$) δ 2.32 (6H, s), 3.75 (2H, s), 7.24 (1H, t, J=7.9 Hz), 7.33 (1H, t, J=7.9 Hz), 7.41 (1H, d, J=7.9 Hz), 7.50 (1H, dd, J=7.9 and 1.1 Hz), 7.63 (1H, d, J=8.4 Hz), 7.73 (1H, d, J=7.6 Hz), 8.05 (1H, d, J=8.4 Hz), 8.10 (1H, dd, J=7.9 and 1.3 Hz); ESI-MS: m/z calcd for $C_{18}H_{17}Cl_2N_3O_2S$: 409.0; found [M+H]$^+$: 410.1.

Example 194: N-(2-((Dimethylamino)methyl)quinolin-8-yl)-2,4,5-trifluorobenzenesulfonamide—Compound (ZDR337)

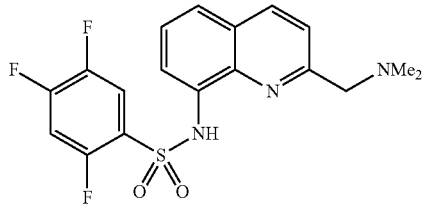 [SMILES: CN(C)Cc1ccc2cccc(NS(=O)(=O)c3cc(F)c(F)cc3F)c2n1]

A similar procedure to that described for the preparation of compound (ZDR018) was followed using compound (ZDR059) (100 mg, 0.50 mmol), 2,4,5-trifluorobenzenesulfonyl chloride (76 μL, 0.55 mmol) and triethylamine (76 μL, 0.55 mmol) in dichloromethane (4 mL). Purification by flash chromatography (dichloromethane/methanol, 50:1→20:1) afforded compound (ZDR337) as a pale yellow solid (190 mg, 0.48 mmol, 97%). $^1$H NMR (400 MHz, CDCl$_3$) δ 2.32 (6H, s), 3.75 (2H, s), 6.85-6.92 (1H, m), 7.40 (1H, t, J=8.0 Hz), 7.49 (1H, dd, J=8.4 and 1.2 Hz), 7.63 (1H, d, J=8.5 Hz), 7.76 (1H, dd, J=7.6 and 1.1 Hz), 7.81 (1H, td, J=8.8 and 6.4 Hz), 8.09 (1H, d, J=8.5 Hz); ESI-MS: m/z calcd for $C_{18}H_{16}F_3N_3O_2S$: 395.1; found [M+H]$^+$: 396.1.

Example 195: N-(2-((Dimethylamino)methyl)quinolin-8-yl)-3,4-difluorobenzenesulfonamide—Compound (ZDR338)

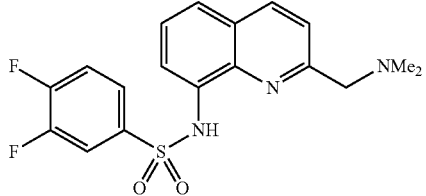

A similar procedure to that described for the preparation of compound (ZDR018) was followed using compound (ZDR059) (100 mg, 0.50 mmol), 3,4-difluorobenzenesulfonyl chloride (73 μL, 0.55 mmol) and triethylamine (76 μL, 0.55 mmol) in dichloromethane (4 mL). Purification by flash chromatography (dichloromethane/methanol, 50:1→20:1) afforded compound (ZDR338) as a pale orange solid (180 mg, 0.48 mmol, 96%). $^1$H NMR (400 MHz, CDCl$_3$) δ 2.30 (6H, s), 3.72 (2H, s), 7.06-7.12 (1H, m), 7.41-7.44 (1H, m), 7.49 (1H, dd, J=8.4 and 1.3 Hz), 7.57 (1H, d, J=8.5 Hz), 7.63-7.67 (1H, m), 7.73-7.78 (1H, m), 7.82 (1H, dd, J=7.5 and 1.3 Hz), 8.07 (1H, d, J=8.5 Hz); ESI-MS: m/z calcd for $C_{18}H_{17}F_2N_3O_2S$: 377.1; found [M+H]$^+$: 378.1.

Example 196: N-(2-((Dimethylamino)methyl)quinolin-8-yl)isoquinoline-5-sulfonamide—Compound (ZDR339)

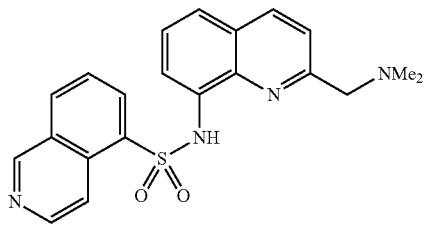 [SMILES: CN(C)Cc1ccc2cccc(NS(=O)(=O)c3cccc4cnccc34)c2n1]

A similar procedure to that described for the preparation of compound (ZDR018) was followed using compound (ZDR059) (100 mg, 0.50 mmol), isoquinoline-5-sulfonylchloride hydrochloride (144 mg, 0.55 mmol) and triethylamine (152 μL, 1.09 mmol) in dichloromethane (4 mL). Purification by flash chromatography (dichloromethane/methanol, 50:1→20:1) afforded compound (ZDR339) as a pale yellow solid (88 mg, 0.22 mmol, 44%). $^1$H NMR (400 MHz, CDCl$_3$) δ 2.25 (6H, s), 3.62 (2H, s), 7.32-7.39 (2H, m), 7.50 (1H, d, J=8.4 Hz), 7.55 (1H, t, J=7.8 Hz), 7.74 (1H, dd, J=7.5 and 1.6 Hz), 7.97 (1H, d, J=8.4 Hz), 8.03-8.05 (1H, m), 8.47 (1H, dd, J=7.5 and 1.6 Hz), 8.61-8.67 (2H, m), 9.20 (1H, d, J=0.7 Hz); ESI-MS: m/z calcd for $C_{21}H_{20}N_4O_2S$: 392.1; found [M+H]$^+$: 393.1.

Example 197: N-(2-((Dimethylamino)methyl)quinolin-8-yl)quinoline-8-sulfonamide—Compound (ZDR340)

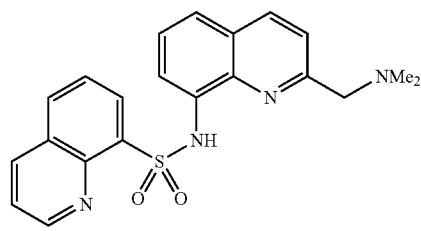 [SMILES: CN(C)Cc1ccc2cccc(NS(=O)(=O)c3cccc4cccnc34)c2n1]

A similar procedure to that described for the preparation of compound (ZDR018) was followed using compound (ZDR059) (100 mg, 0.50 mmol), 8-quinolinesulfonyl chloride (124 mg, 0.55 mmol) and triethylamine (76 μL, 0.55 mmol) in dichloromethane (4 mL). Purification by flash chromatography (dichloromethane/methanol, 50:1→20:1) afforded compound (ZDR340) as a grey solid (70 mg, 0.17 mmol, 34%). $^1$H NMR (400 MHz, d$_6$-DMSO) δ 2.30 (6H, s), 3.81 (2H, s), 7.41 (1H, t, J=8.0 Hz), 7.50 (1H, dd, J=8.8 and 1.5 Hz), 7.57 (1H, d, J=8.4 Hz), 7.64-7.72 (2H, m), 7.83 (1H, dd, J=7.5 and 1.7 Hz), 8.20-8.23 (2H, m), 8.42-8.46 (2H, m), 9.14 (1H, dd, J=4.0 and 1.5 Hz); ESI-MS: m/z calcd for $C_{21}H_{20}N_4O_2S$: 392.1; found [M+H]$^+$: 393.1.

Example 198: N-(2-((Butylamino)methyl)quinolin-8-yl)-4-(trifluoromethyl)benzenesulfonamide— Compound (ZDR401)

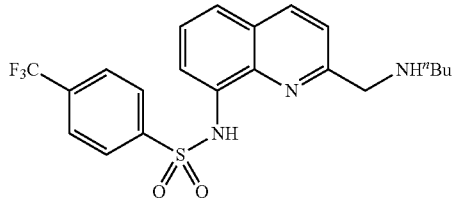

A similar procedure to that described for the preparation of compound (ZDR022) was followed using compound (ZDR019) (100 mg, 0.26 mmol), n-butylamine (80 μL, 0.81 mmol) and sodium triacetoxyborohydride (122 mg, 0.58 mmol) in dichloromethane (5 mL). Purification by flash chromatography (dichloromethane/methanol, 50:1→15:1) afforded compound (ZDR401) as a pale yellow solid (76 mg, 0.17 mmol, 66%). $^1$H NMR (400 MHz, CDCl$_3$) δ 0.90 (3H, t, J=7.4 Hz), 1.31-1.40 (2H, m), 1.68-1.75 (2H, m), 2.89 (2H, t, J=7.6 Hz), 4.29 (2H, s), 7.36-7.45 (3H, m), 7.54 (2H, d, J=8.5 Hz), 7.79 (1H, dd, J=7.5 and 1.5 Hz), 8.02-8.08 (3H, m), 8.93 (2H, brs); ESI-MS: m/z calcd for C$_{21}$H$_{22}$F$_3$N$_3$O$_2$S: 437.1; found [M+H]$^+$: 438.1.

Example 199: N-(2-((sec-Butylamino)methyl)quinolin-8-yl)-4-(trifluoromethyl)benzenesulfonamide— Compound (ZDR402)

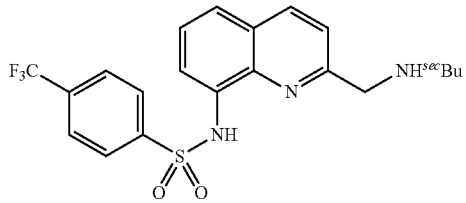

A similar procedure to that described for the preparation of compound (ZDR022) was followed using compound (ZDR019) (100 mg, 0.26 mmol), sec-butylamine (80 μL, 0.79 mmol) and sodium triacetoxyborohydride (120 mg, 0.57 mmol) in dichloromethane (5 mL). Purification by flash chromatography (dichloromethane/methanol, 50:1→15:1) afforded compound (ZDR402) as a pale yellow solid (32 mg, 0.07 mmol, 28%). $^1$H NMR (400 MHz, CDCl$_3$) δ 0.95 (3H, t, J=7.6 Hz), 1.17 (3H, d, J=6.4 Hz), 1.42-1.53 (1H, m), 1.59-1.71 (1H, m), 2.73-2.81 (1H, m), 4.08-4.18 (2H, m), 5.00 (2H, brs), 7.39-7.43 (1H, m), 7.45-7.48 (2H, m), 7.60 (2H, d, J=8.2 Hz), 7.81 (1H, dd, J=7.5 and 1.5 Hz), 8.03-8.07 (3H, m); ESI-MS: m/z calcd for C$_{21}$H$_{22}$F$_3$N$_3$O$_2$S: 437.1; found [M+H]$^+$: 438.2.

Example 200: N-(2-((Iso-Butylamino)methyl)quinolin-8-yl)-4-(trifluoromethyl)benzenesulfonamide— Compound (ZDR403)

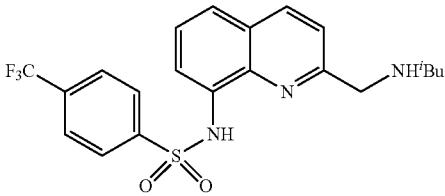

A similar procedure to that described for the preparation of compound (ZDR022) was followed using compound (ZDR019) (100 mg, 0.26 mmol), iso-butylamine (80 μL, 0.81 mmol) and sodium triacetoxyborohydride (111 mg, 0.52 mmol) in dichloromethane (5 mL). Purification by flash chromatography (dichloromethane/methanol, 50:1→15:1) afforded compound (ZDR403) as a yellow oil (73 mg, 0.17 mmol, 63%). $^1$H NMR (400 MHz, CDCl$_3$) δ 0.98 (6H, d, J=6.6 Hz), 1.92 (1H, m), 2.57 (2H, d, J=6.8 Hz), 4.15 (2H, s), 6.21 (2H, brs), 7.40-7.49 (3H, m), 7.59 (2H, d, J=8.4 Hz), 7.82 (1H, dd, J=7.4 and 1.5 Hz), 8.03-8.08 (3H, m); ESI-MS: m/z calcd for C$_{21}$H$_{22}$F$_3$N$_3$O$_2$S: 437.1; found [M+H]$^+$: 438.1.

Example 201: N-(2-((Cyclopentylamino)methyl)quinolin-8-yl)-4-(trifluoromethyl)benzenesulfonamide—Compound (ZDR404)

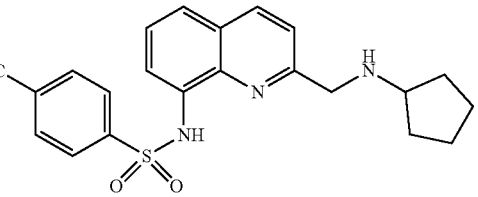

A similar procedure to that described for the preparation of compound (ZDR022) was followed using compound (ZDR019) (100 mg, 0.26 mmol), cyclopentylamine (80 μL, 0.81 mmol) and sodium triacetoxyborohydride (114 mg, 0.54 mmol) in dichloromethane (5 mL). Purification by flash chromatography (dichloromethane/methanol, 50:1→15:1) afforded compound (ZDR404) as a yellow solid (79 mg, 0.18 mmol, 67%). $^1$H NMR (400 MHz, CDCl$_3$) δ 1.03-1.68 (8H, m), 2.71-2.77 (1H, m), 4.21 (2H, s), 7.27-7.36 (3H, m), 7.50 (2H, d, J=8.3 Hz), 7.72 (1H, dd, J=6.7 and 1.9 Hz), 7.93 (1H, d, J=8.3 Hz), 8.03 (2H, d, J=8.3 Hz), 8.50 (2H, brs); ESI-MS: m/z calcd for C$_{22}$H$_{22}$F$_3$N$_3$O$_2$S: 449.1; found [M+H]$^+$: N/A.

Example 202: N-(2-(((Cyclohexylamino)methyl)
quinolin-8-yl)-4-(trifluoromethyl)benzenesulfona-
mide—Compound (ZDR405)

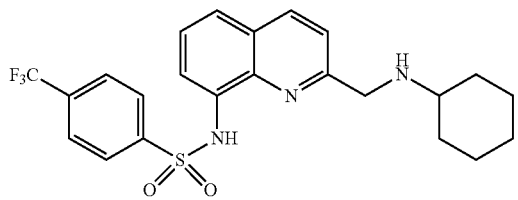 [SMILES: O=S(=O)(Nc1cccc2ccc(CNC3CCCCC3)nc12)c1ccc(C(F)(F)F)cc1]

A similar procedure to that described for the preparation of compound (ZDR022) was followed using compound (ZDR019) (100 mg, 0.26 mmol), cyclohexylamine (90 μL, 0.79 mmol) and sodium triacetoxyborohydride (112 mg, 0.53 mmol) in dichloromethane (5 mL). Purification by flash chromatography (dichloromethane/methanol, 50:1→15:1) afforded compound (ZDR405) as a pale yellow solid (15 mg, 0.03 mmol, 12%). $^1$H NMR (400 MHz, CDCl$_3$) δ 0.83-0.90 (2H, m), 1.48-1.61 (4H, m), 1.70-1.81 (2H, m), 1.87-1.93 (2H, m), 3.20-3.22 (1H, m), 4.11 (2H, s), 7.39-7.48 (3H, m), 7.60 (2H, d, J=8.4 Hz), 7.81 (1H, dd, J=7.5 and 1.5 Hz), 8.02-8.07 (3H, m); ESI-MS: m/z calcd for C$_{23}$H$_{24}$F$_3$N$_3$O$_2$S: 463.2; found [M+H]$^+$: N/A.

Example 203: N-(2-((((Cyclohexylmethyl)amino)
methyl)quinolin-8-yl)-4-(trifluoromethyl)benzene-
sulfonamide—Compound (ZDR406)

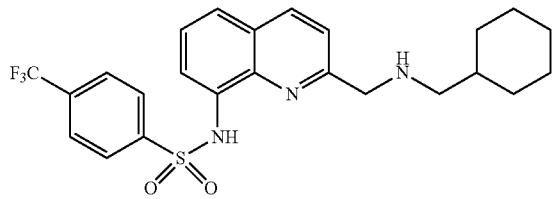 [SMILES: O=S(=O)(Nc1cccc2ccc(CNCC3CCCCC3)nc12)c1ccc(C(F)(F)F)cc1]

A similar procedure to that described for the preparation of compound (ZDR022) was followed using compound (ZDR019) (100 mg, 0.26 mmol), cyclohexanemethylamine (110 μL, 0.85 mmol) and sodium triacetoxyborohydride (118 mg, 0.56 mmol) in dichloromethane (5 mL). Purification by flash chromatography (dichloromethane/methanol, 50:1→15:1) afforded compound (ZDR406) as a pale yellow solid (56 mg, 0.12 mmol, 45%). $^1$H NMR (400 MHz, CDCl$_3$) δ 0.92-1.87 (11H, m), 2.69 (2H, d, J=6.9 Hz), 4.28 (2H, s), 7.38-7.47 (3H, m), 7.58 (2H, d, J=8.5 Hz), 7.81 (1H, dd, J=7.4 and 1.5 Hz), 8.05-8.10 (3H, m), 8.34 (2H, brs); ESI-MS: m/z calcd for C$_{24}$H$_{26}$F$_3$N$_3$O$_2$S: 477.2; found [M+H]$^+$: 478.2.

Example 204: N-(2-(Pyrrolidin-1-ylmethyl)quinolin-
8-yl)-4-(trifluoromethyl)benzenesulfonamide—
Compound (ZDR407)

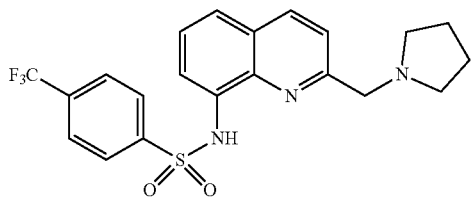 [SMILES: O=S(=O)(Nc1cccc2ccc(CN3CCCC3)nc12)c1ccc(C(F)(F)F)cc1]

A similar procedure to that described for the preparation of compound (ZDR022) was followed using compound (ZDR019) (100 mg, 0.26 mmol), pyrrolidine (70 μL, 0.84 mmol) and sodium triacetoxyborohydride (115 mg, 0.54 mmol) in dichloromethane (5 mL). Purification by flash chromatography (dichloromethane/methanol, 50:1→15:1) afforded compound (ZDR407) as a tan solid (37 mg, 0.09 mmol, 33%). $^1$H NMR (400 MHz, CDCl$_3$) δ 1.85-1.89 (4H, m), 2.64-2.69 (4H, m), 3.99 (2H, s), 7.41-7.45 (1H, m), 7.47-7.50 (1H, m), 7.54 (1H, d, J=8.5 Hz), 7.59 (2H, d, J=8.5 Hz), 7.87 (1H, dd, J=7.5 and 1.5 Hz), 8.02 (2H, d, J=8.5 Hz), 8.07 (1H, d, J=8.5 Hz); ESI-MS: m/z calcd for C$_{21}$H$_{20}$F$_3$N$_3$O$_2$S: 435.1; found [M+H]$^+$: 436.1.

Example 205: N-(2-(Azepan-1-ylmethyl)quinolin-8-
yl)-4-(trifluoromethyl)benzenesulfonamide—Com-
pound (ZDR408)

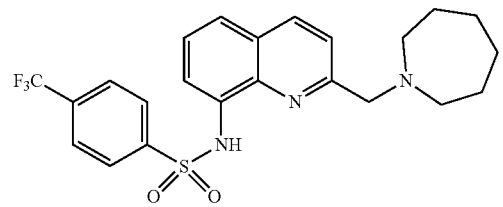 [SMILES: O=S(=O)(Nc1cccc2ccc(CN3CCCCCC3)nc12)c1ccc(C(F)(F)F)cc1]

A similar procedure to that described for the preparation of compound (ZDR022) was followed using compound (ZDR019) (100 mg, 0.26 mmol), hexamethyleneimine (90 μL, 0.80 mmol) and sodium triacetoxyborohydride (117 mg, 0.55 mmol) in dichloromethane (5 mL). Purification by flash chromatography (dichloromethane/methanol, 50:1→15:1) afforded compound (ZDR408) as a brown solid (105 mg, 0.23 mmol, 86%). $^1$H NMR (400 MHz, CDCl$_3$) δ 1.64-1.70 (8H, m), 2.71-2.76 (4H, m), 3.96 (2H, s), 7.41 (1H, t, J=7.9 Hz), 7.46-7.49 (1H, m), 7.59 (2H, d, J=8.4 Hz), 7.64 (1H, d, J=8.4 Hz), 7.84 (1H, dd, J=7.5 and 1.0 Hz), 8.01-8.06 (3H, m), 9.52 (1H, brs); ESI-MS: m/z calcd for C$_{23}$H$_{24}$F$_3$N$_3$O$_2$S: 463.2; found [M+H]$^+$:464.2.

Example 206: N-(2-((Dipropylamino)methyl)quinolin-8-yl)-4-(trifluoromethyl)benzenesulfonamide—Compound (ZDR409)

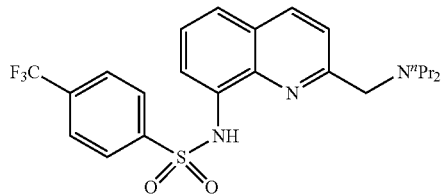

A similar procedure to that described for the preparation of compound (ZDR022) was followed using compound (ZDR019) (100 mg, 0.26 mmol), dipropylamine (110 μL, 0.80 mmol) and sodium triacetoxyborohydride (121 mg, 0.57 mmol) in dichloromethane (5 mL). Purification by flash chromatography (dichloromethane/methanol, 50:1→15:1) afforded compound (ZDR409) as a tan solid (23 mg, 0.05 mmol, 19%). $^1$H NMR (400 MHz, CDCl$_3$) δ 0.86 (6H, t, J=7.2 Hz), 1.45-1.54 (4H, m), 2.44 (4H, t, J=7.2 Hz), 3.81 (2H, s), 7.39-7.43 (1H, m), 7.46-7.49 (1H, m), 7.60 (2H, d, J=8.5 Hz), 7.68 (1H, d, J=8.5 Hz), 7.82 (1H, dd, J=7.5 and 1.3 Hz), 8.00-8.05 (3H, m); ESI-MS: m/z calcd for C$_{23}$H$_{26}$F$_3$N$_3$O$_2$S: 465.2; found [M+H]$^+$: 466.2.

Example 207: N-(2-((Dimethylamino)methyl)quinolin-8-yl)ethenesulfonamide—Compound (ZDR500)

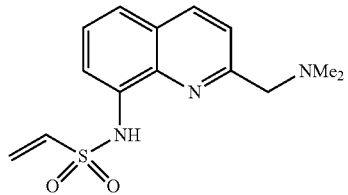 [SMILES: C=CS(=O)(=O)Nc1cccc2ccc(CN(C)C)nc12]

A similar procedure to that described for the preparation of compound (ZDR018) was followed using compound (ZDR059) (79 mg, 0.36 mmol), ethenesulfonyl chloride (50 mg, 0.36 mmol) and triethylamine (56 μL, 0.40 mmol) in dichloromethane (4 mL). Purification by flash chromatography (dichloromethane/methanol, 50:1→20:1) afforded compound (ZDR500) as a yellow oil (58 mg, 0.20 mmol, 55%). $^1$H NMR (400 MHz, CDCl$_3$) δ 2.32 (6H, s), 3.74 (2H, s), 5.88 (1H, d, J=9.8 Hz), 6.36 (1H, d, J=16.6 Hz), 6.56 (1H, dd, J=16.6 and 9.8 Hz), 7.44 (1H, t, J=7.9 Hz), 7.50 (1H, dd, J=8.4 and 1.4 Hz), 7.65 (1H, d, J=8.4 Hz), 7.72 (1H, dd, J=7.5 and 1.4 Hz), 8.12 (1H, d, J=8.4 Hz); ESI-MS: m/z calcd for C$_{14}$H$_{17}$N$_3$O$_2$S: 291.1; found [M+H]$^+$: 292.1.

Example 208: N-(2-((Dimethylamino)methyl)quinolin-8-yl)-1-(5-methylisoxazol-3-yl)methanesulfonamide—Compound (ZDR501)

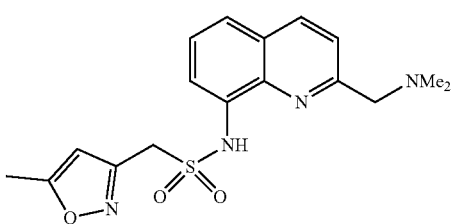 [SMILES: Cc1cc(CS(=O)(=O)Nc2cccc3ccc(CN(C)C)nc23)no1]

A similar procedure to that described for the preparation of compound (ZDR018) was followed using compound (ZDR059) (56 mg, 0.25 mmol), (5-methyl-1,2-oxazol-3-yl)methanesulfonyl chloride (50 mg, 0.25 mmol) and triethylamine (39 μL, 0.28 mmol) in dichloromethane (3 mL). Purification by flash chromatography (dichloromethane/methanol, 50:1→20:1) afforded compound (ZDR501) as a pale yellow oil (47 mg, 0.13 mmol, 51%). $^1$H NMR (400 MHz, CDCl$_3$) δ 2.32 (6H, s), 2.38 (3H, s), 3.70 (2H, s), 4.45 (2H, s), 6.20 (1H, s), 7.45-7.49 (1H, m), 7.55 (1H, d, J=8.0 Hz), 7.65 (1H, d, J=8.5 Hz), 7.86 (1H, d, J=7.5 Hz), 8.14 (1H, d, J=8.5 Hz); ESI-MS: m/z calcd for C$_{17}$H$_{20}$N$_4$O$_3$S: 360.1; found [M+H]$^+$: 361.1.

Example 209: N-(2-((Dimethylamino)methyl)quinolin-8-yl)tetrahydro-2H-pyran-4-sulfonamide—Compound (ZDR502)

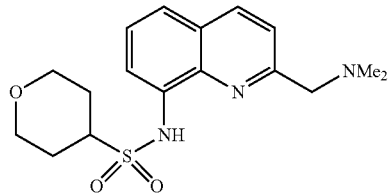 [SMILES: CN(C)Cc1ccc2cccc(NS(=O)(=O)C3CCOCC3)c2n1]

A similar procedure to that described for the preparation of compound (ZDR018) was followed using compound (ZDR059) (55 mg, 0.27 mmol), oxane-4-sulfonyl chloride (50 mg, 0.27 mmol) and triethylamine (38 μL, 0.30 mmol) in dichloromethane (3 mL). Purification by flash chromatography (dichloromethane/methanol, 50:1→20:1) afforded compound (ZDR502) as a pale yellow oil (31 mg, 0.09 mmol, 33%). $^1$H NMR (400 MHz, CDCl$_3$) δ 1.97-2.02 (4H, m), 2.32 (6H, s), 3.20-3.21 (3H, m), 3.75 (2H, s), 3.97-4.01 (2H, m), 7.45-7.49 (1H, m), 7.52-7.55 (1H, m), 7.67 (1H, d, J=8.5 Hz), 7.88 (1H, dd, J=7.5 and 1.5 Hz), 8.15 (1H, d, J=8.5 Hz); ESI-MS: m/z calcd for C$_{17}$H$_{23}$N$_3$O$_3$S: 349.1; found [M+H]$^+$: 350.2.

Example 210: 1-Cyclopropyl-N-(2-((dimethyl-amino)methyl)quinolin-8-yl)methanesulfonamide—Compound (ZDR503)

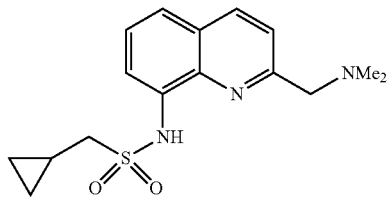 [SMILES: CN(C)Cc1ccc2cccc(NS(=O)(=O)CC3CC3)c2n1]

A similar procedure to that described for the preparation of compound (ZDR018) was followed using compound (ZDR059) (70 mg, 0.32 mmol), cyclopropylmethanesulfonyl chloride (50 mg, 0.32 mmol) and triethylamine (49 µL, 0.35 mmol) in dichloromethane (3 mL). Purification by flash chromatography (dichloromethane/methanol, 50:1→20:1) afforded compound (ZDR503) as a yellow oil (66 mg, 0.20 mmol, 62%). δ $^1$H NMR (400 MHz, CDCl$_3$) δ 0.12-0.16 (2H, m), 0.52-0.57 (2H, m), 1.10-1.18 (1H, m), 2.31 (6H, s), 3.08 (2H, d, J=7.1 Hz), 3.74 (2H, s), 7.46 (1H, t, J=7.8 Hz), 7.41 (1H, dd, J=8.4 and 1.5 Hz), 7.67 (1H, d, J=8.4 Hz), 7.86 (1H, dd, J=7.5 and 1.5 Hz), 8.14 (1H, d, J=8.4 Hz), 9.09 (1H, brs); ESI-MS: m/z calcd for C$_{16}$H$_{21}$N$_3$O$_2$S: 319.1; found [M+H]$^+$: 320.1.

Example 211: N-(2-((Dimethylamino)methyl)quinolin-8-yl)-1-(tetrahydro-2H-pyran-4-yl)methanesulfonamide—Compound (ZDR504)

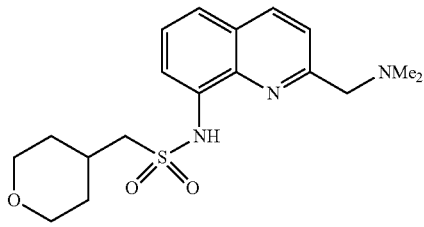 [SMILES: CN(C)Cc1ccc2cccc(NS(=O)(=O)CC3CCOCC3)c2n1]

A similar procedure to that described for the preparation of compound (ZDR018) was followed using compound (ZDR059) (51 mg, 0.25 mmol), oxan-4-ylmethanesulfonyl chloride (50 mg, 0.25 mmol) and triethylamine (36 µL, 0.27 mmol) in dichloromethane (4 mL). Purification by flash chromatography (dichloromethane/methanol, 50:1→20:1) afforded compound (ZDR504) as a pale yellow oil (60 mg, 0.17 mmol, 68%). $^1$H NMR (400 MHz, CDCl$_3$) δ 1.30-1.40 (2H, m), 1.76-1.82 (2H, m), 2.24-2.33 (1H, m), 2.33 (6H, s), 3.06 (2H, d, J=6.4 Hz), 3.34-3.38 (2H, m), 3.75 (2H, s), 3.86-3.90 (2H, m), 7.46-7.50 (1H, m), 7.52-7.56 (1H, m), 7.67 (1H, d, J=8.5 Hz), 7.82 (1H, dd, J=7.5 and 1.5 Hz), 8.15 (1H, d, J=8.5 Hz); ESI-MS: m/z calcd for C$_{18}$H$_{25}$N$_3$O$_3$S: 363.2; found [M+H]$^+$: 364.2.

Example 212: 1-(6-Chloropyridin-3-yl)-N-(2-((dimethylamino)methyl)quinolin-8-yl)methanesulfonamide—Compound (ZDR505)

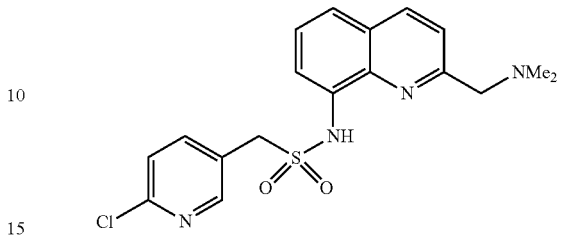

A similar procedure to that described for the preparation of compound (ZDR018) was followed using compound (ZDR059) (45 mg, 0.22 mmol), (6-chloropyridin-3-yl)methanesulfonyl chloride (50 mg, 0.22 mmol) and triethylamine (30 µL, 0.24 mmol) in dichloromethane (4 mL). Purification by flash chromatography (dichloromethane/methanol, 20:1) afforded compound (ZDR505) as a pale yellow oil (36 mg, 0.09 mmol, 40%). $^1$H NMR (400 MHz, CDCl$_3$) δ 2.30 (6H, s), 3.65 (2H, s), 4.35 (2H, s), 7.17 (1H, d, J=8.0 Hz), 7.45-7.49 (1H, m), 7.54-7.57 (2H, m), 7.67 (1H, d, J=8.5 Hz), 7.82-7.85 (2H, m), 8.15 (1H, d, J=8.5 Hz); ESI-MS: m/z calcd for C$_{18}$H$_{19}$ClN$_4$O$_2$S: 390.1; found [M+H]$^+$: 391.1.

Example 213: N-(2-((Dimethylamino)methyl)quinolin-8-yl)prop-2-yne-1-sulfonamide—Compound (ZDR506)

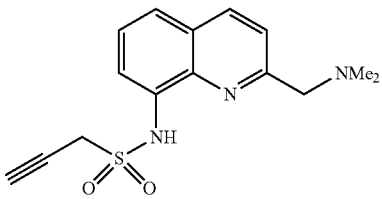

A similar procedure to that described for the preparation of compound (ZDR018) was followed using compound (ZDR059) (73 mg, 0.36 mmol), prop-2-yne-1-sulfonyl chloride (50 mg, 0.36 mmol) and triethylamine (51 µL, 0.39 mmol) in dichloromethane (4 mL). Purification by flash chromatography (dichloromethane/methanol, 20:1) afforded compound (ZDR506) as an orange oil (17 mg, 0.05 mmol, 13%). $^1$H NMR (400 MHz, d$_6$-DMSO) δ 2.75 (1H, s), 3.17 (6H, s), 3.76 (2H, s), 4.64 (2H, s), 7.54-7.56 (1H, m), 7.65-7.74 (3H, m), 8.38 (1H, d, J=8.5 Hz); ESI-MS: m/z calcd for C$_{15}$H$_{17}$N$_3$O$_2$S: 303.1; found [M+H]$^+$: 304.1.

Example 214: Antibacterial Susceptibility and Synergy Determination Methods

Antibacterial susceptibility testing was performed in triplicate (biological) by measuring minimum inhibitory concentrations (MICs) by broth microdilution in 96-well flat bottom microtiter plates (ThermoFisher Scientific, New Zealand). *S. uberis* ATCC 19436, *S. aureus* ATCC 6538, or *E. coli* ATCC 10596 cells grown overnight were diluted to an OD600 of approximately 0.025, so that the final concentration of cells in the MIC assay was approximately 5×10⁵ cfu/mL in media as follows: *S. uberis*; Todd Hewitt Broth (THB), *S. aureus*; Tryptic Soy Broth (TSB) and Cation Adjusted Muller Hinton Broth (CAMHB), and *E. coli*; Lysogeny Borth (LB) and CAMHB, before being dispensed into microtiter wells. As required additional sterile Zinc Sulphate (Heptahydrate) was supplemented into the media, so the final concentration was 50 µM. Test compounds were added to starting wells and two-fold serial dilutions were undertaken to generate a range of inhibitor concentrations at a final volume of 200 µl. Media and test compound-free (untreated) controls were included in each microtiter plate in triplicate. After 24 h incubation at 37° C. and 200 rpm, the OD600 of wells were read using a Varioskan Flash plate reader (ThermoFisher Scientific, New Zealand). The MIC was reported as the lowest concentration of the test compound for which no growth occurred, as determined by OD600 readings. The minimum bactericidal concentration (MBC) was determined using the Miles-Misra drop-plate method to measure the viability of cells in response to test compound challenge.

The MIC and MBC data are shown in Tables 1 and 2.

TABLE 1

Minimum Inhibitory Concentrations (MIC) of Zincaphore (ZDR) molecules

| Compound | M (g/mol) | *S. uberis* ATCC 19436 MIC (µg/ml) | | *S. aureus* ATCC 6538 MIC (µg/ml) | | *E. coli* ATCC 10536 MIC (µg/ml) | |
|---|---|---|---|---|---|---|---|
| | | No Zinc | Zinc (50 µM) | No Zinc | Zinc (50 µM) | No Zinc | Zinc (50 µM) |
| ZDR018 | 366.4 | >256 | 0.125 | >256 | >256 | >256 | >256 |
| ZDR019 | 380.3 | 16 | 1 | 8 | 8 | 128 | 128 |
| ZDR022 | 409.4 | 64 | 0.125 | 16 | 8 | >256 | >256 |
| ZDR022-HCl | 445.9 | 256 | 0.125 | 64 | 4 | >256 | >256 |
| ZDR024 | 395.4 | 64 | 0.25 | 16 | 8 | 256 | ≥256 |
| ZDR025 | 409.4 | 64 | 0.125 | 32 | >256 | 256 | ≥256 |
| ZDR026 | 423.4 | 64 | 0.125 | 32 | >256 | >256 | >256 |
| ZDR027 | 423.4 | 64 | 0.125 | 16 | 16 | >256 | >256 |
| ZDR028 | 437.4 | 128 | 0.125 | 256 | >256 | >256 | >256 |
| ZDR029 | 451.4 | >256 | 0.25 | >256 | >256 | >256 | >256 |
| ZDR030 | 452.5 | 16 | 1 | 16 | 16 | 128 | ≥256 |
| ZDR031 | 425.4 | 16 | 0.5 | 32 | 32 | ≥256 | >256 |
| ZDR033 | 449.4 | >256 | 0.125 | >256 | >256 | >256 | >256 |
| ZDR035 | 472.4 | 2 | 1 | 4 | 4 | 32 | >256 |
| ZDR036 | 816.8 | >256 | >256 | >256 | >256 | >256 | >256 |
| ZDR037 | 759.7 | >256 | 2 | >256 | >256 | >256 | >256 |
| ZDR041 | 495.5 | >256 | 0.5 | 64 | >256 | >256 | >256 |
| ZDR043 | 439.4 | >256 | >256 | >256 | >256 | >256 | >256 |
| ZDR045 | 498.4 | >256 | 0.125 | >256 | >256 | >256 | >256 |
| ZDR046 | 453.4 | 4 | 1 | 4 | 4 | >256 | >256 |
| ZDR061 | 341.4 | >256 | 0.25 | >256 | 256 | >256 | >256 |
| ZDR062 | 355.4 | 256 | 0.25 | 256 | >256 | >256 | >256 |
| ZDR063 | 371.4 | >256 | 0.25 | >256 | >256 | >256 | >256 |
| ZDR064 | 375.8 | >256 | 0.0625 | 128 | 256 | >256 | >256 |
| ZDR065 | 359.4 | >256 | 0.125 | 256 | 256 | >256 | >256 |
| ZDR066 | 425.4 | 128 | 0.0625 | 256 | >256 | >256 | >256 |
| ZDR067 | 386.4 | 128 | 0.125 | 128 | 256 | >256 | >256 |
| ZDR068 | 366.4 | >256 | 1 | >256 | >256 | >256 | >256 |
| ZDR069 | 399.4 | >256 | 0.25 | 256 | >256 | >256 | >256 |
| ZDR070 | 383.4 | >256 | 0.5 | >256 | >256 | >256 | >256 |
| ZDR071 | 419.5 | >256 | 4 | >256 | >256 | >256 | >256 |
| ZDR072 | 398.4 | 256 | 32 | >256 | >256 | >256 | >256 |
| ZDR073 | 384.4 | >256 | 8 | >256 | >256 | >256 | >256 |
| ZDR074 | 409.4 | >256 | 0.0625 | >256 | >256 | 256 | 256 |
| ZDR075 | 409.4 | 256 | 0.125 | >256 | >256 | >256 | >256 |
| ZDR076 | 366.4 | >256 | 1 | >256 | >256 | >256 | >256 |
| ZDR077 | 366.4 | >256 | 1 | >256 | >256 | >256 | >256 |
| ZDR078 | 279.3 | >256 | 2 | >256 | >256 | >256 | >256 |
| ZDR079 | 333.3 | >256 | 0.5 | >256 | 256 | >256 | 64 |
| ZDR080 | 347.4 | >256 | 0.25 | >256 | >256 | >256 | >256 |
| ZDR081 | 347.4 | 256 | 0.25 | >256 | >256 | >256 | >256 |
| ZDR082 | 360.4 | >256 | 0.125 | >256 | >256 | >256 | >256 |
| ZDR084 | 375.8 | 128 | 0.0625 | 256 | >256 | 256 | >256 |
| ZDR085 | 425.4 | 128 | <0.125 | 256 | >256 | 256 | >256 |
| ZDR086 | 421.4 | 64 | 0.25 | 64 | >256 | 128 | 256 |
| ZDR087 | 435.4 | 256 | 0.25 | 128 | >256 | 256 | >256 |
| ZDR088 | 467.5 | >256 | 0.0625 | >256 | >256 | >256 | >256 |
| ZDR089 | 464.5 | 64 | 0.5 | 256 | 128 | >256 | >256 |
| ZDR090 | 466.5 | 4 | 0.5 | 16 | 16 | 16 | 16 |
| ZDR091 | 439.4 | 32 | 0.125 | 64 | 32 | 256 | 256 |
| ZDR092 | 455.4 | 64 | 16 | 32 | 32 | >256 | >256 |
| ZDR093 | 455.4 | 64 | 16 | 64 | 128 | 256 | >256 |
| ZDR094 | 469.4 | 32 | 4 | 62 | 32 | 256 | 256 |
| ZDR095 | 486.5 | >256 | 0.125 | 64 | 8 | 128 | >256 |
| ZDR096 | 563.5 | 64 | 4 | >256 | >256 | >256 | >256 |
| ZDR097 | 421.4 | >256 | 0.0625 | >256 | >256 | >256 | 256 |

TABLE 1-continued

Minimum Inhibitory Concentrations (MIC) of Zincaphore (ZDR) molecules

| Compound | M (g/mol) | S. uberis ATCC 19436 MIC (μg/ml) | | S. aureus ATCC 6538 MIC (μg/ml) | | E. coli ATCC 10536 MIC (μg/ml) | |
|---|---|---|---|---|---|---|---|
| | | No Zinc | Zinc (50 μM) | No Zinc | Zinc (50 μM) | No Zinc | Zinc (50 μM) |
| ZDR098 | 419.4 | 64 | 0.125 | 64 | >256 | >256 | >256 |
| ZDR099 | 427.4 | 64 | 0.25 | 64 | >256 | >256 | 256 |
| ZDR100 | 445.4 | 128 | 0.25 | 32 | 256 | >256 | >256 |
| ZDR101 | 472.4 | >256 | 4 | 64 | 64 | 128 | >256 |
| ZDR102 | 485.4 | 32 | 16 | 32 | 16 | 256 | 64 |
| ZDR103 | 471.5 | >256 | 0.125 | 128 | >256 | >256 | >256 |
| ZDR106 | 461.4 | 64 | 0.25 | >256 | >256 | >256 | >256 |
| ZDR107 | 477.5 | 64 | 0.125 | >256 | 64 | >256 | >256 |
| ZDR108 | 457.4 | >256 | 0.25 | 64 | >256 | >256 | >256 |
| ZDR109 | 458.4 | >256 | 0.5 | >256 | >256 | >256 | >256 |
| ZDR110 | 472.4 | >256 | 4 | >256 | >256 | >256 | >256 |
| ZDR111 | 492.5 | 8 | 0.5 | 16 | 16 | 64 | >256 |
| ZDR112 | 494.5 | 64 | 1 | 16 | 32 | >256 | >256 |
| ZDR113 | 510.5 | 128 | 1 | >256 | >256 | >256 | >256 |
| ZDR114 | 701.6 | 32 | 4 | 64 | 64 | 64 | 64 |
| ZDR115 | 700.6 | 4 | 2 | 16 | 16 | 16 | 16 |
| ZDR116 | 508.5 | 32 | 2 | 64 | 64 | >256 | >256 |
| ZDR117 | 715.6 | 16 | 4 | 64 | 64 | 128 | 32 |
| ZDR118 | 437.4 | 32 | 2 | 128 | 8 | >256 | >256 |
| ZDR119 | 566.6 | 4 | 0.125 | 4 | 4 | >256 | >256 |
| ZDR120 | 436.4 | 32 | 0.5 | 16 | 16 | >256 | >256 |
| ZDR121 | 499.5 | 32 | 2 | 16 | 16 | >256 | >256 |
| ZDR122 | 499.5 | 32 | 2 | 16 | 16 | >256 | >256 |
| ZDR123 | 605.6 | >256 | 0.125 | >256 | >256 | >256 | >256 |
| ZDR124 | 602.5 | 32 | 16 | 16 | 16 | 128 | 32 |
| ZDR125 | 395.4 | 8 | 0.125 | 4 | 4 | >256 | >256 |
| ZDR126 | 409.4 | >256 | 0.125 | >256 | >256 | >256 | >256 |
| ZDR127 | 394.4 | >256 | 1 | 16 | 16 | >256 | >256 |
| ZDR129 | 469.4 | 64 | 1 | 32 | 32 | 256 | 256 |
| ZDR130 | 513.5 | 64 | 1 | 128 | 256 | 256 | 256 |
| ZDR131 | 483.5 | 64 | 1 | 64 | 128 | 256 | 256 |
| ZDR132 | 527.5 | 64 | 1 | 64 | 256 | 256 | 256 |
| ZDR133 | 439.4 | 64 | 0.25 | 64 | 256 | 256 | 256 |
| ZDR135 | 437.4 | 128 | 0.25 | 32 | 64 | >256 | >256 |
| ZDR136 | 465.5 | >256 | 8 | >256 | >256 | >256 | >256 |
| ZDR137 | 485.5 | >256 | 0.125 | >256 | >256 | >256 | >256 |
| ZDR138 | 484.5 | >256 | 0.5 | 128 | 128 | >256 | >256 |
| ZDR139 | 666.7 | 64 | 0.125 | 256 | 256 | >256 | >256 |
| ZDR143 | 660.5 | 8 | 4 | 8 | 8 | 16 | 16 |
| ZDR145 | 511.5 | >256 | >256 | 64 | 128 | 128 | 256 |
| ZDR148 | 466.5 | 64 | 1 | 64 | 128 | 128 | 256 |
| ZDR153 | 408.4 | >256 | 0.5 | 64 | 64 | >256 | >256 |
| ZDR154 | 420.5 | >256 | 16 | >256 | >256 | >256 | >256 |
| ZDR155 | 420.5 | >256 | >256 | >256 | >256 | >256 | >256 |
| ZDR160 | 356.4 | 256 | >256 | >256 | >256 | >256 | >256 |
| ZDR162 | 356.4 | 256 | 16 | >256 | >256 | >256 | >256 |
| ZDR163 | 357.4 | >256 | 8 | >256 | >256 | >256 | >256 |
| ZDR164 | 357.4 | >256 | >256 | >256 | >256 | >256 | >256 |
| ZDR167 | 524.5 | 2 | 0.5 | 2 | 2 | >256 | >256 |
| ZDR170 | 518.5 | 8 | 1 | 8 | 4 | 256 | 256 |
| ZDR171 | 473.5 | 8 | 0.5 | 4 | 4 | >256 | >256 |
| ZDR176 | 382.4 | >256 | 0.5 | 4 | 4 | >256 | >256 |
| ZDR180 | 502.4 | >256 | 0.5 | 64 | 256 | 128 | >256 |
| ZDR181 | 564.5 | >256 | 0.5 | 64 | >256 | 64 | >256 |
| ZDR184 | 381.4 | 32 | 0.5 | 8 | 4 | 64 | 128 |
| ZDR185 | 423.5 | >256 | 0.125 | 256 | 32 | >256 | >256 |
| ZDR186 | 623.6 | >256 | 0.25 | >256 | >256 | >256 | >256 |
| ZDR187 | 408.4 | 16 | 0.5 | 8 | 8 | 32 | 16 |
| ZDR188 | 468.4 | >256 | 0.5 | >256 | >256 | >256 | >256 |
| ZDR190 | 375.9 | 256 | 1 | >256 | >256 | >256 | >256 |
| ZDR191 | 425.4 | 256 | 0.125 | >256 | >256 | >256 | >256 |
| ZDR192 | 350.4 | >256 | 1 | >256 | >256 | >256 | >256 |
| ZDR193 | 348.5 | 128 | 0.25 | >256 | >256 | >256 | >256 |
| ZDR194 | 345.4 | >256 | 4 | >256 | >256 | >256 | >256 |
| ZDR195 | 345.4 | >256 | 32 | >256 | >256 | >256 | >256 |
| ZDR196 | 399.5 | 256 | 0.0625 | >256 | 32 | >256 | >256 |
| ZDR201 | 359.4 | 128 | 0.0625 | >256 | 32 | >256 | >256 |
| ZDR202 | 420.3 | 256 | 0.125 | 256 | >256 | >256 | >256 |
| ZDR203 | 376.5 | 256 | 0.5 | >256 | 64 | >256 | >256 |
| ZDR204 | 334.4 | 256 | 0.5 | >256 | 256 | >256 | >256 |
| ZDR205 | 563.5 | 256 | 0.125 | 128 | 64 | >256 | >256 |

TABLE 1-continued

Minimum Inhibitory Concentrations (MIC) of Zincaphore (ZDR) molecules

| Compound | M (g/mol) | S. uberis ATCC 19436 MIC (μg/ml) | | S. aureus ATCC 6538 MIC (μg/ml) | | E. coli ATCC 10536 MIC (μg/ml) | |
|---|---|---|---|---|---|---|---|
| | | No Zinc | Zinc (50 μM) | No Zinc | Zinc (50 μM) | No Zinc | Zinc (50 μM) |
| ZDR209 | 459.5 | >256 | 1 | >256 | >256 | >256 | >256 |
| ZDR210 | 521.5 | >256 | 0.25 | >256 | >256 | >256 | >256 |
| ZDR211 | 591.5 | 64 | 16 | 128 | 64 | 128 | 128 |
| ZDR224 | 577.5 | 64 | 16 | 128 | 32 | 256 | 256 |
| ZDR257 | 387.5 | >256 | 0.0625 | >256 | >256 | >256 | >256 |
| ZDR258 | 372.4 | 256 | 0.125 | >256 | >256 | >256 | >256 |
| ZDR259 | 305.4 | >256 | 0.25 | >256 | 256 | >256 | >256 |
| ZDR261 | 717.6 | 32 | 16 | 32 | 32 | 64 | 64 |
| ZDR262 | 757.7 | 8 | 16 | 64 | 128 | 32 | 64 |
| ZDR263 | 542.5 | >256 | 256 | >256 | >256 | >256 | >256 |
| ZDR265 | 639.5 | 128 | 256 | 64 | 64 | 256 | 256 |
| ZDR266 | 535.4 | 16 | 16 | 64 | 32 | 128 | 256 |
| ZDR267 | 551.4 | 256 | 256 | 256 | 128 | >256 | >256 |
| ZDR268 | 703.6 | 32 | 16 | 64 | 128 | 64 | 64 |
| ZDR269 | 743.6 | 4 | 8 | 32 | 64 | 64 | 64 |
| ZDR270 | 549.5 | 16 | 4 | 32 | 32 | 128 | 256 |
| ZDR305 | 420.3 | >256 | 0.0625 | 64 | 128 | >256 | >256 |
| ZDR306 | 407.4 | 128 | 0.125 | 128 | 128 | >256 | >256 |
| ZDR307 | 397.5 | >256 | 0.0625 | >256 | >256 | >256 | >256 |
| ZDR308 | 399.5 | 256 | 0.25 | 256 | >256 | 256 | >256 |
| ZDR309 | 420.3 | 128 | 0.125 | 64 | 128 | >256 | >256 |
| ZDR310 | 419.5 | 256 | 4 | >256 | >256 | >256 | >256 |
| ZDR311 | 383.5 | 256 | 0.0625 | >256 | 256 | >256 | >256 |
| ZDR312 | 359.4 | 128 | 0.125 | 256 | 256 | >256 | >256 |
| ZDR313 | 386.4 | 128 | 0.25 | 128 | >256 | >256 | >256 |
| ZDR314 | 371.5 | 128 | 0.25 | 256 | >256 | >256 | >256 |
| ZDR315 | 355.5 | >256 | 0.25 | 256 | >256 | >256 | >256 |
| ZDR316 | 361.4 | >256 | 0.125 | >256 | >256 | >256 | >256 |
| ZDR317 | 355.5 | 256 | 0.25 | >256 | 128 | >256 | >256 |
| ZDR318 | 307.4 | 256 | 32 | >256 | >256 | >256 | >256 |
| ZDR319 | 405.5 | >256 | 1 | >256 | >256 | >256 | >256 |
| ZDR320 | 423.5 | 256 | 0.0625 | >256 | 128 | >256 | >256 |
| ZDR321 | 321.4 | 256 | 0.25 | >256 | 128 | >256 | >256 |
| ZDR322 | 376.9 | >256 | 0.25 | 128 | >256 | >256 | >256 |
| ZDR323 | 305.4 | >256 | 1 | >256 | 256 | >256 | >256 |
| ZDR324 | 369.4 | 256 | 1 | 256 | 256 | >256 | >256 |
| ZDR326 | 381.9 | 128 | 0.125 | 32 | 128 | 256 | >256 |
| ZDR327 | 398.5 | 256 | 8 | >256 | >256 | >256 | >256 |
| ZDR328 | 342.4 | >256 | 1 | >256 | >256 | >256 | >256 |
| ZDR330 | 441.5 | 128 | 0.125 | 32 | 32 | >256 | >256 |
| ZDR331 | 384.5 | >256 | 16 | >256 | >256 | >256 | >256 |
| ZDR332 | 414.5 | 256 | 2 | >256 | >256 | >256 | >256 |
| ZDR333 | 456.6 | 64 | 0.125 | 128 | 128 | >256 | >256 |
| ZDR335 | 410.3 | 64 | 0.0312 | 32 | 8 | >256 | >256 |
| ZDR336 | 410.3 | 64 | 0.0625 | 64 | 128 | >256 | >256 |
| ZDR337 | 395.4 | 256 | 0.0625 | >256 | >256 | >256 | >256 |
| ZDR338 | 377.4 | 128 | 0.0625 | >256 | >256 | >256 | >256 |
| ZDR339 | 392.5 | 256 | 2 | >256 | >256 | >256 | >256 |
| ZDR340 | 392.5 | 64 | 0.25 | >256 | 32 | >256 | >256 |
| ZDR401 | 437.5 | 16 | 0.125 | 32 | 128 | 64 | >256 |
| ZDR402 | 437.5 | 16 | 0.125 | 32 | 128 | 256 | >256 |
| ZDR403 | 437.5 | 16 | 0.125 | 32 | 128 | 64 | 256 |
| ZDR404 | 449.5 | 16 | 0.125 | 32 | 256 | 128 | >256 |
| ZDR405 | 463.5 | 16 | 0.125 | 64 | 128 | 128 | >256 |
| ZDR406 | 477.5 | 16 | 0.125 | 32 | 128 | 64 | 256 |
| ZDR407 | 435.5 | 128 | 0.125 | 64 | 256 | 256 | 256 |
| ZDR408 | 463.5 | 32 | 0.125 | 64 | 256 | >256 | 256 |
| ZDR409 | 465.5 | 256 | 0.125 | 64 | 256 | >256 | >256 |
| ZDR500 | 291.4 | >256 | 0.5 | 256 | >256 | >256 | >256 |
| ZDR501 | 360.4 | >256 | 0.25 | 256 | >256 | >256 | >256 |
| ZDR502 | 349.4 | >256 | 0.25 | >256 | >256 | >256 | >256 |
| ZDR503 | 319.4 | >256 | 0.125 | >256 | 256 | >256 | >256 |
| ZDR504 | 363.5 | >256 | 0.5 | >256 | 256 | >256 | >256 |
| ZDR505 | 390.9 | >256 | 0.25 | >256 | 256 | >256 | >256 |
| ZDR506 | 303.4 | 256 | 2 | >256 | >256 | >256 | >256 |

TABLE 2

Bactericidal (MBC) activity of selected Zincaphore (ZDR) molecules

| Compound | M (g/mol) | S. uberis ATCC 19436 MBC (μg/ml) | | S. aureus ATCC 6538 MBC (μg/ml) | | E. coli ATCC 10536 MBC (μg/ml) | |
|---|---|---|---|---|---|---|---|
| | | No Zinc | Zinc (50 μM) | No Zinc | Zinc (50 μM) | No Zinc | Zinc (50 μM) |
| ZDR022-HCl | 445.9 | >256 | 0.125 | 128 | 256 | >256 | >256 |
| ZDR090 | 466.5 | 8 | 0.5 | 16 | 32 | 16 | 16 |
| ZDR091 | 439.4 | 16 | 0.5 | >256 | 128 | 256 | 128 |
| ZDR092 | 455.4 | 64 | 8 | 256 | 32 | 256 | >256 |
| ZDR095 | 486.5 | >256 | 1 | >128 | >256 | 128 | 256 |
| ZDR102 | 485.4 | 32 | 16 | 128 | 32 | 256 | >256 |
| ZDR111 | 492.5 | 8 | 1 | 16 | 16 | >256 | >256 |
| ZDR112 | 494.5 | 64 | 2 | >256 | 256 | 128 | >256 |
| ZDR114 | 701.6 | 32 | 4 | 128 | 64 | >256 | 64 |
| ZDR115 | 700.6 | 8 | 4 | 16 | 16 | 16 | 16 |
| ZDR116 | 508.5 | 64 | 2 | 128 | >256 | >256 | >256 |
| ZDR117 | 715.6 | 16 | 4 | 64 | 64 | 256 | 64 |
| ZDR119 | 566.6 | 16 | 1 | >256 | 32 | >256 | >256 |
| ZDR120 | 436.4 | >256 | 1 | >256 | >256 | >256 | >256 |
| ZDR121 | 499.5 | 256 | 32 | 64 | 256 | >256 | >256 |
| ZDR122 | 499.5 | 128 | 32 | 32 | 128 | >256 | >256 |
| ZDR124 | 602.5 | 16 | 16 | >256 | >256 | 128 | 32 |
| ZDR125 | 395.4 | 8 | 0.5 | >256 | >256 | >256 | >256 |
| ZDR127 | 394.4 | >256 | 2 | >256 | >256 | >256 | >256 |
| ZDR143 | 660.5 | 8 | 8 | 16 | 16 | 32 | 32 |
| ZDR167 | 524.5 | 8 | 0.5 | 8 | 8 | >256 | >256 |
| ZDR170 | 518.5 | 16 | 2 | 128 | 128 | >256 | >256 |
| ZDR171 | 473.5 | 8 | 0.5 | 16 | 32 | >256 | >256 |
| ZDR187 | 408.4 | 16 | 8 | 32 | 32 | 64 | 16 |
| ZDR224 | 577.5 | 64 | 8 | 128 | 32 | >256 | 256 |
| ZDR261 | 717.6 | 16 | 16 | 128 | 64 | >256 | >256 |
| ZDR269 | 743.6 | 4 | 16 | 64 | 128 | 64 | 64 |
| ZDR335 | 410.3 | 64 | 2 | >256 | >256 | >256 | >256 |

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A compound of Formula I:

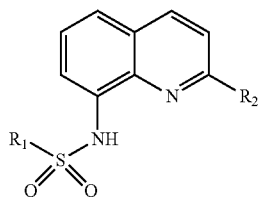

Formula I wherein $R_1$ is selected from the group comprising: saturated or unsaturated $C_1$-$C_6$ alkyl, $C_1$-$C_6$ haloalkyl, $C_1$-$C_6$ cycloalkyl, $C_3$-$C_6$ cycloalkylmethyl, phenyl or benzyl optionally substituted with one or more halogen, $C_1$-$C_6$ alkyl, $C_1$-$C_6$ haloalkyl, $OR_3$, $SR_3$, $SO_2R_3$, $SO_2NR_3R_4$, $NR_3R_4$, $NR_3CO_2R_4$, $NO_2$, CN, CHO, $COR_3$, $CO_2R_3$ or $CONR_3R_4$, 5- or 6-membered heterocyclyl or heterocyclylmethyl, 5- or 6-membered heteroaryl optionally substituted with one or more halogen, hydroxy, $OR_3$, $C_1$-$C_6$ alkyl or $CO_2R_3$, and 5- or 6-membered heteroarylmethyl optionally substituted with one or more halogen or $C_1$-$C_6$ alkyl;

$R_2$ is selected from the group comprising $C_1$-$C_6$ alkyl (heterocyclyl), ($C_1$-$C_6$ alkyl)$NR_7R_8$, ($C_1$-$C_6$ alkyl)$NR_7$ ($C_1$-$C_6$ alkyl)$NR_8R_9$, ($C_1$-$C_6$ alkyl)N(($C_1$-$C_6$ alkyl)$NR_8R_9$)$_2$, ($C_1$-$C_6$ alkyl)$NR_7$($C_1$-$C_6$ alkyl)$OR_8$, ($C_1$-$C_6$ alkyl)$NR_7$($C_1$-$C_6$ alkyl)O($C_1$-$C_6$ alkyl)$OR_8$, ($C_1$-$C_6$ alkyl)$NR_7$C(=O)$R_8$, ($C_1$-$C_6$ alkyl)$NR_7$($C_1$-$C_6$ alkyl)C (=O)$NR_8R_9$, ($C_1$-$C_6$alkyl)$NR_3$C(=NNO$_2$)$NR_4R_5$, ($C_1$-$C_6$ alkyl)$NR_3$C(=NR$_4$)$NR_5R_6$, ($C_1$-$C_6$ alkyl) $NR_3$C(=NR$_4$)$R_5$, ($C_1$-$C_6$ alkyl)$NR_3SO_2R_4$, ($C_0$-$C_3$ alkyl)CH=NOR$_7$, ($C_0$-$C_3$ alkyl)CH=NNR$_7R_8$, ($C_0$-$C_3$ alkyl)CH=NNR$_3$C(=O)R$_7$, ($C_0$-$C_3$ alkyl) CH=NNR$_3$C(=S)R$_7$, ($C_0$-$C_3$ alkyl)CH=NNR$_3$C (=O)$NR_7R_8$, ($C_0$-$C_3$ alkyl)CH=NNR$_3$C(=S)$NR_7R_8$, ($C_0$-$C_3$ alkyl)C(=O)$NR_7R_8$, ($C_0$-$C_3$ alkyl)C(=O) $NR_3OR_7$, ($C_0$-$C_3$ alkyl)C(=O)$NR_3NR_7R_8$;

provided that $R_1$ is not methyl or ethyl when $R_2$ is a methyl(heterocyclyl) group;

$R_3$, $R_4$, $R_5$ and $R_6$ are each selected from the group comprising hydrogen, $C_1$-$C_6$ alkyl, $C_1$-$C_6$ haloalkyl, and aryl; and $R_7$, $R_8$ and $R_9$ are each selected from the group comprising hydrogen, saturated or unsaturated $C_1$-$C_6$ alkyl, cycloalkyl, aryl, heterocyclyl, heteroaryl, $C_1$-$C_6$ alkyl (cycloalkyl), aralkyl, $C_1$-$C_6$ alkyl(heterocyclyl), $C_1$-$C_6$ alkyl(heteroaryl), each of which is optionally substituted with one or more of halogen, $OR_3$, $NR_3R_4$, $NR_3COR_4$, $NR_3C$(=NR$_4$) $NR_5R_6$, $NR_3C$(=NNO$_2$)$NR_4R_5$, $NR_3SO_2R_4$, $NO_2$, and $CO_2R_3$;

or a pharmaceutically acceptable salt or hydrate thereof.

2. A compound as claimed in claim 1 wherein $R_1$ is $C_1$-$C_6$ alkyl or $C_1$-$C_6$ haloalkyl, or $R_1$ is phenyl, benzyl, or 5- to 6-membered heteroaryl, each of which is optionally substituted with halogen, $C_1$-$C_6$ haloalkyl or $C_1$-$C_6$ haloalkoxy.

3. A compound as claimed in claim 1 wherein $R_1$ is (trifluoromethyl)phenyl.

4. A compound as claimed in claim 1 wherein $R_2$ is:

(i) ($C_1$-$C_6$ alkyl)$NR_7R_8$;

(ii) ($C_1$-$C_6$ alkyl)$NR_7$($C_1$-$C_6$ alkyl)$NR_8R_9$;

(iii) ($C_0$-$C_3$ alkyl)CH=$NOR_7$;

(iv) ($C_0$-$C_3$ alkyl)CH=$NNR_7R_8$;

(v) ($C_0$-$C_3$ alkyl)CH=$NNR_3$C(=O)$R_7$;

(vi) ($C_0$-$C_3$ alkyl)CH=$NNR_3$C(=O)$NR_7R_8$; or (vii) ($C_0$-$C_3$ alkyl)CH=$NNR_3$C(=S)$NR_7R_8$.

5. A compound as claimed in claim 1, which is selected from the group comprising:

ZDR022
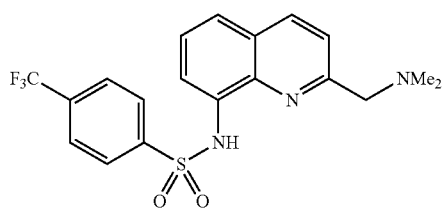

ZDR022-HCl
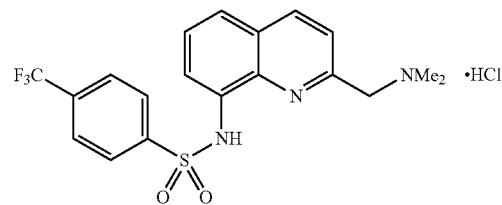

ZDR024
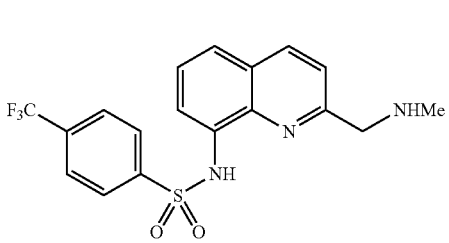

ZDR025
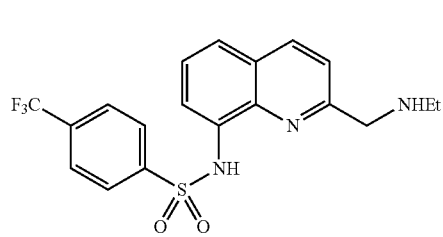

ZDR026
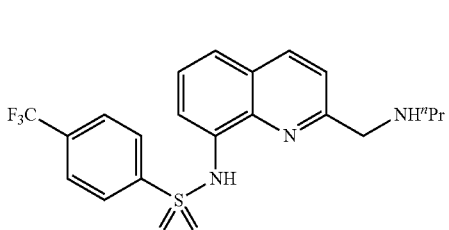

ZDR027
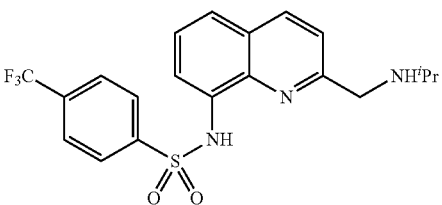

ZDR028
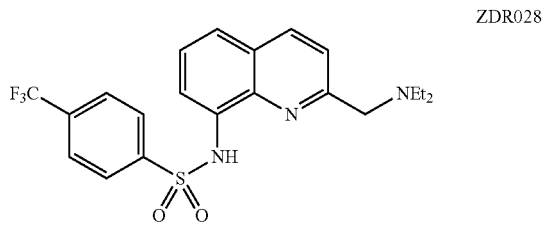

ZDR029
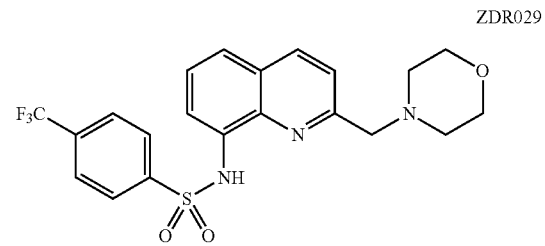

ZDR030
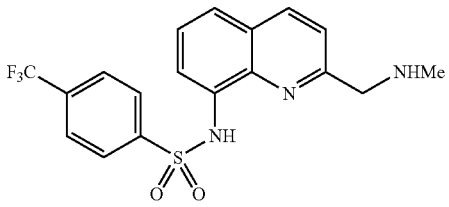

ZDR031

ZDR033

ZDR035
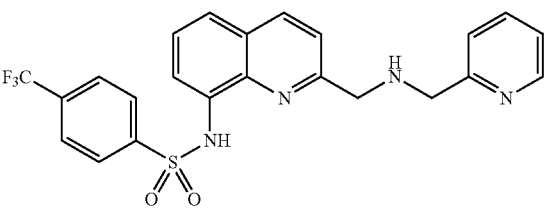

ZDR041
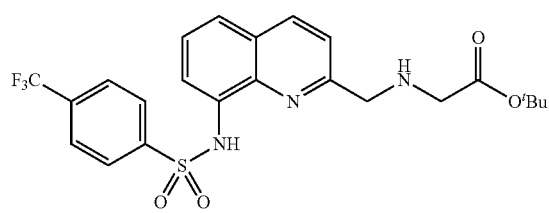
ZDR043
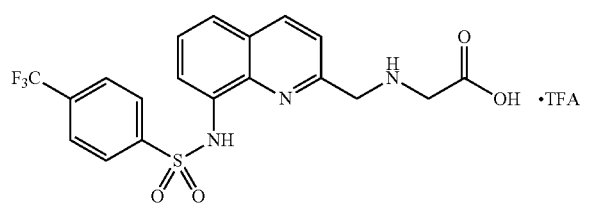
ZDR045
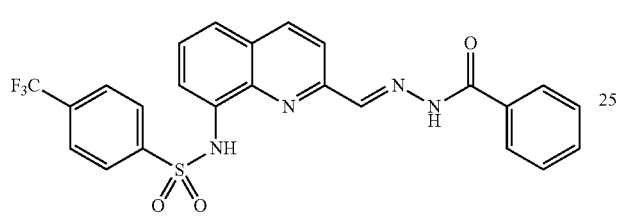
ZDR046
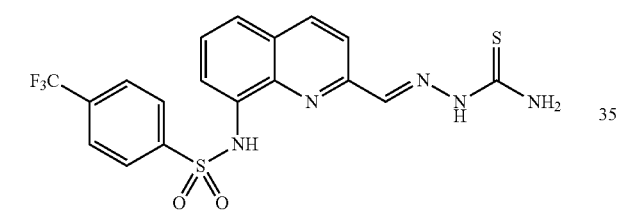
ZDR061
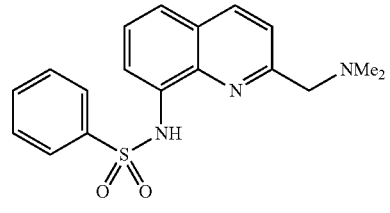
ZDR062
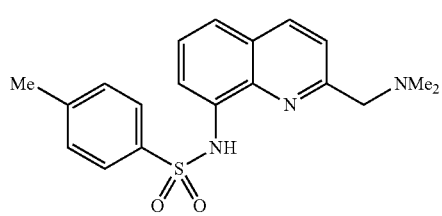
ZDR063
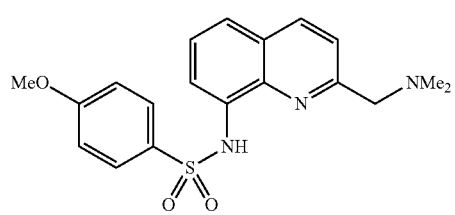
ZDR064
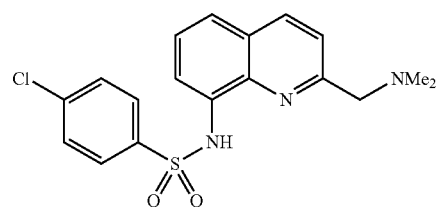
ZDR065
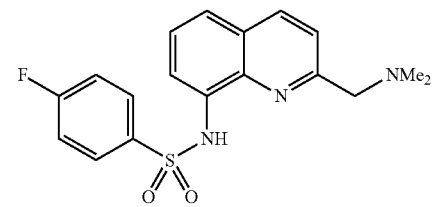
ZDR066
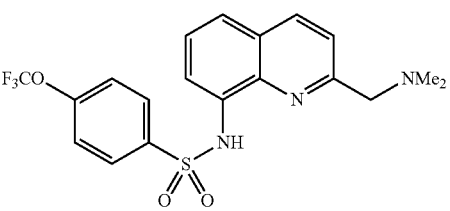
ZDR067
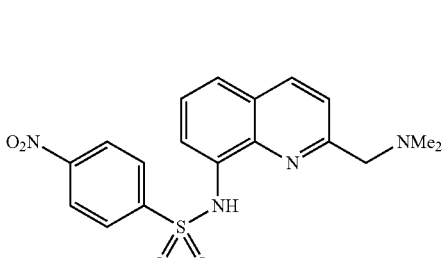
ZDR068
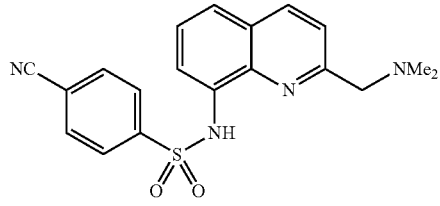
ZDR069
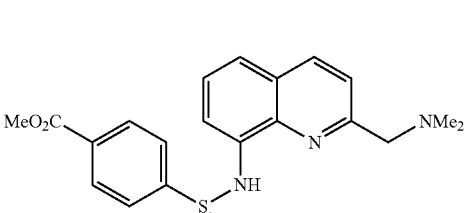
ZDR070
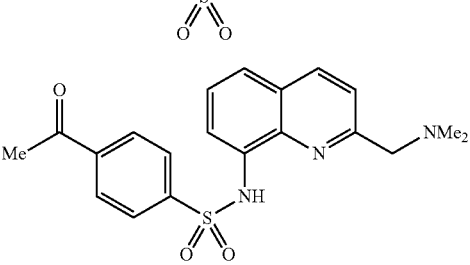

ZDR071
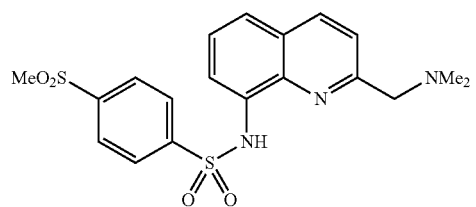
ZDR073
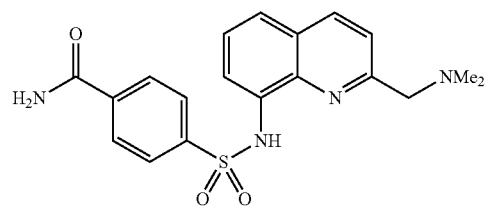
ZDR074
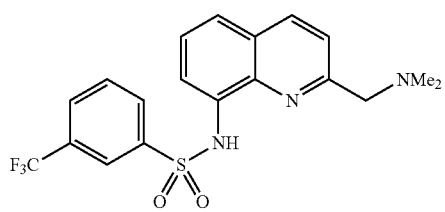
ZDR075
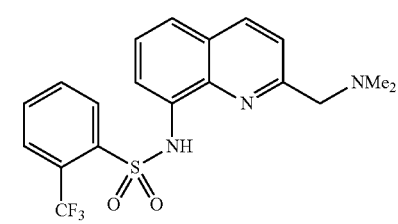
ZDR076
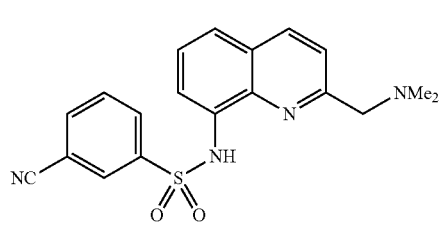
ZDR077
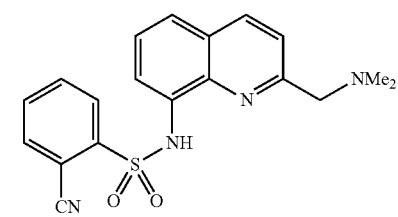
ZDR078
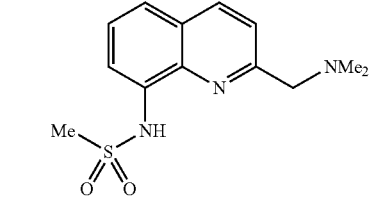
ZDR079
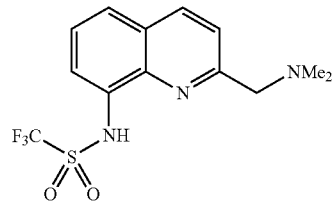
ZDR080
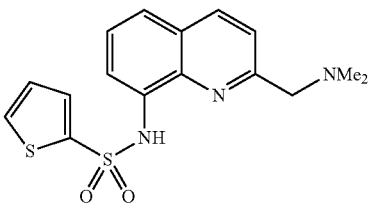
ZDR081
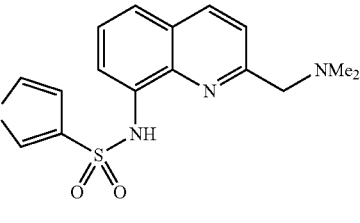
ZDR082
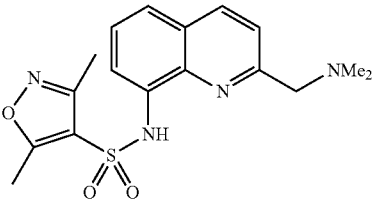
ZDR084
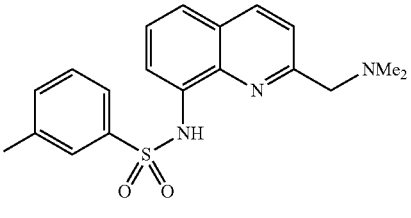
ZDR085
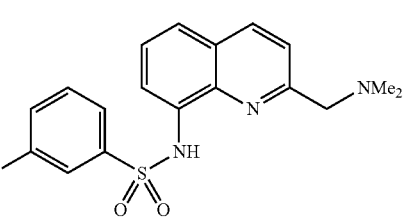
ZDR086
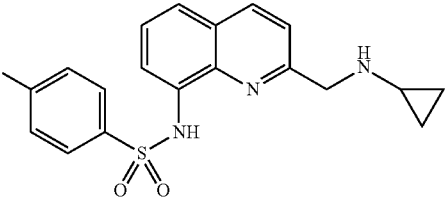

ZDR087
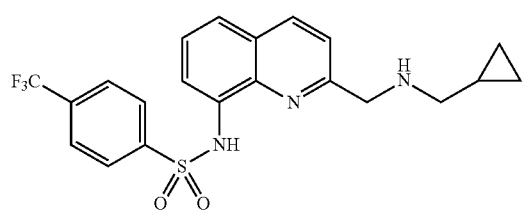
ZDR094
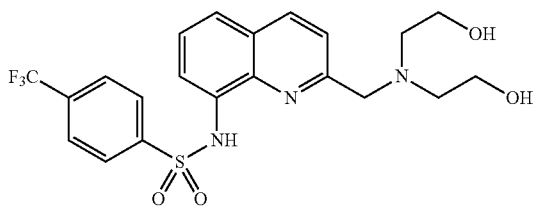
ZDR088
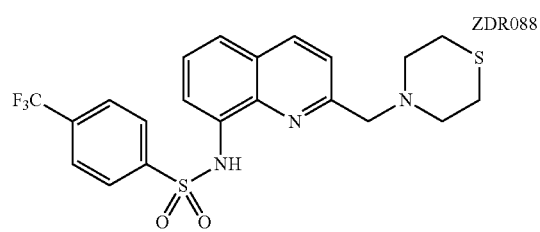
ZDR095
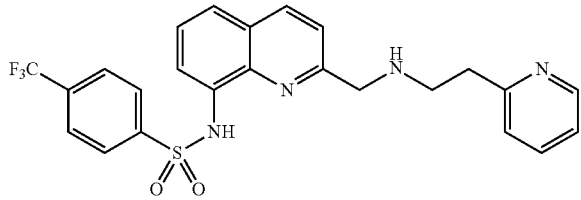
ZDR089
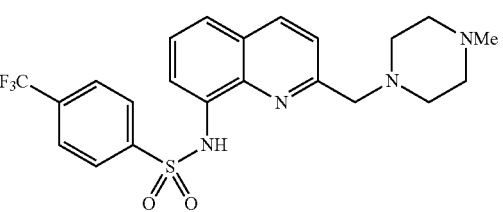
ZDR096
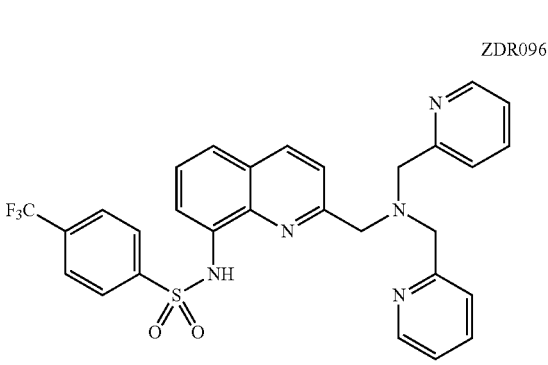
ZDR090
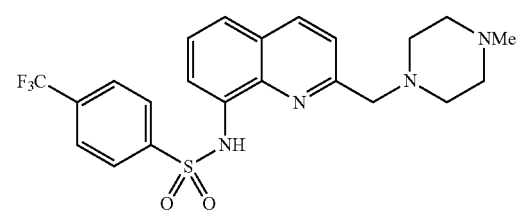
ZDR091
ZDR097
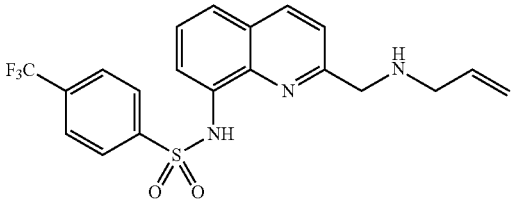
ZDR092
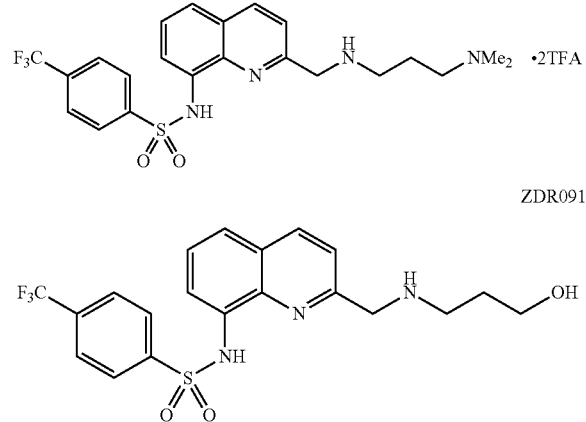
ZDR098
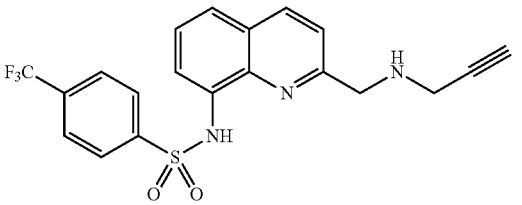
ZDR093
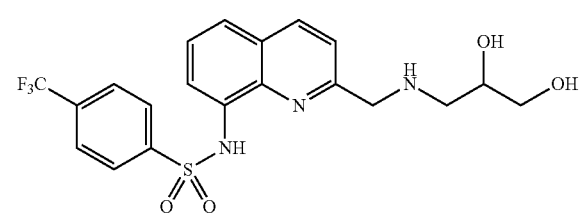
ZDR099
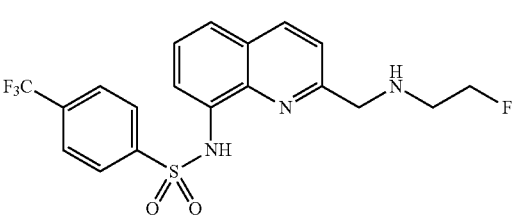

| ZDR100 | ZDR109 |
| ZDR101 | ZDR110 |
| ZDR102 | ZDR111 |
| ZDR103 | ZDR112 |
| ZDR106 | ZDR113 |
| ZDR107 | ZDR114 |
| ZDR108 | ZDR115 |

-continued
ZDR116
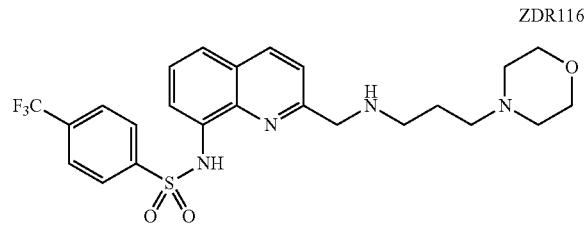
ZDR123
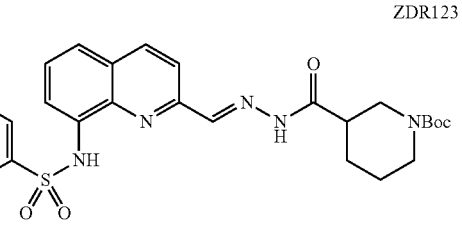
ZDR117
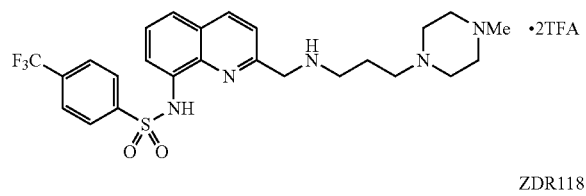
ZDR124
ZDR118
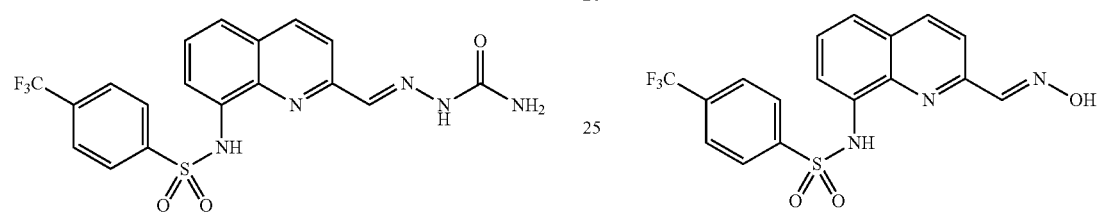
ZDR125
ZDR119
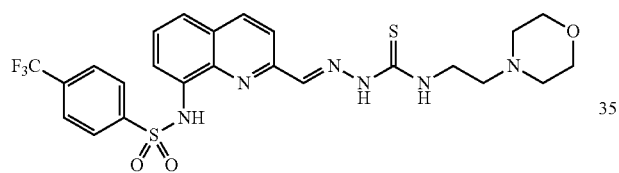
ZDR126
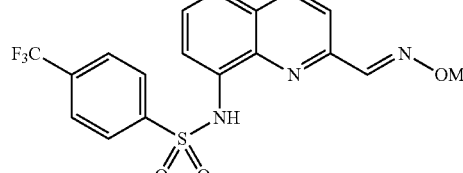
ZDR120
ZDR127
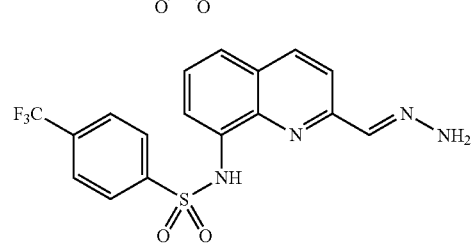
ZDR121
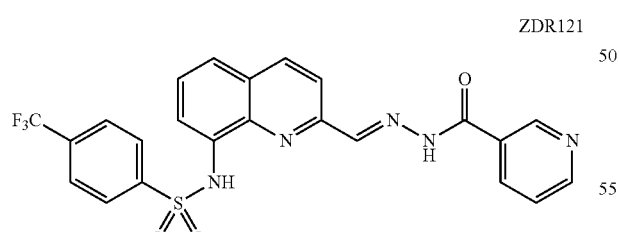
ZDR129
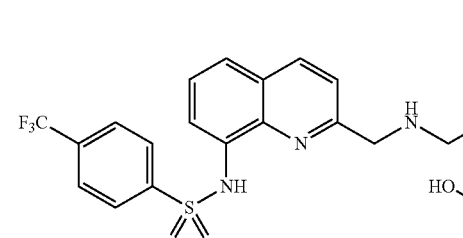
ZDR122
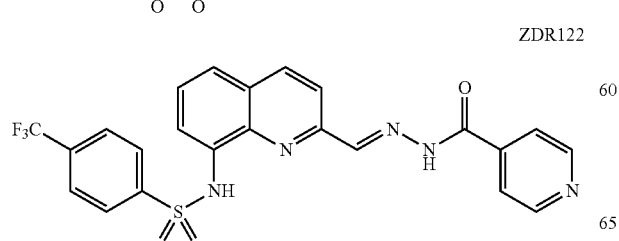
ZDR130
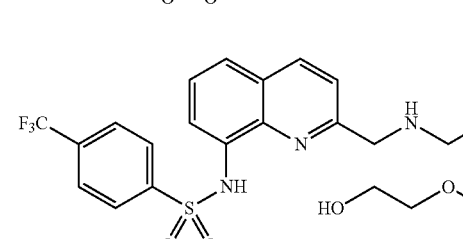

223
-continued

ZDR131, ZDR132, ZDR133, ZDR135, ZDR136, ZDR137, ZDR138

224
-continued

ZDR143, ZDR145, ZDR148, ZDR153, ZDR154, ZDR155, ZDR160

ZDR162
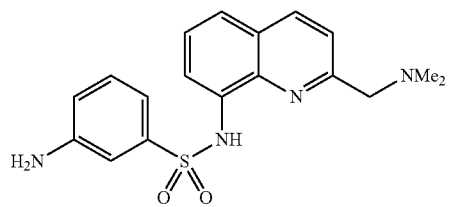
ZDR163
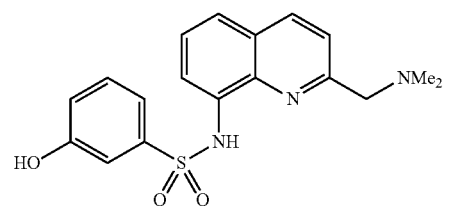
ZDR164
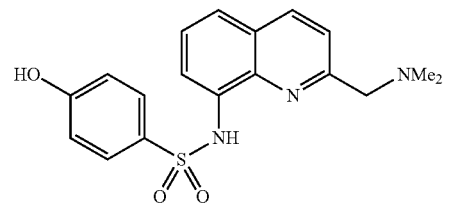
ZDR167
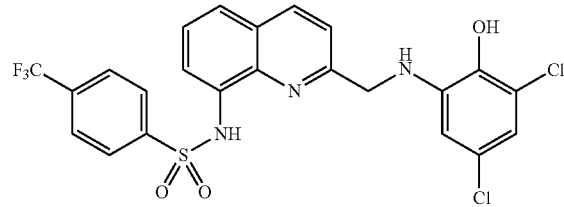
ZDR170
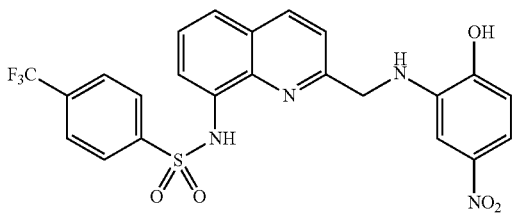
ZDR171
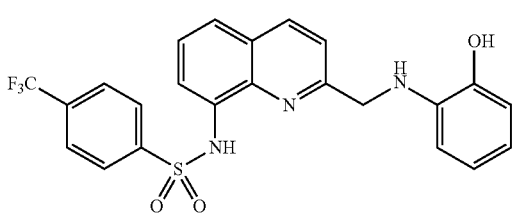
ZDR180
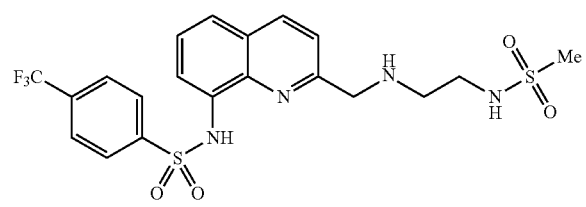
ZDR181
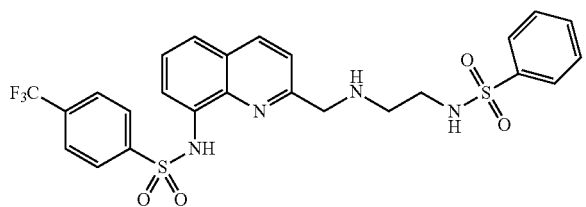
ZDR184
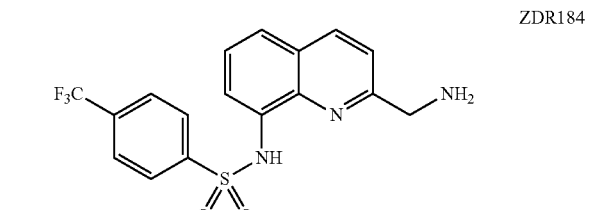
ZDR185
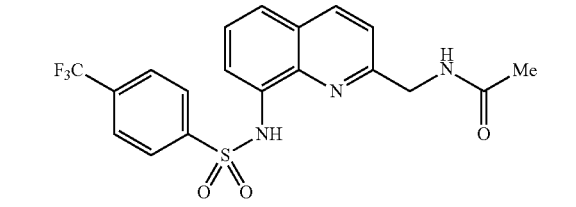
ZDR187
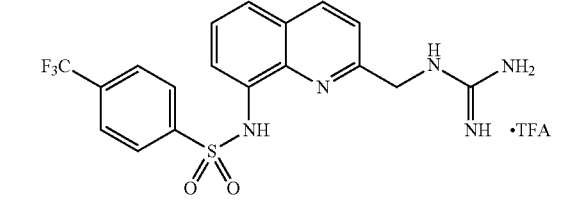
ZDR188
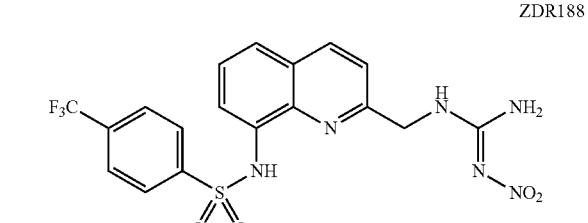
ZDR190
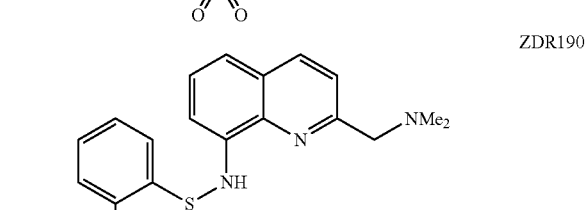
ZDR191
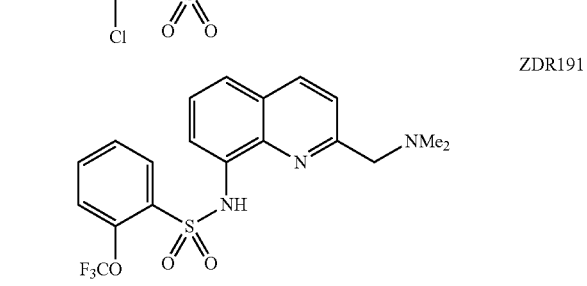

227
-continued
ZDR192
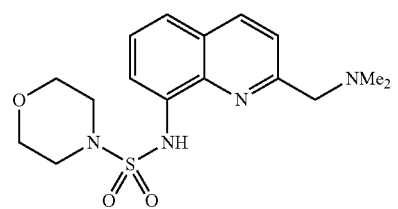
ZDR193
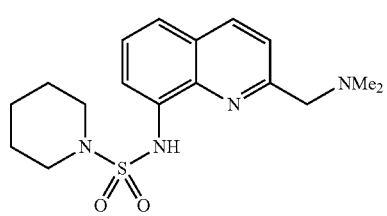
ZDR194
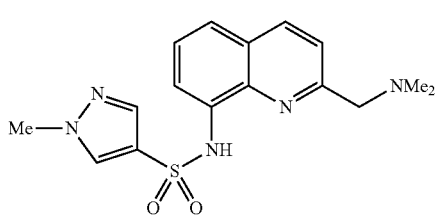
ZDR195
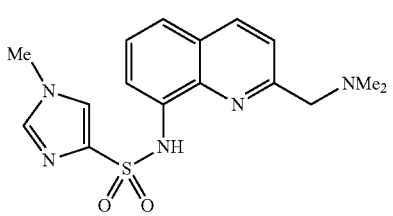
ZDR196
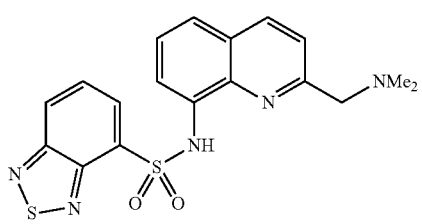
ZDR201
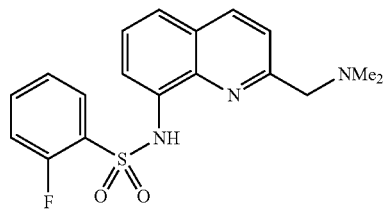
ZDR202
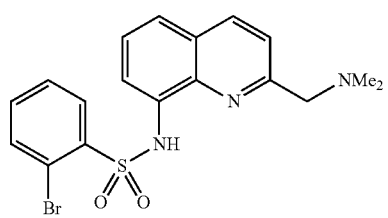
228
-continued
ZDR203
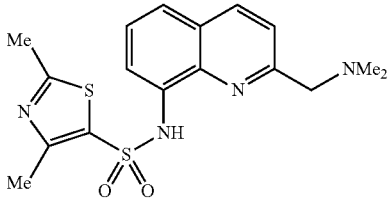
ZDR204
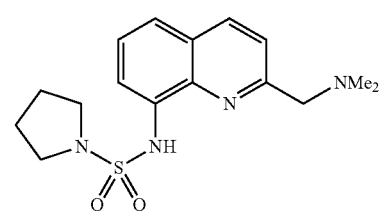
ZDR205
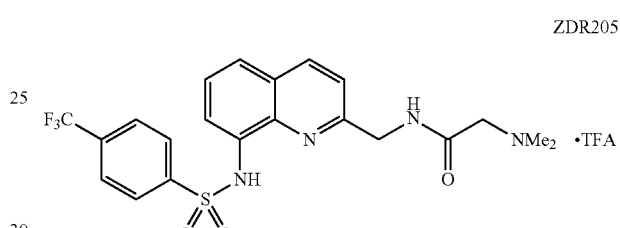
ZDR209
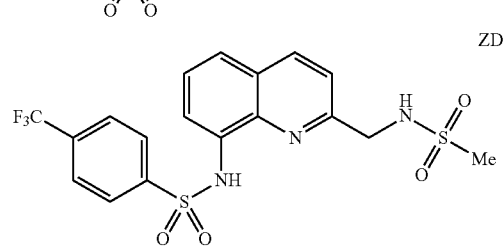
ZDR210
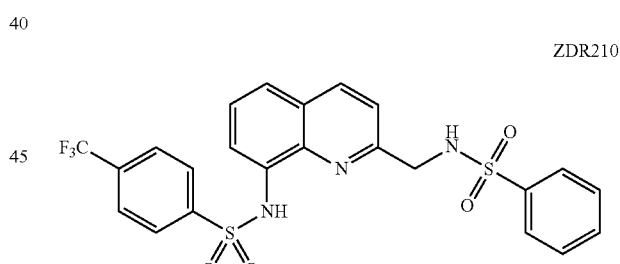
ZDR211
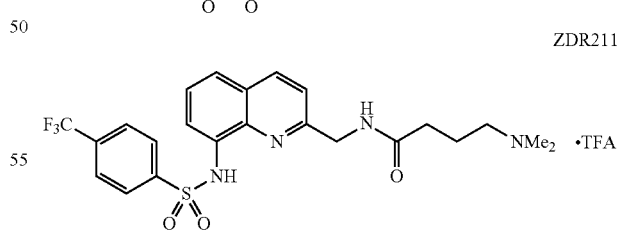
ZDR224
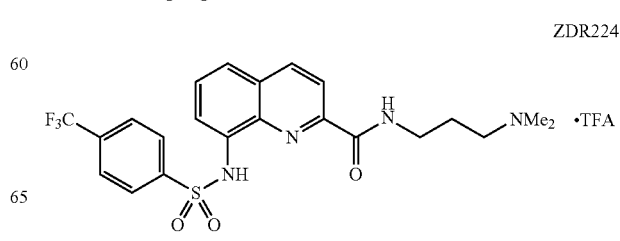

ZDR257
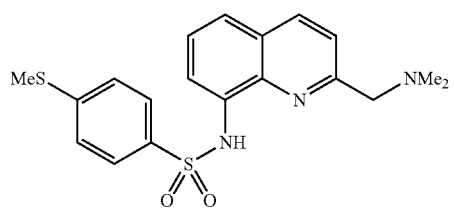
ZDR258
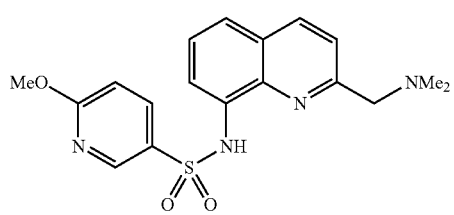
ZDR259
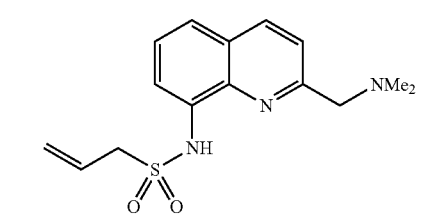
ZDR261
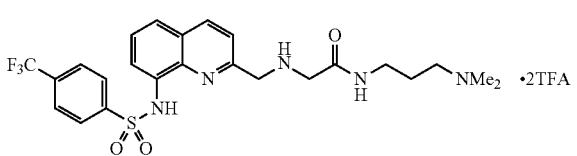
ZDR262
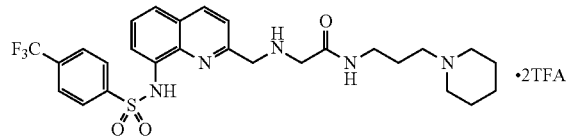
ZDR263
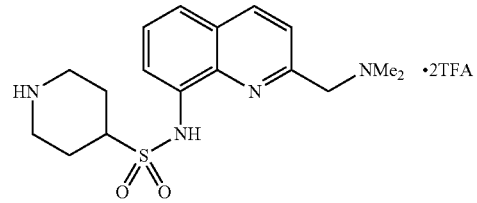
ZDR265
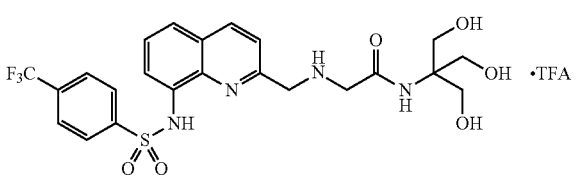
ZDR266
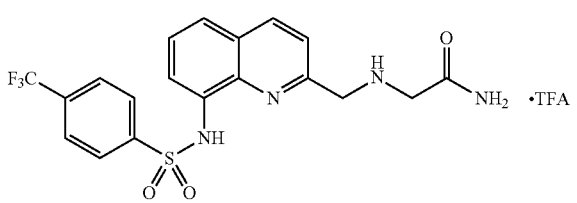
ZDR267
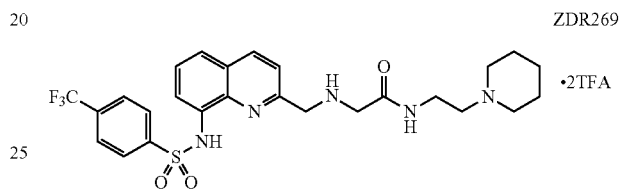
ZDR268
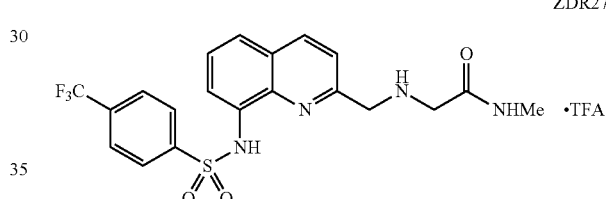
ZDR269
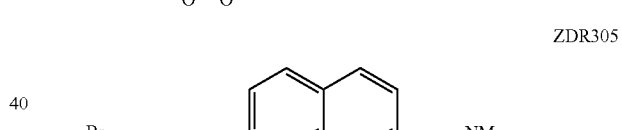
ZDR270
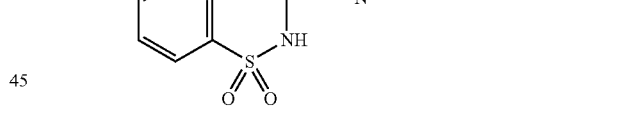
ZDR305
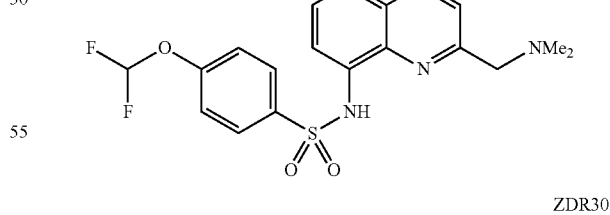
ZDR306
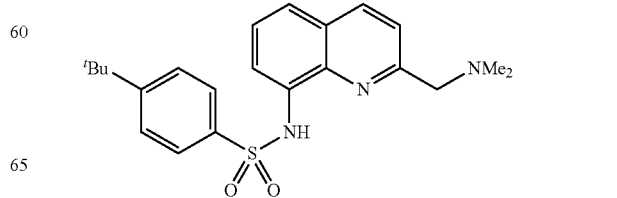
ZDR307

ZDR308
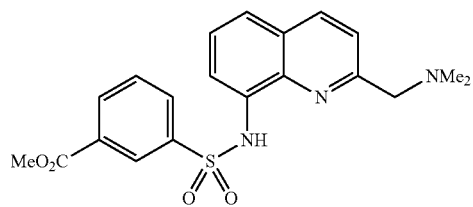
ZDR309
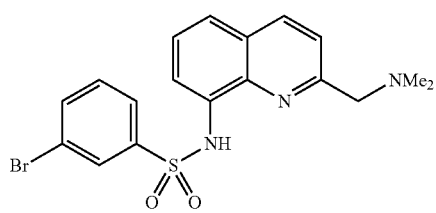
ZDR310
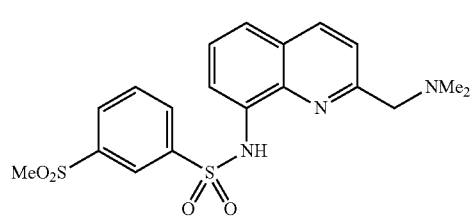
ZDR311
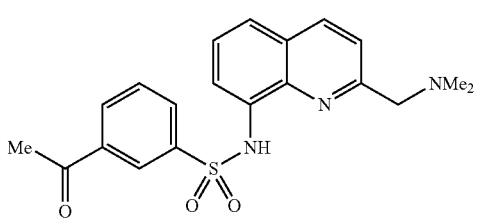
ZDR312
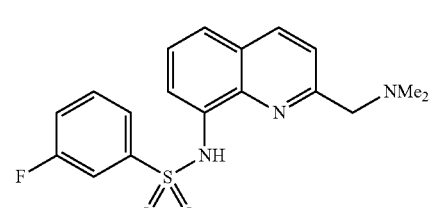
ZDR313
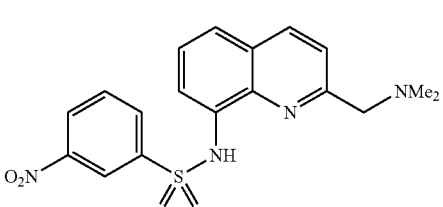
ZDR314
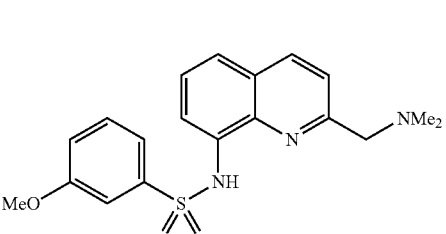
ZDR315
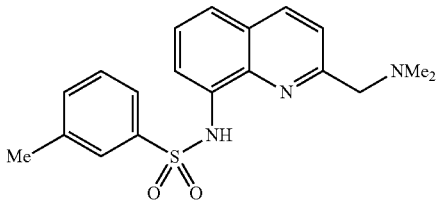
ZDR316
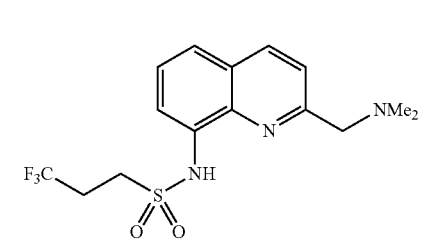
ZDR317
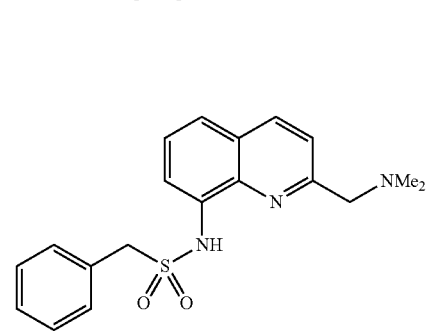
ZDR318
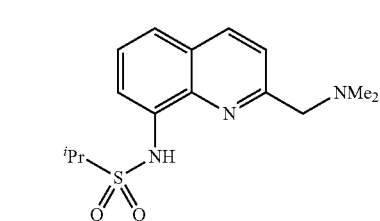
ZDR319
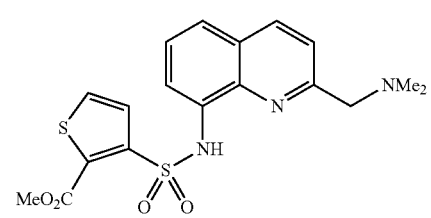
ZDR320
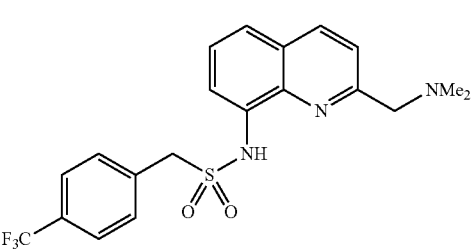

ZDR321
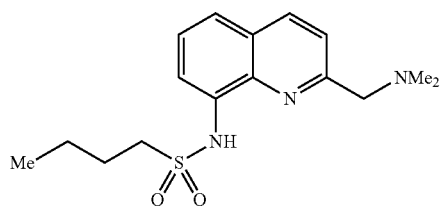
ZDR331
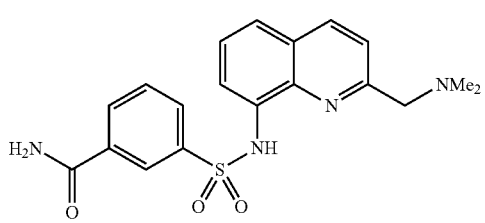
ZDR322
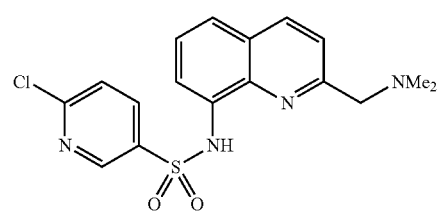
ZDR332
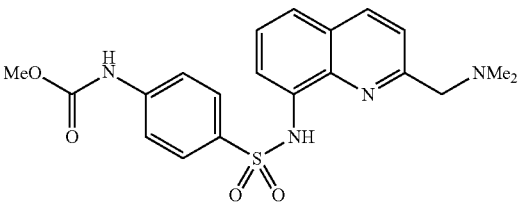
ZDR323
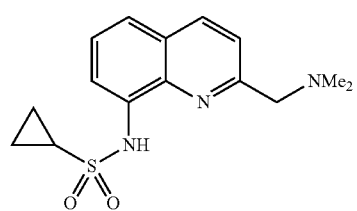
ZDR333
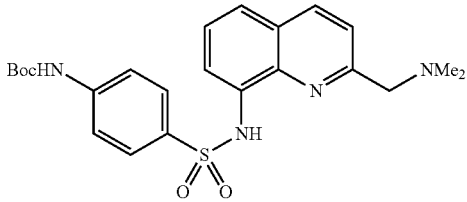
ZDR324
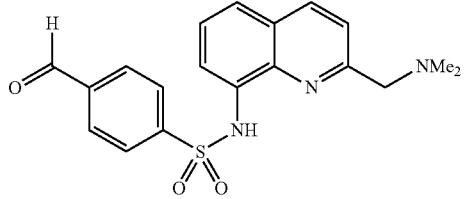
ZDR335
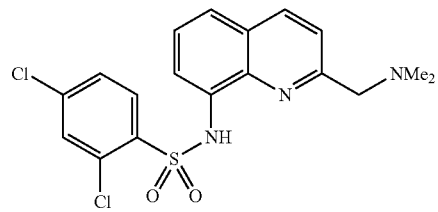
ZDR326
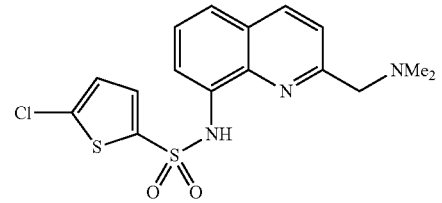
ZDR336
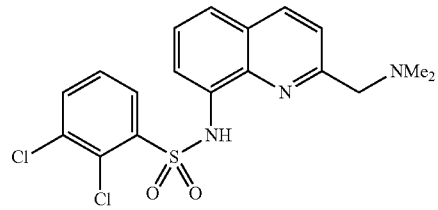
ZDR328
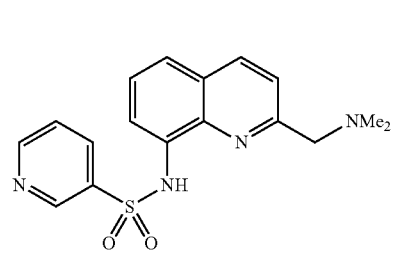
ZDR330
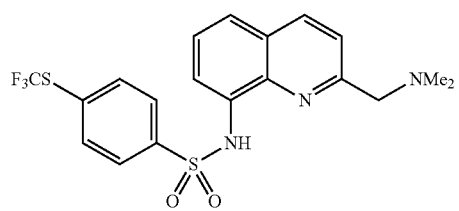
ZDR337
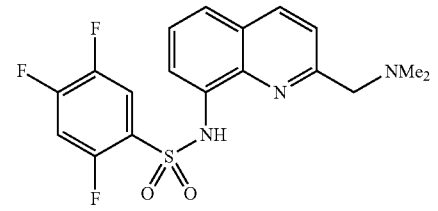

ZDR338
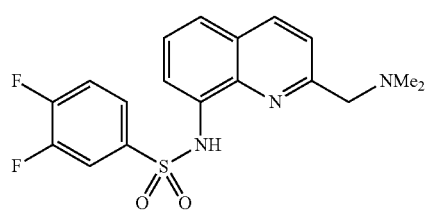
ZDR339
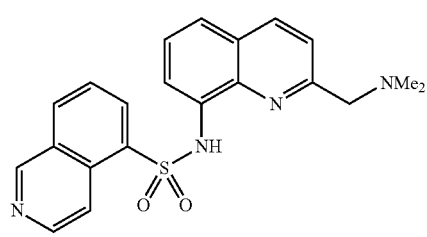
ZDR340
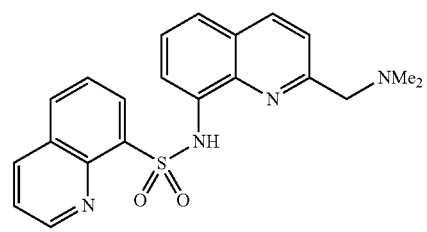
ZDR401
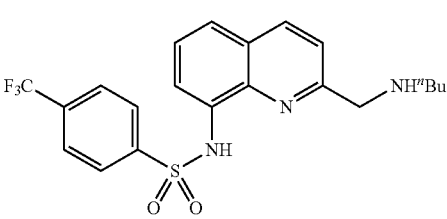
ZDR402
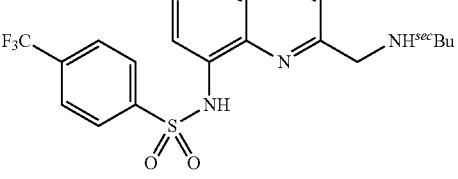
ZDR403
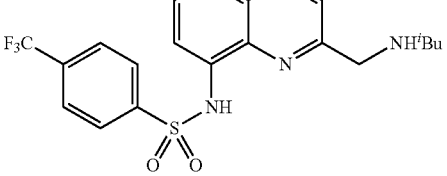
ZDR404
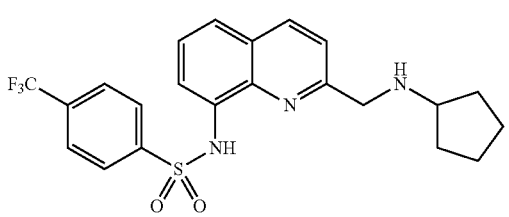
ZDR405
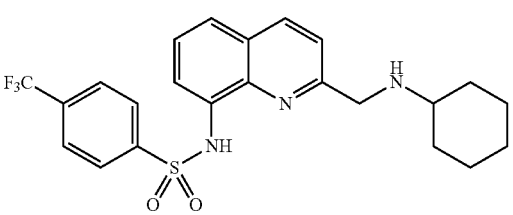
ZDR406
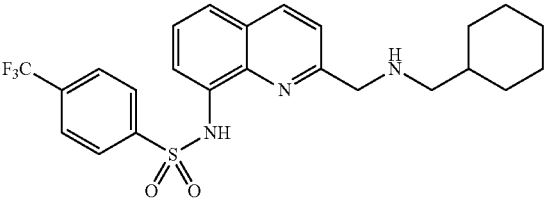
ZDR407
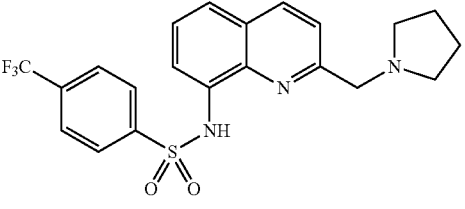
ZDR408
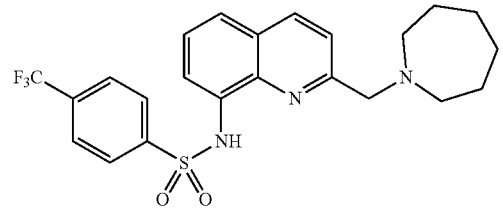
ZDR409
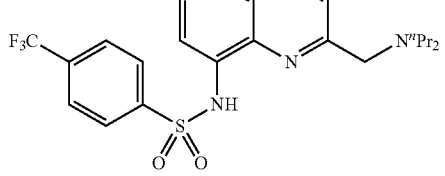
ZDR500
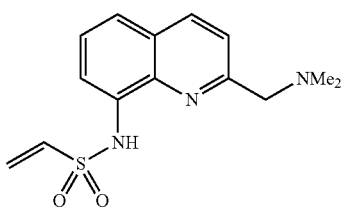

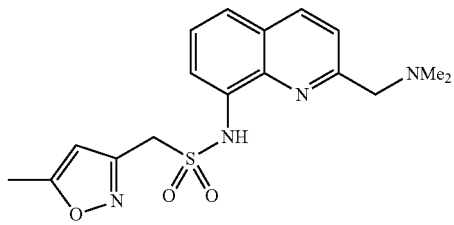

ZDR501

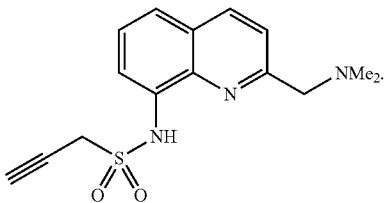

ZDR506

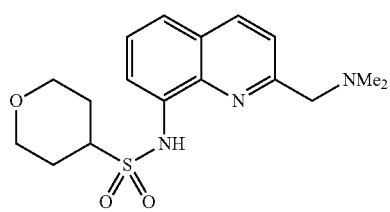

ZDR502

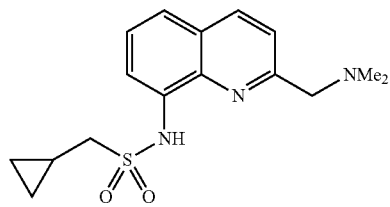

ZDR503

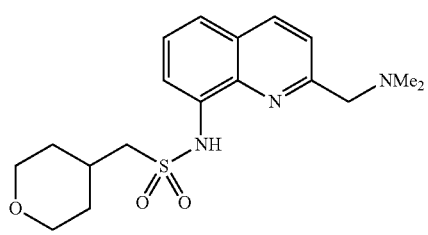

ZDR504

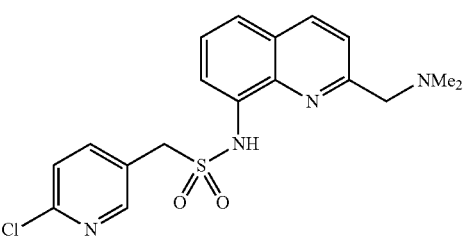 [SMILES: CN(C)Cc1ccc2cccc(NS(=O)(=O)Cc3ccc(Cl)nc3)c2n1]

ZDR505

6. A pharmaceutical composition comprising a compound of claim 1 and a pharmaceutically acceptable carrier.

7. A composition as claimed in claim 6 which is a veterinary pharmaceutical composition.

8. A composition as claimed in claim 6 further comprising an antimicrobial compound selected from the group comprising chlorhexidine, iodine, lactic acid, cetrimide, BZK (benzylalkonium chloride), amoxicillin, erythromycin, cloxacillin, pirlimycin, cephapirin, hetacillin, penicillin, nicin and lacticin.

9. A composition as claimed in claim 6 which is formulated as a tablet, capsule or powder, or as a solution, suspension or dispersion for oral, injectable or sprayable administration.

10. A pharmaceutical composition comprising a compound of claim 5 and a pharmaceutically acceptable carrier.

11. A composition as claimed in claim 10 which is a veterinary pharmaceutical composition.

12. A method of treating or preventing a bacterial infection in an animal comprising administering to an animal a pharmaceutically effective amount of a compound of claim 1.

13. A method of treating or preventing a bacterial infection in an animal comprising administering to an animal a pharmaceutically effective amount of a compound of claim 5.

14. A method as claimed in claim 13 wherein the bacterial infection is caused by *Streptococcus uberis, Staphylococcus aureus, Staphylococcus agalactiae* or *Escherichia coli*.

15. A method as claimed in claim 12 wherein the animal is a bovine cow.

* * * * *